(12) United States Patent
Bartók et al.

(10) Patent No.: US 6,599,735 B1
(45) Date of Patent: Jul. 29, 2003

(54) CONTINUOUS FERMENTATION SYSTEM

(75) Inventors: Attila Bartók, Zurich (CH); Thorsten Mueh, Leverkusen (DE); Markus Rueckel, Penzberg (DE)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/684,855

(22) Filed: Oct. 6, 2000

(30) Foreign Application Priority Data

Oct. 11, 1999 (EP) .............................................. 99120289
Sep. 8, 2000 (EP) .............................................. 00119676

(51) Int. Cl.[7] .................................................. C12M 1/36
(52) U.S. Cl. .................................. 435/286.5; 435/289.1; 435/299.2; 435/810
(58) Field of Search ....................... 435/3, 286.1, 286.5, 435/286.6, 286.7, 287.1, 289.1, 296.1, 299.1, 299.2, 813

(56) References Cited

U.S. PATENT DOCUMENTS 3,338,792 A * 8/1967 Patton et al. .................... 422/4
4,840,902 A * 6/1989 Lawford ...................... 435/161
5,081,035 A * 1/1992 Halberstadt et al. ... 210/321.79

FOREIGN PATENT DOCUMENTS

| EP | 0 684 313 A2 | 11/1995 |
| EP | 0 897 010 A2 | 2/1999 |
| EP | 0 897 985 A2 | 2/1999 |

* cited by examiner

Primary Examiner—William H. Beisner
(74) Attorney, Agent, or Firm—Bryan Cave LLP

(57) ABSTRACT

A fermentation assembly comprising: (a) a vessel for culturing living cells; (b) at least two storage flasks in fluid communication with the vessel for supply of liquids and a first transport means for transferring the liquids from the storage flasks to the vessel; (c) individual appliances operably connected to the transport means for monitoring the supply of the contents of the storage flasks to the vessel; (d) a harvest flask in fluid communication with the vessel and a second transport means for transferring the fermentation broth from the vessel to the harvest flask; and (e) a device operably connected to the first transport means for controlling and maintaining a constant dilution rate in the vessel with varying rates of individual supply of liquid from the storage flasks to the vessel is disclosed.

6 Claims, 93 Drawing Sheets

```
                         1
              50
    A. terreus 9A-1        KhsDCNSVDh GYQCFPELSH kWG1YAPYFS
LQDESPFP1D VPEDChITFV
    A. terreus cbs         NhsDCTSVDr GYQCFPELSH kWG1YAPYFS
LQDESPFP1D VPDDChITFV
    A. niger var.awamori   NqsTCDTVDQ GYQCFSETSH LWGQYAPFFS
LANESAISPD VPAGCrVTFA
    A. niger T213          NqsSCDTVDQ GYQCFSETSH LWGQYAPFFS
LANESVISPD VPAGCrVTFA
    A. niger NRRL3135      NqsSCDTVDQ GYQCFSETSH LWGQYAPFFS
LANESVISPE VPAGCrVTFA
    A. fumigatus 13073     GSkSCDTVD1 GYQCsPATSH LWGQYSPFFS
LEDE1SVSSK LPKDCrITLV
    A. fumigatus 32722     GSkSCDTVD1 GYQCsPATSH LWGQYSPFFS
LEDE1SVSSK LPKDCrITLV
    A. fumigatus 58128     GSkSCDTVD1 GYQCsPATSH LWGQYSPFFS
LEDE1SVSSK LPKDCrITLV
    A. fumigatus 26906     GSkSCDTVD1 GYQCsPATSH LWGQYSPFFS
LEDE1SVSSK LPKDCrITLV
    A. fumigatus 32239     GSkACDTVE1 GYQCsPGTSH LWGQYSPFFS
LEDE1SVSSD LPKDCrVTFV
    E. nidulans            QNHSCNTADG GYQCFPNVSH VWGQYSPYFS
IEQESAISeD VPHGCeVTFV
    T. thermophilus        DSHSCNTVEG GYQCrPEISH sWGQYSPFFS
LADQSEISPD VPQNCkITFV
    M. thermophila         ESRPCDTpD1 GFQCgTAISH FWGQYSPYFS
VpSE1DaS.. IPDDCeVTFA Consensus                  NSHSCDTVDG GYQCFPEISH LWGQYSPYFS LEDESAISPD
VPDDC-VTFV
Consensus phytase          NSHSCDTVDG GYQCFPEISH LWGQYSPYFS
LEDESAISPD VPDDCRVTFV 51
             100
    A. terreus 9A-1        QVLARHGARs PThSKtKAYA AtIAAIQKSA
TaFpGKYAFL QSYNYSLDSE
    A. terreus cbs         QVLARHGARs PTDSKtKAYA AtIAAIQKNA
TaLpGKYAFL KSYNYSMGSE
    A. niger var. awamori  QVLSRHGARY PTESKgKkYS ALIEEIQQNV
TtFDGKYAFL KTYNYSLGAD
    A. niger T213          QVLSRHGARY PTESKgKkYS ALIEEIQQNV
TtFDGKYAFL KTYNYSLGAD
    A. niger NRRL3135      QVLSRHGARY PTDSKgKkYS ALIEEIQQNA
TtFDGKYAFL KTYNYSLGAD
    A. fumigatus 13073     QVLSRHGARY PTSSKsKkYK kLVTAIQaNA
TdFKGKFAFL KTYNYTLGAD
    A. fumigatus 32722     QVLSRHGARY PTSSKsKkYK kLVTAIQaNA
TdFKGKFAFL KTYNYTLGAD
    A. fumigatus 58128     QVLSRHGARY PTSSKsKkYK kLVTAIQaNA
TdFKGKFAFL KTYNYTLGAD
    A. fumigatus 26906     QVLSRHGARY PTSSKsKkYK kLVTAIQKNA
TdFKGKFAFL KTYNYTLGAD
    A. fumigatus 32239     QVLSRHGARY PTASKsKkYK kLVTAIQKNA
TeFKGKFAFL ETYNYTLGAD
    E. nidulans            QVLSRHGARY PTESKsKAYS GLIEAIQKNA
TsFwGQYAFL ESYNYTLGAD
```

FIG. 2A

```
                                           51
       A. terreus 9A-1          QLLSRHGARY PTSSKtElYS QLISrIQKTA
TaYKGyYAFL KDYrYqLGAN
       M. thermophila           QVLSRHGARa PTlKRaaSYv DLIDrIHhGA
IsYgPgYEFL RTYDYTLGAD Consensus                       QVLSRHGARY PTSSK-KAYS ALIEAIQKNA
T-FKGKYAFL KTYNYTLGAD
       Consensus phytase        QVLSRHGARY PTSSKSKAYS ALIEAIQKNA
TAFKGKYAFL KTYNYTLGAD 101
           150
       A. terreus 9A-1          ELTPFGrNQL rDlGaQFYeR YNALTRhInP
FVRATDASRV hESAEKFVEG
       A. terreus cbs           NLTPFGrNQL qDlGaQFYRR YDTLTRhInP
FVRAADSSRV hESAEKFVEG
       A. niger var. awamori    DLTPFGEQEL VNSGIKFYQR YESLTRNIIP
FIRSSGSSRV IASGEKFIEG
       A. niger T213            DLTPFGEQEL VNSGIKFYQR YESLTRNIIP
FIRSSGSSRV IASGEKFIEG
       A. niger NRRL3135        DLTPFGEQEL VNSGIKFYQR YESLTRNIVP
FIRSSGSSRV IASGKKFIEG
       A. fumigatus 13073       DLTPFGEQQL VNSGIKFYQR YKALARSVVP
FIRASGSDRV IASGEKFIEG
       A. fumigatus 32722       DLTPFGEQQL VNSGIKFYQR YKALARSVVP
FIRASGSDRV IASGEKFIEG
       A. fumigatus 58128       DLTPFGEQQL VNSGIKFYQR YKALARSVVP
FIRASGSDRV IASGEKFIEG
       A. fumigatus 26906       DLTAFGEQQL VNSGIKFYQR YKALARSVVP
FIRASGSDRV IASGEKFIEG
       A. fumigatus 32239       DLTPFGEQQM VNSGIKFYQK YKALAgSVVP
FIRSSGSDRV IASGEKFIEG
       E. nidulans              DLTiFGENQM VDSGaKFYRR YKNLARKnTP
FIRASGSDRV VASAEKFING
       T. thermophilus          DLTPFGENQM IQlGIKFYnH YKSLARNaVP
FVRCSGSDRV IASGrlFIEG
       M. thermophila           ELTRtGQQQM VNSGIKFYRR YRALARKsIP
FVRTAGqDRV VhSAENFTQG Consensus                       DLTPFGENQM VNSGIKFYRR YKALARK-VP
FVRASGSDRV IASAEKFIEG
       Consensus phytase        DLTPFGENQM VNSGIKFYRR YKALARKIVP
FIRASGSDRV IASAEKFIEG 151
           200
       A. terreus 9A-1          FQTARqDDHh ANpHQPSPrV DVaIPEGSAY
NNTLEHSlCT AFES...STV
       A. terreus cbs           FQNARqGDPh ANpHQPSPrV DVVIPEGTAY
NNTLEhSICT AFEA...STV
       A. niger var. awamori    FQSTKLkDPr AqpgQSSPkI DVVISEASSs
NNTLDPGTCT VFED...SEL
       A. niger T213            FQSTKLkDPr AqpgQSSPkI DVVISEASSs
NNTLDPGTCT VFED...SEL
       A. niger NRRL3135        FQSTKLkDPr AqpgQSSPkI DVVISEASSs
NNTLDPGTCT VFED...SEL
```

FIG. 2B

```
         A. fumigatus 13073       FQqAKLADPG A.TNRAAPAI SVIIPESETF
NNTLDHGVCT kFEA...SQL
         A. fumigatus 32722       FQqAKLADPG A.TNRAAPAI SVIIPESETF
NNTLDHGVCT kFEA...SQL
         A. fumigatus 58128       FQqAKLADPG A.TNRAAPAI SVIIPESETF
NNTLDHGVCT kFEA...SQL
         A. fumigatus 26906       FQqAKLADPG A.TNRAAPAI SVIIPESETF
NNTLDHGVCT kFEA...SQL
         A. fumigatus 32239       FQqANVADPG A.TNRAAPVI SVIIPESETY
NNTLDHSVCT NFEA...SEL
         E. nidulans              FRKAQLhDHG S..gQATPVV NVIIPEiDGF
NNTLDHSTCV SFEN...DEr
         T. thermophilus          FQSAKVlDPh SDkHDAPPTI NVIIeEGPSY
NNTLDtGSCP VFED...SSg
         M. thermophila           FHSAlLADRG STvRPTlPyd mVVIPETAGa
NNTLHNDlCT AFEEgpySTI Consensus                         FQSAKLADPG S-PHQASPVI NVIIPEGSGY NNTLDHGTCT
AFED---SEL
     Consensus phytase            FQSAKLADPG SQPHQASPVI DVIIPEGSGY
NNTLDHGTCT AFED...SEL 201
         250
         A. terreus 9A-1          GDDAvANFTA VFAPAIaQRL EADLPGVqLS
TDDVVnLMAM CPFETVSlTD
         A. terreus cbs           GDAAADNFTA VFAPAIakRL EADLPGVqLS
ADDVVnLMAM CPFETVSlTD
         A. niger var. awamori    ADTVEANFTA TFAPSIRQRL ENDLSGVTLT
DTEVTyLMDM CSFDTIStST
         A. niger T213            ADTVEANFTA TFAPSIRQRL ENDLSGVTLT
DTEVTyLMDM CSFDTIStST
         A. niger NRRL3135        ADTVEANFTA TFVPSIRQRL ENDLSGVTLT
DTEVTyLMDM CSFDTIStST
         A. fumigatus 13073       GDEVAANFTA lFAPDIRARa EkHLPGVTLT
DEDVVsLMDM CSFDTVARTS
         A. fumigatus 32722       GDEVAANFTA lFAPDIRARa EkHLPGVTLT
DEDVVsLMDM CSFDTVARTS
         A. fumigatus 58128       GDEVAANFTA lFAPDIRARa EkHLPGVTLT
DEDVVsLMDM CSFDTVARTS
         A. fumigatus 26906       GDEVAANFTA lFAPDIRARa KkHLPGVTLT
DEDVVsLMDM CSFDTVARTS
         A. fumigatus 32239       GDEVEANFTA lFAPAIRARI EkHLPGVqLT
DDDVVsLMDM CSFDTVARTA
         E. nidulans              ADEiEANFTA IMGPPIRkRL ENDLPGIKLT
NENVIyLMDM CSFDTMARTA
         T. thermophilus          GHDAQEKFAk qFAPAIlEKI KDHLPGVDLA
vSDVpyLMDL CPFETLARNh
         M. thermophila           GDDAQDTYlS TFAGPItARV NANLPGANLT
DADTVaLMDL CPFETVAsSS
```

FIG. 2C

```
Consensus              GDDAEANFTA TFAPAIRARL EADLPGVTLT DEDVV-LMDM
  CPFETVARTS
       Consensus phytase   GDDVEANFTA LFAPAIRARL EADLPGVTLT
  DEDVVYLMDM CPFETVARTS 251
         300
    A. terreus 9A-1        ........ ...DAhTLSPFC DLFTAtEWtq
  YNYLlSLDKY YGYGGGNPLG
    A. terreus cbs         ........ ...DAhTLSPFC DLFTAaEWtq
  YNYLlSLDKY YGYGGGNPLG
    A. niger var. awamori  ........ ...vDTKLSPFC DLFTHdEWih
  YDYLQSLkKY YGHGAGNPLG
    A. niger T213          ........ ...vDTKLSPFC DLFTHdEWih
  YDYLRSLkKY YGHGAGNPLG
    A. niger NRRL3135      ........ ...vDTKLSPFC DLFTHdEWin
  YDYLQSLkKY YGHGAGNPLG
    A. fumigatus 13073     ........ ...DASQLSPFC QLFTHnEWkk
  YNYLQSLGKY YGYGAGNPLG
    A. fumigatus 32722     ........ ...DASQLSPFC QLFTHnEWkk
  YNYLQSLGKY YGYGAGNPLG
    A. fumigatus 58128     ........ ...DASQLSPFC QLFTHnEWkk
  YNYLQSLGKY YGYGAGNPLG
    A. fumigatus 26906     ........ ...DASQLSPFC QLFTHnEWkk
  YNYLQSLGKY YGYGAGNPLG
    A. fumigatus 32239     ........ ...DASELSPFC AIFTHnEWkk
  YDYLQSLGKY YGYGAGNPLG
    E. nidulans            ........ ...HGTELSPFC AIFTEkEWlq
  YDYLQSLSKY YGYGAGSPLG
    T. thermophilus        ........ ...TDT.LSPFC ALsTQeEWqa
  YDYYQSLGKY YGnGGGNPLG
    M. thermophila         sdpatadagg gNGrpLSPFC rLFSEsEWra
  YDYLQSVGKW YGYGPGNPLG Consensus              ---------- -DATELSPFC ALFTE-EW-- YDYLQSLGKY
  YGYGAGNPLG
       Consensus phytase   .......... .DATELSPFC ALFTHDEWRQ
  YDYLQSLGKY YGYGAGNPLG 301
         350
    A. terreus 9A-1        PVQGVGWaNE LMARLTRAPV HDHTCVNNTL
  DASPATFPLN ATLYADFSHD
    A. terreus cbs         PVQGVGWaNE LIARLTRSPV HDHTCVNNTL
  DANPATFPLN ATLYADFSHD
    A. niger var. awamori  PTQGVGYaNE LIARLTHSPV HDDTSSNHTL
  DSNPATFPLN STLYADFSHD
    A. niger T213          PTQGVGYaNE LIARLTHSPV HDDTSSNHTL
  DSNPATFPLN STLYADFSHD
    A. niger NRRL3135      PTQGVGYaNE LIARLTHSPV HDDTSSNHTL
  DSSPATFPLN STLYADFSHD
    A. fumigatus 13073     PAQGIGFtNE LIARLTRSPV QDHTSTNsTL
  vSNPATFPLN ATMYVDFSHD
```

FIG. 2D

```
A. fumigatus 32722     PAQGIGFtNE LIARLTRSPV QDHTSTNsTL vSNPATFPLN ATMYVDFSHD
A. fumigatus 58128     PAQGIGFtNE LIARLTRSPV QDHTSTNsTL vSNPATFPLN ATMYVDFSHD
A. fumigatus 26906     PAQGIGFtNE LIARLTRSPV QDHTSTNsTL vSNPATFPLN ATMYVDFSHD
A. fumigatus 32239     PAQGIGFtNE LIARLTNSPV QDHTSTNsTL DSDPATFPLN ATIYVDFSHD
E. nidulans            PAQGIGFtNE LIARLTQSPV QDNTSTNHTL DSNPATFPLD rKLYADFSHD
T. thermophilus        PAQGVGFvNE LIARMTHSPV QDYTTVNHTL DSNPATFPLN ATLYADFSHD
M. thermophila         PTQGVGFvNE LLARLAgvPV RDgTSTNRTL DGDPrTFPLG rPLYADFSHD Consensus              PAQGVGF-NE LIARLTHSPV QDHTSTNHTL DSNPATFPLN ATLYADFSHD
Consensus phytase      PAQGVGFANE LIARLTRSPV QDHTSTNHTL DSNPATFPLN ATLYADFSHD 351                                              400
A. terreus 9A-1        SNLVSIFWAL GLYNGTAPLS qTSVESVSQT DGYAAAWTVP FAARAYVEMM
A. terreus cbs         SNLVSIFWAL GLYNGTkPLS qTTVEDITrT DGYAAAWTVP FAARAYIEMM
A. niger var. awamori  NGIISILFAL GLYNGTkPLS TTTVENITQT DGFSSAWTVP FASRlYVEMM
A. niger T213          NGIISILFAL GLYNGTkPLS TTTVENITQT DGFSSAWTVP FASRlYVEMM
A. niger NRRL3135      NGIISILFAL GLYNGTkPLS TTTVENITQT DGFSSAWTVP FASRlYVEMM
A. fumigatus 13073     NSMVSIFFAL GLYNGTEPLS rTSVESaKEl DGYSASWVVP FGARAYFEtM
A. fumigatus 32722     NSMVSIFFAL GLYNGTGPLS rTSVESaKEl DGYSASWVVP FGARAYFEtM
A. fumigatus 58128     NSMVSIFFAL GLYNGTEPLS rTSVESaKEl DGYSASWVVP FGARAYFEtM
A. fumigatus 26906     NSMVSIFFAL GLYNGTEPLS rTSVESaKEl DGYSASWVVP FGARAYFEtM
A. fumigatus 32239     NGMIPIFFAM GLYNGTEPLS qTSeESTKES NGYSASWAVP FGARAYFEtM
E. nidulans            NSMISIFFAM GLYNGTQPLS mDSVESIQEm DGYAASWTVP FGARAYFELM
T. thermophilus        NTMTSIFaAL GLYNGTAkLS TTEIKSIEET DGYSAAWTVP FGGRAYIEMM
M. thermophila         NDMMGVLgAL GaYDGVPPLD KTArrDpEEl GGYAASWAVP FAARiYVEKM Consensus              NSMISIFFAL GLYNGTAPLS TTSVESIEET DGYAASWTVP FGARAYVEMM
Consensus phytase      NSMISIFFAL GLYNGTAPLS TTSVESIEET DGYSASWTVP FGARAYVEMM
```

FIG. 2E

```
                                401
            450
    A. terreus 9A-1      QC.............RAEKE PLVRVLVNDR
VMPLHGCPTD KLGRCKrDAF
    A. terreus cbs       QC.............RAEKQ PLVRVLVNDR
VMPLHGCAVD NLGRCKrDDF
    A. niger var. awamori QC............QAEQE PLVRVLVNDR
VVPLHGCPID aLGRCTrDSF
    A. niger T213        QC.............QAEQE PLVRVLVNDR
VVPLHGCPID aLGRCTrDSF
    A. niger NRRL3135    QC.............QAEQE PLVRVLVNDR
VVPLHGCPVD aLGRCTrDSF
    A. fumigatus 13073   QC.............KSEKE PLVRALINDR
VVPLHGCDVD KLGRCKLNDF
    A. fumigatus 32722   QC.............KSEKE PLVRALINDR
VVPLHGCDVD KLGRCKLNDF
    A. fumigatus 58128   QC.............KSEKE SLVRALINDR
VVPLHGCDVD KLGRCKLNDF
    A. fumigatus 26906   QC.............KSEKE PLVRALINDR
VVPLHGCDVD KLGRCKLNDF
    A. fumigatus 32239   QC.............KSEKE PLVRALINDR
VVPLHGCAVD KLGRCKLKDF
    E. nidulans          QC.............E.KKE PLVRVLVNDR
VVPLHGCAVD KFGRCTLDDW
    T. thermophilus      QC.............DDSDE PVVRVLVNDR
VVPLHGCEVD SLGRCKrDDF
    M. thermophila       RCsggggggg ggegrQEKDE eMVRVLVNDR
VMTLkGCGAD ErGMCTLErF Consensus            QC--------- -----QAEKE PLVRVLVNDR VVPLHGCAVD
KLGRCKLDDF
    Consensus phytase    QC.............QAEKE PLVRVLVNDR
VVPLHGCAVD KLGRCKRDDF 451
        471
    A. terreus 9A-1      VAGLSFAQAG GNWADCF~~~ ~
    A. terreus cbs       VEGLSFARAG
GNWAECF~~~ ~
    A. niger var. awamori VrGLSFARSG GDWAECsA~~ ~
    A. niger T213        VrGLSFARSG GDWAECFA~~ ~
    A. niger NRRL3135    VrGLSFARSG
GDWAECFA~~ ~
    A. fumigatus 13073   VKGLSWARSG GNWGECFS~~ ~
    A. fumigatus 32722   VKGLSWARSG GNWGECFS~~ ~
    A. fumigatus 58128   VKGLSWARSG GNWGECFS~~ ~
    A. fumigatus 26906   VKGLSWARSG GNWGECFS~~ ~
    A. fumigatus 32239   VKGLSWARSG
GNSEQSFS~~ ~
    E. nidulans          VEGLNFARSG GNWkTCFT1~ ~
    T. thermophilus      VrGLSFARqG GNWEGCYAas e
    M. thermophila       IESMAFARGN GKWD1CFA~~ ~

Consensus            VEGLSFARSG GNWAECFA-- -
    Consensus phytase    VEGLSFARSG GNWAECFA.. .
```

EcoRI  M  G  V  F  V  V  L  L  S  I  A  T  L  F  G  S  T
        TATATGAATTCATGGGCGTGTTCGTCGTGCTACTGTCCATTGCCACCTTGTTCGGTTCCA

1   ---------+---------+---------+---------+---------+---------+
                                                                  60
        ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G

CATCCGGTACCGCCTTGGGTCCTCGTGGTAATTCTCACTCTTGTGACACTGTTGACGGTG

61   ---------+---------+---------+---------+---------+---------+
                                                                 120
        GTAGGCCATGGCGGAACCCAGGAGCACCATTAAGAGTGAGAACACTGTGACAACTGCCAC

CP-2
                    CP-3

Y  Q  C  F  P  E  I  S  H  L  W  G  Q  Y  S  P  Y  F  S  L
        GTTACCAATGTTTCCCAGAAATTTCTCACTTGTGGGGTCAATACTCTCCATACTTCTCTT

121   ---------+---------+---------+---------+---------+---------+
                                                                 180

CAATGGTTACAAAGGGTCTTTTAAAGAGTGAACACCCCAGTTATGAGAGGTATGAAGAGAA

E  D  E  S  A  I  S  P  D  V  P  D  D  C  R  V  T  F  V  Q

TGGAAGACGAATCTGCTATTTCTCCAGACGTTCCAGACGACTGTAGAGTTACTTTCGTTC

```
                ACCTTCTGCTTAGACGATAAAGAGGTCTGCAAGGTCTGCTGACATCTCAATGAAAGCAAG

CP-4
                                              CP-5

V  L  S  R  H  G  A  R  Y  P  T  S  S  K  S  K  A  Y  S  A

AAGTTTTGTCTAGACACGGTGCTAGATACCCAACTTCTTCTAAGTCTAAGGCTTACTCTG
         241 ---------+---------+---------+---------+---------+---------+---------+
         300
         TTCAAAACAGATCTGTGCCACGATCTATGGGTTGAAGAAGATTCAGATTCCGAATGAGAC

L  I  E  A  I  Q  K  N  A  T  A  F  K  G  K  Y  A  F  L  K

CTTTGATTGAAGCTATTCAAAAGAACGCTACTGCTTTCAAGGGTAAGTACGCTTTCTTGA
         301 ---------+---------+---------+---------+---------+---------+---------+
         360
         GAAACTAACTTCGATAAGTTTTCTTGCGATGACGAAAGTTCCCATTCATGCGAAAGAACT

CP-6
                                              CP-7

T  Y  N  Y  T  L  G  A  D  D  L  T  P  F  G  E  N  Q  M  V

AGACTTACAACTACACTTTGGGTGCTGACGACTTGACTCCATTCGGTGAAAACCAAATGG
         361 ---------+---------+---------+---------+---------+---------+---------+
         420
         TCTGAATGTTGATGTGAAACCCACGACTGCTGAACTGAGGTAAGCCACTTTTGGTTTACC

N  S  G  I  K  F  Y  R  R  Y  K  A  L  A  R  K  I  V  P  F
         TTAACTCTGGTATTAAGTTCTACAGAAGATACAAGGCTTTGGCTAGAAAGATTGTTCCAT
```

FIG. 3B

```
                421 ---------+---------+---------+---------+---------+---------+
                480
                    AATTGAGACCATAATTCAAGATGTCTTCTATGTTCCGAAACCGATCTTTCTAACAAGGTA

CP-8

CP-9

I  R  A  S  G  S  D  R  V  I  A  S  A  E  K  F  I  E  G  F
                    TCATTAGAGCTTCTGGTTCTGACAGAGTTATTGCTTCTGCTGAAAAGTTCATTGAAGGTT
                481 ---------+---------+---------+---------+---------+---------+ 540
                    AGTAATCTCGAAGACCAAGACTGTCTCAATAACGAAGACGACTTTTCAAGTAACTTCCAA

Q  S  A  K  L  A  D  P  G  S  Q  P  H  Q  A  S  P  V  I  D
                    TCCAATCTGCTAAGTTGGCTGACCCAGGTTCTCAACCACACCAAGCTTCTCCAGTTATTG
                541 ---------+---------+---------+---------+---------+---------+
                600
                    AGGTTAGACGATTCAACCGACTGGGTCCAAGAGTTGGTGTGGTTCGAAGAGGTCAATAAC

CP-10
                                                                        CP-11

V  I  I  P  E  G  S  G  Y  N  N  T  L  D  H  G  T  C  T  A
                    ACGTTATTATTCCAGAAGGaTCcGGTTACAACAACACTTTGGACCACGGTACTTGTACTG
                601 ---------+---------+---------+---------+---------+---------+
                660
                    TGCAATAATAAGGTCTTCCtAGgCCAATGTTGTTGTGAAACCTGGTGCCATGAACATGAC

F  E  D  S  E  L  G  D  D  V  E  A  N  F  T  A  L  F  A  P
                    CTTTCGAAGACTCTGAATTGGGTGACGACGTTGAAGCTAACTTCACTGCTTTGTTCGCTC
```

FIG. 3C

```
661 ---------+---------+---------+---------+---------+---------+
                                                                720
    GAAAGCTTCTGAGACTTAACCCACTGCTGCAACTTCGATTGAAGTGACGAAACAAGCGAG
                                                           CP-12
     A  I  R  A  R  L  E  A  D  L  P  G  V  T  L  T  D  E  D  V
    CAGCTATTAGAGCTAGATTGGAAGCTGACTTGCCAGGTGTTACTTTGACTGACGAAGACG
721 ---------+---------+---------+---------+---------+---------+
                                                                780
    GTCGATAATCTCGATCTAACCTTCGACTGAACGGTCCACAATGAAACTGACTGCTTCTGC

CP-13
     V  Y  L  M  D  M  C  P  F  E  T  V  A  R  T  S  D  A  T  E
    TTGTTTACTTGATGGACATGTGTCCATTCGAAACTGTTGCTAGAACTTCTGACGCTACTG
781 ---------+---------+---------+---------+---------+---------+
                                                                840
    AACAAATGAACTACCTGTACACAGGTAAGCTTTGACAACGATCTTGAAGACTGCGATGAC

L  S  P  F  C  A  L  F  T  H  D  E  W  R  Q  Y  D  Y  L  Q
    AATTGTCTCCATTCTGTGCTTTGTTCACTCACGACGAATGGAGACAATACGACTACTTGC
841 ---------+---------+---------+---------+---------+---------+
                                                                900
    TTAACAGAGGTAAGACACGAAACAAGTGAGTGCTGCTTACCTCTGTTATGCTGATGAACG

AATCTTTGGGTAAGTACTACGGTTACGGTGCTGGTAACCCATTGGGTCCAGCTCAAGGTG
             901 ---------+---------+---------+---------+---------+---------+
         960

TTAGAAACCCATTCATGATGCCAATGCCACGACCATTGGGTAACCCAGGTCGAGTTCCAC

G  F  A  N  E  L  I  A  R  L  T  R  S  P  V  Q  D  H  T  S

TTGGTTTCGCTAACGAATTGATTGCTAGATTGACTAGATCTCCAGTTCAAGACCACACTT
             961 ---------+---------+---------+---------+---------+---------+
         1020

AACCAAAGCGATTGCTTAACTAACGATCTAACTGATCTAGAGGTCAAGTTCTGGTGTGAA
                                    CP-16
                                    CP-17

T  N  H  T  L  D  S  N  P  A  T  F  P  L  N  A  T  L  Y  A

CTACTAACCACACTTTGGACTCTAACCCAGCTACTTTCCCATTGAACGCTACTTTGTACG
             1021 ---------+---------+---------+---------+---------+---------+
         1080

GATGATTGGTGTGAAACCTGAGATTGGGTCGATGAAAGGGTAACTTGCGATGAAACATGC

D  F  S  H  D  N  S  M  I  S  I  F  F  A  L  G  L  Y  N  G

CTGACTTCTCTCACGACAACTCTATGATTTCTATTTTCTTCGCTTTGGGTTTGTACAACG
             1081 ---------+---------+---------+---------+---------+---------+
         1140

GACTGAAGAGAGTGCTGTTGAGATACTAAAGATAAAAGAAGCGAAACCCAAACATGTTGC
```

T  A  P  L  S  T  T  S  V  E  S  I  E  E  T  D  G  Y  S  A
           GTACTGCTCCATTGTCTACTACTTCTGTTGAATCTATTGAAGAAACTGACGGTTACTCTG
    1141   ---------+---------+---------+---------+---------+---------+
    1200
           CATGACGAGGTAACAGATGATGAAGACAACTTAGATAACTTCTTTGACTGCCAATGAGAC

S  W  T  V  P  F  G  A  R  A  Y  V  E  M  M  Q  C  Q  A  E
           CTTCTTGGACTGTTCCATTCGGTGCTAGAGCTTACGTTGAAATGATGCAATGTCAAGCTG
    1201   ---------+---------+---------+---------+---------+---------+ 1260

GAAGAACCTGACAAGGTAAGCCACGATCTCGAATGCAACTTTACTACGTTACAGTTCGAC

CP-20
                                                        CP-21

K  E  P  L  V  R  V  L  V  N  D  R  V  V  P  L  H  G  C  A
              AAAAGGAACCATTGGTTAGAGTTTTGGTTAACGACAGAGTTGTTCCATTGCACGGTTGTG
    1261   ---------+---------+---------+---------+---------+---------+
    1320
              TTTTCCTTGGTAACCAATCTCAAAACCAATTGCTGTCTCAACAAGGTAACGTGCCAACAC

V  D  K  L  G  R  C  K  R  D  D  F  V  E  G  L  S  F  A  R
           CTGTTGACAAGTTGGGTAGATGTAAGAGAGACGACTTCGTTGAAGGTTTGTCTTTCGCTA
    1321   ---------+---------+---------+---------+---------+---------+
    1380
```

FIG. 3F

```
                    GACAACTGTTCAACCCATCTACATTCTCTCTGCTGAAGCAACTTCCAAACAGAAAGCGAT

CP-22

S  G  G  N  W  A  E  C  F  A  *  Eco RI

GATCTGGTGGTAACTGGGCTGAATGTTTCGCTTAAGAATTCATATA 5     1381 ---------+---------+---------+---------+------ 1426

CTAGACCACCATTGACCCGACTTACAAAGCGAATTCTTAAGTATAT
```

P. involutus (phyA1)  SvP.KnTAPt FPIPeseQrn WSPYSPYFPL AeYkAPPAGC
 5  QInQVNIIQR P. involutus (phyA2)  SvP.RniAPK FSIPeseQrn WSPYSPYFPL AeYkAPPAGC
    EInQVNIIQR T. pubescens          hiPlRdTSAc LdVTrDvQqs WSmYSPYFPa AtYvAPPASC
    QInQVHIIQR 10     A. pediades           GgvvQaTfvQ pfFPpQiQds WAAYTPYYPV qaYtPPPkDC
    KItQVNIIQR P. lycii              StQfsfvAAQ LPIPaQntsn WGPYdPFFPV EpYaAPPEGC
    tVtQVNLIQR 15  Basidio        S-P-R-TAAQ LPIP-Q-Q-- WSPYSPYFPV A-Y-APPAGC QI-QVNIIQR 51
       100

20     P. involutus (phyA1)  HGARFPTSGA TTRIKAGLTK LQGvqnfTDA KFNFIkSfkY
    dLGnsDLVPF P. involutus (phyA2)  HGARFPTSGA ATRIKAGLSK LQSvqnfTDP KFDFIkSfTY
    dLGtsDLVPF T. pubescens          HGARFPTSGA AkRIQTAVAK LKAAsnyTDP lLAFVtNyTY
25  sLGqDsLVeL A. pediades           HGARFPTSGA GTRIQAAVkK LQSAktyTDP RLDFLtNyTY
    tLGhDDLVPF
```

FIG. 4A

```
    P. lycii              HGARWPTSGA rSRqvAAVAK IQmArpfTDP KYEFLnDfvY
kFGvADLLPF Basidio               HGARFPTSGA ATRIQAAVAK LQSA---TDP KLDFL-N-TY -LG-DDLVPF 101                                       150

P. involutus (phyA1)  GAaQSfDAGQ EAFARYSkLV SkNNLPFIRA dGSDRVVDSA
TNWTAGFAsA

P. involutus (phyA2)  GAaQSfDAG1 EvFARYSkLV SsDNLPFIRS dGSDRVVDTA
TNWTAGFAsA

T. pubescens          GAtQSSEAGQ EAFTRYSsLV SaDELPFVRA SGSDRVVATA
nNWTAGFA1A

A. pediades           GA1QSSQAGE ETFqRYSfLV SkENLPFVRA SSSNRVVDSA
TNWTEGFSaA

P. lycii              GAnQShQTGt DmYTRYStLf egGDVPFVRA AGdQRVVDSS
TNWTAGFGdA

Basidio               GA-QSSQAGQ EAFTRYS-LV S-DNLPFVRA SGSDRVVDSA TNWTAGFA-A 151                                       200

P. involutus (phyA1)  ShNTvqPkLn LILPQtGNDT LEDNMCPaAG DSDPQvNaWL
AVafPSITAR
```

FIG. 4B

```
     P. involutus (phyA2)  SrNAiqPkLd LILPQtGNDT LEDNMCPaAG ESDPQvDaWL
  AsafPSVTAQ T. pubescens          SsNSitPvLs VIISEaGNDT LDDNMCPaAG DSDPQvNqWL
  AqFAPPMTAR 5    A. pediades           ShHvlnPiLf VILSEslNDT LDDaMCPnAG sSDPQtGiWt
  SIYGTPIAnR P. lycii              SgETvlPtLq VVLqEeGNcT LcNNMCPnEv DGDest.tWL
  GVFAPnITAR 10 Basidio                 S-NT--P-L- VILSE-GNDT LDDNMCP-AG DSDPQ-N-WL AVFAPPITAR 201
   250

15   P. involutus (phyA1)  LNAAAPSvNL TDtDAfNLvs LCAFlTVSkE kkSdFCtLFE
  giPGsFeAFa P. involutus (phyA2)  LNAAAPGANL TDaDAfNLvs LCPFmTVSkE qkSdFCtLFE
  giPGsFeAFa T. pubescens          LNAGAPGANL TDtDTyNLlt LCPFETVAtE rrSeFCDIYE
20 elQAE.dAFa A. pediades           LNqqAPGANI TAaDvsNLip LCAFETIvkE tpSpFCNLF.
  .tPEEFaqFe P. lycii              LNAAAPSANL SDsDAltLmd MCPFDTLSsG naSpFCDLF.
  .tAEEYvSYe 25 Basidio                 LNAAAPGANL TD-DA-NL-- LCPFETVS-E --S-FCDLFE --PEEF-AF-
```

FIG. 4C 251
300

P. involutus (phyA1)   YgGDLDKFYG TGYGQeLGPV QGVGYVNELI ARLTnsAVRD NTQTNRTLDA

P. involutus (phyA2)   YaGDLDKFYG TGYGQALGPV QGVGYINELL ARLTnsAVnD NTQTNRTLDA

T. pubescens           YnADLDKFYG TGYGQPLGPV QGVGYINELI ARLTaQnVsD HTQTNsTLDS

A. pediades            YfGDLDKFYG TGYGQPLGPV QGVGYINELL ARLTemPVRD NTQTNRTLDS

P. lycii               YyyDLDKYYG TGpGNALGPV QGVGYVNELL ARLTgQAVRD ETQTNRTLDS

Basidio            Y-GDLDKFYG TGYGQPLGPV QGVGYINELL ARLT-QAVRD NTQTNRTLDS

301
350

P. involutus (phyA1)   SPvTFPLNKT FYADFSHDN1 MVAVFSAMGL FrQPAPLsTS vPNPwRTWrT

P. involutus (phyA2)   APdTFPLNKT MYADFSHDN1 MVAVFSAMGL FrQSAPLsTS tPDPNRTWLT

T. pubescens           SPeTFPLNRT LYADFSHDNQ MVAIFSAMGL FNQSAPLDPT tPDPaRTFLv

FIG. 4D

```
    A. pediades            SP1TFPLDRS IYADLSHDNQ MIAIFSAMGL FNQSSPLDPS
fPNPKRTWVT P. lycii               dPaTFPLNRT FYADFSHDNt MVPIFAALGL FNaTA.LDP1
kPDeNRlWVd Basidio                    SP-TFPLNRT FYADFSHDNQ MVAIFSAMGL FNQSAPLDPS -PDPNRTWVT 351                                    400

P. involutus (phyA1)   SsLVPFSGRM VVERLsC..f GT........ ........tkV
RVLVQDqVQP

P. involutus (phyA2)   SsVVPFSARM aVERLsC..a GT........ ........tkV
RVLVQDqVQP

T. pubescens           kKIVPFSARM VVERLdC..g GA........ ........qsV
RLLVNDAVQP

A. pediades            SRLtPFSARM VtERLlCqrd GTgsggpsri mrngnvqtfV
RILVNDALQP

P. lycii               SKLVPFSGHM tVEKLaC... .......... ....sgkeaV
RVLVNDAVQP

Basidio                    SKLVPFSARM VVERL-C--- GT-------- ---------V RVLVNDAVQP 401                                    441

P. involutus (phyA1)   LEFCGGDrNG lCTLAkFVES QtFARsDGaG DFEKCFATSa ~
```

FIG. 4E

```
P. involutus (phyA2)    LEFCGGDqDG lCALDkFVES QaYARsGGaG DFEKCLATTv ~

T. pubescens            LAFCGADtsG vCTLDAFVES QaYARNDGEG DFEKCFAT~~ ~

A. pediades             LKFCGGDmDS lCTLEAFVES QkYAREDGQG DFEKCFD~~~ ~

P. lycii                LEFCGG.vDG vCeLsAFVES QtYARENGQG DFAKCgfvPs e

Basidio                 LEFCGGD-DG -CTLDAFVES Q-YAREDGQG DFEKCFATP- -
```
5

5       A. terreus 9al         KhsdCNSVDh GYQCfPELSH kWGlYAPYFS LqDESPFPlD
     VPeDCHITFV A. terreus cbs         NhsdCtSVDr GYQCfPELSH kWGlYAPYFS LqDESPFPlD
     VPdDCHITFV A. niger var. awamori  NqsTCDTVDq GYQCfSEtSH LWGQYAPFFS LANESAISPD
10   VPaGCRVTFa A. niger NRRL3135      NqsSCDTVDq GYQCfSEtSH LWGQYAPFFS LANESvISPE
     VPaGCRVTFa A. fumigatus 13073     GSkSCDTVDl GYQCsPAtSH LWGQYSPFFS LEDElSVSSK
     LPkDCRITLV 15       A. fumigatus 32722     GSkSCDTVDl GYQCsPAtSH LWGQYSPFFS LEDElSVSSK
     LPkDCRITLV A. fumigatus 58128     GSkSCDTVDl GYQCsPAtSH LWGQYSPFFS LEDElSVSSK
     LPkDCRITLV A. fumigatus 26906     GSkSCDTVDl GYQCsPAtSH LWGQYSPFFS LEDElSVSSK
20   LPkDCRITLV A. fumigatus 32239     GSkACDTVEl GYQCsPGtSH LWGQYSPFFS LEDElSVSSD
     LPkDCRVTFV E. nidulans            QNHSCNTaDG GYQCfPNVSH VWGQYSPYFS IEQESAISeD
     VPhGCeVTFV 25       T. thermophilus        DSHSCNTVEG GYQCrPEISH sWGQYSPFFS LADQSEISPD
     VPqNCKITFV
```

FIG. 5A

```
T. lanuginosa      ~~~~~~~~~~ ~~~~nvDIAR hWGQYSPFFS LAEvSEISPA
VPkGCRVeFV

M. thermophila     ESRPCDTpDl GFQCgTAISH FWGQYSPYFS VPsElDaS..
IPdDCeVTFa

Basidio            xSxPxrxtAA qLPipxQxqx xWSPYSPYFP VAxyxA....
pPaGCQIxqV

Consensus  NSHSCDTVDG GYQC-PEISH LWGQYSPFFS LADESAISPD VP-
GCRVTFV

Fcp10    NSHSCDTVDG GYQCFPEISH LWGQYSPFFS LADESAISPD
VPKGCRVTFV 51
                              100

A. terreus 9a1     QVLARHGARs PThSKTKaYA AtIaAIQKSA TaFpGKYAFL
QSYNYSLDSE

A. terreus cbs     QVLARHGARs PTdSKTKaYA AtIaAIQKNA TaLpGKYAFL
KSYNYSMGSE

A. niger var. awamori QVLSRHGARY PTeSKGKKYS ALIeEIQQNv TtFDGKYAFL
KTYNYSLGAD

A. niger NRRL3135  QVLSRHGARY PTdSKGKKYS ALIeEIQQNA TtFDGKYAFL
KTYNYSLGAD

A. fumigatus 13073 QVLSRHGARY PTSSKSKKYk kLVtAIQaNA TdFKGKFAFL
KTYNYTLGAD

A. fumigatus 32722 QVLSRHGARY PTSSKSKKYk kLVtAIQaNA TdFKGKFAFL
KTYNYTLGAD
```

FIG. 5B

```
    A. fumigatus 58128     QVLSRHGARY PTSSKSKKYk kLVtAIQaNA TdFKGKFAFL
KTYNYTLGAD A. fumigatus 26906     QVLSRHGARY PTSSKSKKYk kLVtAIQaNA TdFKGKFAFL
KTYNYTLGAD 5   A. fumigatus 32239     QVLSRHGARY PTASKSKKYk kLVtAIQKNA TeFKGKFAFL
ETYNYTLGAD E. nidulans            QVLSRHGARY PTeSKSKaYS GLIeAIQKNA TsFwGQYAFL
ESYNYTLGAD T. thermophilus        QLLSRHGARY PTSSKTElYS qLIsrIQKtA TaYKGyYAFL
10  KdYrYqLGAN T. lanuginosa          QVLSRHGARY PTAhKSEvYA ELLqrIQDtA TeFKGDFAFL
RdYaYhLGAD M. thermophila         QVLSRHGARa PTlkRAasYv DLIdrIHhGA isYgPgYEFL
RTYDYTLGAD 15  Basidio                NIIqRHGARF PTSGaAtRiq AaVakLQsax xxtDPKLDFL
xnxtYxLGxD Consensus   QVLSRHGARY PTSSKSKKYS ALI-AIQKNA T-FKGKYAFL
KTYNYTLGAD
20         Fcp10   QVLSRHGARY PTSSKSKKYS ALIEAIQKNA TAFKGKYAFL
KTYNYTLGAD
                                101
    150

A. terreus 9a1      ELTPFGrNQL rDlGaQFYeR YNAL.TRhIn PFVRATDAsR
25  VhESAEKFVE

A. terreus cbs      NLTPFGrNQL qDlGaQFYRR YDTL.TRhIn PFVRAADSsR
VhESAEKFVE
```

FIG. 5C

```
        A. niger var. awamori  DLTPFGEQEL VNSGIKFYQR YESL.TRnII PFIRSSGSsR
VIASGEKFIE A. niger NRRL3135      DLTPFGEQEL VNSGIKFYQR YESL.TRnIV PFIRSSGSsR
VIASGKKFIE 5      A. fumigatus 13073     DLTPFGEQQL VNSGIKFYQR YKAL.ARsVV PFIRASGSDR
VIASGEKFIE A. fumigatus 32722     DLTPFGEQQL VNSGIKFYQR YKAL.ARsVV PFIRASGSDR
VIASGEKFIE A. fumigatus 58128     DLTPFGEQQL VNSGIKFYQR YKAL.ARsVV PFIRASGSDR
10 VIASGEKFIE A. fumigatus 26906     DLTAFGEQQL VNSGIKFYQR YKAL.ARsVV PFIRASGSDR
VIASGEKFIE A. fumigatus 32239     DLTPFGEQQM VNSGIKFYQK YKAL.AgsVV PFIRSSGSDR
VIASGEKFIE 15      E. nidulans            DLTiFGENQM VDSGaKFYRR YKnL.ARknt PFIRASGSDR
VVASAEKFIN T. thermophilus        DLTPFGENQM IQlGIKFYnH YKSL.ARnaV PFVRCSGSDR
VIASGrlFIE T. lanuginosa          NLTRFGEEQM MESGrQFYHR YREq.AReIV PFVRAAGSAR
20 VIASAEfFnr M. thermophila         ELTRtGQQQM VNSGIKFYRR YRAL.ARksI PFVRTAGqDR
VVhSAENFtQ Basidio                DLvPFGAxQs sQAGqEaFtR YsxLvSxdnL PFVRASGSDR
VVDSAtNWtA 25
        Consensus              DLTPFGEQQM VNSGIKFYRR YKAL-AR-IV PFVRASGSDR
VIASAEKFIE                          FIG. 5D
```

Fcp10  DLTPFGEQQM VNSGIKFYRR YKAL.ARKIV PFVRASGSDR
VIASAEKFIE 151
200

5  A. terreus 9a1  GFQTARqDDh hAnphQPSPr VDVaIPEGsA YNNTLEHSLC
TAFEs...St

A. terreus cbs  GFQNARqGDP hAnphQPSPr VDVVIPEGtA YNNTLEHSIC
TAFEa...St

A. niger var. awamori GFQSTKLkDP rAqpgQSSPk IDVVISEAsS sNNTLDpGtC
10 TvFEd...SE

A. niger NRRL3135 GFQSTKLkDP rAqpgQSSPk IDVVISEAsS sNNTLDpGtC
TvFEd...SE

A. fumigatus 13073 GFQqAKLADP gAt.nRAAPa ISVIIPESeT FNNTLDHGVC
TkFEa...SQ

15 A. fumigatus 32722 GFQqAKLADP gAt.nRAAPa ISVIIPESeT FNNTLDHGVC
TkFEa...SQ

A. fumigatus 58128 GFQqAKLADP gAt.nRAAPa ISVIIPESeT FNNTLDHGVC
TkFEa...SQ

A. fumigatus 26906 GFQqAKLADP gAt.nRAAPa ISVIIPESeT FNNTLDHGVC
20 TkFEa...SQ

A. fumigatus 32239 GFQqANVADP gAt.nRAAPV ISVIIPESeT YNNTLDHSVC
TnFEa...SE

E. nidulans  GFRkAQLhDh g.s.gQATPV VNVIIPEidG FNNTLDHStC
vSFEn...dE

25 T. thermophilus GFQSAKVlDP hSdkhDAPPt INVIIeEGpS YNNTLDtGsC
PvFEd...Ss

FIG. 5E

```
     T. lanuginosa        GFQdAKdrDP rSnkdQAePV INVIISEEtG sNNTLDgltC
PAaEe...Ap M. thermophila       GFHSAlLADR gStvrPTlPy dmVVIPETaG aNNTLHNDLC
TAFEegPySt 5   Basidio              GFaxA..... ...sxntxxPx LxVILSExg. .NDTLDDNMC
......PxAG Consensus   GFQSAKLADP -A---QASPV INVIIPEG-G YNNTLDHGLC TAFE--
P-SE 10               Fcp10   GFQSAKLADP GANPHQASPV INVIIPEGAG YNNTLDHGLC
TAFEE...SE 201
250

15   A. terreus 9a1       VGDDavANFT AVFAPAIaqR LEAdLPGVQL StDDVVNLMA
MCPFETVSlT A. terreus cbs       VGDAaADNFT AVFAPAIakR LEAdLPGVQL SADDVVNLMA
MCPFETVSlT A. niger var. awamori LADtVEANFT AtFAPSIRqR LEndLSGVtL TDtEVtyLMD
20 MCSFDTIStS A. niger NRRL3135    LADtVEANFT AtFvPSIRqR LEndLSGVtL TDtEVtyLMD
MCSFDTIStS A. fumigatus 13073   LGDEVAANFT ALFAPdIRAR aEkhLPGVtL TDEDVVSLMD
MCSFDTVArT 25   A. fumigatus 32722   LGDEVAANFT ALFAPdIRAR aEkhLPGVtL TDEDVVSLMD
MCSFDTVArT
```

FIG. 5F

```
          A. fumigatus 58128    LGDEVAANFT ALFAPdIRAR aEkhLPGVtL TDEDVVSLMD
MCSFDTVArT A. fumigatus 26906    LGDEVAANFT ALFAPdIRAR aKkhLPGVtL TDEDVVSLMD
MCSFDTVArT 5         A. fumigatus 32239    LGDEVEANFT ALFAPAIRAR IEkhLPGVQL TDDDVVSLMD
MCSFDTVArT E. nidulans           rADEIEANFT AIMGPPIRkR LEndLPGIKL TNENVIyLMD
MCSFDTMArT T. thermophilus       gGHDaQEKFA kqFAPAIlEK IKDhLPGVDL AvsDVpyLMD
10 LCPFETLArn T. lanuginosa         .DptqpAEFl qVFGPRVlkK ItkhMPGVNL TlEDVplFMD
LCPFDTVGsd M. thermophila        IGDDaQDtYl StFAGPItAR VNAnLPGaNL TDADtVaLMD
LCPFETVAsS 15        Basidio               dSDpqxnxWl AVFAPPItAR LNAaaPGaNL TDxDaxNLxx
LCPFETVS..

Consensus   LGDDVEANFT AVFAPPIRAR LEA-LPGVNL TDEDVVNLMD
MCPFDTVA-T

Fcp10  LGDDVEANFT AVFAPPIRAR LEAHLPGVNL TDEDVVNLMD
20 MCPFDTVART 251
          300
25        A. terreus 9a1        dD..Aht... ......LSPF CDLFTa..tE WtQYNYLlSL
dKYYGYGGGN
```

FIG. 5G

```
              A. terreus cbs       dD..Aht... ......LSPF CDLFTa..aE WtQYNYLlSL
       dKYYGYGGGN A. niger var. awamori Tv..DTK... ......LSPF CDLFTH..dE WiHYDYLQSL
       kKYYGHGAGN 5            A. niger NRRL3135    Tv..DTK... ......LSPF CDLFTH..dE WiNYDYLQSL
       kKYYGHGAGN A. fumigatus 13073   SD..ASQ... ......LSPF CQLFTH..nE WkKYNYLQSL
       gKYYGYGAGN A. fumigatus 32722   SD..ASQ... ......LSPF CQLFTH..nE WkKYNYLQSL
10     gKYYGYGAGN A. fumigatus 58128   SD..ASQ... ......LSPF CQLFTH..nE WkKYNYLQSL
       gKYYGYGAGN A. fumigatus 26906   SD..ASQ... ......LSPF CQLFTH..nE WkKYNYLQSL
       gKYYGYGAGN 15            A. fumigatus 32239   AD..ASE... ......LSPF CAIFTH..nE WkKYDYLQSL
       gKYYGYGAGN E. nidulans          AH..GTE... ......LSPF CAIFTE..kE WlQYDYLQSL
       sKYYGYGAGS T. thermophilus      ht..DT.... ......LSPF CALsTQ..eE WqaYDYYQSL
20     gKYYGnGGGN T. lanuginosa        PvlfPrQ... ......LSPF CHLFTa..dD WmaYDYYyTL
       dKYYSHGGGS M. thermophila       SsdpATadag ggngrpLSPF CrLFSE..sE WraYDYLQSV
       gKWYGYGPGN 25     Basidio                     .......... ...xexxSxF CDLFexxpeE FxaFxYxgdL
       dKFYGtGyGQ
```

FIG. 5H

```
Consensus   SD--ATQ---  ------LSPF CDLFTH---E W-QYDYLQSL -KYYGYGAGN

Fcp10    SD..ATQ...  ......LSPF CDLFTH..DE WIQYDYLQSL GKYYGYGAGN 301                                      350

A. terreus 9a1           PLGPvQGVGW aNELMARLTR A.PVHDHTCv NNTLDASPAT FPLNATLYAD

A. terreus cbs           PLGPvQGVGW aNELIARLTR S.PVHDHTCv NNTLDANPAT FPLNATLYAD

A. niger var. awamori    PLGPTQGVGY aNELIARLTH S.PVHDDTSS NHTLDSNPAT FPLNSTLYAD

A. niger NRRL3135        PLGPTQGVGY aNELIARLTH S.PVHDDTSS NHTLDSSPAT FPLNSTLYAD

A. fumigatus 13073       PLGPAQGIGF tNELIARLTR S.PVQDHTST NsTLvSNPAT FPLNATMYvD

A. fumigatus 32722       PLGPAQGIGF tNELIARLTR S.PVQDHTST NsTLvSNPAT FPLNATMYvD

A. fumigatus 58128       PLGPAQGIGF tNELIARLTR S.PVQDHTST NsTLvSNPAT FPLNATMYvD

A. fumigatus 26906       PLGPAQGIGF tNELIARLTR S.PVQDHTST NsTLvSNPAT FPLNATMYvD

A. fumigatus 32239       PLGPAQGIGF tNELIARLTN S.PVQDHTST NsTLDSDPAT FPLNATIYvD
```

FIG. 5I

```
         E. nidulans         PLGPAQGIGF tNELIARLTQ S.PVQDNTST NHTLDSNPAT
    FPLDrkLYAD T. thermophilus     PLGPAQGVGF vNELIARMTH S.PVQDYTTv NHTLDSNPAT
    FPLNATLYAD 5        T. lanuginosa       AFGPSRGVGF vNELIARMTg NlPVKDHTTv NHTLDdNPET
    FPLDAvLYAD M. thermophila      PLGPTQGVGF vNELLARLA. GvPVRDgTST NRTLDGDPrT
    FPLGrPLYAD Basidio             PLGPvQGVGY iNELLARLTx qa.VRDNTqT NRTLDSSPxT
10  FPLNrTFYAD Consensus  PLGPAQGVGF -NELIARLTH S-PVQDHTST NHTLDSNPAT
    FPLNATLYAD Fcp10    PLGPAQGVGF VNELIARLTH S.PVQDHTST NHTLDSNPAT
15  FPLNATLYAD 351
    400
         A. terreus 9a1      FSHDSnLVSI FWALGLYNGT aPLSqTSVE. .SvsQTDGYA
20  AAWTVPFAAR A. terreus cbs      FSHDSnLVSI FWALGLYNGT kPLSqTTVE. .ditrTDGYA
    AAWTVPFAAR A. niger var. awamori FSHDNGIISI LFALGLYNGT kPLSTTTVE. .NitQTDGFS
    SAWTVPFASR 25       A. niger NRRL3135   FSHDNGIISI LFALGLYNGT kPLSTTTVE. .NitQTDGFS
    SAWTVPFASR
```

FIG. 5J

```
              A. fumigatus 13073    FSHDNSMVSI FFALGLYNGT ePLSrTSVE. .SaKElDGYS
        ASWvVPFGAR A. fumigatus 32722    FSHDNSMVSI FFALGLYNGT gPLSrTSVE. .SaKElDGYS
        ASWvVPFGAR 5           A. fumigatus 58128    FSHDNSMVSI FFALGLYNGT ePLSrTSVE. .SaKElDGYS
        ASWvVPFGAR A. fumigatus 26906    FSHDNSMVSI FFALGLYNGT ePLSrTSVE. .SaKElDGYS
        ASWvVPFGAR A. fumigatus 32239    FSHDNGMIPI FFAMGLYNGT ePLSqTSeE. .StKESNGYS
 10     ASWAVPFGAR E. nidulans           FSHDNSMISI FFAMGLYNGT qPLSmdSVE. .SiQEmDGYA
        ASWTVPFGAR T. thermophilus       FSHDNTMtSI FaALGLYNGT akLSTTeIK. .SiEETDGYS
        AAWTVPFGGR 15           T. lanuginosa         FSHDNTMtGI FsAMGLYNGT kPLSTSkIQP pTgAAADGYA
        ASWTVPFAAR M. thermophila        FSHDNdMMGV LgALGaYDGv pPLdkTA..R rdpEElGGYA
        ASWAVPFAAR Basidio               FSHDNqMVAI FsAMGLFNqS aPLdPSxpDP nrt.....Wv
 20     TSklVPFSAR Consensus   FSHDNTMVSI FFALGLYNGT -PLSTTSVEP -S-EETDGYA
        ASWTVPFAAR Fcp10   FSHDNTMVSI FFALGLYNGT KPLSTTSVE. .SIEETDGYA
 25     ASWTVPFAAR           FIG. 5K
```

```
                                         450
         A. terreus 9a1            AYVEMMQC.. ra........ .....EKEPL VRVLVNDRVM
    PLHGCPtDKL A. terreus cbs            AYIEMMQC.. ra........ .....EKQPL VRVLVNDRVM
    PLHGCAVDNL A. niger var. awamori     lYVEMMQC.. Qa........ .....EQEPL VRVLVNDRVV
    PLHGCPIDaL A. niger NRRL3135         lYVEMMQC.. Qa........ .....EQEPL VRVLVNDRVV
    PLHGCPVDaL A. fumigatus 13073        AYfEtMQC.. Ks........ .....EKEPL VRaLINDRVV
    PLHGCDVDKL A. fumigatus 32722        AYfEtMQC.. Ks........ .....EKEPL VRaLINDRVV
    PLHGCDVDKL A. fumigatus 58128        AYfEtMQC.. Ks........ .....EKESL VRaLINDRVV
    PLHGCDVDKL A. fumigatus 26906        AYfEtMQC.. Ks........ .....EKEPL VRaLINDRVV
    PLHGCDVDKL A. fumigatus 32239        AYfEtMQC.. Ks........ .....EKEPL VRaLINDRVV
    PLHGCAVDKL E. nidulans               AYfELMQC.. E......... .....KKEPL VRVLVNDRVV
    PLHGCAVDKF T. thermophilus           AYIEMMQC.. Dd........ .....sDEPV VRVLVNDRVV
    PLHGCEVDsL T. lanuginosa             AYVELLRC.. Etetsseeee EG...EDEPF VRVLVNDRVV
    PLHGCrVDRW
```

FIG. 5L

```
        M. thermophila       iYVEkMRC.. sggggggggg EGrqeKDEeM VRVLVNDRVM
TLkGCGaDEr Basidio              mvVErLxCxx xgtxxxxxxx xxxxxxxxxx VRVLVNDaVq
PLEfCGgDxd Consensus            AYVEMMQC-- E--------- EG---EKEPL VRVLVNDRVV
PLHGCGVDKL Fcp10    AYVEMMQC.. EA........ .....EKEPL VRVLVNDRVV
PLHGCGVDKL 451                           482

A. terreus 9a1        GRCKrDAFVA GLSFAQAG.. GNWADCF~~~ ~~

A. terreus cbs        GRCKrDDFVE GLSFARAG.. GNWAECF~~~ ~~

A. niger var. awamori GRCtrDsFVr GLSFARSG.. GDWAECsA~~ ~~

A. niger NRRL3135     GRCtrDsFVr GLSFARSG.. GDWAECFA~~ ~~

A. fumigatus 13073    GRCKlNDFVK GLSWARSG.. GNWGECFS~~ ~~

A. fumigatus 32722    GRCKlNDFVK GLSWARSG.. GNWGECFS~~ ~~

A. fumigatus 58128    GRCKlNDFVK GLSWARSG.. GNWGECFS~~ ~~

A. fumigatus 26906    GRCKlNDFVK GLSWARSG.. GNWGECFS~~ ~~

A. fumigatus 32239    GRCKlKDFVK GLSWARSG.. GNSEQSFS~~ ~~

E. nidulans           GRCtlDDWVE GLNFARSG.. GNWKtCFTl~ ~~

T. thermophilus       GRCKrDDFVr GLSFARqG.. GNWEGCYAas e~

T. lanuginosa         GRCRrDEWIK GLTFARqG.. GHWDrCF~~~ ~~

M. thermophila        GmCtlErFIE SMAFARGN.. GKWDlCFA~~ ~~
```

FIG. 5M

```
Basidio          GxCtlDAFVE SqxYAReDgq GDFEKCFAtp xx

Consensus  GRCK-DDFVE GLSFARSG-- GNWEECFA-- --

Fcp10  GRCKRDDFVE GLSFARSG.. GNWEECFA.. ..
```

EcoRI  M  G  V  F  V  V  L  L  S  I  A  T  L  F  G  S  T
           17
    TATATGAATTCATGGGCGTGTTCGTCGTGCTACTGTCCATTGCCACCTTGTTCGGTTCCA

1 ---------+---------+---------+---------+---------+---------+
           60

ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G  37

CATCCGGTACCGCCTTGGGTCCTCGTGGTAATTCTCACTCTTGTGACACTGTTGACGGTG

61 ---------+---------+---------+---------+---------+---------+
          120

GTAGGCCATGGCGGAACCCAGGAGCACCATTAAGAGTGAGAACACTGTGACAACTGCCAC

CP-2

CP-3.10

Y  Q  C  F  P  E  I  S  H  L  W  G  Q  Y  S  P  F  S  L
           57
    GTTACCAATGTTTCCCAGAAATTTCTCACTTGTGGGGTCAATACTCTCCATTCTTCTCTT

121 ---------+---------+---------+---------+---------+---------+
          180

CAATGGTTACAAAGGGTCTTTAAAGAGTGAACACCCCAGTTATGAGAGGTAAGAAGAGAA

A  D  E  S  A  I  S  P  D  V  P  K  G  C  R  V  T  F  V  Q  77

TGGCTGACGAATCTGCTATTTCTCCAGACGTTCCAAAGGGTTGTAGAGTTACTTTCGTTC
```

FIG. 6A

```
181 ---------+---------+---------+---------+---------+---------+
                                                              240
    ACCGACTGCTTAGACGATAAAGAGGTCTGCAAGGTTTCCCGACATCTCAATGAAAGCAAG

CP-4.10
                              CP-5.10

V  L  S  R  H  G  A  R  Y  P  T  S  S  K  S  K  K  Y  S  A
                                                                 97

AAGTTTTGTCTAGACACGGTGCTAGATACCCAACTTCTTCTAAGTCTAAGAAGTACTCTG

241 ---------+---------+---------+---------+---------+---------+
                                                              300

TTCAAAACAGATCTGTGCCACGATCTATGGGTTGAAGAAGATTCAGATTCTTCATGAGAC

L  I  E  A  I  Q  K  N  A  T  A  F  K  G  K  Y  A  F  L  K 117

CTTTGATTGAAGCTATTCAAAAGAACGCTACTGCTTTCAAGGGTAAGTACGCTTTCTTGA

301 ---------+---------+---------+---------+---------+---------+
                                                              360

GAAACTAACTTCGATAAGTTTTCTTGCGATGACGAAAGTTCCCATTCATGCGAAAGAACT

CP-6
                              CP-7.10

T  Y  N  Y  T  L  G  A  D  D  L  T  P  F  G  E  Q  Q  M  V
                                                                  137

AGACTTACAACTACACTTTGGGTGCTGACGACTTGACTCCATTCGGTGAACAACAAATGG

361 ---------+---------+---------+---------+---------+---------+
                                                              420

TCTGAATGTTGATGTGAAACCCACGACTGCTGAACTGAGGTAAGCCACTTGTTGTTTACC
```

TTAACTCTGGTATTAAGTTCTACAGAAGATACAAGGCTTTGGCTAGAAAGATTGTTCCAT
   421 ---------+---------+---------+---------+---------+---------+ 480
       AATTGAGACCATAATTCAAGATGTCTTCTATGTTCCGAAACCGATCTTTCTAACAAGGTA
                                         ─────────────────
                                              CP-8.10
                                                    ────────────
                                                       CP-9.10

V  R  A  S  G  S  D  R  V  I  A  S  A  E  K  F  I  E  G  F
       ─
   177

TCGTTAGAGCTTCTGGTTCTGACAGAGTTATTGCTTCTGCTGAAAAGTTCATTGAAGGTT
   481 ---------+---------+---------+---------+---------+---------+ 540
       AGCAATCTCGAAGACCAAGACTGTCTCAATAACGAAGACGACTTTTCAAGTAACTTCCAA

Q  S  A  K  L  A  D  P  G  A  N  P  H  Q  A  S  P  V  I  N
   197                                  ─  ─                          ─

TCCAATCTGCTAAGTTGGCTGACCCAGGTGCTAACCCACACCAAGCTTCTCCAGTTATTA
   541 ---------+---------+---------+---------+---------+---------+ 600
       AGGTTAGACGATTCAACCGACTGGGTCCACGATTGGGTGTGGTTCGAAGAGGTCAATAAT
                                                     ───────────────
                                                        CP-10.10
                                                     ───────────────
                                                        CP-11.10

V  I  I  P  E  G  A  G  Y  N  N  T  L  D  H  G  L  C  T  A
   217                      ─                             ─

ACGTTATTATTCCAGAAGGTGCTGGTTACAACAACACTTTGGACCACGGTTTGTGTACTG
   601 ---------+---------+---------+---------+---------+---------+ 660
```

FIG. 6C

```
                    TGCAATAATAAGGTCTTCCACGACCAATGTTGTTGTGAAACCTGGTGCCAAACACATGAC

F  E  E  S  E  L  G  D  D  V  E  A  N  F  T  A  V  F  A  P
              237

CTTTCGAAGAATCTGAATTGGGTGACGACGTTGAAGCTAACTTCACTGCTGTTTTCGCTC

661 ---------+---------+---------+---------+---------+---------+
              720

GAAAGCTTCTTAGACTTAACCCACTGCTGCAACTTCGATTGAAGTGACGACAAAAGCGAG
                                                                              CP-
              12.10

P  I  R  A  R  L  E  A  H  L  P  G  V  N  L  T  D  E  D  V 257

CACCTATTAGAGCTAGATTGGAAGCTCACTTGCCAGGTGTTAACTTGACTGACGAAGACG

721 ---------+---------+---------+---------+---------+---------+
              780

GTGGATAATCTCGATCTAACCTTCGAGTGAACGGTCCACAATTGAACTGACTGCTTCTGC

CP-13.10

V  N  L  M  D  M  C  P  F  D  T  V  A  R  T  S  D  A  T  Q
              277

TTGTTAACTTGATGGACATGTGTCCATTCGACACTGTTGCTAGAACTTCTGACGCTACTC

781 ---------+---------+---------+---------+---------+---------+
              840

AACAATTGAACTACCTGTACACAGGTAAGCTGTGACAACGATCTTGAAGACTGCGATGAG
```

FIG. 6D

```
              L  S  P  F  C  D  F  T  H  D  E  W  I  Q  Y  D  Y  L  Q 297
                                    ─
              AATTGTCTCCATTCTGTGACTTGTTCACTCACGACGAATGGATTCAATACGACTACTTGC

841 ---------+---------+---------+---------+---------+---------+
             900

TTAACAGAGGTAAGACACTGAACAAGTGAGTGCTGCTTACCTAAGTTATGCTGATGAACG

CP-14.10
                     CP-15.10

S  L  G  K  Y  Y  G  Y  G  A  G  N  P  L  G  P  A  Q  G  V
             317

AATCTTTGGGTAAGTACTACGGTTACGGTGCTGGTAACCCATTGGGTCCAGCTCAAGGTG

901 ---------+---------+---------+---------+---------+---------+
             960

TTAGAAACCCATTCATGATGCCAATGCCACGACCATTGGGTAACCCAGGTCGAGTTCCAC

G  F  V  N  E  L  I  A  R  L  T  H  S  P  V  Q  D  H  T  S 337
                    ─                             ─
              TTGGTTTCGTTAACGAATTGATTGCTAGATTGACTCACTCTCCAGTTCAAGACCACACTT

961 ---------+---------+---------+---------+---------+---------+
             1020

AACCAAAGCAATTGCTTAACTAACGATCTAACTGAGTGAGAGGTCAAGTTCTGGTGTGAA

CP-16.10
                              CP-17.10

T  N  H  T  L  D  S  N  P  A  T  F  P  L  N  A  T  L  Y  A
             357

CTACTAACCACACTTTGGACTCTAACCCAGCTACTTTCCCATTGAACGCTACTTTGTACG
```

FIG. 6E

```
1021 ---------+---------+---------+---------+---------+---------+
                                                                  1080
     GATGATTGGTGTGAAACCTGAGATTGGGTCGATGAAAGGGTAACTTGCGATGAAACATGC

D  F  S  H  D  N  T  M  V  S  I  F  F  A  L  G  L  Y  N  G 377

CTGACTTCTCTCACGACAACACTATGGTTTCTATTTTCTTCGCTTTGGGTTTGTACAACG

1081 ---------+---------+---------+---------+---------+---------+
                                                                  1140
     GACTGAAGAGAGTGCTGTTGTGATACCAAAGATAAAAGAAGCGAAACCCAAACATGTTGC
                                   CP-18.10
                                   CP-19.10

T  K  P  L  S  T  T  S  V  E  S  I  E  E  T  D  G  Y  A  A
     397

GTACTAAGCCATTGTCTACTACTTCTGTTGAATCTATTGAAGAAACTGACGGTTACGCTG

1141 ---------+---------+---------+---------+---------+---------+
                                                                  1200
     CATGATTCGGTAACAGATGATGAAGACAACTTAGATAACTTCTTTGACTGCCAATGCGAC

S  W  T  V  P  F  A  A  R  A  Y  V  E  M  M  Q  C  E  A  E 417

CTTCTTGGACTGTTCCATTCGCTGCTAGAGCTTACGTTGAAATGATGCAATGTGAAGCTG
1201 ---------+---------+---------+---------+---------+---------+ 1260
     GAAGAACCTGACAAGGTAAGCCACGATCTCGAATGCAACTTTACTACGTTACACTTCGAC
                                            CP-20.10
                                            CP-21.10
```

AAAAGGAACCATTGGTTAGAGTTTTGGTTAACGACAGAGTTGTTCCATTGCACGGTTGTG
       1261  ---------+---------+---------+---------+---------+---------+
       1320
              TTTTCCTTGGTAACCAATCTCAAAACCAATTGCTGTCTCAACAAGGTAACGTGCCAACAC

V  D  K  L  G  R  C  K  R  D  D  F  V  E  G  L  S  F  A  R
       457

GTGTTGACAAGTTGGGTAGATGTAAGAGAGACGACTTCGTTGAAGGTTTGTCTTTCGCTA
       1321  ---------+---------+---------+---------+---------+---------+
       1380
              CACAACTGTTCAACCCATCTACATTCTCTCTGCTGAAGCAACTTCCAAACAGAAAGCGAT

CP-22.10
              S  G  G  N  W  E  E  C  F  A  *   Eco RI                467

GATCTGGTGGTAACTGGGAAGAATGTTTCGCTTAAGAATTCATATA
       1381  ---------+---------+---------+---------+------  1426
              CTAGACCACCATTGACCCTTCTTACAAAGCGAATTCTTAAGTATAT
```

P. involutus (phyA1)    ~~~~~~~~~~ ~FPipeseqR nWSPYSPYFP LAEykA....
  5   pPaGCQInqV P. involutus (phyA2)    ~~~~~~~~~~ ~FsipeseqR nWSPYSPYFP LAEykA....
      pPaGCeInqV T. pubescens            ~~~~~~~~~~ ~LDvtRDVqQ sWSmYSPYFP aAtyvA....
      pPaSCQInqV 10      A. pediades             ~~~~~~~~~~ ~pffpPQIqD sWAaYTPYYP VqAyTP....
      pPKDCKITqV P. lycii                ~~~~~~~~~~ ~LPipAQnTs nWGPYdPFFP VEpyAA....
      pPEGCtVTqV A. terreus 9a1          KhsdCNSVDh GYQCfPELSH kWGlYAPYFS LqDESPFP1D
 15   VPEDCHITFV A. terreus cbs          NhsdCtSVDr GYQCfPELSH kWGlYAPYFS LqDESPFP1D
      VPDDCHITFV A. niger var. awamori   NqsTCDTVDq GYQCfSEtSH LWGQYAPFFS LANESAISPD
      VPaGCRVTFa 20      A. niger T213           NqsSCDTVDq GYQCfSEtSH LWGQYAPFFS LANESvISPD
      VPaGCRVTFa A. niger NRRL3135       NqsSCDTVDq GYQCfSEtSH LWGQYAPFFS LANESvISPE
      VPaGCRVTFa A. fumigatus ATCC13073  GSkSCDTVDl GYQCsPAtSH LWGQYSPFFS LEDElSVSSK
 25   LPKDCRITLV A. fumigatus ATCC32722  GSkSCDTVDl GYQCsPAtSH LWGQYSPFFS LEDElSVSSK
      LPKDCRITLV
```

FIG. 7A

```
        A. fumigatus ATCC58128   GSkSCDTVDl GYQCsPAtSH LWGQYSPFFS LEDElSVSSK
   LPKDCRITLV A. fumigatus ATCC26906   GSkSCDTVDl GYQCsPAtSH LWGQYSPFFS LEDElSVSSK
   LPKDCRITLV 5      A. fumigatus ATCC32239   GSkACDTVEl GYQCsPGtSH LWGQYSPFFS LEDElSVSSD
   LPKDCRVTFV E. nidulans              QNHSCNTaDg GYQCfPNVSH VWGQYSPYFS IEQESAISeD
   VPhGCeVTFV T. thermophilus          DSHSCNTVEg GYQCrPEISH sWGQYSPFFS LADQSEISPD
10 VPQNCKITFV T. lanuginosa            ~~~~~~~~~~ ~~~~nvDIAR hWGQYSPFFS LAEvSEISPA
   VPKGCRVeFV M. thermophila           ESRPCDTpDl GFQCgTAISH FWGQYSPYFS VPsElDaS..
   IPDDCeVTFa 15
        Consensus Seq. 11        NSHSCDTVD- GYQC-PEISH LWGQYSPFFS LADESAISPD
   VPKGCRVTFV 51
20                                                                      100

P. involutus (phyA1)     NIIqRHGARF PTSGaTtRik AgLtKLQgvq nftDAKFnFI
   KSFKYdLGns P. involutus (phyA2)     NIIqRHGARF PTSGaAtRik AgLsKLQsvq nftDPKFDFI
   KSFtYdLGTs 25      T. pubescens             HIIqRHGARF PTSGaAKRiq TaVAKLKaaS nytDPlLAFV
   tnYtYSLGqD
                           FIG. 7B
```

```
         A. pediades           NIIqRHGARF PTSGaGtRiq AaVKKLQsak TytDPRLDFL
   tnYtYTLGhD P. lycii              NLIqRHGARW PTSGarsRqv AaVAKIQmar PftDPKYEFL
   NdFvYkFGvA 5        A. terreus 9a1        QVLARHGARs PThSKTKaYA AtIAaIQKSA TaFpGKYAFL
   QSYNYSLDSE A. terreus cbs        QVLARHGARs PTdSKTKaYA AtIAaIQKNA TaLpGKYAFL
   KSYNYSMGSE A. niger var. awamori QVLSRHGARY PTeSKGKKYS ALIEeIQQNv TtFDGKYAFL
10 KTYNYSLGAD A. niger T213         QVLSRHGARY PTeSKGKKYS ALIEeIQQNv TtFDGKYAFL
   KTYNYSLGAD.

A. niger NRRL3135     QVLSRHGARY PTdSKGKKYS ALIEeIQQNA TtFDGKYAFL
   KTYNYSLGAD

15       A. fumigatus ATCC13073 QVLSRHGARY PTSSKSKKYk kLVtaIQaNA TdFKGKFAFL
   KTYNYTLGAD A. fumigatus ATCC32722 QVLSRHGARY PTSSKSKKYk kLVtaIQaNA TdFKGKFAFL
   KTYNYTLGAD A. fumigatus ATCC58128 QVLSRHGARY PTSSKSKKYk kLVtaIQaNA TdFKGKFAFL
20 KTYNYTLGAD A. fumigatus ATCC26906 QVLSRHGARY PTSSKSKKYk kLVtaIQaNA TdFKGKFAFL
   KTYNYTLGAD A. fumigatus ATCC32239 QVLSRHGARY PTASKSKKYk kLVtaIQKNA TeFKGKFAFL
   ETYNYTLGAD 25       E. nidulans           QVLSRHGARY PTeSKSKaYS GLIEaIQKNA TsFwGQYAFL
   ESYNYTLGAD
```

FIG. 7C

|   |   |   |
|---|---|---|
| | T. thermophilus<br>KdYrYqLGAN | QLLSRHGARY PTSSKTElYS qLIsRIQKtA TaYKGyYAFL |
| | T. lanuginosa<br>RdYaYhLGAD | QVLSRHGARY PTAhKSEvYA ELLQRIQDtA TeFKGDFAFL |
| 5 | M. thermophila<br>RTYDYTLGAD | QVLSRHGARa PTlkRAasYv DLIDRIHhGA isYgPgYEFL |
| | Consensus Seq. 11<br>KTYNYTLGAD | QVLSRHGARY PTSSKSKKYS ALIERIQKNA T-FKGKYAFL |
| 10 | | |
| | | 101 |
| | 150 | |
| | P. involutus (phyA1)<br>VVDSAtNWtA | DLvPFGAaQs fDAGqEaFaR YskLvSKNnL PFIRAdGSDR |
| 15 | P. involutus (phyA2)<br>VVDTAtNWtA | DLvPFGAaQs fDAGLEvFaR YskLvSsDnL PFIRSdGSDR |
| | T. pubescens<br>VVATANNWtA | sLveLGAtQs sEAGqEaFtR YsSLvSaDeL PFVRASGSDR |
| 20 | A. pediades<br>VVDSAtNWtE | DLvPFGAlQs sQAGeEtFQR YsfLvSKEnL PFVRASSSNR |
| | P. lycii<br>VVDSStNWtA | DLlPFGANQs hQTGtDMYtR YsTLfEgGdV PFVRAAGdQR |
| | A. terreus 9a1<br>VhESAEKFVE | ELTPFGrNQL rDlGaQFYeR YNAL.TRHIn PFVRATDAsR |
| 25 | A. terreus cbs<br>VhESAEKFVE | NLTPFGrNQL qDlGaQFYRR YDTL.TRHIn PFVRAADSsR |

FIG. 7D

```
         A. niger var. awamori    DLTPFGEQEL VNSGIKFYQR YESL.TRNII PFIRSSGSsR
     VIASGEKFIE A. niger T213            DLTPFGEQEL VNSGIKFYQR YESL.TRNII PFIRSSGSsR
     VIASGEKFIE 5      A. niger NRRL3135        DLTPFGEQEL VNSGIKFYQR YESL.TRNIV PFIRSSGSsR
     VIASGKKFIE A. fumigatus ATCC13073   DLTPFGEQQL VNSGIKFYQR YKAL.ARSVV PFIRASGSDR
     VIASGEKFIE A. fumigatus ATCC32722   DLTPFGEQQL VNSGIKFYQR YKAL.ARSVV PFIRASGSDR
 10  VIASGEKFIE A. fumigatus ATCC58128   DLTPFGEQQL VNSGIKFYQR YKAL.ARSVV PFIRASGSDR
     VIASGEKFIE A. fumigatus ATCC26906   DLTAFGEQQL VNSGIKFYQR YKAL.ARSVV PFIRASGSDR
     VIASGEKFIE 15      A. fumigatus ATCC32239   DLTPFGEQQM VNSGIKFYQK YKAL.AgSVV PFIRSSGSDR
     VIASGEKFIE E. nidulans              DLTiFGENQM VDSGaKFYRR YKnL.ARKnt PFIRASGSDR
     VVASAEKFIN T. thermophilus          DLTPFGENQM IQlGIKFYnH YKSL.ARNaV PFVRCSGSDR
 20  VIASGrlFIE T. lanuginosa            NLTRFGEEQM MESGrQFYHR YREq.AREIV PFVRAAGSAR
     VIASAEfFnr M. thermophila           ELTRtGQQQM VNSGIKFYRR YRAL.ARKsI PFVRTAGqDR
     VVhSAENFtQ

25

Consensus Seq. 11         DLTPFGENQM VNSGIKFYRR YKAL-ARNIV PFVRASGSDR
     VIASAEKFIE
```

P. involutus (phyA1)       GFaSA..... ..shNtvqPk LNLILPQ..T gNDTLEDNMC
  5   PAaGD.....

P. involutus (phyA2)       GFaSA..... ..srNaiqPk LDLILPQ..T gNDTLEDNMC
      PAaGE.....

T. pubescens               GFalA..... ..ssNsiTPV LSVIISE..A gNDTLDDNMC
      PAaGD.....

10       A. pediades                GFsAA..... ..shHvlNPI LfVILSE..S LNDTLDDAMC
      PnaGs.....

P. lycii                   GFgdA..... ..sgEtvlPt LQVVLQE..E gNcTLcNNMC
      PnevD.....

A. terreus 9al             GFQTARqDDh hAnpHQPSPr VDVaIPEGSA YNNTLEHSLC
 15   TAFEs...ST A. terreus cbs             GFQNARqGDP hAnpHQPSPr VDVVIPEGTA YNNTLEHSIC
      TAFEA...ST A. niger var. awamori      GFQSTKLkDP rAqpgQSSPk IDVVISEASS sNNTLDpGtC
      TvFED...Se 20       A. niger T213              GFQSTKLkDP rAqpgQSSPk IDVVISEASS sNNTLDpGtC
      TvFED...Se A. niger NRRL3135          GFQSTKLkDP rAqpgQSSPk IDVVISEASS sNNTLDpGtC
      TvFED...Se A. fumigatus ATCC13073     GFQqAKLADP gAt.NRAAPa ISVIIPESeT FNNTLDHGVC
 25   TkFEA...Sq A. fumigatus ATCC32722     GFQqAKLADP gAt.NRAAPa ISVIIPESeT FNNTLDHGVC
      TkFEA...Sq
```

FIG. 7F

|   |   |   |
|---|---|---|
|   | *A. fumigatus* ATCC58128 | GFQqAKLADP gAt.NRAAPa ISVIIPESeT FNNTLDHGVC TkFEA...Sq |
|   | *A. fumigatus* ATCC26906 | GFQqAKLADP gAt.NRAAPa ISVIIPESeT FNNTLDHGVC TkFEA...Sq |
| 5 | *A. fumigatus* ATCC32239 | GFQqANVADP gAt.NRAAPV ISVIIPESeT YNNTLDHSVC TnFEA...Se |
|   | *E. nidulans* | GFRkAQLhDh g.s.gQATPV VNVIIPEidG FNNTLDHStC vSFEN...de |
| 10 | *T. thermophilus* | GFQSAKVlDP hSdkHDAPPt INVIIeEGPS YNNTLDtGsC PvFED...SS |
|   | *T. lanuginosa* | GFQdAKdrDP rSnkDQAePV INVIISEETG sNNTLDgltC PAaEE...AP |
|   | *M. thermophila* | GFHSAlLADR gStvRPTlPy dmVVIPETAG aNNTLHNDLC TAFEEgpyST |
| 15 |   |   |
|   | Consensus Seq. 11 | GFQSAKLADP -A--HQASPV INVIIPEGSG YNNTLDHGLC TAFED---ST |

```
                                      201
20                                          250

P. involutus (phyA1)    .SDpqvnaWl AVafPSItAR LNAaaPSVNL TDtDafNLVs
   LCAFlTVSK.

P. involutus (phyA2)    .SDpqvDaWl AsafPSVtAQ LNAaaPGaNL TDADafNLVs
   LCPFmTVSK.

25       T. pubescens            .SDpqvnQWl AqFAPPMtAR LNAgaPGaNL TDtDtyNLLt
   LCPFETVAt.
```

FIG. 7G

```
     A. pediades         .SDpqtGiWT SIYGTPIanR LNqqaPGaNI TAADVsNLIp
LCAFETIvK.

P. lycii            .GDESt.tWl GVFAPnItAR LNAaaPSaNL SDsDaLtLMD
MCPFDTLSs.

5    A. terreus 9a1      VGDDAvANFT AVFAPAIaqR LEAdLPGVQL StDDVVNLMA
MCPFETVSlT

A. terreus cbs      VGDAAADNFT AVFAPAIakR LEAdLPGVQL SADDVVNLMA
MCPFETVSlT

A. niger var. awamori  LADtvEANFT AtFAPSIRqR LEndLSGVtL TDtEVtyLMD
10   MCSFDTIStS A. niger T213       LADtvEANFT AtFAPSIRqR LEndLSGVtL TDtEVtyLMD
MCSFDTIStS A. niger NRRL3135   LADtvEANFT AtFvPSIRqR LEndLSGVtL TDtEVtyLMD
MCSFDTIStS 15   A. fumigatus ATCC13073  LGDEvAANFT ALFAPdIRAR aEkhLPGVtL TDEDVVSLMD
MCSFDTVART A. fumigatus ATCC32722  LGDEvAANFT ALFAPdIRAR aEkhLPGVtL TDEDVVSLMD
MCSFDTVART A. fumigatus ATCC58128  LGDEvAANFT ALFAPdIRAR aEkhLPGVtL TDEDVVSLMD
20   MCSFDTVART A. fumigatus ATCC26906  LGDEvAANFT ALFAPdIRAR aKkhLPGVtL TDEDVVSLMD
MCSFDTVART A. fumigatus ATCC32239  LGDEvEANFT ALFAPAIRAR IEkhLPGVQL TDDDVVSLMD
MCSFDTVART 25   E. nidulans         rADEiEANFT AIMGPPIRkR LEndLPGIKL TNENVIyLMD
MCSFDTMART
```

FIG. 7H

```
           T. thermophilus        gGHDAQEKFA kqFAPAIlEK IKDhLPGVDL AvsDVpyLMD
    LCPFETLARn T. lanuginosa          .DptqpAEFl qVFGPRVlkK ItkhMPGVNL TlEDVplFMD
    LCPFDTVGsd 5         M. thermophila         IGDDAQDtYl StFAGPItAR VNAnLPGaNL TDADtVaLMD
    LCPFETVAsS Consensus Seq. 11      LGDDAEANFT AVFAPPIRAR LEA-LPGVNL TDEDVVNLMD
    MCPFDTVART 10
                                  251
    300

P. involutus (phyA1)   .......... ....ekkSdF CtLFegiPGs FeaFAYggdL
    dKFYGtGyGQ 15        P. involutus (phyA2)   .......... ....eqkSdF CtLFegiPGs FeaFAYagdL
    dKFYGtGyGQ T. pubescens           .......... ....errSeF CDIYeelqAE .daFAYnadL
    dKFYGtGyGQ A. pediades            .......... ....etpSPF CNLF..TPEE FaQFEYFgdL
 20 dKFYGtGyGQ P. lycii               .......... ....gnaSPF CDLF..TAEE YvsYEYYydL
    dKYYGtGPGN A. terreus 9a1         dD..Aht... ......LSPF CDLF..TAtE WtQYNYLlSL
    dKYYGYGGGN 25        A. terreus cbs         dD..Aht... ......LSPF CDLF..TAAE WtQYNYLlSL
    dKYYGYGGGN
```

FIG. 71

```
          A. niger var. awamori   Tv..DTK... ......LSPF CDLF..ThDE WiHYDYLQSL
     kKYYGHGAGN A. niger T213           Tv..DTK... ......LSPF CDLF..ThDE WiHYDYLRSL
     kKYYGHGAGN 5        A. niger NRRL3135       Tv..DTK... ......LSPF CDLF..ThDE WiNYDYLQSL
     kKYYGHGAGN A. fumigatus ATCC13073  SD..ASQ... ......LSPF CQLF..ThNE WkKYNYLQSL
     gKYYGYGAGN A. fumigatus ATCC32722  SD..ASQ... ......LSPF CQLF..ThNE WkKYNYLQSL
10   gKYYGYGAGN A. fumigatus ATCC58128  SD..ASQ... ......LSPF CQLF..ThNE WkKYNYLQSL
     gKYYGYGAGN A. fumigatus ATCC26906  SD..ASQ... ......LSPF CQLF..ThNE WkKYNYLQSL
     gKYYGYGAGN 15        A. fumigatus ATCC32239  AD..ASE... ......LSPF CAIF..ThNE WkKYDYLQSL
     gKYYGYGAGN E. nidulans             AH..GTE... ......LSPF CAIF..TEKE WlQYDYLQSL
     sKYYGYGAGS T. thermophilus         ht..DT.... ......LSPF CALs..TqEE WqaYDYYQSL
20   gKYYGnGGGN T. lanuginosa           PvlfPrQ... ......LSPF CHLF..TADD WmaYDYYyTL
     dKYYSHGGGS M. thermophila          SsdpATadag ggngrpLSPF CrLF..SEsE WraYDYLQSV
     gKWYGYGPGN 25
          Consensus Seq. 11       SD--ATQ--- ------LSPF CDLF--TADE W-QYDYLQSL -
     KYYGYGAGN
                                              FIG. 7J
```

```
                                    301
                   350
        P. involutus (phyA1)    eLGPvQGVGY vNELIARLTN S.AVRDNTqT NRTLDASPvT
        FPLNkTFYAD P. involutus (phyA2)    ALGPvQGVGY iNELLARLTN S.AVNDNTqT NRTLDAaPDT
        FPLNkTMYAD T. pubescens            PLGPvQGVGY iNELIARLTa q.nVsDHTqT NsTLDSSPET
        FPLNrTLYAD A. pediades             PLGPvQGVGY iNELLARLTE m.PVRDNTqT NRTLDSSPlT
        FPLDrSIYAD P. lycii                ALGPvQGVGY vNELLARLTg q.AVRDETqT NRTLDSDPAT
        FPLNrTFYAD A. terreus 9a1          PLGPvQGVGW aNELMARLTR A.PVHDHTCv NNTLDASPAT
        FPLNATLYAD A. terreus cbs          PLGPvQGVGW aNELIARLTR S.PVHDHTCv NNTLDANPAT
        FPLNATLYAD A. niger var. awamori   PLGPTQGVGY aNELIARLTH S.PVHDDTSS NHTLDSNPAT
        FPLNSTLYAD A. niger T213           PLGPTQGVGY aNELIARLTH S.PVHDDTSS NHTLDSNPAT
        FPLNSTLYAD A. niger NRRL3135       PLGPTQGVGY aNELIARLTH S.PVHDDTSS NHTLDSSPAT
        FPLNSTLYAD A. fumigatus ATCC13073  PLGPAQGIGF tNELIARLTR S.PVQDHTST NsTLvSNPAT
        FPLNATMYvD A. fumigatus ATCC32722  PLGPAQGIGF tNELIARLTR S.PVQDHTST NsTLvSNPAT
        FPLNATMYvD
```

FIG. 7K

|  |  |
|---|---|
| *A. fumigatus* ATCC58128 | PLGPAQGIGF tNELIARLTR S.PVQDHTST NsTLvSNPAT FPLNATMYvD |
| *A. fumigatus* ATCC26906 | PLGPAQGIGF tNELIARLTR S.PVQDHTST NsTLvSNPAT FPLNATMYvD |
| *A. fumigatus* ATCC32239 | PLGPAQGIGF tNELIARLTN S.PVQDHTST NsTLDSDPAT FPLNATIYvD |
| *E. nidulans* | PLGPAQGIGF tNELIARLTQ S.PVQDNTST NHTLDSNPAT FPLDrkLYAD |
| *T. thermophilus* | PLGPAQGVGF vNELIARMTH S.PVQDYTTv NHTLDSNPAT FPLNATLYAD |
| *T. lanuginosa* | AFGPSRGVGF vNELIARMTg NlPVKDHTTv NHTLDdNPET FPLDAvLYAD |
| *M. thermophila* | PLGPTQGVGF vNELLARLA. GvPVRDgTST NRTLDGDPrT FPLGrPLYAD |
| Consensus Seq. 11 | PLGPAQGVGF -NELIARLTH S-PVQDHTST NHTLDSNPAT FPLNATLYAD |

351
400

|  |  |
|---|---|
| *P. involutus* (phyA1) | FSHDNlMVAV FsAMGLFrqP aPLSTSvpNP wrt.....Wr TSSlVPFSGR |
| *P. involutus* (phyA2) | FSHDNlMVAV FsAMGLFrqS aPLSTSTpDP nrt.....Wl TSSvVPFSAR |
| *T. pubescens* | FSHDNqMVAI FsAMGLFNqS aPLdPTTpDP art.....Fl vkkiVPFSAR |

FIG. 7L

| | | |
|---|---|---|
| | A. pediades<br>TSRltPFSAR | LSHDNqMIAI FsAMGLFNqS sPLdPSfpNP krt.....Wv |
| | P. lycii<br>DSklVPFSGH | FSHDNTMVPI FaALGLFNAT a.LdPlkpDe nrl.....Wv |
| 5 | A. terreus 9a1<br>AAWTVPFAAR | FSHDSnLVSI FWALGLYNGT aPLSqTSVES Vs..QTDGYA |
| | A. terreus cbs<br>AAWTVPFAAR | FSHDSnLVSI FWALGLYNGT KPLSqTTVEd It..rTDGYA |
| 10 | A. niger var. awamori<br>SAWTVPFASR | FSHDNGIISI LFALGLYNGT KPLSTTTVEN It..QTDGFS |
| | A. niger T213<br>SAWTVPFASR | FSHDNGIISI LFALGLYNGT KPLSTTTVEN It..QTDGFS |
| | A. niger NRRL3135<br>SAWTVPFASR | FSHDNGIISI LFALGLYNGT KPLSTTTVEN It..QTDGFS |
| 15 | A. fumigatus ATCC13073<br>ASWvVPFGAR | FSHDNSMVSI FFALGLYNGT EPLSrTSVES ak..ElDGYS |
| | A. fumigatus ATCC32722<br>ASWvVPFGAR | FSHDNSMVSI FFALGLYNGT gPLSrTSVES ak..ElDGYS |
| 20 | A. fumigatus ATCC58128<br>ASWvVPFGAR | FSHDNSMVSI FFALGLYNGT EPLSrTSVES ak..ElDGYS |
| | A. fumigatus ATCC26906<br>ASWvVPFGAR | FSHDNSMVSI FFALGLYNGT EPLSrTSVES ak..ElDGYS |
| | A. fumigatus ATCC32239<br>ASWAVPFGAR | FSHDNGMIPI FFAMGLYNGT EPLSqTSeES tk..ESNGYS |
| 25 | E. nidulans<br>ASWTVPFGAR | FSHDNSMISI FFAMGLYNGT QPLSmdSVES Iq..EmDGYA |

FIG. 7M

|   |   |   |
|---|---|---|
| | *T. thermophilus* AAWTVPFGGR | FSHDNTMtSI FaALGLYNGT akLSTTeIKS Ie..ETDGYS |
| | *T. lanuginosa* ASWTVPFAAR | FSHDNTMtGI FsAMGLYNGT KPLSTSkIQP ptgaAADGYA |
| 5 | *M. thermophila* ASWAVPFAAR | FSHDNdMMGV LgALGaYDGv pPLdkTArrd ..peElGGYA |
| | Consensus Seq. 11 ASWTVPFAAR | FSHDNTMVSI FFALGLYNGT KPLSTTSVES I---ETDGYA |
| 10 | | |
| | | 401                                              450 |
| | *P. involutus* (phyA1) PLEfCGgDRn | mvVErLsC.. fGt....... ........Tk VRVLVQDQVq |
| 15 | *P. involutus* (phyA2) PLEfCGgDQd | maVErLsC.. AGt....... ........Tk VRVLVQDQVq |
| | *T. pubescens* PLafCGaDts | mvVErLDC.. GGa....... ........Qs VRLLVNDaVq |
| 20 | *A. pediades* PLkfCGgDmd | mvtErLlCQr DGtGsGGpsr imrNgnvQTF VRILVNDaLq |
| | *P. lycii* PLEfCGg.vd | mtVEkLaC.. .......... .....sgKea VRVLVNDaVq |
| | *A. terreus* 9a1 PLHGCPtDKL | AYVEMMQCrA .......... ..EK...EPL VRVLVNDRVM |
| 25 | *A. terreus* cbs PLHGCAVDNL | AYIEMMQCrA .......... ..EK...QPL VRVLVNDRVM |

FIG. 7N

```
         A. niger var. awamori    lYVEMMQCQA .......... ..EQ...EPL VRVLVNDRVV
     PLHGCPIDaL A. niger T213            lYVEMMQCQA .......... ..EQ...EPL VRVLVNDRVV
     PLHGCPIDaL 5       A. niger NRRL3135        lYVEMMQCQA .......... ..EQ...EPL VRVLVNDRVV
     PLHGCPVDaL A. fumigatus ATCC13073   AYfEtMQCKS .......... ..EK...EPL VRaLINDRVV
     PLHGCDVDKL A. fumigatus ATCC32722   AYfEtMQCKS .......... ..EK...EPL VRaLINDRVV
10   PLHGCDVDKL A. fumigatus ATCC58128   AYfEtMQCKS .......... ..EK...ESL VRaLINDRVV
     PLHGCDVDKL A. fumigatus ATCC26906   AYfEtMQCKS .......... ..EK...EPL VRaLINDRVV
     PLHGCDVDKL 15       A. fumigatus ATCC32239   AYfEtMQCKS .......... ..EK...EPL VRaLINDRVV
     PLHGCAVDKL E. nidulans              AYfELMQCE. .......... ..KK...EPL VRVLVNDRVV
     PLHGCAVDKF T. thermophilus          AYIEMMQCDD .......... ...sD...EPV VRVLVNDRVV
20   PLHGCEVDsL T. lanuginosa            AYVELLRCET ETsSeEEeEG ..ED...EPF VRVLVNDRVV
     PLHGCrVDRW M. thermophila           iYVEkMRCsG GGgGgGGgEG ..rQekdEeM VRVLVNDRVM
     TLkGCGaDEr 25
         Consensus Seq. 11        AYVEMMQCEA GG-G-GG-EG --EK---EPL VRVLVNDRVV
     PLHGCGVDKL
```

FIG. 70

|   |   | 451 | 482 |
|---|---|---|---|
|   | P. involutus (phyA1) | GlCtLAKFVE SqTFARSDga | GDFEKCFAts a~ |
|   | P. involutus (phyA2) | GlCaLDKFVE SqAYARSGga | GDFEKCLAtt v~ |
| 5 | T. pubescens | GvCtLDAFVE SqAYARNDge | GDFEKCFAt~ ~~ |
|   | A. pediades | SlCtLEAFVE SqkYAReDgq | GDFEKCFD~~ ~~ |
|   | P. lycii | GvCELsAFVE SqTYAReNgq | GDFAKCgfvp se |
|   | A. terreus 9a1 | GRCKrDAFVA GLSFAQAG.. | GNWADCF~~ ~~ |
|   | A. terreus cbs | GRCKrDDFVE GLSFARAG.. | GNWAECF~~ ~~ |
| 10 | A. niger var. awamori | GRCtrDsFVr GLSFARSG.. | GDWAECsA~~ ~~ |
|   | A. niger T213 | GRCtrDsFVr GLSFARSG.. | GDWAECFA~~ ~~ |
|   | A. niger NRRL3135 | GRCtrDsFVr GLSFARSG.. | GDWAECFA~~ ~~ |
|   | A. fumigatus ATCC13073 | GRCKLNDFVK GLSWARSG.. | GNWGECFS~~ ~~ |
|   | A. fumigatus ATCC32722 | GRCKLNDFVK GLSWARSG.. | GNWGECFS~~ ~~ |
| 15 | A. fumigatus ATCC58128 | GRCKLNDFVK GLSWARSG.. | GNWGECFS~~ ~~ |
|   | A. fumigatus ATCC26906 | GRCKLNDFVK GLSWARSG.. | GNWGECFS~~ ~~ |
|   | A. fumigatus ATCC32239 | GRCKLKDFVK GLSWARSG.. | GNSEQSFS~~ ~~ |
|   | E. nidulans | GRCtLDDWVE GLNFARSG.. | GNWktCFTl~ ~~ |
|   | T. thermophilus | GRCKrDDFVr GLSFARqG.. | GNWEGCYAas e~ |
| 20 | T. lanuginosa | GRCRrDEWIK GLTFARqG.. | GHWDrCF~~~ ~~ |
|   | M. thermophila | GmCtLErFIE SMAFARGN.. | GKWDlCFA~~ ~~ |

FIG. 7P

Consensus Seq. 11    GRCKLDDFVE GLSFARSG-- GNWAECFA-- --

ATGGGCGTGTTCGTCGTGCTACTGTCCATTGCCACCTTGTTCGGTTCCACATCCGGTACC

1 ---+---------+---------+---------+---------+---------+------
                                                                      60

TACCCGCACAAGCAGCACGATGACAGGTAACGGTGGAACAAGCCAAGGTGTAGGCCATGG

A  L  G  P  R  G  N  S  H  S  C  D  T  V  D  G  G  Y  Q  C    40

GCCTTGGGTCCTCGTGGTAATTCTCACTCTTGTGACACTGTTGACGGTGGTTACCAATGT

61 ---+---------+---------+---------+---------+---------+------
                                                                     120

CGGAACCCAGGAGCACCATTAAGAGTGAGAACACTGTGACAACTGCCACCAATGGTTACA

F  P  E  I  S  H  L  W  G  T  Y  S  P  Y  F  S  L  A  D  E    60

TTCCCAGAAATTTCTCACTTGTGGGGTACCTACTCTCCATACTTCTCTTTGGCAGACGAA

121 ---+---------+---------+---------+---------+---------+------
                                                                     180

AAGGGTCTTTAAAGAGTGAACACCCCATGGATGAGAGGTATGAAGAGAAACCGTCTGCTT

S  A  I  S  P  D  V  P  D  D  C  R  V  T  F  V  Q  V  L  S    80

TCTGCTATTTCTCCAGACGTTCCAGACGACTGTAGAGTTACTTTCGTTCAAGTTTTGTCT

187 ---+---------+---------+---------+---------+---------+------
                                                                     240

AGACGATAAAGAGGTCTGCAAGGTCTGCTGACATCTCAATGAAAGCAAGTTCAAAACAGA
```

AGACACGGTGCTAGATACCCAACTTCTTCTGCGTCTAAGGCTTACTCTGCTTTGATTGAA

241 ---+---------+---------+---------+---------+---------+------
         300

TCTGTGCCACGATCTATGGGTTGAAGAAGACGCAGATTCCGAATGAGACGAAACTAACTT

A  I  Q  K  N  A  T  A  F  K  G  K  Y  A  F  L  K  T  Y  N     120

GCTATTCAAAAGAACGCTACTGCTTTCAAGGGTAAGTACGCTTTCTTGAAGACTTACAAC

301 ---+---------+---------+---------+---------+---------+------
         360

CGATAAGTTTTCTTGCGATGACGAAAGTTCCCATTCATGCGAAAGAACTTCTGAATGTTG

Y  T  L  G  A  D  D  L  T  P  F  G  E  N  Q  M  V  N  S  G     140

TACACTTTGGGTGCTGACGACTTGACTCCATTCGGTGAAAACCAAATGGTTAACTCTGGT

361 ---+---------+---------+---------+---------+---------+------
         420

ATGTGAAACCCACGACTGCTGAACTGAGGTAAGCCACTTTTGGTTTACCAATTGAGACCA

I  K  F  Y  R  R  Y  K  A  L  A  R  K  I  V  P  F  I  R  A     160

ATTAAGTTCTACAGAAGATACAAGGCTTTGGCTAGAAAGATTGTTCCATTCATTAGAGCT

421 ---+---------+---------+---------+---------+---------+------
         480

TAATTCAAGATGTCTTCTATGTTCCGAAACCGATCTTTCTAACAAGGTAAGTAATCTCGA
```

TCTGGTTCTGACAGAGTTATTGCTTCTGCTGAAAAGTTCATTGAAGGTTTCCAATCTGCT

481 ---+---------+---------+---------+---------+---------+------
             540

AGACCAAGACTGTCTCAATAACGAAGACGACTTTTCAAGTAACTTCCAAAGGTTAGACGA

K  L  A  D  P  G  S  Q  P  H  Q  A  S  P  V  I  N  V  I  I        200

AAGTTGGCTGACCCAGGTTCTCAACCACACCAAGCTTCTCCAGTTATTAACGTGATCATT

541 ---+---------+---------+---------+---------+---------+------
             600

TTCAACCGACTGGGTCCAAGAGTTGGTGTGGTTCGAAGAGGTCAATAATTGCACTAGTAA

P  E  G  S  G  Y  N  N  T  L  D  H  G  T  C  T  A  F  E  D        220

CCAGAAGGATCCGGTTACAACAACACTTTGGACCACGGTACTTGTACTGCTTTCGAAGAC

601 ---+---------+---------+---------+---------+---------+------
             660

GGTCTTCCTAGGCCAATGTTGTTGTGAAACCTGGTGCCATGAACATGACGAAAGCTTCTG

S  E  L  G  D  D  V  E  A  N  F  T  A  L  F  A  P  A  I  R        240

TCTGAATTAGGTGACGACGTTGAAGCTAACTTCACTGCTTTGTTCGCTCCAGCTATTAGA

661 ---+---------+---------+---------+---------+---------+------
             720

AGACTTAATCCACTGCTGCAACTTCGATTGAAGTGACGAAACAAGCGAGGTCGATAATCT
```

GCTAGATTGGAAGCTGACTTGCCAGGTGTTACTTTGACTGACGAAGACGTTGTTTACTTG

721 ---+---------+---------+---------+---------+---------+------
        780

CGATCTAACCTTCGACTGAACGGTCCACAATGAAACTGACTGCTTCTGCAACAAATGAAC

M  D  M  C  P  F  D  T  V  A  R  T  S  D  A  T  E  L  S  P   280

ATGGACATGTGTCCATTCGACACTGTCGCTAGAACTTCTGACGCTACTGAATTGTCTCCA

781 ---+---------+---------+---------+---------+---------+------
        840

TACCTGTACACAGGTAAGCTGTGACAGCGATCTTGAAGACTGCGATGACTTAACAGAGGT

F  C  A  L  F  T  H  D  E  W  I  Q  Y  D  Y  L  Q  S  L  G   300

TTCTGTGCTTTGTTCACTCACGACGAATGGATCCAATACGACTACTTGCAAAGCTTGGGT

841 ---+---------+---------+---------+---------+---------+------
        900

AAGACACGAAACAAGTGAGTGCTGCTTACCTAGGTTATGCTGATGAACGTTTCGAACCCA

K  Y  Y  G  Y  G  A  G  N  P  L  G  P  A  Q  G  V  G  F  A   320

AAGTACTACGGTTACGGTGCTGGTAACCCATTGGGTCCAGCTCAAGGTGTTGGTTTCGCT

901 ---+---------+---------+---------+---------+---------+------
        960

TTCATGATGCCAATGCCACGACCATTGGGTAACCCAGGTCGAGTTCCACAACCAAAGCGA
```

AACGAATTGATTGCTAGATTGACTCACTCTCCAGTTCAAGACCACACTTCTACTAACCAC
        961 ---+---------+---------+---------+---------+---------+------
                                                                     1020

TTGCTTAACTAACGATCTAACTGAGTGAGAGGTCAAGTTCTGGTGTGAAGATGATTGGTG

T  L  D  S  N  P  A  T  F  P  L  N  A  T  L  Y  A  D  F  S    360

ACTTTGGACTCTAACCCAGCTACTTTCCCATTGAACGCTACTTTGTACGCTGACTTCTCT
       1021 ---+---------+---------+---------+---------+---------+------
                                                                     1080

TGAAACCTGAGATTGGGTCGATGAAAGGGTAACTTGCGATGAAACATGCGACTGAAGAGA

H  D  N  T  M  I  S  I  F  F  A  L  G  L  Y  N  G  T  K  P    380

CACGACAACACTATGATATCTATTTTCTTCGCTTTGGGTTTGTACAACGGTACCAAGCCA
       1081 ---+---------+---------+---------+---------+---------+------
                                                                     1140

GTGCTGTTGTGATACTATAGATAAAAGAAGCGAAACCCAAACATGTTGCCATGGTTCGGT

L  S  T  T  S  V  E  S  I  E  E  T  D  G  Y  S  A  S  W  T    400

TTGTCTACTACTTCTGTTGAATCTATTGAAGAAACTGACGGTTACTCTGCTTCTTGGACT
       1141 ---+---------+---------+---------+---------+---------+------
                                                                     1200

AACAGATGATGAAGACAACTTAGATAACTTCTTTGACTGCCAATGAGACGAAGAACCTGA
```

GTTCCATTCGCTGCTAGAGCTTACGTTGAAATGATGCAATGTCAAGCTGAAAAGGAACCA

1201 ---+---------+---------+---------+---------+---------+------
                                                                     1260

CAAGGTAAGCGACGATCTCGAATGCAACTTTACTACGTTACAGTTCGACTTTTCCTTGGT

L  V  R  V  L  V  N  D  R  V  V  P  L  H  G  C  A  V  D  K   440

TTGGTTAGAGTTTTGGTTAACGACAGAGTTGTTCCATTGCACGGTTGTGCTGTTGACAAG

1261 ---+---------+---------+---------+---------+---------+------
                                                                     1320

AACCAATCTCAAAACCAATTGCTGTCTCAACAAGGTAACGTGCCAACACGACAACTGTTC

L  G  R  C  K  R  D  D  F  V  E  G  L  S  F  A  R  S  G  G   460

TTGGGTAGATGTAAGAGAGACGACTTCGTTGAAGGTTTGTCTTTCGCTAGATCTGGTGGT

1321 ---+---------+---------+---------+---------+---------+------
                                                                     1380

AACCCATCTACATTCTCTCTGCTGAAGCAACTTCCAAACAGAAAGCGATCTAGACCACCA

N  W  A  E  C  F  *    467

AACTGGGCTGAATGTTTCGCTTAA

1381 ---+---------+---------+ 1410

TTGACCCGACTTACAAAGCGAATT
```

ATGGGCGTGTTCGTCGTGCTACTGTCCATTGCCACCTTGTTCGGTTCCACATCCGGTACC

1 ---------+---------+---------+---------+---------+---------+
                                                                    60

TACCCGCACAAGCAGCACGATGACAGGTAACGGTGGAACAAGCCAAGGTGTAGGCCATGG

A   L   G   P   R   G   N   S   H   S   C   D   T   V   D   G   G   Y   Q   C       40

GCCTTGGGTCCTCGTGGTAACTCTCACTCTTGTGACACTGTTGACGGTGGTTACCAATGT

61 ---------+---------+---------+---------+---------+---------+
                                                                    120

CGGAACCCAGGAGCACCATTGAGAGTGAGAACACTGTGACAACTGCCACCAATGGTTACA

A   F   P   E   I   S   H   L   W   G   T   Y   S   P   F   F   S   L   A   D   E   60

TTCCCAGAAATTTCTCACTTGTGGGGTACATACTCTCCATTCTTCTCTTTGGCTGACGAA

121 ---------+---------+---------+---------+---------+---------+
                                                                    180

AAGGGTCTTTAAAGAGTGAACACCCCATGTATGAGAGGTAAGAAGAGAAACCGACTGCTT

S   A   I   S   P   D   V   P   K   G   C   R   V   T   F   V   Q   V   L   S       80

TCTGCTATTTCTCCAGACGTTCCAAAGGGTTGTAGAGTTACTTTCGTTCAAGTTTTGTCT

181 ---------+---------+---------+---------+---------+---------+
                                                                    240

AGACGATAAAGAGGTCTGCAAGGTTTCCCAACATCTCAATGAAAGCAAGTTCAAAACAGA
```

FIG. 9A

```
           R  H  G  A  R  Y  P  T  S  S  A  S  K  A  Y  S  A  L  I  E     100
                                          ̲              ̲
           AGACACGGTGCTAGATACCCAACTTCTTCTGCGTCTAAGGCGTACTCTGCTTTGATTGAA

241 ---------+---------+---------+---------+---------+---------+
       300

TCTGTGCCACGATCTATGGGTTGAAGAAGACGCAGATTCCGCATGAGACGAAACTAACTT

A  I  Q  K  N  A  T  A  F  K  G  K  Y  A  F  L  K  T  Y  N     120

GCTATTCAAAAGAACGCTACTGCTTTCAAGGGTAAGTACGCTTTCTTGAAGACTTACAAC

301 ---------+---------+---------+---------+---------+---------+
       360

CGATAAGTTTTCTTGCGATGACGAAAGTTCCCATTCATGCGAAAGAACTTCTGAATGTTG

A     Y  T  L  G  A  D  D  L  T  P  F  G  E  Q  Q  M  V  N  S  G  140

TACACTTTGGGTGCTGACGACTTGACTCCATTCGGTGAACAACAAATGGTTAACTCTGGT

361 ---------+---------+---------+---------+---------+---------+
       420

ATGTGAAACCCACGACTGCTGAACTGAGGTAAGCCACTTGTTGTTTACCAATTGAGACCA

I  K  F  Y  R  R  Y  K  A  L  A  R  K  I  V  P  F  I  R  A     160
                                                                ̲
           ATTAAGTTCTACAGAAGATACAAGGCTTTGGCTAGAAAGATTGTTCCATTCATTAGAGCT

421 ---------+---------+---------+---------+---------+---------+
       480

TAATTCAAGATGTCTTCTATGTTCCGAAACCGATCTTTCTAACAAGGTAAGTAATCTCGA
```

TCTGGTTCTGACAGAGTTATTGCTTCTGCTGAAAAGTTCATTGAAGGTTTCCAATCTGCT

481 ---------+---------+---------+---------+---------+---------+
   540

AGACCAAGACTGTCTCAATAACGAAGACGACTTTTCAAGTAACTTCCAAAGGTTAGACGA

K  L  A  D  P  G  A  N  P  H  Q  A  S  P  V  I  N  V  I  I    200

AAGTTGGCTGACCCAGGTGCTAACCCACACCAAGCTTCTCCAGTTATTAACGTTATTATT

541 ---------+---------+---------+---------+---------+---------+
   600

TTCAACCGACTGGGTCCACGATTGGGTGTGGTTCGAAGAGGTCAATAATTGCAATAATAA

P  E  G  A  G  Y  N  N  T  L  D  H  G  L  C  T  A  F  E  E    220

CCAGAAGGTGCTGGTTACAACAACACTTTGGACCACGGTTTGTGTACTGCTTTCGAAGAA

601 ---------+---------+---------+---------+---------+---------+
   660

GGTCTTCCACGACCAATGTTGTTGTGAAACCTGGTGCCAAACACATGACGAAAGCTTCTT

S  E  L  G  D  D  V  E  A  N  F  T  A  V  F  A  P  P  I  R    240

TCTGAATTGGGTGACGACGTTGAAGCTAACTTCACTGCTGTTTTCGCTCCACCAATTAGA

661 ---------+---------+---------+---------+---------+---------+
   720

AGACTTAACCCACTGCTGCAACTTCGATTGAAGTGACGACAAAAGCGAGGTGGTTAATCT
```

FIG. 9C

```
              A  R  L  E  A  H  L  P  G  V  N  L  T  D  E  D  V  V  N  L
        260
              GCTAGATTGGAAGCTCACTTGCCAGGTGTTAACTTGACTGACGAAGACGTTGTTAACTTG
        721 ---------+---------+---------+---------+---------+---------+
        780
              CGATCTAACCTTCGAGTGAACGGTCCACAATTGAACTGACTGCTTCTGCAACAATTGAAC

M  D  M  C  P  F  D  T  V  A  R  T  S  D  A  T  Q  L  S  P   280
              ATGGACATGTGTCCATTCGACACTGTTGCTAGAACTTCTGACGCTACTCAATTGTCTCCA
        781 ---------+---------+---------+---------+---------+---------+
        840
              TACCTGTACACAGGTAAGCTGTGACAACGATCTTGAAGACTGCGATGAGTTAACAGAGGT

F  C  D  L  F  T  H  D  E  W  I  Q  Y  D  Y  L  Q  S  L  G   300
              TTCTGTGACTTGTTCACTCACGACGAATGGATTCAATACGACTACTTGCAATCTTTGGGT
        841 ---------+---------+---------+---------+---------+---------+
        900
              AAGACACTGAACAAGTGAGTGCTGCTTACCTAAGTTATGCTGATGAACGTTAGAAACCCA

K  Y  Y  G  Y  G  A  G  N  P  L  G  P  A  Q  G  V  G  F  V   320
              AAGTACTACGGTTACGGTGCTGGTAACCCATTGGGTCCAGCTCAAGGTGTTGGTTTCGTT
        901 ---------+---------+---------+---------+---------+---------+
        960
              TTCATGATGCCAATGCCACGACCATTGGGTAACCCAGGTCGAGTTCCACAACCAAAGCAA
```

AACGAATTGATTGCTAGATTGACTCACTCTCCAGTTCAAGACCACACTTCTACTAACCAC

961 ---------+---------+---------+---------+---------+---------+
                                                                          1020

TTGCTTAACTAACGATCTAACTGAGTGAGAGGTCAAGTTCTGGTGTGAAGATGATTGGTG

T  L  D  S  N  P  A  T  F  P  L  N  A  T  L  Y  A  D  F  S    360

ACTTTGGACTCTAACCCAGCTACTTTCCCATTGAACGCTACTTTGTACGCTGACTTCTCT

1021 ---------+---------+---------+---------+---------+---------+
                                                                          1080

TGAAACCTGAGATTGGGTCGATGAAAGGGTAACTTGCGATGAAACATGCGACTGAAGAGA

H  D  N  T  M  V  S  I  F  F  A  L  G  L  Y  N  G  T  K  P    380

CACGACAACACTATGGTTTCTATTTTCTTCGCTTTGGGTTTGTACAACGGTACTAAGCCA

1081 ---------+---------+---------+---------+---------+---------+
                                                                          1140

GTGCTGTTGTGATACCAAAGATAAAAGAAGCGAAACCCAAACATGTTGCCATGATTCGGT

L  S  T  T  S  V  E  S  I  E  E  T  D  G  Y  S  A  S  W  T    400

TTGTCTACTACTTCTGTTGAATCTATTGAAGAAACTGACGGTTACTCTGCTTCTTGGACT

1141 ---------+---------+---------+---------+---------+---------+
                                                                          1200

AACAGATGATGAAGACAACTTAGATAACTTCTTTGACTGCCAATGAGACGAAGAACCTGA
```

GTTCCATTCGCTGCTAGAGCTTACGTTGAAATGATGCAATGTGAAGCTGAAAAGGAACCA

1201 ---------+---------+---------+---------+---------+---------+
         1260

CAAGGTAAGCGACGATCTCGAATGCAACTTTACTACGTTACACTTCGACTTTTCCTTGGT

L  V  R  V  L  V  N  D  R  V  V  P  L  H  C  G  V  D  K         440

TTGGTTAGAGTTTTGGTTAACGACAGAGTTGTTCCATTGCACGGTTGTGGTGTTGACAAG

1261 ---------+---------+---------+---------+---------+---------+
         1320

AACCAATCTCAAAACCAATTGCTGTCTCAACAAGGTAACGTGCCAACACCACAACTGTTC

L  G  R  C  K  R  D  D  F  V  E  G  L  S  F  A  R  S  G  G      460

TTGGGTAGATGTAAGAGAGACGACTTCGTTGAAGGTTTGTCTTTCGCTAGATCTGGTGGT

1321 ---------+---------+---------+---------+---------+---------+
         1380

AACCCATCTACATTCTCTCTGCTGAAGCAACTTCCAAACAGAAAGCGATCTAGACCACCA

N  W  E  E  C  F  A  *    467

AACTGGGAAGAATGTTTCGCTTAA

1381 ---------+---------+---- 1404

TTGACCCTTCTTACAAAGCGAATT
```

ATGGGGGTTTTCGTCGTTCTATTATCTATCGCGACTCTGTTCGGCAGCACATCGGGCACT
    1 ---------+---------+---------+---------+---------+---------+
                                                                  60

TACCCCCAAAAGCAGCAAGATAATAGATAGCGCTGAGACAAGCCGTCGTGTAGCCCGTGA

A   L   G   P   R   G   N   H   S   K   S   C   D   T   V   D   L   G   Y   Q    40

GCGCTGGGCCCCCGTGGAAATCACTCCAAGTCCTGCGATACGGTAGACCTAGGGTACCAG
   61 ---------+---------+---------+---------+---------+---------+
                                                                  120

CGCGACCCGGGGGCACCTTTAGTGAGGTTCAGGACGCTATGCCATCTGGATCCCATGGTC

C   S   P   A   T   S   H   L   W   G   T   Y   S   P   Y   F   S   L   E   D    60
                                          ‾               ‾
      TGCTCCCCTGCGACTTCTCATCTATGGGGCACGTACTCGCCATaCTTTTCGCTCGAGGAC
  121 ---------+---------+---------+---------+---------+---------+
                                                                  180

ACGAGGGGACGCTGAAGAGTAGATACCCCGtgCATGAGCGGTAtGAAAAGCGAGCTCCTG

E   L   S   V   S   S   K   L   P   K   D   C   R   I   T   L   V   Q   V   L    80

GAGCTGTCCGTGTCGAGTAAGCTTCCCAAGGATTGCCGGATCACCTTGGTACAGGTGCTA
  181 ---------+---------+---------+---------+---------+---------+
                                                                  240

CTCGACAGGCACAGCTCATTCGAAGGGTTCCTAACGGCCTAGTGGAACCATGTCCACGAT
```

TCGCGCCATGGAGCGCGGTACCCAACCAGCTCCAAGAGCAAAAAGTATAAGAAGCTTaTt

241 ---------+---------+---------+---------+---------+---------+
                                                                              300

AGCGCGGTACCTCGCGCCATGGGTTGGTCGAGGTTCTCGTTTTTCATATTCTTCGAAtAa

T  A  I  Q  A  N  A  T  D  F  K  G  K  Y  A  F  L  K  T  Y   120

ACGGCGATCCAGGCCAATGCCACCGACTTCAAGGGCAAGTacGCCTTTTTGAAGACGTAC

301 ---------+---------+---------+---------+---------+---------+
                                                                              360

TGCCGCTAGGTCCGGTTACGGTGGCTGAAGTTCCCGTTCAtgCGGAAAAACTTCTGCATG

N  Y  T  L  G  A  D  D  L  T  P  F  G  E  Q  Q  L  V  N  S   140

AACTATACTCTGGGTGCGGATGACCTCACTCCCTTTGGGGAGCAGCAGCTGGTGAACTCG

361 ---------+---------+---------+---------+---------+---------+
                                                                              420

TTGATATGAGACCCACGCCTACTGGAGTGAGGGAAACCCCTCGTCGTCGACCACTTGAGC

G  I  K  F  Y  Q  R  Y  K  A  L  A  R  S  V  V  P  F  I  R   160

GGCATCAAGTTCTACCAGAGGTACAAGGCTCTGGCGCGCAGTGTGGTGCCGTTTATTCGC

421 ---------+---------+---------+---------+---------+---------+
                                                                              480

CCGTAGTTCAAGATGGTCTCCATGTTCCGAGACCGCGCGTCACACCACGGCAAATAAGCG
```

GCCTCAGGCTCGGACCGGGTTATTGCTTCGGGAGAGAAGTTCATCGAGGGGTTCCAGCAG

481 ---------+---------+---------+---------+---------+---------+
        540

CGGAGTCCGAGCCTGGCCCAATAACGAAGCCCTCTCTTCAAGTAGCTCCCCAAGGTCGTC

A  K  L  A  D  P  G  A  T  N  R  A  A  P  A  I  S  V  I  I
        200

GCGAAGCTGGCTGATCCTGGCGCGACGAACCGCGCCGCTCCGGCGATTAGTGTGATTATT

541 ---------+---------+---------+---------+---------+---------+
        600

CGCTTCGACCGACTAGGACCGCGCTGCTTGGCGCGGCGAGGCCGCTAATCACACTAATAA

P  E  S  E  T  F  N  N  T  L  D  H  G  V  C  T  K  F  E  A   220

CCGGAGAGCGAGACGTTCAACAATACGCTGGACCACGGTGTGTGCACGAAGTTTGAGGCG

601 ---------+---------+---------+---------+---------+---------+
        660

GGCCTCTCGCTCTGCAAGTTGTTATGCGACCTGGTGCCACACACGTGCTTCAAACTCCGC

S  Q  L  G  D  E  V  A  A  N  F  T  A  L  F  A  P  D  I  R   240

AGTCAGCTGGGAGATGAGGTTGCGGCCAATTTCACTGCGCTCTTTGCACCCGACATCCGA

661 ---------+---------+---------+---------+---------+---------+
        720

TCAGTCGACCCTCTACTCCAACGCCGGTTAAAGTGACGCGAGAAACGTGGGCTGTAGGCT
```

GCTCGCctCGAGAAGCATCTTCCTGGCGTGACGCTGACAGACGAGGACGTTGTCAGTCTA
 5    721   ---------+---------+---------+---------+---------+---------+
      780

CGAGCGgaGCTCTTCGTAGAAGGACCGCACTGCGACTGTCTGCTCCTGCAACAGTCAGAT

M  D  M  C  P  F  D  T  V  A  R  T  S  D  A  S  Q  L  S  P   280

ATGGACATGTGTcCGTTTGATACGGTAGCGCGCACCAGCGACGCAAGTCAGCTGTCACCG
10    781   ---------+---------+---------+---------+---------+---------+
      840

TACCTGTACACAgGCAAACTATGCCATCGCGCGTGGTCGCTGCGTTCAGTCGACAGTGGC

F  C  Q  L  F  T  H  N  E  W  K  K  Y  D  Y  L  Q  S  L  G   300
15
            TTCTGTCAACTCTTCACTCACAATGAGTGGAAGAAGTACgACTACCTTCAGTCCTTGGGC
      841   ---------+---------+---------+---------+---------+---------+
      900

AAGACAGTTGAGAAGTGAGTGTTACTCACCTTCTTCATGcTGATGGAAGTCAGGAACCCG
20
            K  Y  Y  G  Y  G  A  G  N  P  L  G  P  A  Q  G  I  G  F  T   320

AAGTACTACGGCTACGGCGCAGGCAACCCTCTGGGACCGGCTCAGGGGATAGGGTTCACC
      901   ---------+---------+---------+---------+---------+---------+
      960

25          TTCATGATGCCGATGCCGCGTCCGTTGGGAGACCCTGGCCGAGTCCCCTATCCCAAGTGG
```

AACGAGCTGATTGCCCGGTTGACgCGTTCGCCAGTGCAGGACCACACCAGCACTAACTCG
     961   ---------+---------+---------+---------+---------+---------+
    1020
           TTGCTCGACTAACGGGCCAACTGcGCAAGCGGTCACGTCCTGGTGTGGTCGTGATTGAGC

T  L  V  S  N  P  A  T  F  P  L  N  A  T  M  Y  V  D  F  S    360

ACTCTAGTCTCCAACCCGGCCACCTTCCCGTTGAACGCTACCATGTACGTCGACTTTTCA
    1021   ---------+---------+---------+---------+---------+---------+
    1080
           TGAGATCAGAGGTTGGGCCGGTGGAAGGGCAACTTGCGATGGTACATGCAGCTGAAAAGT

H  D  N  S  M  V  S  I  F  F  A  L  G  L  Y  N  G  T  E  P
     380

CACGACAACAGCATGGTTTCCATCTTCTTTGCATTGGGCCTGTACAACGGCACTGAACCC
    1081   ---------+---------+---------+---------+---------+---------+
    1140
           GTGCTGTTGTCGTACCAAAGGTAGAAGAAACGTAACCCGGACATGTTGCCGTGACTTGGG

L  S  R  T  S  V  E  S  A  K  E  L  D  G  Y  S  A  S  W  V    400

TTGTCCCGGACCTCGGTGGAAAGCGCCAAGGAATTGGATGGGTATTCTGCATCCTGGGTG
    1141   ---------+---------+---------+---------+---------+---------+
    1200
           AACAGGGCCTGGAGCCACCTTTCGCGGTTCCTTAACCTACCCATAAGACGTAGGACCCAC
```

GTGCCTTTCGGCGCGCGAGCCTACTTCGAGACGATGCAATGCAAGTCGGAAAAGGAGCCT

1201    ---------+---------+---------+---------+---------+---------+
        1260

CACGGAAAGCCGCGCGCTCGGATGAAGCTCTGCTACGTTACGTTCAGCCTTTTCCTCGGA

L  V  R  A  L  I  N  D  R  V  V  P  L  H  G  C  D  V  D  K     440

CTTGTTCGCGCTTTGATTAATGACCGGGTTGTGCCACTGCATGGCTGCGATGTGGACAAG

1261    ---------+---------+---------+---------+---------+---------+
        1320

GAACAAGCGCGAAACTAATTACTGGCCCAACACGGTGACGTACCGACGCTACACCTGTTC

L  G  R  C  K  L  N  D  F  V  K  G  L  S  W  A  R  S  G  G     460

CTGGGGCGATGCAAGCTGAATGACTTTGTCAAGGGATTGAGTTGGGCCAGATCTGGGGGC

1321    ---------+---------+---------+---------+---------+---------+
        1380

GACCCCGCTACGTTCGACTTACTGAAACAGTTCCCTAACTCAACCCGGTCTAGACCCCCG

N  W  G  E  C  F  S  *     467

AACTGGGGAGAGTGCTTTAGTTGA

1381    ---------+---------+---- 1404

TTGACCCCTCTCACGAAATCAACT
```

FIG. 10F

```
                    CP-1
             EcoRI  M  G  V  F  V  V  L  L  S  I  A  T  L  F  G  S  T
         TATATGAATTCATGGGCGTGTTCGTCGTGCTACTGTCCATTGCCACCTTGTTCGGTTCCA
       1 ---------+---------+---------+---------+---------+---------+
                                                                   60
         ATATACTTAAGTACCCGCACAAGCAGCACGATGACAGGTAACGGTGGAACAAGCCAAGGT

S  G  T  A  L  G  P  R  G  N  S  H  S  C  D  T  V  D  G  G
         CATCCGGTACCGCCTTGGGTCCTCGTGGTAATTCTCACTCTTGTGACACTGTTGACGGTG
      61 ---------+---------+---------+---------+---------+---------+
                                                                  120
         GTAGGCCATGGCGGAACCCAGGAGCACCATTAAGAGTGAGAACACTGTGACAACTGCCAC
                  CP-2
                   CP-3
           Y  Q  C  F  P  E  I  S  H  L  W  G  Q  Y  S  P  Y  F  S  L
         GTTACCAATGTTTCCCAGAAATTTCTCACTTGTGGGGTCAATACTCTCCATACTTCTCTT
     121 ---------+---------+---------+---------+---------+---------+
                                                                  180
         CAATGGTTACAAAGGGTCTTTAAAGAGTGAACACCCCAGTTATGAGAGGTATGAAGAGAA

E  D  E  S  A  I  S  P  D  V  P  D  D  C  R  V  T  F  V  Q
         TGGAAGACGAATCTGCTATTTCTCCAGACGTTCCAGACGACTGTAGAGTTACTTTCGTTC
     181 ---------+---------+---------+---------+---------+---------+
                                                                  240
         ACCTTCTGCTTAGACGATAAAGAGGTCTGCAAGGTCTGCTGACATCTCAATGAAAGCAAG
                                      CP-4.7
                                      CP-5.7
           V  L  S  R  H  G  A  R  Y  P  T  D  S  K  G  K  K  Y  S  A
         AAGTTTTGTCTAGACACGGTGCTAGATACCCAACTgacTCTAAGgggtAAGaagTACTCTG
     241 ---------+---------+---------+---------+---------+---------+
                                                                  300
         TTCAAAACAGATCTGTGCCACGATCTATGGGTTGActgAGATTCccaTTCttcATGAGAC
```

FIG. 11A

```
              L   I   E   A   I   Q   K   N   A   T   A   F   K   G   K   Y   A   F   L   K
          CTTTGATTGAAGCTATTCAAAAGAACGCTACTGCTTTCAAGGGTAAGTACGCTTTCTTGA
      301 ---------+---------+---------+---------+---------+---------+ 360
          GAAACTAACTTCGATAAGTTTTCTTGCGATGACGAAAGTTCCCATTCATGCGAAAGAACT
                                        CP-6
                                        CP-7

T   Y   N   Y   T   L   G   A   D   D   L   T   P   F   G   E   N   Q   M   V
          AGACTTACAACTACACTTTGGGTGCTGACGACTTGACTCCATTCGGTGAAAACCAAATGG
      361 ---------+---------+---------+---------+---------+---------+ 420
          TCTGAATGTTGATGTGAAACCCACGACTGCTGAACTGAGGTAAGCCACTTTTGGTTTACC

N   S   G   I   K   F   Y   R   R   Y   K   A   L   A   R   K   I   V   P   F
          TTAACTCTGGTATTAAGTTCTACAGAAGATACAAGGCTTTGGCTAGAAAGATTGTTCCAT
      421 ---------+---------+---------+---------+---------+---------+ 480
          AATTGAGACCATAATTCAAGATGTCTTCTATGTTCCGAAACCGATCTTTCTAACAAGGTA
                                                   CP-8.7
                                                    CP-9

I   R   A   S   G   S   S   R   V   I   A   S   A   E   K   F   I   E   G   F
          TCATTAGAGCTTCTGGTTCTtctAGAGTTATTGCTTCTGCTGAAAAGTTCATTGAAGGTT
      481 ---------+---------+---------+---------+---------+---------+ 540
          AGTAATCTCGAAGACCAAGAagaTCTCAATAACGAAGACGACTTTTCAAGTAACTTCCAA Q   S   A   K   L   A   D   P   G   S   Q   P   H   Q   A   S   P   V   I   D
          TCCAATCTGCTAAGTTGGCTGACCCAGGTTCTCAACCACACCAAGCTTCTCCAGTTATTG
      541 ---------+---------+---------+---------+---------+---------+ 600
          AGGTTAGACGATTCAACCGACTGGGTCCAAGAGTTGGTGTGGTTCGAAGAGGTCAATAAC
                                                              CP-10.7
                                                               CP-11.7
              V   I   I   S   E   A   S   S   Y   N   N   T   L   D   P   G   T   C   T   A
```

FIG. 11B

```
           ACGTTATTATTtctGAcgctTCTtctTACAACAACACTTTGGACccaGGTACTTGTACTG
       601 ---------+---------+---------+---------+---------+---------+
660
           TGCAATAATAAagaCTgcgaAGGagaATGTTGTTGTGAAACCTGggtCCATGAACATGAC
```

FIG. 11C

```
              F  E  D  S  E  L  A  D  T  V  E  A  N  F  T  A  L  F  A  P
            CTTTCGAAGACTCTGAATTGgctGACactGTTGAAGCTAACTTCACTGCTTTGTTCGCTC
       661  ---------+---------+---------+---------+---------+---------+  720
            GAAAGCTTCTGAGACTTAACcgaCTGtgaCAACTTCGATTGAAGTGACGAAACAAGCGAG
                                                                 CP-12.7

A  I  R  A  R  L  E  A  D  L  P  G  V  T  L  T  D  T  E  V
            CAGCTATTAGAGCTAGATTGGAAGCTGACTTGCCAGGTGTTACTTTGACTGACactgaaG
       721  ---------+---------+---------+---------+---------+---------+  780
            GTCGATAATCTCGATCTAACCTTCGACTGAACGGTCCACAATGAAACTGACTGtgacttC CP-13.7
             T  Y  L  M  D  M  C  S  F  E  T  V  A  R  T  S  D  A  T  E
            TTactTACTTGATGGACATGTGTtctTTCGAAACTGTTGCTAGAACTTCTGACGCTACTG
       781  ---------+---------+---------+---------+---------+---------+  840
            AAtgaATGAACTACCTGTACACAagaAAGCTTTGACAACGATCTTGAAGACTGCGATGAC L  S  P  F  C  A  L  F  T  H  D  E  W  R  H  Y  D  Y  L  Q
            AATTGTCTCCATTCTGTGCTTTGTTCACTCACGACGAATGGAGAcacTACGACTACTTGC
       841  ---------+---------+---------+---------+---------+---------+  900
            TTAACAGAGGTAAGACACGAAACAAGTGAGTGCTGCTTACCTCTgtgATGCTGATGAACG CP-14.7
                        CP-15.7
             S  L  K  K  Y  Y  G  H  G  A  G  N  P  L  G  P  T  Q  G  V
            AATCTTTGaagAAGTACTACGGTcacGGTGCTGGTAACCCATTGGGTCCAactCAAGGTG
       901  ---------+---------+---------+---------+---------+---------+  960
            TTAGAAACttcTTCATGATGCCAgtgCCACGACCATTGGGTAACCCAGGTtgaGTTCCAC G  F  A  N  E  L  I  A  R  L  T  R  S  P  V  Q  D  H  T  S
            TTGGTTTCGCTAACGAATTGATTGCTAGATTGACTAGATCTCCAGTTCAAGACCACACTT
```

FIG. 11D

```
                    961 ---------+---------+---------+---------+---------+---------+
                         AACCAAAGCGATTGCTTAACTAACGATCTAACTGATCTAGAGGTCAAGTTCTGGTGTGAA
                                              CP-16
                                              CP-17.7
                           T  N  H  T  L  D  S  N  P  A  T  F  P  L  N  A  T  L  Y  A
                         CTACTAACCACACTTTGGACTCTAACCCAGCTACTTTCCCATTGAACGCTACTTTGTACG
                    1021 ---------+---------+---------+---------+---------+---------+
                         GATGATTGGTGTGAAACCTGAGATTGGGTCGATGAAAGGGTAACTTGCGATGAAACATGC

D  F  S  H  D  N  G  I  I  S  I  F  F  A  L  G  L  Y  N  G
                         CTGACTTCTCTCACGACAACggtattATTTCTATTTTCTTCGCTTTGGGTTTGTACAACG
                    1081 ---------+---------+---------+---------+---------+---------+
                         GACTGAAGAGAGTGCTGTTGccataaTAAAGATAAAAGAAGCGAAACCCAAACATGTTGC
                                                 CP-18.7
                                                 CP-19.7
                           T  A  P  L  S  T  T  S  V  E  S  I  E  E  T  D  G  Y  S  S
                         GTACTGCTCCATTGTCTACTACTTCTGTTGAATCTATTGAAGAAACTGACGGTTACTCTt
                    1141 ---------+---------+---------+---------+---------+---------+
                         CATGACGAGGTAACAGATGATGAAGACAACTTAGATAACTTCTTTGACTGCCAATGAGAa A  W  T  V  P  F  A  S  R  A  Y  V  E  M  M  Q  C  Q  A  E
                         ctgctTGGACTGTTCCATTCgcttctAGAGCTTACGTTGAAATGATGCAATGTCAAGCTG
                    1201 ---------+---------+---------+---------+---------+---------+ 1260
                         gacgaACCTGACAAGGTAAGcgaagaTCTCGAATGCAACTTTACTACGTTACAGTTCGAC
                                                                            CP-20
                                                                            CP-21
                           K  E  P  L  V  R  V  L  V  N  D  R  V  V  P  L  H  G  C  A
                         AAAAGGAACCATTGGTTAGAGTTTTGGTTAACGACAGAGTTGTTCCATTGCACGGTTGTG
                    1261 ---------+---------+---------+---------+---------+---------+
                         TTTTCCTTGGTAACCAATCTCAAAACCAATTGCTGTCTCAACAAGGTAACGTGCCAACAC
```

FIG. 11E

```
              V  D  K  L  G  R  C  K  R  D  D  F  V  E  G  L  S  F  A  R
           CTGTTGACAAGTTGGGTAGATGTAAGAGAGACGACTTCGTTGAAGGTTTGTCTTTCGCTA
     1321 ---------+---------+---------+---------+---------+---------+
1380
           GACAACTGTTCAACCCATCTACATTCTCTCTGCTGAAGCAACTTCCAAACAGAAAGCGAT
                                                             CP-22
            S  G  G  N  W  A  E  C  F  A  *  Eco RI
           GATCTGGTGGTAACTGGGCTGAATGTTTCGCTTAAGAATTCATATA
     1381 ---------+---------+---------+---------+------ 1426
           CTAGACCACCATTGACCCGACTTACAAAGCGAATTCTTAAGTATAT
```

FIG. 11F

```
  1  MGVFVVLLSI ATLFGSTSGT ALGPRGNSHS CDTVDGGYQC FPEISSNWSP
 51  YSPYFSLADE SAISPDVPKG CRVTFVQVLQ RHGARFPTSG AATRISALIE
101  AIQKNATAFK GKYAFLKTYN YTLGADDLVP FGANQSSQAG IKFYRRYKAL
151  ARKIVPFIRA SGSDRVIDSA TNWIEGFQSA KLADPGANPH QASPVINVII
201  PEGAGYNNTL DHGLCTAFEE SELGDDVEAN FTAVFAPPIR ARLEAHLPGV
251  NLTDEDVVNL MDMCPFDTVA RTSDATELSP FCDLFTHDEW IQYDYLGDLD
301  KYYGTGAGNP LGPAQGVGFV NELIARLTHS PVQDHTSTNH TLDSNPATFP
351  LNATLYADFS HDNTMVAIFF ALGLYNGTKP LSTTSVESIE ETDGYSASWL
401  VPFSARMYVE MMQCEAEKEP LVRVLVNDRV VPLHGCGVDK LGRCKRDDFV
451  EGLSFARSGG NWEECFA
```

FIG. 22 form agents, a circuit 12 for monitoring gas supply and taking samples including an outlet tube from the fermentor, which circuit is operably connected to the outlet to be pump 13, and gas inlet and outlet flow control devices 14 and 15 operably connected to the gas inlet and outlet tubes 9, 10.

CONTINUOUS FERMENTATION SYSTEM

FIELD OF THE INVENTION

The present invention relates to a continuous process for the manufacture of proteins. In particular, the invention relates to fermentation assemblies and processes for manufacturing proteins.

SUMMARY OF THE INVENTION

In accordance with the present invention it has been found that splitting of cultivation media used in a continuous fermentation process allows one to study the influence on growth and metabolite-production of microorganisms, and thus to determine optimal conditions for the fermentation process. A continuously delivered fermentation medium can generally be split into as many fractions as it contains ingredients. Examples of such ingredients are carbon, nitrogen, phosphorus, and sulfur sources as well as vitamins and complex substrates such as corn steep, yeast extract, and other natural products. Furthermore, every required mineral, micro- or trace element can be provided separately as a solution of a water-soluble salt, such as a chloride, sulfate or nitrate. In this manner, a fermentation medium of any desired composition can be obtained, provided that the desired amounts of the ingredients are (water)-soluble and no disturbing interactions (e.g., precipitation, reaction) occur in the individual feed solutions or in the fermentation medium.

One embodiment of the invention is a fermentation assembly containing a vessel for culturing living cells, at least two storage flasks in fluid communication with the vessel for supply of liquids and a first transport means for transferring the liquids from the storage flasks to the vessel, individual appliances operably connected to the transport means for monitoring the supply of the contents of the storage flasks to the vessel, a harvest flask in fluid communication with the vessel and a second transport means for transferring the fermentation broth from the vessel to the harvest flask, and a device operably connected to the first transport means for controlling and maintaining a constant dilution rate in the vessel with varying rates of individual supply of liquid from the storage flasks to the vessel.

Another embodiment of the invention is a process for the manufacture of a protein. This process includes providing a continuous culture of living cells in a fermentation reactor; and individually feeding nutrients and other agents required for the growth of the cells into the reactor at a constant dilution rate to achieve optimal production of the protein.

A further embodiment of the invention is a fermentation assembly. This fermentation assembly includes a fermentor 1 equipped with inlet tubes 2a in fluid communication with a storage flask 2 for supply of liquids to the fermentor, a pump 3 operably connected to the inlet tubes for transporting liquids from the storage flask 2 to the fermentor 1, a scale 4 in contact with each storage flask for monitoring the amount of liquid supplied to and discharged from the fermentor, a gas inlet 9 and outlet tubes 10 in communication with the fermentor for introducing and removing gas therefrom, a pump 6 operably connected to an outlet tube 5a which is in fluid connection with the fermentor, wherein the pump discharges fermentation broth from the fermentor to a harvest flask 5, a main controlling unit 7 operably connected to the fermentation assembly for overall process monitoring and steering, a controlling unit 11 operably connected to individual control systems 17 for monitoring and steering temperature, pH, gas pressure, fermentor content, and anti-foam agents, a circuit 12 for monitoring gas supply and taking samples including an outlet tube from the fermentor, which circuit is operably connected to the outlet to be pump 13, and gas inlet and outlet flow control devices 14 and 15 operably connected to the gas inlet and outlet tubes 9, 10.

BRIEF DESCRIPTION OF DRAWINGS

FIGS. 2A–2F depicts the design of a consensus phytase amino acid sequence. (SEQ ID NOs.: 101 through 115)

FIGS. 3A–3G depicts the nucleotide sequence of the consensus phytase-1 gene (fcp) and of the primers used to construct it. (SEQ. ID NOs.: 116 and 117)

FIGS. 4A–4F depicts the alignment and consensus sequences of five Basidiomycetes phytases. (SEQ. ID. NOs.: 118 through 123)

FIGS. 5A–5N depicts the design of the consensus phytase-10 amino acid sequence. (SEQ. ID. NOs.: 124 through 139)

FIGS. 6A–6G depicts the nucleotide and amino acid sequences of consensus phytase-10. (SEQ. ID NOs.: 140 and 141)

FIGS. 7A–7Q depicts the amino acid alignment for the design of consensus phytase-11. (SEQ. ID. NOs.: 142 through 160)

FIGS. 8A–8F depicts the nucleotide and amino acid sequence of phytase-1 thermo-[8]-Q50T-K91A. (SEQ. ID NOs.: 161 and 162)

FIGS. 9A–9F depicts the nucleotide and amino acid sequence of consensus phytase-10-thermo[3]-Q50T-K91A. (SEQ. ID NOs.: 163 and 164)

FIGS. 10A–10F depicts the nucleotide and amino acid sequence of *A. fumigatus* ATCC 13073 phytase α-mutant. (SEQ. ID. NOs: 165 and 166)

FIGS. 11A–11F depicts the nucleotide and amino acid sequence of consensus phytase-7. (SEQ. ID. NOs.: 167 and 168)

FIG. 22 depicts the amino acid sequence of consensus phytase-12 (consphy 12) (SEQ ID. NO.: 169)

DETAILED DESCRIPTION OF THE INVENTION

Figure 1:
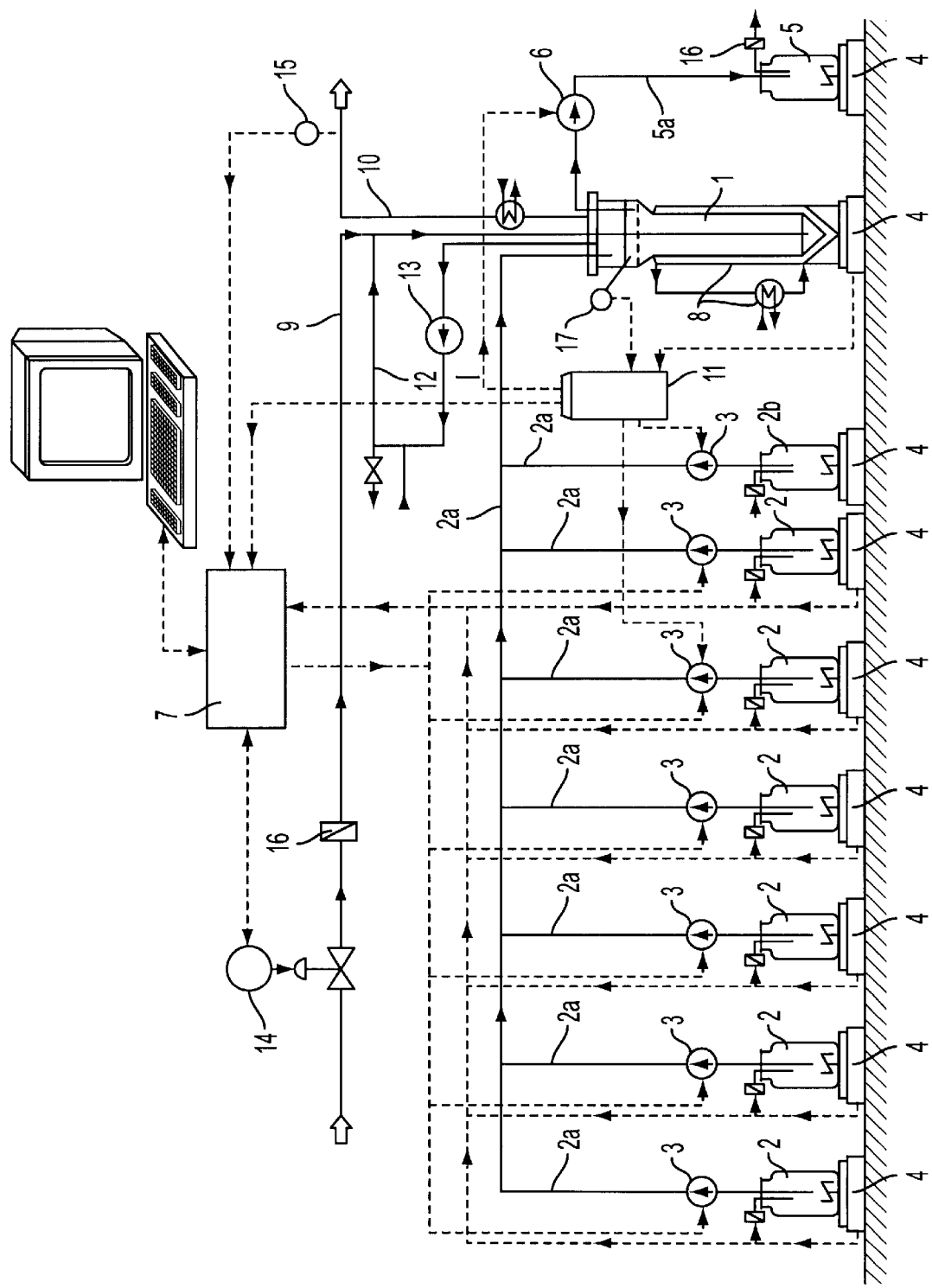
FIG. 1 is a diagram depicting a fermentation assembly according to the present invention.

In one aspect, the present invention is a continuous process for the manufacture of proteins by means of a protein-producing microorganism.

More particularly, the invention is a continuous process for the manufacture of a protein using a protein-producing microorganism that may be immobilized on a solid carrier and/or the nutrients and other agents required for growth of the microorganism and optimal production of protein therefrom are fed into a reactor individually at a constant dilution rate.

In a preferred aspect, the invention is a process for the manufacture of a protein using a fermentation assembly that includes (a) a vessel suitable for carrying out reactions with living or inactivated cells; (b) at least two storage flasks connected to the vessel for supply of liquids and means to transport the liquids from the storage flasks to the vessel; (c) individual appliances monitoring the supply of the contents of the storage flasks to the vessel; (d) a harvest flask connected to the vessel and means to transport fermentation broth from the vessel to the harvest flask; and (e) a device for controlling and maintaining a constant dilution rate in the vessel with varying rates of supply of individual liquids from the storage flasks to the vessel.

Any conventional fermentation vessel can be used as the vessel in step (a) above for the purpose of this invention. The vessel may be made of materials such as stainless steel, glass or ceramics, and may have a volume of from e.g., 100 ml to 2500 m$^3$ although these figures are not critical to the invention. For continuous operation, the inside of the vessel is optionally equipped with a receptacle or sieve plate for uptake of immobilized living cells. These cells may be present in the vessel as a bed of immobilized cells, such as one selected from the group consisting of a fixed bed, an expanded bed, a moving bed, and combinations thereof.

Further, the fermentation vessel is connected to a series of storage flasks that contain nutrient solutions and solutions for maintaining and controlling a desired pH and other parameters, such as foam formation, redox potential, etc., in the fermentation broth. Depending on the particular needs of the fermentation, there may be separate storage flasks for individual supply of substrates to the vessel, which substrates serve as the carbon, nitrogen or mineral source for the living cells in the vessel. In a particular embodiment, at least one of the at least two storage flasks contains a controlling agent. Said controlling agent has the purpose of regulating the pH of the contents of the flask containing it, and may be an acid, e.g., hydrochloric acid, or a base, e.g., sodium hydroxide.

The present process is advantageously carried out at a constant dilution rate in the fermentation vessel. As used herein, the term "dilution rate" means the total volume of liquids supplied to the fermentation vessel per volume of the fermentation vessel per hour ($h^{-1}$).

Accordingly, it is a particular feature of the present invention to carry out the fermentation process at a constant dilution rate in the fermentation vessel while varying the supply of individual nutrient components or other additives during the fermentation process. To facilitate this task, a storage flask containing an inert component, e.g., water is optionally provided in the fermentation vessel to complement the supply of liquids added to the fermentation vessel, thus keeping the total supply of liquid constant in the fermentation vessel.

The assembly that is preferably used to carry out the process of this invention further includes means to transport the individual components of the fermentation medium from the storage flasks to the fermentation vessel, and appliances for monitoring the amount of liquid supplied to the fermentation vessel. Every combination of measuring instruments (e.g., volumetric or mass flow rate by either gravimetric, anemometric, magnetic, ultrasonic, Venturi, J, cross-relation, thermal, Coriolis, or radiometric) and transfer units (e.g., pumps or pressure difference) can be used for this purpose. Additionally, every transfer unit can be applied as a dosing unit (e.g., gear, peristaltic, piston, membrane or excenter pump). For operation on a small scale, the supply is suitably monitored by weighing the storage flasks that contain nutrient or additive solutions in a predetermined concentration.

As used herein, the "means to transport" individual components of the fermentation medium from the storage flasks to the fermentation vessel includes tubing, piping, and other types of conventional liquid transfer apparatus.

The device for controlling and maintaining a constant dilution rate in the fermentation vessel is suitably a system containing a measuring instrument that monitors the flow from the storage flasks and a controlling unit, e.g., a computer-software control that calculates the actual mass flow rates, compares them to the desired value, and adjusts the pump setting accordingly. An appropriate system is, e.g., the Process Automation System, National Instruments, Bridge View, USA, for Windows NT 4.0 (represented by National Instruments, Sonnenbergstrasse 53, 5408 Ennetbaden, Switzerland) that is connected to the various operating units (scales, pumps) through a serial-interface box (Rocket Port, Comtrol Europe Ltd, Great Britain, represented by Technosoftware AG Rothackerstrasse 13, 5702 Niederlenz, Switzerland).

An assembly that can be used in the process of this invention is depicted in FIG. 1. As FIG. 1 shows, the fermentation vessel 1 (Fermentor) is equipped with inlet tubes 2a from storage flasks 2 (e.g., suitably equipped with a stirrer) for supply of salt solution (Salts), nutrient solution (Nutrients), particular substrates (e.g., Substrate 1 and Substrate 2) for supply of, e.g., distinct carbon sources, agents for controlling the pH (Base), water for controlling a constant dilution rate, and antifoam agents. Pumps 3 transport liquids from the storage flasks 2 to the fermentor 1. Scales 4 monitor the amount of liquids supplied to and discharged from the fermentor. Further, the fermentor has inlet tubes 9 for oxygen supply and outlet tubes 10 for exhaust controlled by units 14 and 15, respectively. Pump 6 discharges fermentation broth via outlet tubes 5a to a harvest flask 5. A main controlling unit 7 monitors and steers the overall process. Controlling unit 11 monitors and steers individual control systems 17 for temperature, pH, gas pressure, fermentor content, and supply of antifoam agents. Circuit 12 including pump 13 is used for taking samples from the fermentation broth and for providing a controlled gas flow for moving the fermentation broth. Inlet and outlet gas flow is controlled by flow control 14 and 15. Sterile filters 16 are provided optionally. Optionally, the fermentation vessel 1 is equipped with a thermostating unit 8.

In the process of the present invention, any protein-producing microorganism either of natural origin, e.g. naturally occurring fungal or bacterial microorganisms or microorganisms which have been transformed by protein encoding DNA whereby such transformed microorganisms can be bacteria, fungi or yeast, preferably from the genus Peniophora, Aspergillus, Hansenula or Pichia, especially *Aspergillus niger, Aspergillus awanari, Aspergillus sojae, Aspergillus oryzae, Hansenula polymorpha* or *Pichia pastoris*.

In this context, the skilled person in the art selects such a protein-producing microorganism which is known to be useful for the production of a desired protein.

In a preferred embodiment of the present invention the protein has the activity of an enzyme such as catalase, lactase, phenoloxidase, oxidase, oxidoreductase, glucanase cellulase, xylanase and other polysaccharides, peroxidase, lipase, hydrolase, esterase, cutinase, protease and other proteolytic enzymes, aminopeptidase, carboxypeptidase, phytase, lyase, pectinase and other pectinolytic enzymes, amylase, glucosidase, mannosidase, isomerase, invertase, transferase, ribonuclease, chitinase, and desoxyribonuclease. In another preferred embodiment of the present invention, the protein is a therapeutic protein such as an antibody, a vaccine, an antigen, or an antibacterial and/or a health-beneficial protein such as lactoternin, lactoperoxidase or lysozyme.

It will be understood by those skilled in the art that the term "activity" includes not only native activities referring to naturally occurring enzymes or therapeutic functions, but also those activities or functions which have been modified by amino acid substitutions, deletions, additions, or other modifications which may be made to enhance or modify the desired activity, the thermostability, pH tolerance, and/or further properties.

In a most preferred embodiment of the invention, the selected protein is a protein having the activity of a phytase. Examples of proteins having the activity of a phytase are described in EP 684 313, EP 897 010, EP 897 985 or in Examples 6 to 16 and FIGS. 2A–22 of the present invention.

FIGS. 2A–2F: Design of the consensus phytase sequence. The letters represent the amino acid residues in the one-letter code. The following sequences were used for the alignment: phyA from *Aspergillus terreus* 9A-1 (Mitchell et al, 1997; from amino acid (aa) 27), phyA from *A. terreus* cbs116.46; (van Loon et al., 1998; from aa 27), phyA from *Aspergillus niger* var. awamori (Piddington et al, 1993; from aa 27), phyA from *A. niger* T213; Mitchell et al. 1997 from aa 27), phyA from *A. niger* strain NRRL3135 (van Hartingsveldt et al, 1993; from aa 27), phyA from *Aspergillus fumigatus* ATCC 13073 (Pasamontes et al, 1997; from aa 25), phyA from *A. fumigatus* ATCC 32722 (EP 897 985; FIG. 1; from aa 27), phyA from *A. fumigatus* ATCC 58128 (EP 897 985; FIG. 1; from aa 27), phyA from *A. fumigatus* ATCC 26906 (EP 897 985; FIG. 1; from aa 27), phyA from *A. fumigatus* ATCC 32239 (EP 897 985; FIG. 1; from aa 30), phyA from *Emericella nidulans* (Pasamontes et al, 1997a; from aa 25), phyA from *Talaromyces thermophilus* (Pasamontes et al, 1997a; from aa 24), and phyA from *Myceliophthora thermophila* (Mitchell et al, 1997; from aa 19). As used herein, the phrase "from aaX" means that the sequence used to generate a consensus sequence began at amino acid number X counting from the start codon. The alignment was calculated using the program PILEUP (program menu for the Wisconsin Package, version 8, September 1994, Genetics Computer Group, 575 Science Drive, Madison, Wis., USA 53711; see also Devereux et al., 1984). The location of the gaps was refined by hand. Capitalized amino acid residues in the alignment at a given position belong to the amino acid coalition that establish the consensus residue. In bold, beneath the calculated consensus sequence, the amino acid sequence of the finally constructed consensus phytase (Fcp) is shown. The gaps in the calculated consensus sequence were filled by hand according to principals stated in Example 6.

FIGS. 3A–3G: DNA sequence of the consensus phytase-1 gene (fcp) and of the primers used for the gene construction. The calculated amino acid sequence (FIGS. 2A–2F) was converted into a DNA sequence using the program BACK-TRANSLATE (Devereux et al., 1984) and the codon frequency table of highly expressed yeast genes (GCG program package, 9.0). The signal peptide of the phytase from *A. terreus* cbs. 116.46 was fused to the N-terminus. The bold bases represent the sequences of the oligonucleotides used to generate the gene. The names of the respective oligonucleotides are alternately noted above or below the sequence. The underlined bases represent the start and stop codon of the gene. The bases written in italics show the two introduced Eco RI sites.

FIGS. 4A–4F: Alignment and consensus sequence of five Basidiomycetes phytases. The letters represent the amino acid residues in the one-letter code. The amino acid sequences of the phytases from *Paxillus involutus*, phyA1 (from aa 21) and phyA2 (from aa 21, WO 98/28409), *Trametes pubecens* (from aa 24, WO 98/28409), *Agrocybe pediades* (from aa 19, WO 98/28409), and *Peniophora lycii* (from aa 21, WO 98/28409) starting with the amino acid residues mentioned in parentheses, were used for the alignment and the calculation of the corresponding consensus sequence called "Basidio" (Example 7). The alignment was performed by the program PILEUP. The location of the gaps was refined by hand. The consensus sequence was calculated by the program PRETTY from the Sequence Analysis Package Release 9.0 (Devereux et al., 1984). PRETTY prints sequences with their columns alligned and can display a consensus sequence for the alignment. While a vote weight of 0.5 was assigned to the two *P. involutus* phytases, all other genes were used with a vote weight of 1.0 for the consensus sequence calculation. At positions where the program was not able to determine a consensus residue, the Basidio sequence contains a dash. Capitalized amino acid residues in the alignment at a given position belong to the amino acid coalition that establish the consensus residue.

FIGS. 5A–5N: Design of consensus phytase-10 amino acid sequence. Adding the phytase sequence of *Thermomyces lanuginosus* (Berka et al. 1998) and the consensus sequence of the phytases from five Basidiomycetes (FIGS. 4A–4F) to the alignment of FIGS. 2A–2F, an improved consensus sequence was calculated by the program PRETTY. Additionally, the amino acid sequence of *A. niger* T213 was omitted; therefore, a vote weight of 0.5 was used for the remaining *A. niger* phytase sequences. For further information see Example 8.

FIGS. 6A–6G: DNA and amino acid sequence of consensus phytase-10. The amino acid sequence is written above the corresponding DNA sequences using the one-letter code. The sequence of the oligonucleotides which were used to assemble the gene are in bold letters. The labels of oligonucleotides and the amino acids which were changed compared to those for consensus phytase-1 are underlined. The fcp10 gene was assembled from the following oligonucleotides: CP-1, CP-2, CP-3.10, CP-4.10, CP-5.10, CP-6, CP-7.10, CP-8.10, CP-9.10, CP-10.10, CP-11.1,0, CP-12.10, CP-13.10, CP-14.10, CP-15.10, CP-16.10, CP-17.10, CP18.10, CP-19.10, CP-20.10, CP-21.10, and CP-22.10. The newly synthesized oligonucleotides are additionally marked by the number 10. The phytase contains the following 32 exchanges relative to consensus phytase-1: Y54F, E58A, D69K, D70G, A94K, N134Q, I158V, S187A, Q188N, D197N, S204A, T214L, D220E, L234V, A238P, D246H, T251N, Y259N, E267D, E277Q, A283D, R291I, A320V, R329H, S364T, I366V, A379K, S396A, G404A, Q415E, A437G, A463E. The mutations accentuated in bold letters revealed a stabilizing effect on consensus phytase-1 when tested as single mutations in consensus phytase-1.

FIGS. 7A–7Q: Alignment for the design of consensus phytase-11. In contrast to the design of consensus phytase-10, for the design of the amino acid sequence of consensus phytase-11, all Basidiomycete phytases (FIGS. 4A–4F) were used as independent sequences using an assigned vote weight of 0.2 for each Basidiomycete sequence. Additionally, the amino acid sequence of A. niger T213 phytase was used in that alignment, again.

FIGS. 8A–8F: DNA and amino acid sequence of consensus phytase-1-thermo[8]-Q50T-K91A. The amino acid sequence is written above the corresponding DNA sequence using the one-letter code. The replaced amino acid residues are underlined. The stop codon of the gene is marked by a star (*)

FIGS. 9A–9F: DNA and amino acid sequence of consensus phytase-10-thermo[3]-Q50T-K91A. The amino acid sequence is written above the corresponding DNA sequence using the one-letter code. The replaced amino acid residues are underlined. The stop codon of the gene is marked by a star (*).

FIGS. 10A–10F: DNA and amino acid sequence of A. fumigatus ATCC 13073 phytase α-mutant. The amino acid sequence is written above the corresponding DNA sequence using the one-letter code. The replaced amino acid residues are underlined. The stop codon of the gene is marked by a star (*).

FIGS. 11A–11F: DNA and amino acid sequence of consensus phytase-7. The amino acids are written above the corresponding DNA sequence using the one-letter code. The sequences of the oligonucleotides used to assemble the gene are in bold letters. Oligonucleotides and amino acids that were exchanged are underlined and their corresponding triplets are highlighted in small cases. The fcp7 gene was assembled from the following oligonucleotides: CP-1, CP-2, CP-3, CP-4.7, CP-5.7, CP-6, CP-7, CP-8.7, CP-9, CP-10.7, CP-11.7, CP-12.7, CP-13.7, CP-14.7, CP-15.7, CP-16, CP-17.7, CP-18.7, CP-19.7, CP-20, CP-21, and CP-22. The newly synthesized oligonucleotides are additionally marked by number 7. The phytase contains the following 24 exchanges in comparison to the original consensus phytase-1: S89D, S92G, A94K, D164S, P201S, G203A, G205S, H212P, G224A, D226T, E255T, D256E, V258T, P265S, Q292H, G300K, Y305H, A314T, S364G, M365I, A397S, S398A, G404A, and A405S.

Figure 12A:
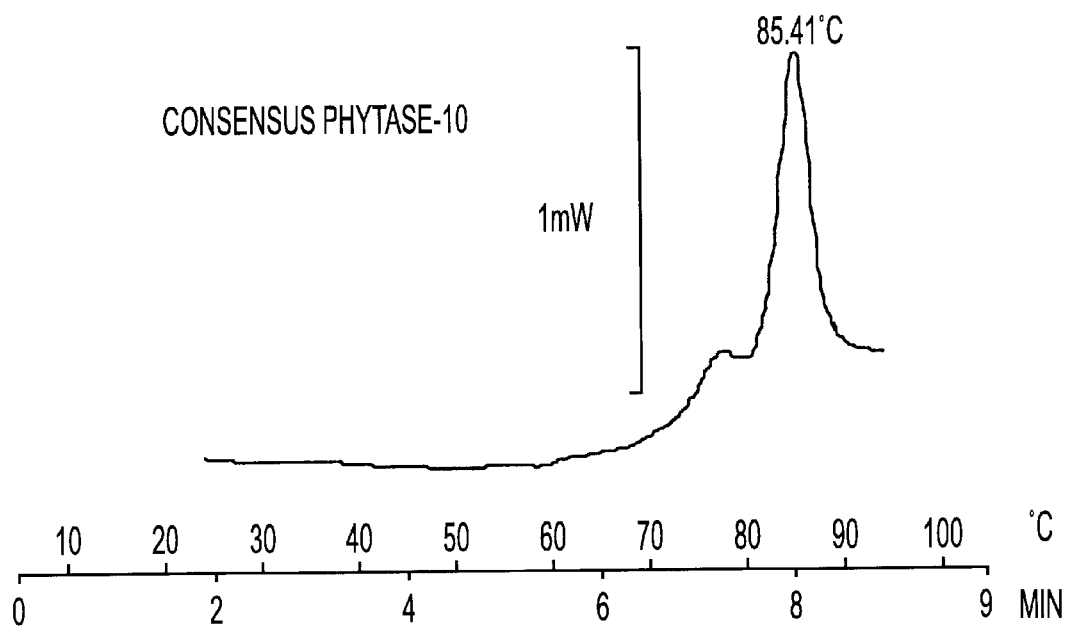
FIGS. 12A–12B depicts a differential scanning calorimetry (DSC) of consensus phytase-10 (12A) and consensus phytase-1 (12B).
Figure 12B:
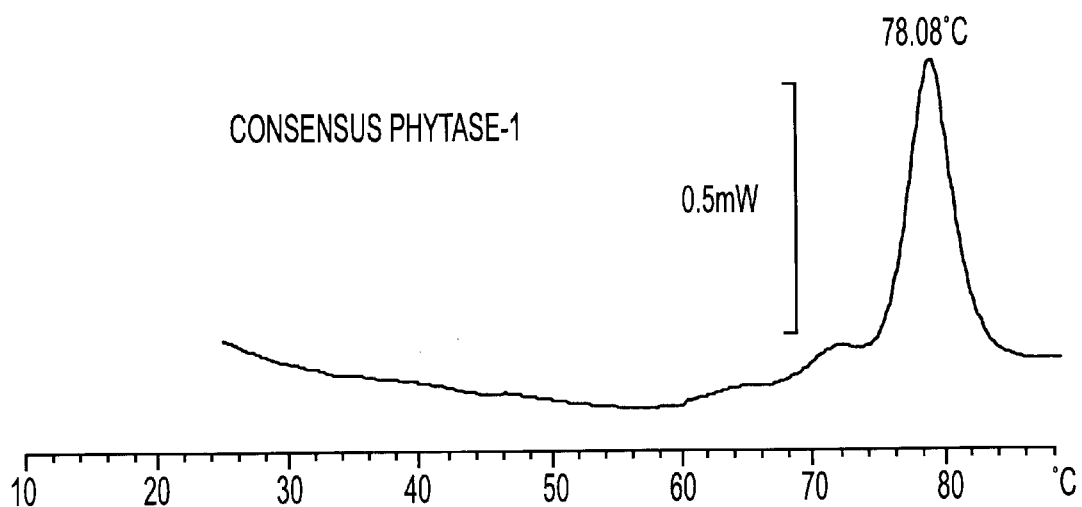

FIGS. 12A–12B: Differential scanning calorimetry (DSC) of consensus phytase-1 and consensus phytase-10. The protein samples were concentrated to about 50–60 mg/ml and extensively dialyzed against 10 mM sodium acetate, pH 5.0. A constant heating rate of 10° C./min was applied up to 95° C. DSC of consensus phytase-10 (12A) yielded a melting temperature of 85.4° C., which is 7.3° C. higher than the melting point of consensus phytase-1 (78.1° C., 12B).

Figure 13A:
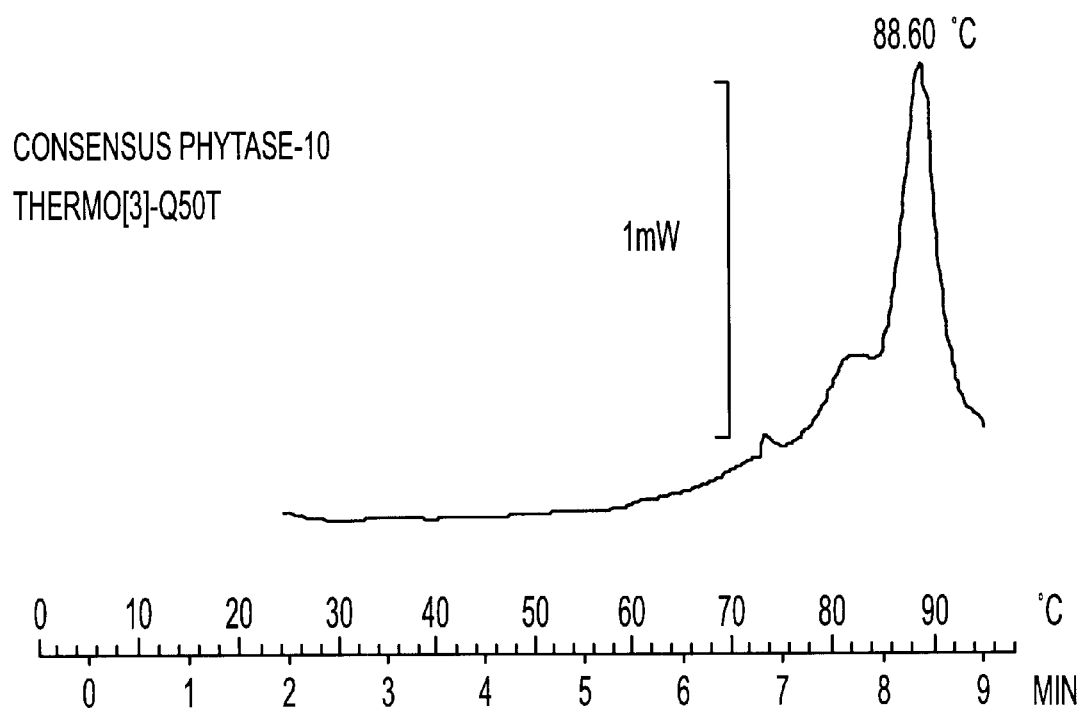
FIGS. 13A–13B depicts DSC of consensus phytase-10-thermo[3]-Q50T (13A) and consensus phytase-10-thermo-[3]-Q50T-K91A (13B).
Figure 13B:
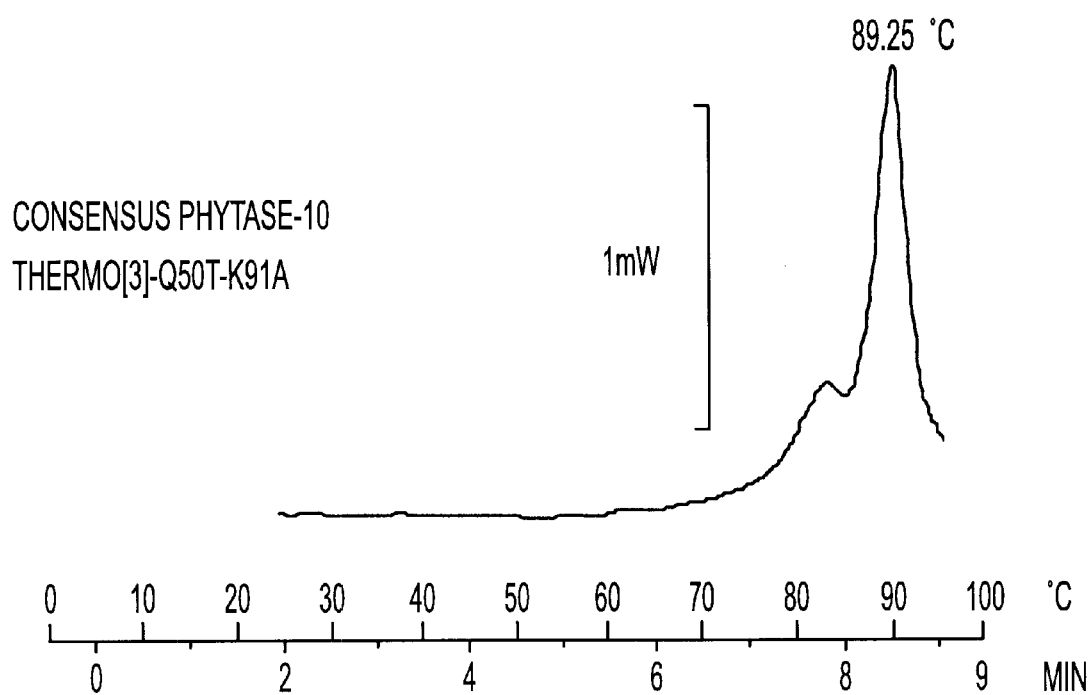

FIGS. 13A–13B: Differential scanning calorimetry (DSC) of consensus phytase-10-thermo[3]-Q50T and consensus phytase-10-thermo[3]-Q50T-K91A. The protein samples were concentrated to about 50–60 mg/ml and extensively dialyzed against 10 mM sodium acetate, pH 5.0. A constant heating rate of 10° C./min was applied up to 95° C. DSC of consensus phytase-10-thermo-[3]-Q50T (13A) yielded a melting temperature of 88.6° C., while the melting point of consensus phytase-10-thermo[3]-Q50T-K91A was found at 89.25° C. (13B).

Figure 14:
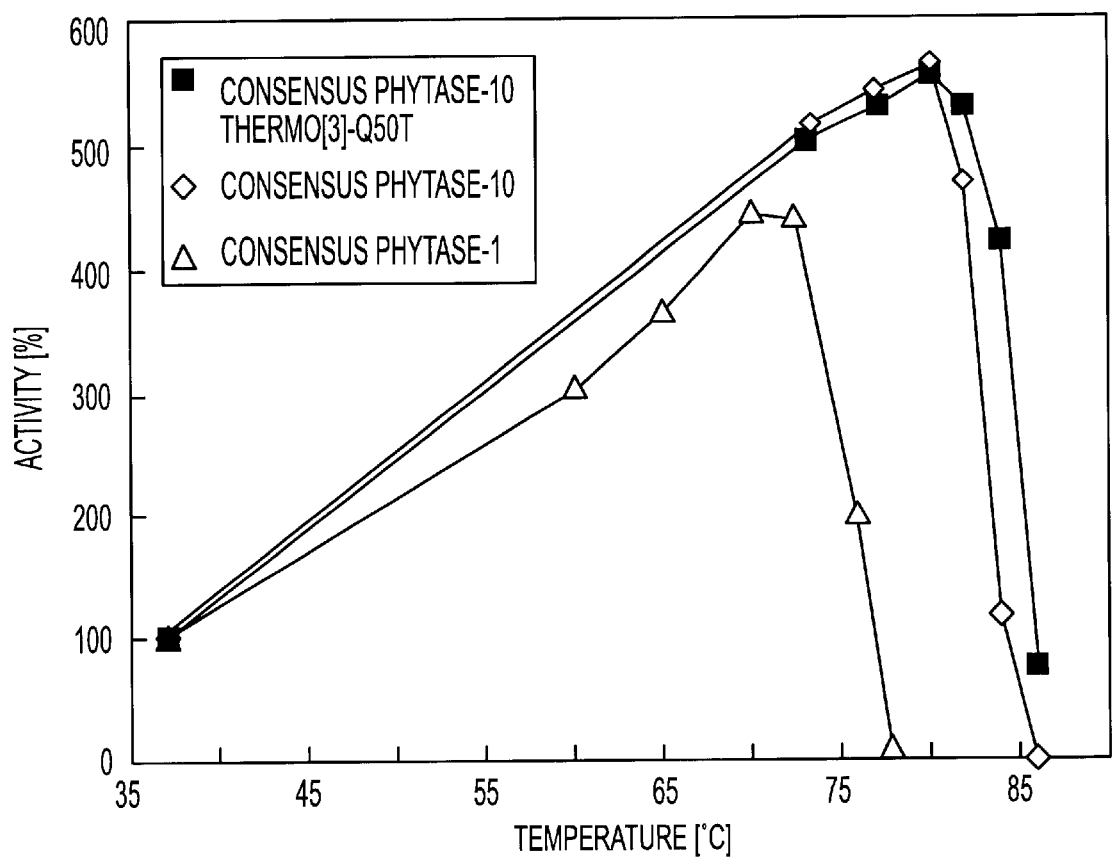
FIG. 14 is a graph comparing the temperature optima between consensus phytase-1, consensus phytase-10, and consensus phytase-10-thermo[3]-Q50T.

FIG. 14: Comparison of the temperature optimum between consensus phytase-1, consensus phytase-10 and consensus phytase-10-thermo[3]-Q50T. For the determination of the temperature optimum, the phytase standard assay was performed at a series of temperatures between 37° C. and 86° C. (see Mitchell et al., 1997, Lehmann et al., 2000 and further references mentioned therein). The diluted supernatant of transformed S. cerevisiae strains was used for the determination. The other components of the supernatant showed no influence on the determination of the temperature optimum: Δ, consensus phytase-1; ◇, consensus phytase-10; ■, consensus phytase 10-thermo[3]-Q50T.

Figure 15A:
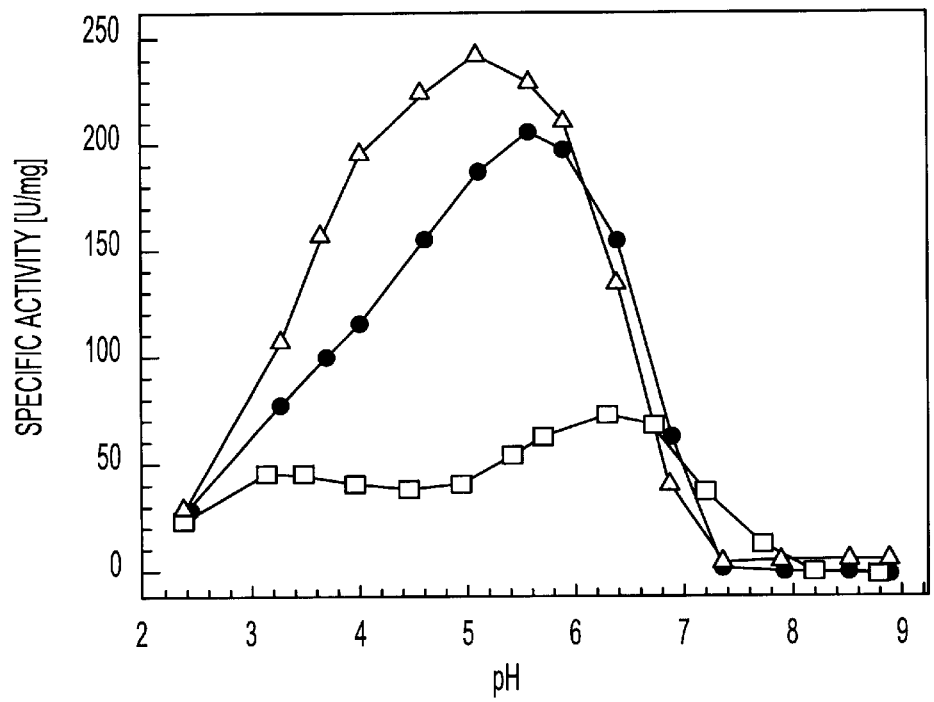
FIGS. 15A–15B is a graph depicting the pH-dependent activity profile (15A) and substrate specificity (15B) of consensus phytase 10, consensus phytase-10-thermo[3]-Q50T, and consensus phytase-10-thermo[3]-Q50T-K91A.
Figure 15B:
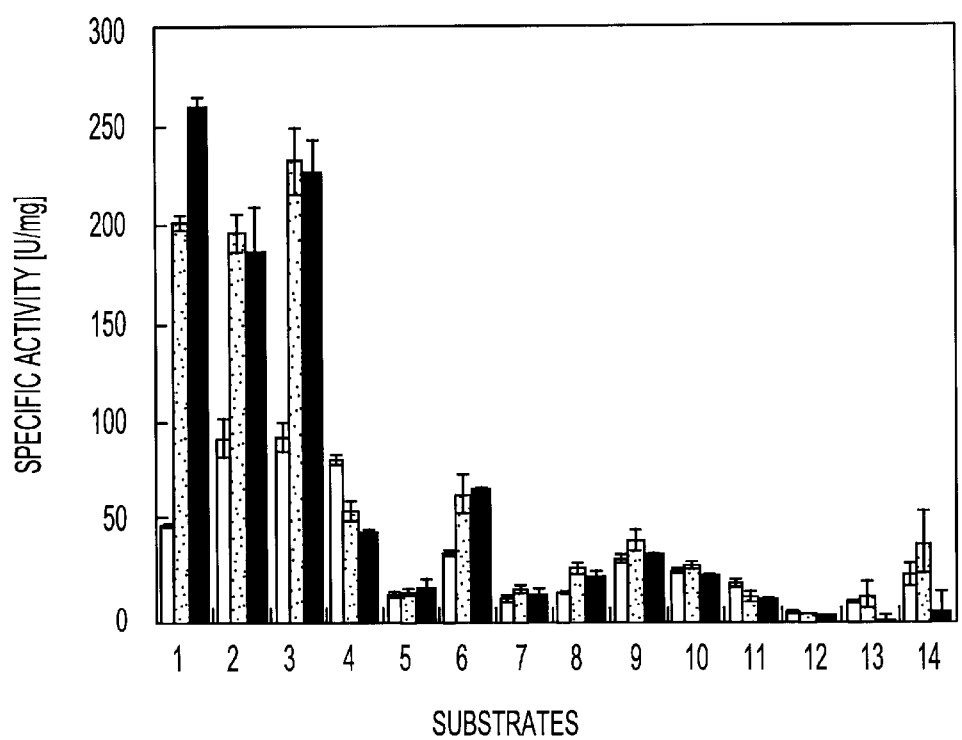

FIGS. 15A–15B: pH-dependent activity profile and substrate specificity of consensus phytase-10 and its variants thermo[3]-Q50T and thermo[3]-Q50T-K91A. FIG. 15A) shows the pH-dependent activity profile of consensus phytase-10 (□), consensus phytase-10-thermo[3]-Q50T (Δ), and consensus phytase-10-thermo[3]-Q50T-K91A (▲). The phytase activity was determined using a standard assay in appropriate buffers (see Example 15) at different pH-values (see Mitchell et al., 1997, Lehmann et al., 2000 and further references mentioned therein). FIG. 15B) shows the corresponding substrate specificity tested by replacement of phytate by the indicated compounds in a standard assay; open bars, consensus phytase-10 (white bars, consensus phytase-10-thermo-Q50T; dark bars, consensus phytase-10-thermo-Q50T-K91A). The numbers correspond to the following compounds: 1, phytate; 2, p-nitrophenyl phosphate; 3, phenyl phosphate; 4, fructose-1,6-bisphosphate; 5, fructose-6-phosphate; 6, glucose-6-phosphate; 7, ribose-5-phosphate; 8, DL-glycerol-3-phosphate; 9, glycerol-2-phosphate; 10,3-phosphoglycerate; 11, phosphoenolpyruvate; 12, AMP; 13, ADP; 14, ATP.

Figure 16A:
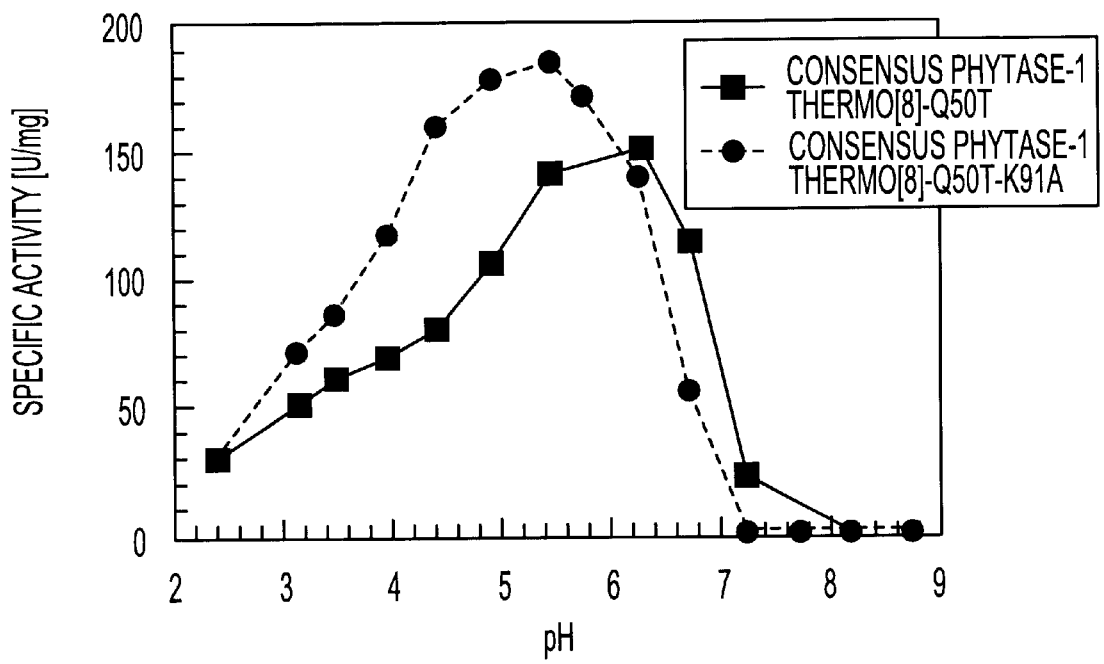
FIGS. 16A–16B depicts the pH-dependent activity profile (16A) and substrate specificity (16B) of consensus phytase-1-thermo[8]-Q50T and consensus phytase-1-thermo[8]-Q50T-K91A.
Figure 16B:
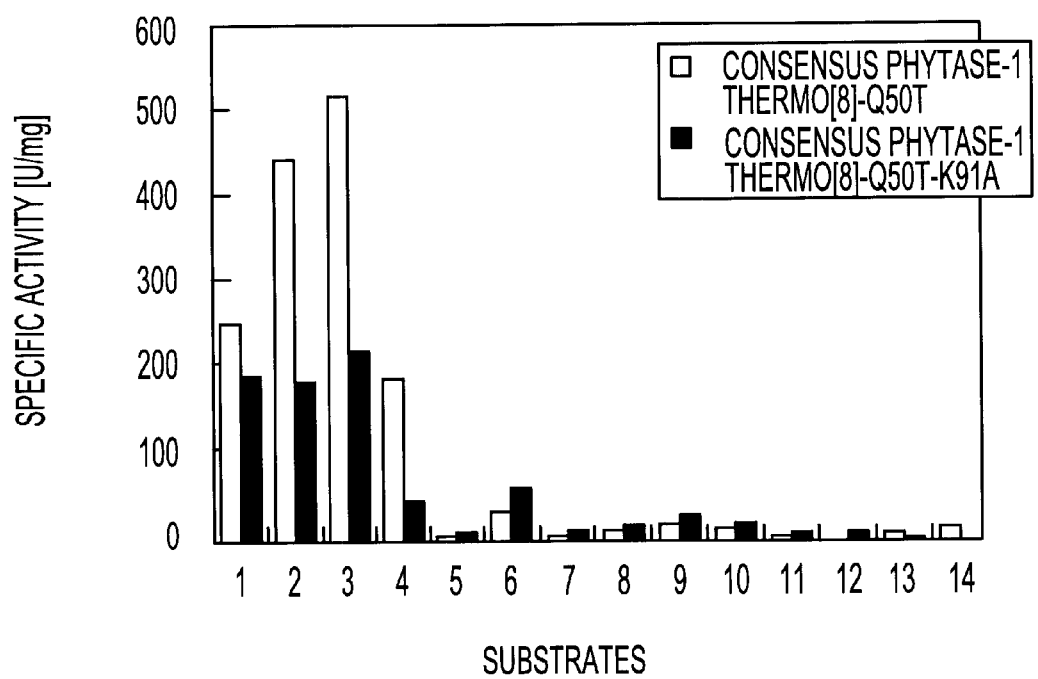

FIGS. 16A–16B: pH-dependent activity profile and substrate specificity of consensus phytase-1-thermo[8]-Q50T and of consensus phytase-1-thermo[8]-Q50T-K91A. FIG. 16A) shows the pH-dependent activity profile of the Q50T- (■) and the Q50T-K91A-variant (Δ). The phytase activity was determined using the standard assay in appropriate buffers (see Example 15) at different pH-values (see Mitchell et al., 1997, Lehmann et al., 2000 and further references mentioned -therein). FIG. 16B) shows the corresponding substrate specificities tested by replacement of phytate by the indicated compounds in the standard assay (open bars, consensus phytase-1-thermo[8]-Q50T; filled bars, consensus phytase-1-thermo[8]-Q50T-K91A). The substrates are listed in the legend of FIGS. 15A–15B.

Figure 17A:
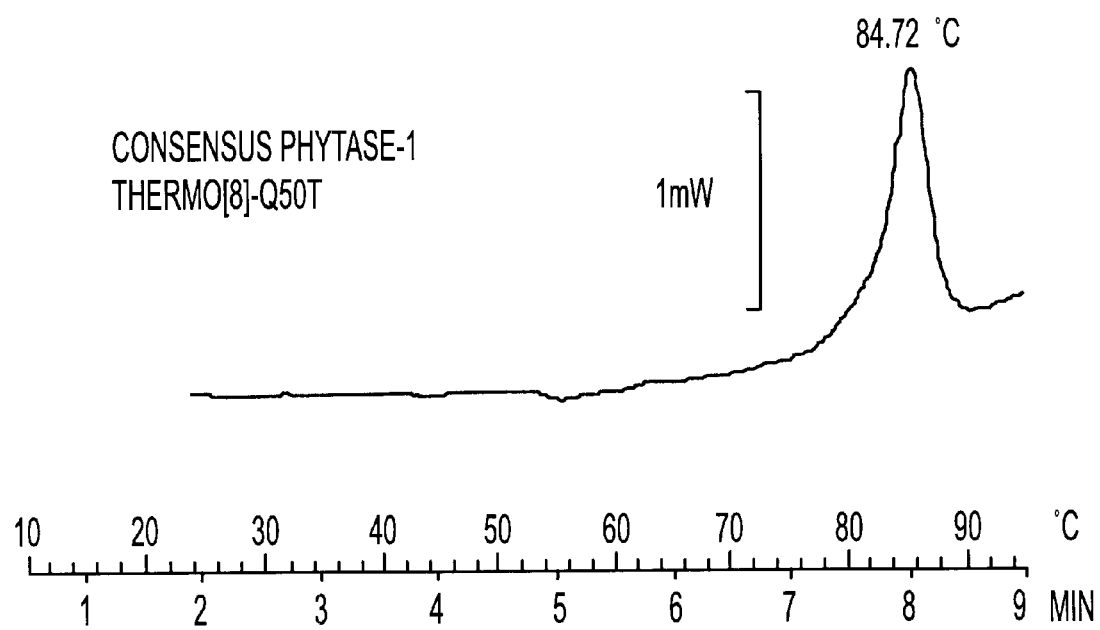
FIGS. 17A–17B depicts DSC of consensus phytase-1-thermo[8]-Q50T (17A) and consensus phytase-1-thermo[8]-Q50T-K91A (17B).
Figure 17B:
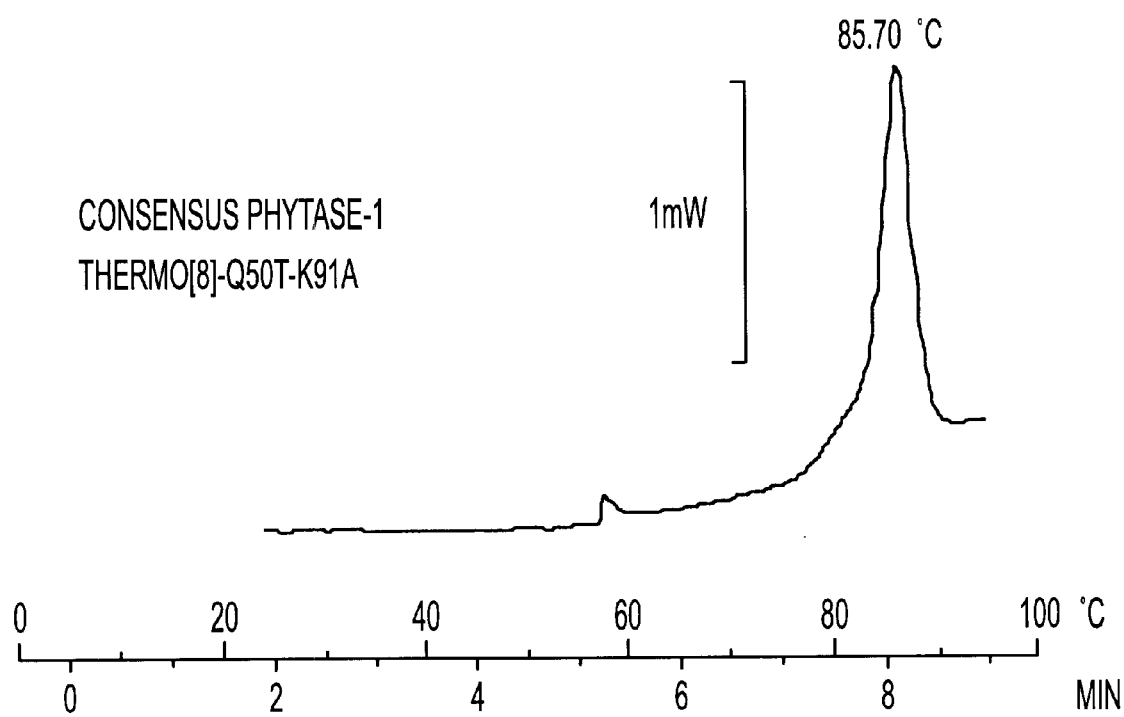

FIGS. 17A–17B: Differential scanning calorimetry (DSC) of consensus phytase-1-thermo[8]-Q50T (FIG. 17A) and consensus phytase-1-thermo[8]-Q50T-K91A (FIG. 17B). The protein samples were concentrated to about 50–60 mg/ml and extensively dialyzed against 10 mM sodium acetate, pH 5.0. A constant heating rate of 10° C./min was applied up to 95° C. DSC of consensus phytase-1-thermo [8]-Q50T (FIG. 17A) showed a melting temperature of 84.72° C., while the melting point of consensus phytase-1-thermo[8]-Q50T-K91A (FIG. 17B) was found at 85.70° C.

Figure 18:
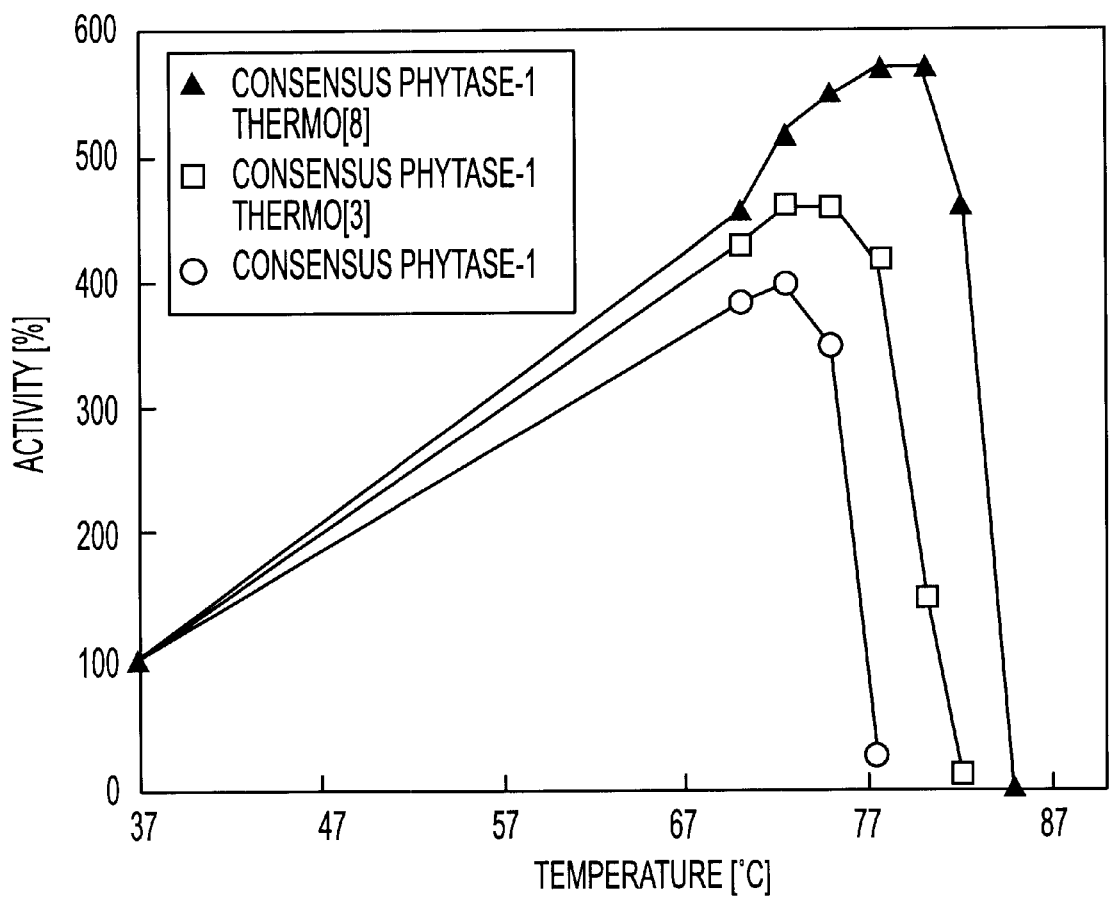
FIG. 18 is a graph comparing the temperature optima between consensus phytase-1, consensus phytase-1-thermo[3], and consensus phytase-1-thermo[8].

FIG. 18: Comparison of the temperature optimum between consensus phytase-1, consensus phytase-1-thermo

[3] and consensus phytase-1-thermo[8]. For the determination of the temperature optimum, the phytase standard assay was performed at a series of temperatures between 37° C. and 86° C. (see Mitchell et al., 1997, Lehmann et al., 2000 and further references mentioned therein). Purified protein from the supernatant of transformed *S. cerevisiae* strains was used for the determination. O, consensus phytase-1; □, consensus phytase-1-thermo[3]; Δ, consensus phytase-1-thermo[8].

Figure 19A:
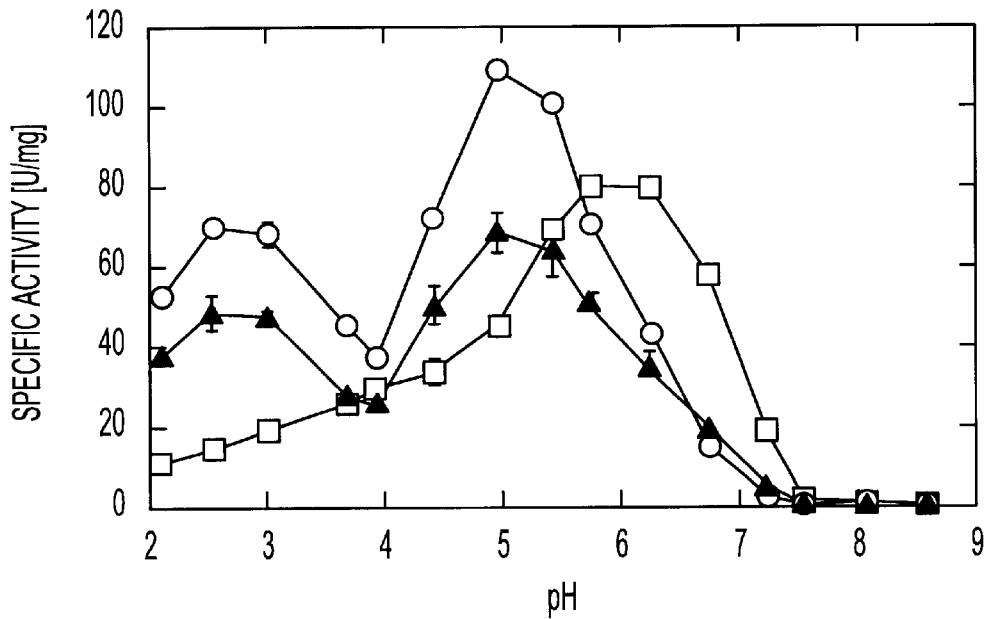
FIGS. 19A–19B depicts the pH-dependent activity profile (19A) and substrate specificity (19B) of consensus phytase-1, consensus phytase-7, and the phytase from *A. niger* NRRL 3135.
Figure 19B:
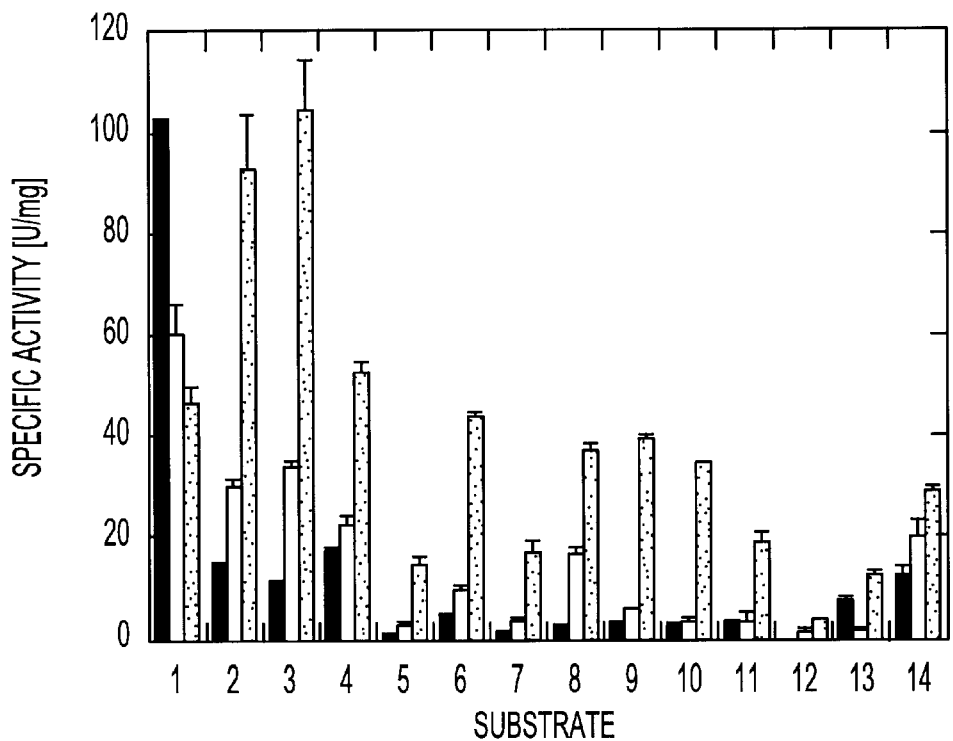

FIGS. 19A–19B: Comparison of the pH-dependent activity profile (FIG. 19A) and substrate specificity (FIG. 19B) of consensus phytase-1, consensus phytase-7, and of the phytase from *A. niger* NRRL 3135. FIG. 19A) shows the pH-dependent activity profile of consensus phytase-1 (■), the phytase from *A. niger* NRRL 3135 (O), and of consensus phytase-7 (Δ). The phytase activity was determined using the standard assay in appropriate buffers (see Example 15) at different pH-values (see Mitchell et al., 1997, Lehmann et al., 2000 and further references mentioned therein). FIG. 19B) shows the corresponding substrate specificity tested by replacement of phytate by the indicated compounds in the standard assay (black bars, *A. niger* NRRL 3135 phytase; grey bars, consensus phytase-1, dashed bars, consensus phytase-7). The substrates are listed in the legend of FIGS. 15A–15B.

Figure 20A:
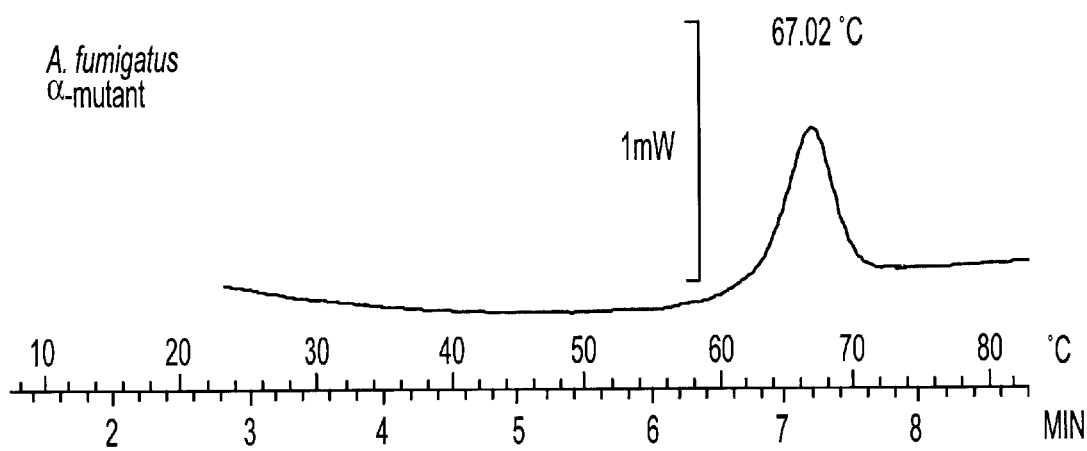
FIGS. 20A–20B depicts DSC of the phytase from *A. fumigatus* ATCC 13073 (20B) and of its stabilized α-mutant (20A).
Figure 20B:
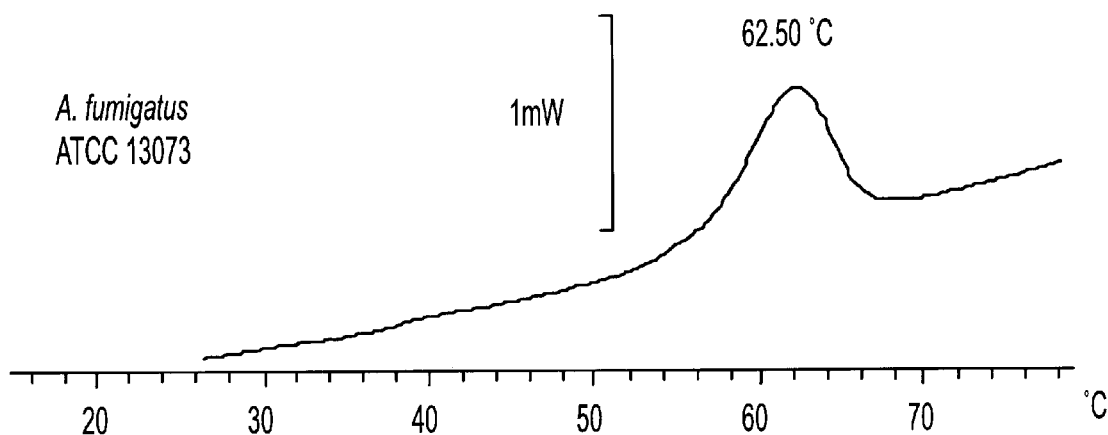

FIGS. 20A–20B: Differential scanning calorimetry (DSC) of the phytase from *A. fumigatus* ATCC 13073 (FIG. 20B) and of its stabilized α-mutant (FIG. 20A), which contains the following amino acid exchanges: F55Y, V100I, F114Y, A243L, S265P, N294D.

The protein samples were concentrated to about 50–60 mg/ml and extensively dialyzed against 10 mM sodium acetate, pH 5.0. A constant heating rate of 10° C./min was applied up to 95° C. DSC of consensus *A. fumigatus* 13073 phytase (FIG. 20B) revealed a melting temperature of 62.50° C., while the melting point of the α-mutant (FIG. 20A) was found at 67.02° C.

Figure 21:
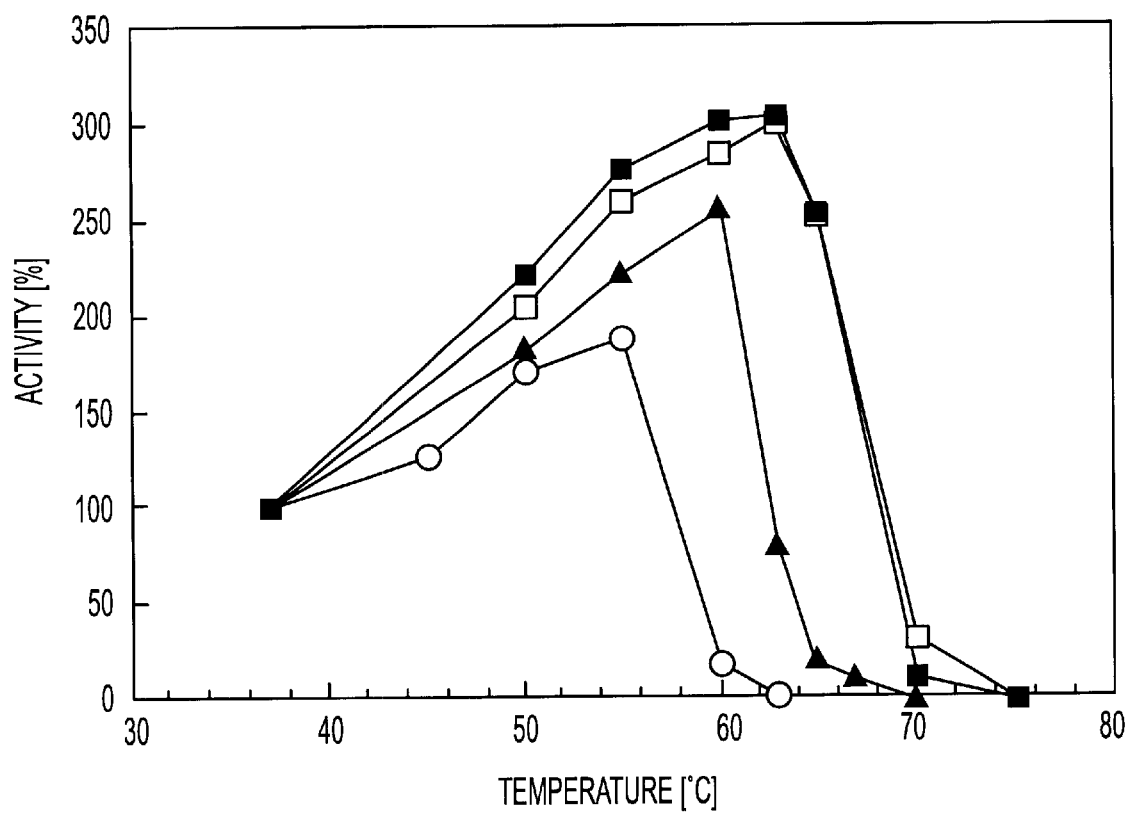
FIG. 21 is a graph depicting the temperature optima of *A. fumigatus* ATCC 13073 wild type phytase, its α-mutant, and a further stabilized α-mutant.

FIG. 21: Comparison of the temperature optimum of *A. fumigatus* 13073 wild-type phytase, its α-mutant, and a further stabilized α-mutant (E59A-S126N-R329H-S364T-G404A). For the determination of the temperature optimum, the phytase standard assay was performed at a series of temperatures between 37° C. and 75° C. (see Mitchell et al., 1997, Lehmann et al., 2000 and further references mentioned therein). The diluted supernatants of transformed *S. cerevisiae* strains were used for the determination. The other components of the supernatant showed no influence on the determination of the temperature optimum. O, *A. fumigatus* ATCC 13073 phytase; Δ, *A. fumigatus* ATCC 13073 α-mutant; □, *A. fumigatus* ATCC 13073 alpha-mutant-(E59A-S126N-R329H-S364T-G404A)-Q27T; ■, *A. fumigatus* ATCC 13073 α-mutant-(E59A-S126N-R329H-S364T-G404A)-Q27T-K68A. The mutations Q51T and K92A in the *A. fumigatus* α-mutants correspond to -1 Q50T and K91A in consensus phytase, respectively.

FIG. 22: Amino acid sequence of consensus phytase-12 (consphy12), which contains a number of active site residues transferred from the "basidio" consensus sequence (FIGS. 4A–4F) to consensus phytase-10-thermo[3]-Q50T-K91A.

The culture medium used in the fermentation process in accordance with the present invention includes nutrients for the cells or microorganisms such as digestible nitrogen sources and inorganic substances, vitamins, micro- and trace elements and other growth-promoting factors. In addition, the culture medium contains a carbon source. Various organic or inorganic substances may be used as nitrogen sources in the fermentation process, such as nitrates, ammonium salts, yeast extract, meat extract, peptone, casein, cornsteep liquor, amino acids and urea. Typical inorganic substances that can be used in the fermentation are calcium, iron, zinc, nickel, manganese, cobalt, copper, molybdenum, and alkali salts such as chlorides, sulfates and phosphates as well as boric acid. As a carbon source, glycerol or sugar-like mono-, di-, oligo- or polysaccharides, e.g., glucose, fructose, sucrose, maltose, starch, glycogen, cellulose or substrates containing such substances, e.g., molasses, glucose syrups and fructose syrups can be used. The concentration of glucose and/or methanol in the total feed stream may vary from about 10 to about 500 g/l for each component, and is preferably from about 200 to about 300 g/l. While the fermentation medium is principally an aqueous medium, such medium may contain organic solvents such as alcohols, e.g. methanol, ethanol or isopropanol. Further, the fermentation medium may also be a dispersion or suspension, in which case the fermentation is suitably carried out with stirring.

For continuous operation, the cells are optionally immobilized on a solid porous carrier. Any solid porous carrier with any porosity, size and geometry conventionally used in fermentation processes and exerting no toxic effects on the particular cell or microorganism which is to be immobilized can be used for the purpose of this invention. Examples of such carriers are those made from inorganic material and having a pore diameter of from about 0.5 to about 100 μm, preferably from about 10 to about 30 μm diameter. Examples of inorganic materials are ceramics and natural minerals such as steatite, zeolite, bentonite, silicates (glasses), aluminum silicates, aluminum oxide, magnesium aluminum silicates and magnesium aluminum oxides. Such carriers are commercially available, e.g., from Ceramtec, Marktredwitz, Germany, Schott Engineering GmbH, Mainz, Germany and others. Preferably, the carriers are spherical with a mean diameter of from about 0.2 to about 20 mm diameter. The carriers can be loaded with the living cells in a manner known per se by contacting the carrier particles with an appropriate cell culture. If desired, the carrier particles loaded with the cells can be further processed by applying a membrane-type coating layer, such as described in German Offenlegungsschrift DE 3421049. Suitably, the carrier is present in the fermentation vessel on a fixed bed. Further, the culture medium, its components and their containments, respectively are suitably sterilized prior to use if autosterilization (e.g., by methanol, ethanol, ammonia) cannot be guaranteed. Heat sterilization with steam (e.g., at 121° C. and 1 bar pressure for 20 minutes) and filtration (0.2 μm) for sensitive components are preferred. Alternative sterilization methods may be applied. Media components need not necessarily be sterilized when running the process in continuous mode.

Depending on the particular cell or organism used, the fermentation may be carried out at a pH between about 2 and about 11. In a preferred aspect of the invention, the fermentation process for the manufacture of phytase is carried out using the microorganism, *Hansenula polymorpha* transformed by a phytase encoding DNA sequence as described in EP 897 010, EP 897 985, or Example 11 of the present case. According to that particular aspect of the invention, the preferred carbon source is a mixture of glucose and methanol. Further, in accordance with that particular aspect of the invention, the fermentation may be carried out at a pH between about 4 and 5, preferably at about pH 4.6. A preferred temperature range for carrying out such fermentation process is between about 10° C. and 50° C., more preferably the fermentation temperature is about 30° C. The aeration rate is preferably adjusted to between about 0.01 and about 1.5 volume of gas per volume of liquid with a dissolved oxygen concentration (DO) of between 0.01% and about 500%. A DO of 100% denotes oxygen saturation of the solution at atmospheric pressure (1 bar) and reactor temperature. The fermentation can be carried out at a pressure of from about 0.1 to about 100 bar, preferably, the fermentation is carried out at atmospheric pressure, i.e., at about 1 bar. The dilution rate can vary from about 0.001 to about 0.5 per hour.

The following examples are provided to further illustrate the process of the present invention. These examples are illustrative only and are not intended to limit the scope of the invention in any way.

EXAMPLES

Example 1

Storage solutions for feed medium were prepared as follows:

| 1.1 $CaCl_2/H_3BO_3$ Solution | | |
|---|---|---|
| $CaCl_2 \cdot 2\ H_2O$ | 18.75 | g/l |
| $H_3BO_3$ | 0.0125 | g/l |

This solution was sterilized at 121° C. for 20 minutes.

| 1.2 Microelements Solution | | |
|---|---|---|
| $(NH_4)_2Fe(SO_4)_2 \cdot 6\ H_2O$ | 2.5 | g/l |
| $CuSO_4 \cdot 5\ H_2O$ | 0.2 | g/l |
| $ZnSO_4 \cdot 7\ H_2O$ | 0.75 | g/l |
| $MnSO_4 \cdot 5\ H_2O$ | 1.0 | g/l |
| Na-EDTA | 2.5 | g/l |

This solution was sterilized at 121° C. for 20 minutes.

| 1.3 Trace Elements Solution | | |
|---|---|---|
| $NiSO_4 \cdot 6\ H_2O$ | 0.025 | g/l |
| $CoCl_2 \cdot 6\ H_2O$ | 0.025 | g/l |
| $Na_2MoO_4 \cdot 2\ H_2O$ | 0.025 | g/l |
| KI | 0.025 | g/l |

This solution was sterilized at 121° C. for 20 minutes.

| 1.4 Salts + Vitamin Solution | | |
|---|---|---|
| $KH_2PO_4$ | 50.0 | g/l |
| $NH_4H_2PO_4$ | 100.0 | g/l |
| $MgSO_4 \cdot 7\ H_2O$ | 45.0 | g/l |
| $(NH_4)_2SO_4$ | 50.0 | g/l |
| KCl | 23.0 | g/l |
| NaCl | 5.0 | g/l |
| vitamin solution | 5.0 | ml/l |

(D-biotin, 600 mg/l and thiamin · HCl 200 g/l in 50% isopropanol/water)

The vitamin solution was sterilized by filtration (0.2 μm), and added to the salt solution that was sterilized at 121° C. for 20 minutes.

1.5 Glucose Solution 770 g of D-glucose $H_2O$ were dissolved in 480 g of water and sterilized (121° C., 20 minutes) to yield a 1 liter solution containing 57% (by weight) of D-glucose.

1.6 Methanol

Pure methanol was assumed to be sterile and poured into a sterilized flask.

1.7 Antifoam

A sterilized (121° C., 20 minutes) solution of 10 antifoam (STRUKTOL J 673, Schill & Seilacher, Hamburg, Germany) was provided for supply on demand by foam-control.

1.8 Base

A solution of about 12.5% (by weight) of ammonia in sterile water was poured into a sterilized flask.

Example 2

A fixed bed bioreactor (1 liter) was set up following the principle illustrated in FIG. 1 with individual storage flasks provided for solutions 1.1 to 1.8 of Example 1. The fixed bed of porous steatite spheres (4 mm diameter, pore diameter 10–30 μm, 280 pores per ml, CeramTec, Marktredwitz, Germany) was contained by a sieve plate at the top. The reactor was sterilized (121° C., 20 minutes), and thereafter filled with an inoculum culture of *Hansenula polymorpha* transformed with a phytase encoding DNA as described, e.g. in EP 897 010, EP 897 985 or Example 11. EP 897010 and EP 897985 are incorporated by reference as if recited in full herein. Then the connection to the storage flasks was established. The inoculum culture was grown on a medium containing glycerol as a carbon source instead of glucose. The reactor was switched to batch operation until all glycerol was consumed, which was determined by a rise of the dissolved oxygen concentration. Then the feed stream was turned on and the fermentation was run under process conditions as given below:

| Temperature | 30° C. | |
|---|---|---|
| pH | 4.6 | Diluted oxygen concentration 52–62 |
| % $ox_{otal}$ | $10^5$ | $N/m^2$ |
| $P_{O2}$ | $10^5$ | $N/m^2$ |
| Dilution rate | 0.0067 | $h^{-1}$ |
| Aeration rate | 100 | ml/min |
| $V_{fluid}$ | 1190 | $ml^{-1}$ |
| $V_{fixed\ bed}$ | 950 | $ml^{-1}$ |

Substrate composition as provided by storage flasks 1–8; (actual concentrations in feed stream given):

| D-glucose | 305 | g/l |
|---|---|---|
| Methanol | 264 | g/l |
| $CaCl_2/H_3BO_3$ Solution | 12.2 | g/l |
| Microelement Solution | 20.9 | g/l |
| Trace Element Solution | 17.2 | g/l |
| Salts + vitamin Solution | 44.7 | g/l |

Analytics:

Bio-Rad Protein Assay Kit I (Bio-Rad, Glattbrugg, Switzerland) was used to determine the total protein concentration. A factor for the calculation of phytase concentration ($c_{phyt}$) from total protein concentration ($c_{tp}$) was determined as $c_{phyt}=0.76\ c_{tp}$.

To determine the biomass in the medium two samples of 1 ml were centrifuged, washed with 1 ml of water, centrifuged again, dried at 85° C. for two days and weighed.

Results:

Under the above process conditions, the biomass was 59 g/l. Given a dilution rate of 0.0067 per hour the productivity was 0.078 g of phytase per liter per hour.

In a fermentation that was run fed-batch-wise, the biomass was 125 g/l; the productivity, however, was calculated to 0.054 g phytase per liter per hour.

Example 3

A fermentation was carried out as set forth in Example 2 but omitting the steatite spheres (i.e., without immobilization of the microorganism). A nutrient and a salt and vitamin solution of the following composition were pumped into the reactor separately:

| Nutrient Solution: | | |
|---|---|---|
| $NiSO_4 \cdot 6 H_2O$ | 8.33 | mg/l |
| $CoCl_2 \cdot 6 H_2O$ | 8.33 | mg/l |
| $Na_2MoO_4 \cdot 2 H_2O$ | 8.33 | mg/l |
| KI | 8.33 | mg/l |
| $(NH_4)_2Fe(SO_4)_2 \cdot 6 H_2O$ | 833.33 | mg/l |
| $CuSO_4 \cdot 5 H_2O$ | 66.67 | mg/l |
| $ZnSO_4 \cdot 7 H_2O$ | 250 | mg/l |
| $MnSO_4 \cdot 5 H_2O$ | 333.33 | mg/l |
| Na-EDTA | 833.33 | mg/l |
| $CaCl_2 \cdot 2 H_2O$ | 6250 | mg/l |
| $H_3BO_3$ | 4.17 | mg/l |
| Salts + Vitamins Solution: | | |
| $KH_2PO_4$ | 50.0 | g/l |
| $NH_4H_2PO_4$ | 100.0 | g/l |
| $MgSO_4 \cdot 7 H_2O$ | 45.0 | g/l |
| $(NH_4)_2SO_4$ | 50.0 | g/l |
| KCl | 23.0 | g/l |
| NaCl | 5.0 | g/l |
| vitamin solution | 5.0 | ml/l |

(D-biotin, 600 mg/l and thiamin · HCl 200 g/l in 50% isopropanol/water)

The supply of these two solutions was adjusted to provide in the feed stream a concentration of 51 g/l of the Nutrient Solution and 61 g/l of the Salts+Vitamins Solution. The dilution rate was adjusted to 0.009 $h^{-1}$. The pH was kept at 4.6 by addition of 12.5 wt % ammonium hydroxide. Glucose Solution as in Example 1 and methanol were fed into the reactor separately to maintain a glucose concentration of 275 g/l and a methanol concentration of 260 g/l in the feed stream.

The productivity of this fermentation was 0.088 g phytase per liter per hour. Biomass in outflow was 58 g/l.

Example 4

A fermentation process as set forth in Example 3 was carried out, but adjusting glucose concentration to 290 g/l and methanol concentration to 260 g/l, and keeping the dilution rate constant at 0.009 $h^{-1}$, the productivity was 0.092 g phytase per liter per hour. Biomass in outflow was 60.4 g/l.

Example 5

A fermentation process as set forth in Example 3 was carried out, but adjusting glucose concentration to 270 g/l and methanol concentration to 280 g/l, and keeping the dilution rate constant at 0.009 $h^{-1}$, the productivity was 0.094 g phytase per liter per hour. Biomass in outflow was 56.8 g/l.

Example 6

Design of the Amino Acid Sequence of Consensus Phytase-1

Alignment of the Amino Acid Sequences

The alignment was calculated using the program PILEUP from the GCG Sequence Analysis Package Release 9.0 (Devereux et al., 1984) with the standard parameters (gap creation penalty 12, gap extension penalty 4). The location of the gaps was refined using a text editor. Table 1 shows the sequences (see FIGS. 2A–2F), without the signal sequence, that were used for the performance of the alignment starting with the amino acid (aa) as mentioned in Table 1, e.g., "aa 27" means that the alignment began at the 27 amino acid from the start codon.

TABLE 1

Origin and vote weight of the phytase amino acid sequences used for the design of consensus phytase-1 phyA from *Aspergillus terreus* 9A-1, aa 27, vote weight 0.5 (Mitchell et al., 1997)
phyA from *Aspergillus terreus* cbs116.46, aa 27, vote weight 0.5 (EP 897 985; FIG. 1)
phyA from *Aspergillus niger* var. *awamori*, aa 27, vote weight 0.33 (Piddington et al., 1993)
phyA from *Aspergillus niger* T213, aa 27, vote weight 0.33
phyA from *Aspergillus niger* strain NRRL3135, aa 27, vote weight 0.33 (van Hartingsveldt et al., 1993)
phyA from *Aspergillus fumigatus* ATCC 13073, aa 26, vote weight 0.2 (Pasamontes et al., 1997)
phyA from *Aspergillus fumigatus* ATCC 32722, aa 26, vote weight 0.2 (EP 897 985; FIG. 1)
phyA from *Aspergillus fumigatus* ATCC 58128, aa 26, vote weight 0.2 (EP 897 985; FIG. 1)
phyA from *Aspergillus fumigatus* ATCC 26906, aa 26, vote weight 0.2 (EP 897 985; FIG. 1)
phyA from *Aspergillus fumigatus* ATCC 32239, aa 30, vote weight 0.2 (EP 897 985; FIG. 1)
phyA from *Emericella nidulans*, aa 25, vote weight 1.0 (Pasamontes et al., 1997a)
phyA from *Talaromyces thermophilus* ATCC 20186, aa 24, vote weight 1.0 (Pasamontes et al., 1997a)
phyA from *Myceliophthora thermophila*, aa 19, vote weight 1.0 (Mitchell et al., 1997)

Calculation of the Amino Acid Sequence of Consensus Phytase-1

Using the refined alignment as input, the consensus sequence was calculated by the program PRETTY from the GCG Sequence Analysis Package Release 9.0 (Devereux et al., 1984). PRETTY prints sequences with their columns aligned and can display a consensus sequence for an alignment. A vote weight that pays regard to the similarity between the amino acid sequences of the aligned phytases was assigned to all sequences. The vote weight was set in such a way that the combined impact of all phytases from one sequence subgroup (same species, but from different strains), e.g. the amino acid sequences of all phytases from *A. fumigatus*, on the election was set one, that means that each sequence contributes a value of 1 divided by the number of strain sequences (see Table 1). By this means, it was possible to prevent very similar amino acid sequences, e.g. of the phytases from different *A. fumigatus* strains, from dominating the calculated consensus sequence.

The program PRETTY was started with the following parameters: The plurality defining the number of votes below which there is no consensus was set on 2.0. The threshold, which determines the scoring matrix value below which an amino acid residue may not vote for a coalition of residues, was set on 2. PRETTY used the PrettyPep.Cmp consensus scoring matrix for peptides.

Ten positions of the alignment (positions 46, 66, 82, 138, 162, 236, 276, 279, 280, 308; FIGS. 2A–2F), for which the program was not able to determine a consensus residue, were filled by hand according to the following rules: if a most frequent residue existed, this residue was chosen (positions 138, 236, 280); if a prevalent group of similar equivalent residues occurred, the most frequent or, if not available, one residue of this group was selected (positions 46, 66, 82, 162, 276, 308). If there was neither a prevalent residue nor a prevalent group, one of the occurring residues was chosen according to common assumptions on their influence on the protein stability (position 279). Eight other positions (positions 132, 170, 204, 211, 275, 317, 384, 447; FIGS. 2A–2F) were not filled with the amino acid residue selected by the program but normally with amino acids that occur with the same frequency as the residues that were chosen by the program. In most cases, the slight underrating of the three *A. niger* sequences (sum of the vote weights: 0.99) was eliminated by this correction.

Conversion of the Consensus Phytase-1 Amino Acid Sequence to a DNA Sequence

The first 26 amino acid residues of the *A. terreus* cbs116.46 phytase were used as a signal peptide and, therefore, fused to the N-terminus of all consensus phytases. For this stretch, we used a special method to calculate the corresponding DNA sequence. Purvis et al (1987) proposed that the incorporation of rare codons in a gene has an influence on the folding efficiency of the protein. The DNA sequence for the signal sequence was calculated using the approach of Purvis et al (1987), which is hereby incorporated by reference as if recited in full herein, and optimized for expression in *S. cerevisiae*. For the remaining parts of the protein, we used the codon frequency table of highly expressed *S. cerevisiae* genes, obtained from the GCG program package, to translate the calculated amino acid sequence into a DNA sequence.

The resulting sequence of the fcp gene is shown in FIGS. 3A–3G.

Construction and Cloning of the Consensus Phytase-1 Gene

The calculated DNA sequence of consensus phytase-1 (fcp) was divided into oligonucleotides of 85 bp, alternately using the sequence of the sense and the anti-sense strand. Every oligonucleotide overlaps 20 bp with its previous and its following oligonucleotide of the opposite strand. The location of all primers, purchased from Microsynth, Balgach (Switzerland) and obtained in a PAGE-purified form, is indicated in FIGS. 3A–3G.

PCR-Reactions

In three PCR reactions, the synthesized oligonucleotides were composed to the entire gene. For the PCR, the High Fidelity Kit from Boehringer Mannheim (Boehringer Mannheim, Germany) and the thermo cycler The Protokol (TM) from AMS Biotechnology (Europe) Ltd. (Lugano, Switzerland) were used.

Oligonucleotides CP-1 to CP-10 (Mix 1, FIGS. 3A–3G) were mixed to a concentration of 0.2 pmol/µl of each oligonucleotide. A second oligonucleotide mixture (Mix 2) was prepared with CP-9 to CP-22 (0.2 pmol/µl of each oligonucleotide). Additionally, four short primers were used in the PCR reactions:

CP-a: Eco RI

5'-TATATGAATTCATGGGCGTGTTCGTC-3' (SEQ ID No. 1)

CP-b:

5'-TGAAAAGTTCATTGAAGGTTTC-3' (SEQ ID No. 2)

CP-c:

5'-TCTTCGAAAGCAGTACAAGTAC-3' (SEQ ID No. 3)

CP-e: Eco RI

5'-TATATGAATTCTTAAGCGAAAC-3' (SEQ ID No. 4)

PCR reaction a: 10 µl Mix 1 (2.0 pmol of each oligonucleotide)

2 µl nucleotides (10 mM each nucleotide)

2 µl primer CP-a (10 pmol/µl)

2 µl primer CP-c (10 pmol/µl)

10.0 µl PCR buffer 0.75 µl polymerase mixture (2.6U)

73.25 µl $H_2O$

PCR reaction b: 10 µl Mix 2 (2.0 pmol of each oligonucleotide)

2 µl nucleotides (10 mM each nucleotide)

2 µl primer CP-b (10 pmol/µl)

2 µl primer CP-e (10 pmol/µl)

10.0 µl PCR buffer 0.75 µl polymerase mixture (2.6 U)

73.25 µl $H_2O$

Reaction conditions for PCR reactions a and b:

step 1 2 minutes—45° C.

step 2 30 seconds—72° C.

step 3 30 seconds—94° C.

step 4 30 seconds—52° C.

step 5 1 minute—72° C.

Steps 3 to 5 were repeated 40 times.

The PCR products (670 and 905 bp) were purified by an agarose gel electrophoresis (0.9% agarose) and subsequently subjected to gel extraction (QIAEX II Gel Extraction Kit, Qiagen, Hilden, Germany). The purified DNA fragments were used for the PCR reaction c.

PCR reaction c: 6 µl PCR product of reaction a (≈50 ng)

6 µl PCR product of reaction b (≈50 ng)

2 µl primer CP-a (10 pmol/µl)

2 µl primer CP-e (10 pmol/µl)

10.0 µl PCR buffer 0.75 µl polymerase mixture (2.6 U)

73.25 µl $H_2O$

Reaction conditions for PCR reaction c:

step 1 2 minutes—94° C.

step 2 30 seconds—94° C.

step 3 30 seconds—55° C.

step 4 1 minutes—72° C.

Steps 2 to 4 were repeated 31-times.

The resulting PCR product (1.4 kb) was purified as mentioned above, digested with Eco RI, and ligated in an Eco RI-digested and dephosphorylated pBsk(−)-vector (Stratagene, La Jolla, Calif., USA). 1 µl of the ligation mixture was used to transform *E. coli* XL-1 competent cells (Stratagene, La Jolla, Calif., USA). All standard procedures were carried out as described by Sambrook et al. (1987). The DNA sequence of the constructed consensus phytase gene (fcp, FIGS. 3A–3G) was controlled by sequencing as known in the art.

Example 7

Design of an Improved Consensus Phytase (Consensus Phytase-10) Amino Acid Sequence The alignments used for the design of consensus phytase-10 were calculated using the program PILEUP from the GCG Sequence Analysis Package Release 9.0 (Devereux et al., 1984) with the standard parameters (gap creation penalty 12, gap extension penalty 4). The location of the gaps was refined using a text editor.

The following sequences were used for the alignment of the Basiodiomycete phytases starting with the amino acid (aa) mentioned in Table 2:

TABLE 2

Origin and vote weight of five *Basidiomycete phytases* used for the calculation of the corresponding amino acid consensus sequence (basidio)

phyA1 from *Paxillus involutus* NN005693, aa 21, vote weight 0.5 (WO 98/28409)
phyA2 from *Paxillus involutus* NN005693, aa 21, vote weight 0.5 (WO 98/28409)
phyA from *Trametes pubescens* NN9343, aa 24, vote weight 1.0 (WO 98/28409)
phyA from *Agrocybe pediades* NN009289, aa 19, vote weight 1.0 (WO 98/28409)
phyA from *Peniophora lycii* NN006113, aa 21, vote weight 1.0 (WO 98/28409)

The alignment is shown in FIGS. 4A–4F.

In Table 3 the genes, which were used for the performance of the final alignment, are arranged. The first amino acid (aa) of the sequence, which is used in the alignment is mentioned behind the organism's designation.

TABLE 3

Origin and vote weight of the phytase sequences used for the design of consensus phytase 10 phyA from *Aspergillus terreus* 9A-1, aa 27, vote weight 0.5 (Mitchell et al., 1997)
phyA from *Aspergillus terreus* cbs116.46, aa 27, vote weight 0.5 (EP 897 985; FIG. 1)
phyA from *Aspergillus niger* var. *awamori*, aa 27, vote weight 0.5 (Piddington et al., 1993)
phyA from *Aspergillus niger* strain NRRL3135, aa 27, vote weight 0.5 (van Hartingsveldt et al., 1993)
phyA from *Aspergillus fumigatus* ATCC 13073, aa 26, vote weight 0.2 (Pasamontes et al., 1997)
phyA from *Aspergillus fumigatus* ATCC 32722, aa 26, vote weight 0.2 (EP 897 985; FIG. 1)
phyA from *Aspergillus fumigatus* ATCC 58128, aa 26, vote weight 0.2 (EP 897 985; FIG. 1)
phyA from *Aspergillus fumigatus* ATCC 26906, aa 26, vote weight 0.2 (EP 897 985; FIG. 1)
phyA from *Aspergillus fumigatus* ATCC 32239, aa 30, vote weight 0.2 (EP 897 985; FIG. 1)
phyA from *Emericella nidulans*, aa 25, vote weight 1.0 (Pasamontes et al., 1997a)
phyA from *Talaromyces thermophilus* ATCC 20186, aa 24, vote weight 1.0 (Pasamontes et al, 1997a)
phyA from *Myceliophthora thermophila*, aa 19, vote weight 1.0 (Mitchell et al., 1997)
phyA from *Thermomyces lanuginosa*, aa 36, vote weight 1.0 (Berka et al., 1998)
Consensus sequence of five *Basidiomycete phytases*, vote weight 1.0 (Basidio, FIGS. 4A–4F)

The corresponding alignment is shown in FIGS. 5A–5N. Calculation of the Amino Acid Sequence of Consensus Phytase-10

To improve the alignment, we combined the consensus sequence of five phytases from four different Basidiomycetes, called Basidio, still containing the undefined sequence positions (see FIGS. 4A–4F), nearly all phytase sequences used for calculation of the original consensus phytase, and one new phytase sequence from the Ascomycete *Thermomyces lanuginosus* to a larger alignment. We set plurality on 2.0 and threshold on 3. The vote weights used are listed in Table 3. The alignment and the corresponding consensus sequence are presented in FIGS. 5A–5N. The new consensus phytase-10 sequence has 32 different amino acids in comparison to the original consensus phytase (consensus phytase-1). Positions for which the program PRETTY was not able to calculate a consensus amino acid residue were filled according to rules mentioned in Example 6. None of the residues suggested by the program was replaced.

We included all Basidiomycete phytases as single amino acid sequences but assigning a vote weight of 0.2 in the alignment. The corresponding alignment is shown in FIGS. 7A–7Q. The calculated consensus amino acid sequence (consensus phytase-11) has the following differences to the sequence of consensus phytase-10: D35X, X(K)69K, X(E) 100E, A101R, Q134N, X(K)153N, X(H)190H, X(A)204S, X(E)220D, E222T, V227A, X(R)271R, H287A, X(D)288D, X(K)379K, X(I)389I, E390X, X(E)415E, X(A)416A, X(R) 446L, E463A, where the numbering is as in FIGS. 6A–6G.

As used herein, "X" means that the program was not able to calculate a consensus amino acid; the amino acid in parenthesis corresponds to the amino acid finally included in the consensus phytase-10.

We also checked single amino acid replacements suggested by the improved consensus phytase sequences 10 and 11 on their influence on the stability of the original consensus phytase-1. The approach is described in Example 8.

Conversion of Consensus Phytase-10 Amino Acid Sequence to a DNA Sequence

The first 26 amino acid residues of *A. terreus* cbs116.46 phytase were used as a signal peptide and, therefore, fused to the N-terminus of consensus phytase-10. The procedure used is further described in Example 6.

The resulting sequence of the fcp10 gene is shown in FIGS. 6A–6G.

Construction and Cloning of the Consensus Phytase-10 Gene (fcp10)

The calculated DNA sequence of fcp10 was divided into oligonucleotides of 85 bp, alternately using the sequence of the sense and the anti-sense strand. Every oligonucleotide overlaps 20 bp with its previous and its following oligonucleotide of the opposite strand. The location of all primers, purchased from Microsynth, Balgach (Switzerland) and obtained in a PAGE-purified form, is indicated in FIGS. 6A–6G.

PCR-Reactions

In three PCR reactions, the synthesized oligonucleotides were composed to the entire gene. For the PCR, the High Fidelity Kit from Boehringer Mannheim (Boehringer Mannheim, Mannheim, Germany) and the thermocycler The Protokol™ from AMS Biotechnology (Europe) Ltd. (Lugano, Switzerland) were used. The following oligonucleotides were used in a concentration of 0.2 pmol/ml.

Mix 1.10: CP-1, CP-2, CP-3.10, CP-4.10, CP-5.10, CP-6, CP-7.10, CP-8.10, CP-9.10, CP-10.10

Mix 2.10: CP-9.10, CP-10.10, CP-11.10, CP-12.10, CP-13.10, CP-14.10, CP-15.10, CP-16.10, CP-17.10, CP-18.10, CP-19.10, CP-20.10, CP-21.10, CP-22.10

The newly synthesized oligonucleotides are marked by number 10. The phytase contains the following 32 exchanges, which are underlined in FIGS. 6A–6G, in comparison to the original consensus phytase-1: Y54F, E58A, D69K, D70G, A94K, N134Q, I158V, S187A, Q188N, D197N, S204A, T214L, D220E, L234V, A238P, D246H, T251N, Y259N, E267D, E277Q, A283D, R291I, A320V, R329H, S364T, I366V, A379K, S396A, G404A, Q415E, A437G, A463E.

Four short PCR primers were used for the assembling of the oligonucleotides:

CP-a: Eco RI
5'-TATATGAATTCATGGGCGTGTTCGTC-3' (SEQ ID No. 1)

CP-b:
5'-TGAAAAGTTCATTGAAGGTTTC-3' (SEQ ID No. 2)

CP-c.10:
5'-TCTTCGAAAGCAGTACACAAAC-3' (SEQ ID No. 5)

CP-e: Eco RI
5'-TATATGAATTCTTAAGCGAAAC-3' (SEQ ID No. 4)

PCR reaction a: 10 µl Mix 1.10 (2.0 pmol of each oligonucleotide)
2 µl nucleotides (10 mM each nucleotide)
2 µl primer CP-a (10 pmol/ml)
2 µl primer CP-c.10 (10 pmol/ml)
10.0 µl PCR buffer
0.75 µl polymerase mixture (2.6 U)
73.25 µl H$_2$O PCR reaction b: 10 µl Mix 2.10 (2.0 pmol of each oligonucleotide)
2 µl nucleotides (10 mM each nucleotide)
2 µl primer CP-b (10 pmol/ml)
2 µl primer CP-e (10 pmol/ml)
10.0 µl PCR buffer
0.75 µl polymerase mixture (2.6 U)
73.25 µl H$_2$O Reaction conditions for PCR reactions a and b:
step 1 2 minutes—45° C.
step 2 30 seconds—72° C.
step 3 30 seconds—94° C.
step 4 30 seconds—52° C.
step 5 1 minutes—72° C.

Steps 3 to 5 were repeated 40 times.

The PCR products (670 and 905 bp) were purified by an agarose gel electrophoresis (0.9% agarose) subsequently followed by gel extraction (QIAEX II Gel Extraction Kit, Qiagen, Hilden, Germany). The purified DNA fragments were used for the PCR reaction c.

PCR reaction c:
6 µl PCR product of reaction a(≈50 ng)
6 µl PCR product of reaction b(≈50 ng)
2 µl primer CP-a (10 pmol/ml)
2 µl primer CP-e (10 pmol/ml)
10.0 µl PCR buffer
0.75 µl polymerase mixture (2.6 U)
73.25 µl H$_2$O Reaction conditions for PCR reaction c:
step 1 2 minutes—94° C.
step 2 30 seconds—94° C.
step 3 30 seconds—55° C.
step 4 1 minute—72° C.

Steps 2 to 4 were repeated 31 times.

The resulting PCR product (1.4 kb) was purified as mentioned above, digested with Eco RI, and ligated in an Eco RI-digested and dephosphorylated pBsk(−)-vector (Stratagene, La Jolla, Calif., USA). 1 µl of the ligation mixture was used to transform *E. coli* XL-1 competent cells (Stratagene, La Jolla, Calif., USA). All standard procedures were carried out as described by Sambrook et al. (1987). The DNA sequence of the constructed gene (fcp10) was checked by sequencing as known in the art.

Example 8

Increasing the Thermostability of Consensus Phytase-1 by Introduction of Single Mutations Suggested by the Amino Acid Sequence of Consensus Phytase-10 and/or Consensus Phytase-11

To increase the thermostability of homologous genes, it is also possible to test the stability effect of each differing amino acid residue between the protein of interest and the calculated consensus sequence, and to combine all stabilizing mutations into the protein of interest. We used the consensus phytase-1 as the protein of interest, and tested the effect on the protein stability of 34 amino acids, which differed between consensus phytase-1 on one hand and consensus phytases-10 and/or -11 on the other hand, by single mutation.

To construct muteins for expression in *A. niger*, *S. cerevisiae*, or *H. polymorpha*, the corresponding expression plasmid containing the consensus phytase gene was used as template for site-directed mutagenesis (see Examples 11–13). Mutations were introduced using the "quick exchange™ site-directed mutagenesis kit" from Stratagene (La Jolla, Calif., USA) following the manufacturer's protocol, and using the corresponding primers. All mutations made and their corresponding primers are summarized in Table 4. Plasmids harboring the desired mutation were identified by DNA sequence analysis as known in the art.

TABLE 4

Primers used for site-directed mutagenesis of consensus phytases (Exchanged bases are highlighted in bold. The introduction of a restriction site is marked above the sequence. When a restriction site is written in parenthesis, the mentioned site was destroyed by introduction of the mutation.)

| mutation | Primer set | |
|---|---|---|
| | Kpn I | |
| Q50T | 5'-CACTTGTGGGGTACCTACTCTCCATACTTCTC-3' | (SEQ ID No. 6) |
| | 5'-GAGAAGTATGGAGAGTAGGTACCCCACAAGTG-3' | (SEQ ID No. 7) |
| Y54F | 5'-GGTCAATACTCTCCATTCTTCTCTTTGGAAG-3' | (SEQ ID No. 8) |
| | 5'-CTTCCAAAGAGAAGAATGGAGAGTATTGACC-3' | (SEQ ID No. 9) |
| E58A | 5'-CATACTTCTCTTTGGCAGACGAATCTGC-3' | (SEQ ID No. 10) |
| | 5'-GCAGATTCGTCTGCCAAAGAGAAGTATG-3' | (SEQ ID No. 11) |
| | Aat II | |

TABLE 4-continued

Primers used for site-directed mutagenesis of consensus phytases (Exchanged bases are highlighted in bold. The introduction of a restriction site is marked above the sequence. When a restriction site is written in parenthesis, the mentioned site was destroyed by introduction of the mutation.)

| mutation | Primer set | |
|---|---|---|
| D69K | 5'-CTCCA*GACGT*CCCAAAGGACTGTAGAGTTAC-3' | (SEQ ID No. 12) |
| | 5'-GTAACTCTACAGTCCTTTGG*GACGTC*TGGAG-3' | (SEQ ID No. 13) |
| | Aat II | |
| D70G | 5'-CTCCA*GACGT*CCCAGACGGCTGTAGAGTTAC-3' | (SEQ ID No. 14) |
| | 5'-GTAACTCTACAGCCGTCTGG*GACGTC*TGGAG-3' | (SEQ ID No. 15) |
| K91A | 5'-GATACCCAACTTCTTCTGCGTCTAAGGCTTACTCTG-3' | (SEQ ID No. 16) |
| | 5'-CAGAGTAAGCCTTAGACGCAGAAGAAGTTGGGTATC-3' | (SEQ ID No. 17) |
| | Sca I | |
| A94K | 5'-CTTCTAAGTCTAAGAA*GTACT*CTGCTTTG-3' | (SEQ ID No. 18) |
| | 5'-CAAAGCAG*AGTACT*TCTTAGACTTAGAAG-3' | (SEQ ID No. 19) |
| A101R | 5'-GCTTACTCTGCTTTGATTGAACGGATTCAAAAGAACGCTAC-3' | (SEQ ID No. 20) |
| | 5'-GTAGCGTTCTTTTGAATCCGTTCAATCAAAGCAGAGTAAGC-3' | (SEQ ID No. 21) |
| N134Q | 5'-CCATTCGGTGAACAGCAAATGGTTAACTC-3' | (SEQ ID No. 22) |
| | 5'-GAGTTAACCATTTGCTGTTCACCGAATGG-3' | (SEQ ID No. 23) |
| | Nru I | |
| K153N | 5'-GATACAAGGCTC*TCGCGA*GAAACATTGTTC-3' | (SEQ ID No. 24). |
| | 5'-GGAACAATGTTTC*TCGCGA*GAGCCTTGTATC-3' | (SEQ ID No. 25) |
| | Bss HI | |
| I158V | 5'-GATTGTTCCATTCGT*GCGCGC*TTCTGGTTC-3' | (SEQ ID No. 26) |
| | 5'-GAACCAGAAG*CGCGC*ACGAATGGAACAATC-3' | (SEQ ID No. 27) |
| | Bcl I | |
| D197N | 5'-CTCCAGTTATTAACG*TGATCA*TTCCAGAAGG-3' | (SEQ ID No. 28) |
| | 5'-CCTTCTGGAAT*GATCA*CGTTAATAACTGGAG-3' | (SEQ ID No. 29) |
| | Apa I | |
| S187A | 5'-GGCTGACCCAGG*GGCCC*AACCACACCAAGC-3' | (SEQ ID No. 30) |
| | 5'-GCTTGGTGTGGTT*GGGCCCC*TGGGTCAGCC-3' | (SEQ ID No. 31) |
| | Nco I | |
| T214L | 5'-CACTTTGGA*CCATGG*TCTTTGTACTGCTTTCG-3' | (SEQ ID No. 32) |
| | 5'-CGAAAGCAGTACAAAGA*CCATGG*TCCAAAGTG-3' | (SEQ ID No. 33) |
| | AvrII | |
| E222T | 5'-GCTTTCGAAGACTCTAC*CCTAGG*TGACGACGTTG-3' | (SEQ ID No. 34) |
| | 5'-CAACGTCGTCAC*CCTAGGG*TAGAGTCTTCGAAAGC-3' | (SEQ ID No. 35) |
| V227A | 5'-GGTGACGACGCTGAAGCTAACTTCAC-3' | (SEQ ID No. 36) |
| | 5'-GTGAAGTTAGCTTCAGCGTCGTCACC-3' | (SEQ ID No. 37) |
| | Sac II | |
| L234V | 5'-CTAACTTCAC*CGCGG*TGTTCGCTCCAG-3' | (SEQ ID No. 38) |
| | 5'-CTGGAGCGAACAC*CGCGG*TGAAGTTAG-3' | (SEQ ID No. 39) |
| A238P | 5'-GCTTTGTTCGCTCCACCTATTAGAGCTAGATTGG-3' | (SEQ ID No. 40) |
| | 5'-CCAATCTAGCTCTAATAGGTGGAGCGAACAAAGC-3' | (SEQ ID No. 41) |
| | Hpa I | |
| T251N | 5'-GCCAGGTG*TTAAC*TTGACTGACGAAG-3' | (SEQ ID No. 42) |
| | 5'-TTCGTCAGTCAAG*TTAAC*ACCTGGC-3' | (SEQ ID No. 43) |
| | Aat II | |
| Y259N | 5'-GACGAAG*ACGT*CGTTAACTTGATGGAC-3' | (SEQ ID No. 44) |
| | 5'-GTCCATCAAGTTAAC*GACGT*CTTCGTC-3' | (SEQ ID No. 45) |
| | Asp I | |
| E267D | 5'-GTCCATTC*GACACTGT*CGCTAGAACTTC-3' | (SEQ ID No. 46) |
| | 5'-GAAGTTCTAGCG*ACAGTGT*CGAATGGAC-3' | (SEQ ID No. 47) |
| E277Q | 5'-CTGACGCTACTCAGCTGTCTCCATTC-3' | (SEQ ID No. 48) |
| | 5'-GAATGGAGACAGCTGAGTAGCGTCAG-3' | (SEQ ID No. 49) |
| A283D | 5'-GTCTCCATTCTGTGATTTGTTCACTCAC-3' | (SEQ ID No. 50) |
| | 5'-GTGAGTGAACAAATCACAGAATGGAGAC-3' | (SEQ ID No. 51) |
| | Ksp I | |
| H287A | 5'-GCTTTGTTCAC*CGCGG*ACGAATGGAG-3' | (SEQ ID No. 52) |
| | 5'-CTCCATTCGT*CCGCGG*TGAACAAAGC-3' | (SEQ ID No. 53) |
| | Bam HI | |
| R291I | 5'-CACGACGAATG*GATCC*AATACGACTAC-3' | (SEQ ID No. 54) |
| | 5'-GTAGTCGTATT*GGATCC*ATTCGTCGTG-3' | (SEQ ID No. 55) |
| | Bsi WI | |
| Q292A | 5'-GACGAATGGAGAG*CGTACG*ACTACTTG-3' | (SEQ ID No. 56) |
| | 5'-CAAGTAGT*CGTACG*CTCTCCATTCGTC-3' | (SEQ ID No. 57) |
| | Hpa I | |
| A320V | 5'-GGTGTTGGTTTC*GTTAAC*GAATTGATTGC-3' | (SEQ ID No. 58) |
| | 5'-GCAATCAATTC*GTTAAC*GAAACCAACACC-3' | (SEQ ID No. 59) |
| | (Bgl II) | |
| R329H | 5'-GCTAGATTGACT*CACTCT*CCAGTTCAAG-3' | (SEQ ID No. 60) |
| | 5'-CTTGAACTGGAGA*GTGAGT*CAATCTAGC-3' | (SEQ ID No. 61) |
| | Eco RV | |
| S364T | 5'-CTCACGACAACACTAT*GATATC*TATTTTCTTC-3' | (SEQ ID No. 62) |
| | 5'-GAAGAAAATAGA*TATATC*ATAGTGTTGTCGTGAG-3' | (SEQ ID No. 63) |
| | Nco I | |

TABLE 4-continued

Primers used for site-directed mutagenesis of consensus phytases (Exchanged bases are highlighted in bold. The introduction of a restriction site is marked above the sequence. When a restriction site is written in parenthesis, the mentioned site was destroyed by introduction of the mutation.)

| mutation | Primer set | | |
|---|---|---|---|
| I366V | 5'-CGACAACT*CCATGG*TTTCTATTTTCTTCGC-3' | (SEQ ID No. 64) | |
| | 5'-GCGAAGAAAATAGAAA*CCATGG*AGTTGTCG-3' | (SEQ ID No. 65) | |
| | Kpn I | | |
| A379K | 5'-GTACAAC*GGTACC*AAGCCATTGTCTAC-3' | (SEQ ID No. 66) | |
| | 5'-GTAGACAATGGCTT*GGTACC*GTTGTAC-3' | (SEQ ID No. 67) | |
| S396A | 5'-CTGACGGTTACGCTGCTTCTTGGAC-3' | (SEQ ID No. 68) | |
| | 5'-GTCCAAGAAGCAGCGTAACCGTCAG-3' | (SEQ ID No. 69) | |
| G404A | 5'-CTGTTCCATTCGCTGCTAGAGCTTAC-3' | (SEQ ID No. 70) | |
| | 5'-GTAAGCTCTAGCAGCGAATGGAACAG-3' | (SEQ ID No. 71) | |
| Q415E | 5'-GATGCAATGTGAAGCTGAAAAGGAACC-3' | (SEQ ID No. 72) | |
| | 5'-GGTTCCTTTTCAGCTTCACATTGCATC-3' | (SEQ ID No. 73) | |
| | Sal I | | |
| A437G | 5'-CACGGTTGTGGT*GTCGAC*AAGTTGGG-3' | (SEQ ID No. 74) | |
| | 5'-CCCAACTT*GTCGAC*ACCACAACCGTG-3' | (SEQ ID No. 75) | |
| | Mun I | | |
| A463E | 5'-GATCTGGTGG*CAATTG*GGAGGAATGTTTCG-3' | (SEQ ID No. 76) | |
| | 5'-CGAAACATTCCTCCC*AATTG*CCACCAGATC-3' | (SEQ ID No. 77) | | and accordingly for other mutations.

The temperature optimum of the purified phytases, expressed in *Saccharomyces cerevisiae* (Example 14), was determined as outlined in Example 14. Table 5 shows the effect on the stability of consensus phytase-1 for each mutation introduced.

TABLE 5

Stability effect of the individual amino acid replacements in consensus phytase-1
(+ or − means a positive, respectively, negative effect on the protein stability up to 1° C., ++ and −− means a positive, respectively, negative effect on the protein stability between 1° C. and 3° C.; the number 10 or 11 corresponds to the consensus phytase sequence that suggested the amino acid replacement.)

| stabilizing | | neutral | | destabilizing | |
|---|---|---|---|---|---|
| mutation | effect | Mutation | effect | Mutation | effect |
| E58A (10) | + | D69A | ± | Y54F (10) | − |
| D69K (11) | + | D70G (10) | ± | V73I | − |
| D197N (10) | + | N134Q (10) | ± | A94K (10) | − |
| T214L (10) | ++ | G186H | ± | A101R (11) | − |
| E222T (11) | ++ | S187A (10) | ± | K153N (11) | − |
| E267D (10) | + | T214V | ± | I158V (10) | −− |
| R291I* | + | T251N (10) | ± | G203A | −− |
| R329H (10) | + | Y259N (10) | ± | G205S | − |
| S364T (10) | ++ | A283D (10) | ± | A217V | − |
| A379K (11) | + | A320V (10) | ± | V227A (11) | −− |
| G404A (10) | ++ | K445T | ± | L234V (10) | − |
| | | A463E (10) | ± | A238P (10) | −− |
| | | | | E277Q (10) | − |
| | | | | H287A (11) | − |
| | | | | Q292A (10) | − |
| | | | | I366V (10) | − |
| | | | | S396A (10) | −− |
| | | | | Q415E (11) | − |
| | | | | A437G (10) | −− |
| | | | | E451R | −− |

*This amino acid replacement was found in another round of mutations.

We combined eight positive mutations (E58A, D197N, E267D, R291I, R329H, S364T, A379K, G404A) in consensus phytase-1 using the primers and the technique mentioned above in this example. Furthermore, the mutations Q50T and K91A were introduced which mainly influence the catalytical characteristics of the phytase (see EP 897 985 as well as Example 14). The DNA and amino acid sequence of the resulting phytase gene (consensus phytase-1-thermo[8]-Q50T-K91A) is shown in FIGS. 8A–8F. In this way, the temperature optimum and the melting point of the consensus phytase was increased by 7° C. (FIGS. 16, 17, 18).

Using the results of Table 5, we further improved the thermostability of consensus phytase 10 by the back mutations K94A, V158I, and A396S that revealed a strong negative influence on the stability of consensus phytase-1. The resulting protein is consensus phytase-10-thermo [3]. We also introduced the mutations Q50T and K91A which mainly influence the catalytical characteristics of consensus phytase (see EP 897 485 as well as Example 14 and FIGS. 15A–16B). The resulting DNA and amino acid sequence is shown in FIGS. 9A–9F. The optimized phytase showed a 4° C. higher temperature optimum and melting point than consensus phytase-10 (FIGS. 13A, 13B and 14). The phytase also had a strongly increased specific activity with phytate as substrate of 250 U/mg at pH 5.5 (FIGS. 15A–15B).

Example 9

Stabilization of the Phytase of *A. fumigatus* ATCC 13073 by Replacement of Amino Acid Residues with the Corresponding Consensus Phytase-1 and Consensus Phytase-10 Residues At six typical positions where the *A. fumigatus* 13073 phytase is the only or nearly the only phytase in the alignment of FIGS. 2A–2F that does not contain the corresponding consensus phytase amino acid residue, the non-consensus amino acid residue was replaced by the consensus one. In a first round, the following amino acids were substituted in *A. fumigatus* 13073 phytase, containing the Q51T substitution and the signal sequence of *A. terreus* cbs. 116.46 phytase (see FIGS. 10A–10F):

F55(28)Y, V100(73)I, F114(87)Y, A243(220)L, S265(242)P, N294(282)D.

The numbers in parentheses refer to the numbering of FIG. 2.

In a second round, four of the seven stabilizing amino acid exchanges (E59A, R329H, S364T, G404A) found in the consensus phytase-10 sequence and, tested as single mutations in consensus phytase-1 (Table 5), were additionally introduced into the *A. fumigatus* α-mutant. The amino acid replacement S154N, shown to reduce the protease susceptibility of the phytase, was also introduced.

The mutations were introduced as described in example 8 (see Table 6), and expressed as described in Examples 11 to 13. The resulting *A. fumigatus* 13073 phytase variants were called α-mutant and α-mutant-E59A-S154N-R329H-S364T-G404A.

The temperature optimum (60° C., FIG. 21) and the melting point (67.02° C., FIGS. 20A–20B) of the *A. fumigatus* 13073 phytase α-mutant were increased by 5–7° C. in comparison to the values of the wild-type (temperature optimum: 55° C., $T_m$: 60° C.). The five additional amino acid replacements further increased the temperature optimum by 3° C. (FIG. 21).

TABLE 6

Mutagenesis primers for stabilization of *A. fumigatus* phytase ATCC 13073

| Mutation | Primer | |
|---|---|---|
| F55Y | 5'-CACGTACTCGCCATACTTTTCGCTCGAG-3' | (SEQ ID No. 78) |
|  | 5'-CTCGAGCGAAAAGTATGGCGAGTACGTG-3' | (SEQ ID No. 79) |
|  | (Xho I) | |
| E58A | 5'-CCATACTTTTCG*CTCGC*GGACGAGCTGTCCGTG-3' | (SEQ ID No. 80) |
|  | 5'-CACGGACAGCTCGTC*CGCGA*GCGAAAAGTAGG-3' | (SEQ ID No. 81) |
| V100I | 5'-GTATAAGAAGCTTATTACGGCGATCCAGGCC-3' | (SEQ ID No. 82) |
|  | 5'-GGCCTGGATCGCCGTAATAAGCTTCTTATAC-3' | (SEQ ID No. 83) |
| F114Y | 5'-CTTCAAGGGCAAGTACGCCTTTTTGAAGACG-3' | (SEQ ID No. 84) |
|  | 5'-CGTCTTCAAAAAGGCGTACTTGCCCTTGAAG-3' | (SEQ ID No. 85) |
| A243L | 5'-CATCCGAGCTCGCCTCGAGAAGCATCTTC-3' | (SEQ ID No. 86) |
|  | 5'-GAAGATGCTTCTCGAGGCGAGCTCGGATG-3' | (SEQ ID No. 87) |
| S265P | 5'-CTAATGGATGTGTCCGTTTGATACGGTAG-3' | (SEQ ID No. 88) |
|  | 5'-CTACCGTATCAAACGGACACATGTCCATTAG-3' | (SEQ ID No. 89) |
| N294D | 5'-GTGGAAGAAGTACGACTACCTTCAGTC-3' | (SEQ ID No. 90) |
|  | 5'-GACTGAAGGTAGTCGTACTTCTTCCAC-3' | (SEQ ID No. 91) |
|  | (Mlu I) | |
| R329H | 5'-GCCCGGTTGA*CGCAT*TCGCCAGTGCAGG-3' | (SEQ ID No. 92) |
|  | 5'-CCTGCACTGGCGAA*TGCGT*CAACCGGGC-3' | (SEQ ID No. 93) |
|  | Nco I | |
| S364T | 5'-CACACGACAACAC*CATG*GTTTCCATCTTC-3' | (SEQ ID No. 94) |
|  | 5'-GAAGATGGAAACCATGGTGTTGTCGTGTG-3' | (SEQ ID No. 95) |
|  | (Bss HI) | |
| G404A | 5'-GTGGTGCCTTTCG*CCGCGC*GAGCCTACTTC-3' | (SEQ ID No. 96) |
|  | 5'-GAAGTAGGCTC*GCGCGG*CGAAAGGCACCAC-3' | (SEQ ID No. 97) |

Example 10

Introduction of the Active Site Amino Acid Residues of the *A. niger* NRRL 3135 Phytase Into the Consensus Phytase-1

We used the crystal structure of the *Aspergillus niger* NRRL 3135 phytase to define all active site amino acid residues (see Reference Example and EP 897 010, which is hereby incorporated by reference as if recited in full herein). Using the alignment of FIGS. 2A–2F, we replaced the following active site residues and additionally the non-identical adjacent residues of the consensus phytase-1 by those of the *A. niger* phytase:

S89D, S92G, A94K, D164S, P201S, G203A, G205S, H212P, G224A, D226T, E255T, D256E, V258T, P265S, Q292H, G300K, Y305H, A314T, S364G, M365I, A397S, S398A, G404A, and A405S The new sequence, consensus phytase-7, was backtranslated into a DNA sequence (FIGS. 11A–11F) as described in Example 6. The corresponding gene (fcp7) was generated as described in Example 6 using the following oligonucleotide mixes:

Mix 1.7: CP-1, CP-2, CP-3, CP-4.7, CP-5.7, CP-6, CP-7, CP-8.7, CP-9, CP-10.7

Mix 2.7: CP-9, CP-10.7, CP-11.7, CP-12.7, CP-13.7, CP-14.7, CP-15.7, CP-16, CP-17.7, CP-18.7, CP-19.7, CP-20, CP-21, CP-22.

The DNA sequences of the oligonucleotides are indicated in FIGS. 11A–11F. The newly synthesized oligonucleotides are additionally marked by the number "7." After assembling of the oligonucleotides using the s am e PCR primers as set forth in Example 6, the gene was cloned into an expression vector as described in Examples 11–13.

The pH-profile of consensus phytase-7, purified after expression in Hansenula polymorpha, was very similar to that of *A. niger* NRRL 3135 phytase (see FIGS. 19A–19B).

Example 11

Expression of the Consensus Phytase Genes in *Hansenula polymorpha*

The phytase expression vectors, used to transform *H. polymorpha* RB11 (Gellissen et al., 1994), were constructed by inserting the Eco RI fragment of pBsk-fcp or variants thereof into the multiple cloning site of the *H. polymorpha* expression vector pFPMT121, which is based on an ura3 selection marker from *S. cerevisiae*, a formate dehydrogenase (FMD) promoter element and a methanol oxidase (MO) terminator element from *H. polymorpha*. The 5' end of the fcp gene is fused to the FMD promoter, and the 3' end to the MOX terminator (Gellissen et al., 1996; EP 0299 108 B). The resulting expression vectors were designated pFPMTfcp, pFPMTfcp10, pFPMTfcp7.

The constructed plasmids were propagated in *E. coli*. Plasmid DNA was purified using standard state of the art procedures (see, for example, EP 897 985, Example 5). The expression plasmids were transformed into the *H. polymorpha* strain RP11 deficient in orotidine-5'-phosphate decarboxylase (ura3) using the procedure for preparation of competent cells and for transformation of yeast as described in Gelissen et al. (1996). Each transformation mixture was plated on YNB (0.14% w/v Difco YNB and 0.5% ammonium sulfate) containing 2% glucose and 1.8% agar and incubated at 37° C. After 4 to 5 days individual transformant colonies were picked and grown in the liquid medium described above for 2 days at 37° C. Subsequently, an aliquot of this culture was used to inoculate fresh vials with YNB-medium containing 2% glucose. After seven further passages in selective medium, the expression vector is integrated into the yeast genome in multimeric form. Subsequently, mitotically stable transformants were obtained by two additional cultivation steps in 3 ml non-selective liquid medium (YPD, 2% glucose, 10 g yeast extract, and 20 g peptone). To obtain genetically homogeneous recombinant strains, an aliquot from the last stabilization culture was plated on a selective plate. Single colonies were isolated for analysis of phytase expression in YNB containing 2% glycerol instead of glucose to derepress the fmd promoter. Purification of the consensus phytases was done as described in Example 12.

Example 12

Expression of the Consensus Phytase Genes in *Saccharomyces cerevisiae* and Purification of the Phytases from Culture Supernatant The consensus phytase genes were isolated from the corresponding Bluescript-plasmid (pBsk⁻fcp, pBSK⁻fcp10, pBsk⁻fcp7), and ligated into the Eco RI sites of the expression cassette of the *Saccharomyces cerevisiae* expression vector pYES2 (Invitrogen, San Diego, Calif., USA) or subcloned between the shortened GAPFL (glyceraldhyde-3-phosphate dehydrogenase) promoter and the pho5 terminator as described by Janes et al. (1990). The correct orientation of the gene was checked by PCR. Transformation of *S. cerevisiae* strains, e.g. INVSc1 (Invitrogen, San Diego, Calif., USA) was done according to Hinnen et al. (1978). Single colonies harboring the phytase gene under the control of the GAPFL promoter were picked and cultivated in 5 ml selection medium (SD-uracil, Sherman et al., 1986) at 30° C. under vigorous shaking (250 rpm) for one day. The preculture was then added to 500 ml YPD medium (Sherman et al., 1986) and grown under the same conditions. Induction of the gall promoter was done according to the manufacturer's (Invitrogen) instructions. After four days of incubation, cell broth was centrifuged (7000 rpm, GS3 rotor, 15 min, 5° C.) to remove the cells and the supernatant was concentrated by way of ultrafiltration in Amicon 8400 cells (PM30 membranes) and ultrafree-15 centrifugal filter devices (Biomax-30K, Millipore, Bedford, Mass., USA). The concentrate (10 ml) was desalted on a 40 ml Sephadex G25 Superfine column (Pharmacia Biotech, Freiburg, Germany), with 10 mM sodium acetate, pH 5.0, serving as elution buffer. The desalted sample was brought to 2 M $(NH_4)_2SO_4$ and directly loaded onto a 1 ml Butyl Sepharose 4 Fast Flow hydrophobic interaction chromatography column (Pharmacia Biotech, Freiburg, Germany) which was eluted with a linear gradient from 2 M to 0 M $(NH_4)_2SO_4$ in 10 mM sodium acetate, pH 5.0. Phytase was eluted in the breakthrough, concentrated and loaded on a 120 ml Sephacryl S-300 gel permeation chromatography column (Pharmacia Biotech, Freiburg, Germany). Consensus phytase-1 and consensus phytase-7 eluted as a homogeneous symmetrical peak and was shown by SDS-PAGE to be approximately 95% pure.

Example 13

Expression of the Consensus Phytase Genes in *Aspergillus niger*

The Bluescript-plasmids pBsk⁻fcp, pBSK⁻fcp10, and pBsk⁻fcp7 were used as template for the introduction of a Bsp HI-site upstream of the start codon of the genes and an Eco RV-site downstream of the stop codon. The Expand™ High Fidelity PCR Kit (Boehringer Mannheim, Mannheim, Germany) was used with the following primers:
Primer Asp-1:
 Bsp HI
  5'-TATATCATGAGCGTGTTCGTCGTGCTACT GTTC-3' (SEQ ID No. 98)
Primer Asp-2 used for cloning of fcp and fcp7:
 Eco RV
  3'-ACCCGACTTACAAAGCGAATTCTATAGA TATAT-5' (SEQ ID No. 99)
Primer Asp-3 used for cloning of fcp10:
 Eco RV
  3'-ACCCTTCTTACAAAGCGAATTCTATAG ATATAT-5' (SEQ ID No. 100)

The reaction was performed as described by the supplier. The PCR-amplified fcp-genes had a new Bsp HI site at the start codon, introduced by primer Asp-1, which resulted in a replacement of the second amino acid residue glycine by serine. Subsequently, the DNA-fragment was digested with Bsp HI and Eco RV and ligated into the Nco I site downstream of the glucoamylase promoter of *Aspergillus niger* (glaA) and the Eco RV site upstream of the *Aspergillus nidulans* tryptophan C terminator (trpC) (Mullaney et al., 1985). After this cloning step, the genes were sequenced to detect possible failures introduced by PCR. The resulting expression plasmids which basically correspond to the pGLAC vector as described in Example 9 of EP 684 313 contained the orotidine-5'-phosphate decarboxylase gene (pyr4) of *Neurospora crassa* as a selection marker. Transformation of *Aspergillus niger* and expression of the consensus phytase genes was done as described in EP 684 313. The consensus phytases were purified as described in Example 12.

Example 14

Determination of Phytase Activity and of Temperature Optimum

Phytase activity was determined basically as described by Mitchell et al. (1997). The activity was measured in an assay mixture containing 0.5% phytic acid (≈5 mM) in 200 mM sodium acetate, pH 5.0. After 15 minutes of incubation at 37° C., the reaction was stopped by addition of an equal volume of 15% trichloroacetic acid. The liberated phosphate was quantified by mixing 100 μl of the assay mixture with 900 μl $H_2O$ and 1 ml of 0.6 M $H_2SO_4$, 2% ascorbic acid and 0.5% ammonium molybdate. Standard solutions of potassium phosphate were used as reference. One unit of enzyme activity was defined as the amount of enzyme that releases 1 μmol phosphate per minute at 37° C. The protein concentration was determined using the enzyme extinction coefficient at 280 nm calculated according to Pace et al. (1995): consensus phytase-1.101; consensus phytase-7, 1.068; consensus phytase-1 10, 1.039.

In case of pH-optimum curves, purified enzymes were diluted in 10 mM sodium acetate, pH 5.0. Incubations were started by mixing aliquots of the diluted protein with an equal volume of 1% phytic acid (≈10 mM) in a series of different buffers: 0.4 M glycine/HCl, pH 2.5; 0.4 M acetate/ NaOH, pH 3.0, 3.5, 4.0, 4.5, 5.0, 5.5; 0.4 M imidazole/HCl, pH 6.0, 6.5; 0.4 M Tris/HCl pH 7.0, 7.5, 8.0, 8.5, 9.0. Control experiments showed that the pH was only slightly affected by the mixing step. Incubations were performed for 15 minutes at 37° C. as described above.

For determining the substrate specificities of the phytases, phytic acid in the assay mixture was replaced by 5 mM concentrations of the respective phosphate compounds. The activity tests were performed as described above.

For determination of the temperature optimum, enzyme (100 μl) and substrate solution (100 μl) were pre-incubated for 5 minutes at the given temperature. The reaction was started by addition of the substrate solution to the enzyme. After 15 minutes of incubation, the reaction was stopped with trichloroacetic acid and the amount of phosphate released was determined.

The pH-optimum of the original consensus phytase was about pH 6.0–6.5 (80 U/mg). By introduction of the Q50T mutation, the pH-optimum shifted to pH 6.0 (130 U/mg). After introduction of K91A, the pH optimum shifted one pH-unit into the acidic pH-range showing a higher specific activity between pH 2.5 and pH 6.0. That was shown for the stabilized mutants and for consensus phytase-10, too (FIGS. 15A–16B).

Consensus phytase-7, which was constructed to transfer the catalytic characteristics of the A. niger NRRL 3135 phytase into consensus phytase-1, had a pH-profile very similar to that of A. niger NRRL 3135 phytase (see FIGS. 19A–19B). The substrate specificity of consensus phytase-7 also resembled A. niger NRRL 3135 phytase more than it resembled consensus phytase-1.

The temperature optimum of consensus phytase-1 (71° C.) was 16–26° C. higher than the temperature optimum of the wild-type phytases (45–55° C., Table 7) which were used to calculate the consensus sequence. The improved consensus phytase-10 showed a further increase of its temperature optimum to 80° C. (FIGS. 12A–12B). The temperature optimum of the consensus phytase-1-thermo[8] phytase was found in the same range (78° C.) when using the supernatant of an overproducing S. cerevisiae strain. The highest temperature optimum reached of 82° C. was determined for consensus phytase-10-thermo[3]-Q50T-K91A.

TABLE 7

Temperature optimum and $T_m$-value of consensus phytase and of the phytases from A. fumigatus, A. niger, E. nidulans, and M. thermophila. The determination of the temperature optimum was performed as described in Example 14. The $T_m$-values were determined by differential scanning calorimetry as described in Example 15

| Phytase | Temperature optimum [° C.] | Tm [° C.] |
|---|---|---|
| Consensus phytase-10-thermo[3]-Q50T-K91A | 82 | 89.3 |
| Consensus phytase-10-thermo[3]-Q50T | 82 | 88.6 |
| Consensus phytase-10 | 80 | 85.4 |
| Consensus phytase-1-thermo[8]-Q50T | 78 | 84.7 |
| Consensus phytase-1-thermo[8]-Q50T-K91A | 78 | 85.7 |
| Consensus phytase-1 | 71 | 78.1 |
| A. niger NRRL3135 | 55 | 63.3 |
| A. fumigatus 13073 | 55 | 62.5 |
| A. fumigatus 13073 α-mutant | 60 | 67.0 |
| A. fumigatus 13073 α-mutant (optimized) | 63 | — |
| A. terreus 9A-1 | 49 | 57.5 |
| A. terreus cbs.116.46 | 45 | 58.5 |
| E. nidulans | 45 | 55.7 |

TABLE 7-continued

Temperature optimum and $T_m$-value of consensus phytase and of the phytases from A. fumigatus, A. niger, E. nidulans, and M. thermophila. The determination of the temperature optimum was performed as described in Example 14. The $T_m$-values were determined by differential scanning calorimetry as described in Example 15

| Phytase | Temperature optimum [° C.] | Tm [° C.] |
|---|---|---|
| M. thermophila | 55 | n.d. |
| T. thermophilus | 45 | n.d. |

Example 15

Determination of the Melting Point by Differential Scanning Calorimetry (DSC)

To determine the unfolding temperature of the phytases, differential scanning calorimetry was applied as previously published by Lehmann et al. (2000). Solutions of 50–60 mg/ml homogeneous phytase were used for the tests. A constant heating rate of 10° C./min was applied up to 90–95° C.

The determined melting points reflect the results obtained for the temperature optima (Table 7). The most stable consensus phytase designed is consensus phytase-10-thermo[3]-Q50T-K91A showing a melting temperature under the chosen conditions of 89.3° C. This is 26 to 33.6° C. higher than the melting points of the wild-type phytases used.

Example 16

Transfer of Basidiomycete Phytase Active Site Into Consensus Phytase-10-thermo[3]-Q50T-K91A As described previously (Example 8), mutations derived from the basidiomycete phytase active site were introduced into the consensus phytase-10. The following five constructs a) to e) were prepared:

(a) This construct is called consensus phytase-12, and it contains a selected number of active site residues of the basidio consensus sequence. Its amino acid sequence (conspy 12) is shown in FIG. 22 (the first 26 amino acids form the signal peptide, amended positions are underlined);

(b) a cluster of mutations (Cluster II) was transferred to the consensus phytase 10 sequence, viz.: S80Q, Y86F, S90G, K91A, S92A, K93T, A94R, Y95I;

(c) another cluster of mutations (Cluster III) was transferred to the consensus phytase-10 sequence, viz.: T129V, E133A, Q143N, M136S, V137S, N138Q, S139A;

(d) a further cluster of mutations (Cluster IV) was transferred to the consensus phytase-10 sequence, viz.: A168D, E171T, K172N, F173W;

(e) and finally, a further cluster of mutations (Cluster V) was transferred to the consensus phytase-10 sequence, viz.: Q297G, S298D, G300D, Y305T.

These constructs were expressed as described in Examples 11–13.

The following references are incorporated herein by reference as if recited in full herein:

Akanuma, S., Yamagishi, A., Tanaka, N. & Oshima, T. (1998). Serial increase in the thermal stability of 3-isopropylmalate dehydrogenase from Bacillus subtilis by experimental evolution. Prot. Sci. 7, 698–705.

Arase, A., Yomo, T., Urabe, I., Hata, Y., Katsube, Y. & Okada, H. (1993). Stabilization of xylanase by random mutagenesis. *FEBS Lett*, 316, 123–127.

Berka, R. M., Rey, M. W., Brown, K. M., Byun, T. & Klotz, A. V. (1998). Molecular characterization and expression of a phytase gene from the thermophilic fungus Thermomyces lanuginosus. *Appl. Environ. Microbiol.* 64, 4423–4427.

Blaber, M., Lindstrom, J. D., Gassner, N., Xu, J., Heinz, D. W. & Matthews, B. W. (1993). Energetic cost and structural consequences of burying a hydroxyl group within the core of a protein determined from Ala'Ser and Val'Thr substitutions in T4 lysozyme. *Biochemistry* 32, 11363–11373.

Cosgrove, D. J. (1980) Inositol phosphates—their chemistry, biochemistry and physiology: studies in organic chemistry, chapter 4. Elsevier Scientific Publishing Company, Amsterdam, Oxford, New York.

Devereux, J., Haeberli, P.& Smithies, O. (1984) A comprehensive set of sequence analysis programs for the VAX. *Nucleic Acids Res.* 12, 387–395.

Gellissen, G., Hollenberg, C. P., Janowicz, Z. A. (1994) Gene expression in methylotrophic yeasts . In: Smith, A. (ed.) Gene expression in recombinant microorganisms. Dekker, New York, 395–439.

Gellissen, G., Piontek, M., Dahlems, U., Jenzelewski, V., Gavagan, J. E., DiCosimo, R., Anton, D. I. & Janowicz, Z. A. (1996) Recombinant *Hansenula polymorpha* as a biocatalyst: coexpression of the spinach glycolate oxidase (GO) and the *S. cerevisiae* catalase T (CTT1) gene. *Appl. Microbiol. Biotechnol.* 46, 46–54.

Gerber, P. and Müller, K. (1995) Moloc molecular modeling software. *J. Comput. Aided Mol. Des.* 9, 251–268

Hinnen, A., Hicks, J. B. & Fink, G, R. (1978) Transformation of yeast. *Proc. Natl. Acad. Sci. USA* 75, 1929–1933.

Imanaka, T., Shibazaki, M. & Takagi, M. (1986). A new way of enhancing the thermostability of proteases. *Nature* 324, 695–697.

Janes, M., Meyhack, B., Zimmermann, W. & Hinnen, A. (1990) The influence of GAP promoter variants on hirudine production, average plasmid copy number and cell growth in *Saccharomyces cerevisiae*. *Curr. Genet.* 18, 97–103.

Karpusas, M., Baase, W. A., Matsumura, M. & Matthews, B. W. (1989). Hydrophobic packing in T4 lysozyme probed by cavity-filling mutants. *Proc. Natl. Acad. Sci. (USA)* 86, 8237–8241.

Lehmann, L., Kostrewa, D., Wyss, M., Brugger, R., D'Arcy, A., Pasamontes, L., van Loon, A. (2000), From DNA sequence to improved functionality: using protein sequence comparisons to rapidly design a thermostable consensus phytase, *Protein Engineering* 13, 49–57.

Margarit, I., Campagnoli, S., Frigerio, F., Grandi, G., Fillipis, V. D. & Fontana, A. (1992). Cumulative stabilizing effects of glycine to alanine substitutions in *Bacillus subtilis* neutral protease. *Prot. Eng.* 5, 543–550.

Matthews, B. W. (1987a). Genetic and structural analysis of the protein stability problem. *Biochemistry* 26, 6885–6888.

Matthews, B. W. (1993). Structural and genetic analysis of protein stability. *Annu. Rev. Biochem.* 62, 139–160.

Matthews, B. W., Nicholson, H. & Becktel, W. (1987). Enhanced protein thermostability from site-directed mutations that decrease the entropy of unfolding. *Proc. Natl. Acad. Sci. (USA)* 84, 6663–6667.

Mitchell, D. B., Vogel, K., Weimann, B. J., Pasamontes, L. & van Loon, A. P. G. M. (1997) The phytase subfamily of histidine acid phosphatases: isolation of genes for two novel phytases from the fungi *Aspergillus terreus* and *Myceliophthora thermophila*, *Microbiology* 143, 245–252.

Mullaney, E. J., Hamer, J. E., Roberti, K. A., Yelton, M. M. & Timberlake, W. E. (1985) Primary structure of the trpC gene from *Aspergillus nidulans*. *Mol. Gen. Genet.* 199, 37–46.

Munoz, V. & Serrano, L. (1995). Helix design, prediction and stability. *Curr. Opin. Biotechnol.* 6, 382–386.

Pace, N. C., Vajdos, F., Fee, L., Grimsley, G. & Gray, T. (1995). How to measure and predict the molar absorption coefficient of a protein. *Prot. Sci.* 4, 2411–2423.

Pantoliano, M. W., Landner, R. C., Brian, P. N., Rollence, M. L., Wood, J. F. & Poulos, T. L. (1987). Protein engineering of subtilisin BPN': enhanced stabilization through the introduction of two cysteines to form a disulfide bond. *Biochemistry* 26, 2077–2082.

Pasamontes, L., Haiker, M., Henriquez-Huecas, M., Mitchell, D. B. & van Loon, A. P. G. M. (1997a). Cloning of the phytases from *Emericella nidulans* and the thermophilic fungus *Talaromyces thermophilus*. *Biochim. Biophys. Acta* 1353, 217–223.

Pasamontes, L., Haiker, M., Wyss, M., Tessier, M. & van Loon, A. P. G. M. (1997) Cloning, purification and characterization of a heat stable phytase from the fungus *Aspergillus fumigatus*, *Appl. Environ. Microbiol.* 63, 1696–1700.

Piddington, C. S., Houston, C. S., Paloheimo, M., Cantrell, M., Miettinen-Oinonen, A. Nevalainen, H., & Rambosek, J. (1993) The cloning and sequencing of the genes encoding phytase (phy) and pH 2.5-optimum acid phosphatase (aph) from *Aspergillus niger* var. awamori. *Gene* 133, 55–62.

Purvis, I. J., Bettany, A. J. E., Santiago, T. C., Coggins, J. R., Duncan, K., Eason, R. & Brown, A. J. P. (1987). The efficiency of folding of some proteins is increased by controlled rates of translation in vivo. *J. Mol. Biol.* 193, 413–417.

Risse, B., Stempfer, G., Rudolph, R., Schumacher, G. & Jaenicke, R. (1992). Characterization of the stability effect of point mutations of pyruvate oxidase from *Lactobacillus plantarum*: protection of the native state by modulating coenzyme binding and subunit interaction. *Prot. Sci.* 1, 1710–1718.

Sambrook, J., Fritsch, E. F. & Maniatis, T. (1989) *Molecular Cloning: A Laboratory Manual*, 2nd Ed., Cold Spring Harbor Laboratory, Cold Spring Harbor, N.Y.

Sauer, R., Hehir, K., Stearman, R., Weiss, M., Jeitler-Nilsson, A., Suchanek, E. &

Pabo, C. (1986). An engineered intersubunit disulfide enhances the stability and DNA binding of the N-terminal domain of 1-repressor. *Biochemistry* 25, 5992–5999.

Serrano, L., Day, A. G. & Fersht, A. R. (1993). Step-wise mutation of barnase to binase. A procedure for engineering increased stability of proteins and an experimental analysis of the evolution of protein stability. *J. Mol. Biol.* 233, 305–312.

Sheman, J. P., Finck, G. R. & Hicks, J. B. (1986) Laboratory course manual for methods in yeast genetics. Cold Spring Harbor University.

Steipe, B., Schiller, B., Plueckthun, A. & Steinbach, S. (1994). Sequence statistics reliably predict stabilizing mutations in a protein domain. *J. Mol. Biol.* 240, 188–192.

van den Burg, B., Vriend, G., Veltman, O. R., Venema & G., Eijsink, V. G. H. (1998). Engineering an enzyme to resist boiling. *Proc. Natl. Acad. Sci. (USA)* 95, 2056–2060.

Van Etten, R.L. (1982) Human prostatic acid phosphatase: a histidine phosphatase. *Ann. NY cad. Sci.* 390, 27–50.

van Hartingsveldt, W., van Zeijl, C. M. F., Harteveld, G. M., Gouka, R. J., Suykerbuyk, M. E. G., Luiten, R. G. M., van Paridon, P. A., Selten, G. C. M., Veenstra, A. E., van Gorcom, R. F. M., & van den Hondel, C. A. M. J. J. (1993) Cloning, characterization and overexpression of the phytase-encoding gene (phyA) of *Aspergillus niger*. *Gene* 127, 87–94.

The invention being thus described, it will be obvious that the same may be varied in many ways. Such variations are not to be regarded as a departure from the spirit and scope of the invention and all such modifications are intended to be included within the scope of the following claims.

What is claimed is:

1. A fermentation assembly comprising
   (a) a vessel for culturing living cells;
   (b) at least three storage flasks, wherein one of the storage flasks contains water, in fluid communication with the vessel for supply of liquids and a first transport means for transferring the liquids from the storage flasks to the vessel;
   (c) individual appliances operably connected to the transport means for monitoring the supply of the contents of the storage flasks to the vessel;
   (d) a harvest flask in fluid communication with the vessel and a second transport means for transferring the fermentation broth from the vessel to the harvest flask; and
   (e) a device operably connected to the first transport means for controlling and maintaining a cons ant dilution rate in the vessel with varying rates of indi vidual supply of liquid from the storage flasks to the vessel.

2. A fermentation assembly according to claim 1 wherein the at least three storage flasks comprise individual storage flasks for solutions of carbon, nitrogen, and mineral sources.

3. A fermentation assembly according to claim 1 wherein at least one of the at least three storage flasks contains a controlling agent.

4. A fermentation assembly according to claim 1 wherein the vessel contains a bed of immobilized living cells.

5. A fermentation assembly according to claim 4 wherein the bed of immobilized cells is selected from the group consisting of a fixed bed, an expanded bed, a moving bed, and combinations thereof.

6. An assembly according to claim 4 wherein the living cells are immobilized on a porous carrier.

* * * * *

UNITED STATES PATENT AND TRADEMARK OFFICE
CERTIFICATE OF CORRECTION

PATENT NO.    : 6,599,735 B1
DATED         : July 29, 2003
INVENTOR(S)   : Attila Bartók et al.

It is certified that error appears in the above-identified patent and that said Letters Patent is hereby corrected as shown below:

<u>Column 219,</u>
Line 44, please change "cons ant" to -- constant --.

Signed and Sealed this

Fourteenth Day of October, 2003

JAMES E. ROGAN
*Director of the United States Patent and Trademark Office*

SEQUENCE LISTING

```
<160> NUMBER OF SEQ ID NOS: 169

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 1
tatatgaatt catgggcgtg ttcgtc                                          26

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 2
tgaaaagttc attgaaggtt tc                                              22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 3
tcttcgaaag cagtacaagt ac                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 4
tatatgaatt cttaagcgaa ac                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 5
tcttcgaaag cagtacacaa ac                                              22

<210> SEQ ID NO 6
<211> LENGTH: 32
```

```
<212> TYPE: DNA
<213> ORGANISM: Artificial Sequence
<220> FEATURE:
<223> OTHER INFORMATION: Description of Artificial Sequence:Primer

<400> SEQUENCE: 6
cacttgtggg gtacctactc tccatacttc tc                              32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 7
gagaagtatg gagagtaggt accccacaag tg                              32

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 8
ggtcaatact ctccattctt ctctttggaa g                               31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 9
cttccaaaga gaagaatgga gagtattgac c                               31

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 10
catacttctc tttggcagac gaatctgc                                   28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 11
gcagattcgt ctgccaaaga gaagtatg                                   28

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 12
```
ctccagacgt cccaaaggac tgtagagtta c                   31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 13
gtaactctac agtcctttgg gacgtctgga g                   31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 14
ctccagacgt cccagacggc tgtagagtta c                   31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 15
gtaactctac agccgtctgg gacgtctgga g                   31

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 16
gatacccaac ttcttctgcg tctaaggctt actctg              36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 17
cagagtaagc cttagacgca gaagaagttg ggtatc              36

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 18
cttctaagtc taagaagtac tctgctttg                      29

<210> SEQ ID NO 19
<211> LENGTH: 29
<212> TYPE: DNA
<213> ORGANISM: Artificial Sequence

```
<220> FEATURE:
<223> OTHER INFORMATION: Description of Artificial Sequence:Primer

<400> SEQUENCE: 19
caaagcagag tacttcttag acttagaag                                29

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence:Primer

<400> SEQUENCE: 20
gcttactctg ctttgattga acggattcaa agaacgcta c                   41

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence:Primer

<400> SEQUENCE: 21
gtagcgttct ttgaatccg ttcaatcaaa gcagagtaag c                   41

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 22
ccattcggtg aacagcaaat ggttaactc                                29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 23
gagttaacca tttgctgttc accgaatgg                                29

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 24
gatacaaggc tctcgcgaga acattgttc                                30

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 25
ggaacaatgt ttctcgcgag agccttgtat c                             31
```

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 26
gattgttcca ttcgtgcgcg cttctggttc                               30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 27
gaaccagaag cgcgcacgaa tggaacaatc                               30

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 28
ctccagttat taacgtgatc attccagaag g                             31

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 29
ccttctggaa tgatcacgtt aataactgga g                             31

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 30
ggctgaccca ggggcccaac cacaccaagc                               30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 31
gcttggtgtg gttgggcccc tgggtcagcc                               30

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 32
cactttggac catggtcttt gtactgcttt cg                    32

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 33
cgaaagcagt acaaagacca tggtccaaag tg                    32

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 34
gctttcgaag actctaccct aggtgacgac gttg                  34

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 35
caacgtcgtc acctagggta gagtcttcga aagc                  34

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 36
ggtgacgacg ctgaagctaa cttcac                           26

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 37
gtgaagttag cttcagcgtc gtcacc                           26

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 38
ctaacttcac cgcggtgttc gctccag                          27

<210> SEQ ID NO 39

```
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 39
ctggagcgaa caccgcggtg aagttag                                27

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 40
gctttgttcg ctccacctat tagagctaga ttgg                        34

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence:Primer

<400> SEQUENCE: 41
ccaatctagc tctaataggt ggagcgaaca aagc                        34

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 42
gccaggtgtt aacttgactg acgaag                                 26

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 43
ttcgtcagtc aagttaacac ctggc                                  25

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 44
gacgaagacg tcgttaactt gatggac                                27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 45
```

```
gtccatcaag ttaacgacgt cttcgtc                                        27

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 46
gtccattcga cactgtcgct agaacttc                                       28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 47
gaagttctag cgacagtgtc gaatggac                                       28

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 48
ctgacgctac tcagctgtct ccattc                                         26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 49
gaatggagac agctgagtag cgtcag                                         26

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 50
gtctccattc tgtgatttgt tcactcac                                       28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 51
gtgagtgaac aaatcacaga atggagac                                       28

<210> SEQ ID NO 52
<211> LENGTH: 26
<212> TYPE: DNA
```

```
<213> ORGANISM: Artificial Sequence
<220> FEATURE:
<223> OTHER INFORMATION: Description of Artificial Sequence:Primer

<400> SEQUENCE: 52
gctttgttca ccgcggacga atggag                                          26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 53
ctccattcgt ccgcggtgaa caaagc                                          26

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 54
cacgacgaat ggatccaata cgactac                                         27

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 55
gtagtcgtat tggatccatt cgtcgtg                                         27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 56
gacgaatgga gagcgtacga ctacttg                                         27

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 57
caagtagtcg tacgctctcc attcgtc                                         27

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 58
ggtgttggtt tcgttaacga attgattgc                                       29
```

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 59
gcaatcaatt cgttaacgaa accaacacc                                    29

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 60
gctagattga ctcactctcc agttcaag                                     28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 61
cttgaactgg agagtgagtc aatctagc                                     28

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 62
ctcacgacaa cactatgata tctattttct tc                                32

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 63
gaagaaaata gatatcatag tgttgtcgtg ag                                32

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 64
cgacaactcc atggtttcta ttttcttcgc                                   30

<210> SEQ ID NO 65
<211> LENGTH: 30
<212> TYPE: DNA
<213> ORGANISM: Artificial Sequence
<220> FEATURE:

```
<223> OTHER INFORMATION: Description of Artificial Sequence:Primer

<400> SEQUENCE: 65
gcgaagaaaa tagaaaccat ggagttgtcg                                    30

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 66
gtacaacggt accaagccat tgtctac                                       27

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 67
gtagacaatg gcttggtacc gttgtac                                       27

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 68
ctgacggtta cgctgcttct tggac                                         25

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 69
gtccaagaag cagcgtaacc gtcag                                         25

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 70
ctgttccatt cgctgctaga gcttac                                        26

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 71
gtaagctcta gcagcgaatg gaacag                                        26
```

```
<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 72
gatgcaatgt gaagctgaaa aggaacc                                              27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 73
ggttcctttt cagcttcaca ttgcatc                                              27

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 74
cacggttgtg gtgtcgacaa gttggg                                               26

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 75
cccaacttgt cgacaccaca accgtg                                               26

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 76
gatctggtgg caattgggag gaatgtttcg                                           30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 77
cgaaacattc ctcccaattg ccaccagatc                                           30

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence:Primer
```

-continued

```
<400> SEQUENCE: 78
cacgtactcg ccatactttt cgctcgag                                              28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 79
ctcgagcgaa aagtatggcg agtacgtg                                              28

<210> SEQ ID NO 80
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 80
ccatactttt cgctcgcgga cgagctgtcc gtg                                        33

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 81
cacggacagc tcgtccgcga gcgaaaagta gg                                         32

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 82
gtataagaag cttattacgg cgatccaggc c                                          31

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 83
ggcctggatc gccgtaataa gcttcttata c                                          31

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 84
cttcaagggc aagtacgcct ttttgaagac g                                          31

<210> SEQ ID NO 85
<211> LENGTH: 31
```

```
<212> TYPE: DNA
<213> ORGANISM: Artificial Sequence
<220> FEATURE:
<223> OTHER INFORMATION: Description of Artificial Sequence:Primer

<400> SEQUENCE: 85
cgtcttcaaa aaggcgtact tgcccttgaa g                           31

<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 86
catccgagct cgcctcgaga agcatcttc                              29

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 87
gaagatgctt ctcgaggcga gctcggatg                              29

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 88
ctaatggatg tgtccgtttg atacggtag                              29

<210> SEQ ID NO 89
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 89
ctaccgtatc aaacggacac atgtccatta g                           31

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 90
gtggaagaag tacgactacc ttcagtc                                27

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 91
```
gcccggttga cgcattcgcc agtgcagg                                              28

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 92
gactgaaggt agtcgtactt cttccac                                               27

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 93
cctgcactgg cgaatgcgtc aaccgggc                                              28

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 94
cacacgacaa caccatggtt tccatcttc                                             29

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence:Primer

<400> SEQUENCE: 95
gaagatggaa accatggtgt tgtcgtgtg                                             29

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 96
gtggtgcctt tcgccgcgcg agcctacttc                                            30

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 97
gaagtaggct cgcgcggcga aaggcaccac                                            30

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 98
tatatcatga gcgtgttcgt cgtgctactg ttc                                    33

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 99
acccgactta caaagcgaat tctatagata tat                                    33

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence:Primer

<400> SEQUENCE: 100
acccttctta caaagcgaat tctatagata tat                                    33

<210> SEQ ID NO 101
<211> LENGTH: 440
<212> TYPE: PRT
<213> ORGANISM: A. terreus 9A-1

<400> SEQUENCE: 101

Lys His Ser Asp Cys Asn Ser Val Asp His Gly Tyr Gln Cys Phe Pro
 1               5                  10                  15

Glu Leu Ser His Lys Trp Gly Leu Tyr Ala Pro Tyr Phe Ser Leu Gln
            20                  25                  30

Asp Glu Ser Pro Phe Pro Leu Asp Val Pro Glu Asp Cys His Ile Thr
        35                  40                  45

Phe Val Gln Val Leu Ala Arg His Gly Ala Arg Ser Pro Thr His Ser
    50                  55                  60

Lys Thr Lys Ala Tyr Ala Ala Thr Ile Ala Ala Ile Gln Lys Ser Ala
65                  70                  75                  80

Thr Ala Phe Pro Gly Lys Tyr Ala Phe Leu Gln Ser Tyr Asn Tyr Ser
                85                  90                  95

Leu Asp Ser Glu Glu Leu Thr Pro Phe Gly Arg Asn Gln Leu Arg Asp
           100                 105                 110

Leu Gly Ala Gln Phe Tyr Glu Arg Tyr Asn Ala Leu Thr Arg His Ile
       115                 120                 125

Asn Pro Phe Val Arg Ala Thr Asp Ala Ser Arg Val His Glu Ser Ala
   130                 135                 140

Glu Lys Phe Val Glu Gly Phe Gln Thr Ala Arg Gln Asp Asp His His
145                 150                 155                 160

Ala Asn Pro His Gln Pro Ser Pro Arg Val Asp Val Ala Ile Pro Glu
                165                 170                 175

Gly Ser Ala Tyr Asn Asn Thr Leu Glu His Ser Leu Cys Thr Ala Phe
            180                 185                 190

Glu Ser Ser Thr Val Gly Asp Asp Ala Val Ala Asn Phe Thr Ala Val
        195                 200                 205

Phe Ala Pro Ala Ile Ala Gln Arg Leu Glu Ala Asp Leu Pro Gly Val

-continued

```
                210                 215                 220
Gln Leu Ser Thr Asp Asp Val Val Asn Leu Met Ala Met Cys Pro Phe
225                 230                 235                 240

Glu Thr Val Ser Leu Thr Asp Asp Ala His Thr Leu Ser Pro Phe Cys
                245                 250                 255

Asp Leu Phe Thr Ala Thr Glu Trp Thr Gln Tyr Asn Tyr Leu Leu Ser
                260                 265                 270

Leu Asp Lys Tyr Tyr Gly Tyr Gly Gly Asn Pro Leu Gly Pro Val
                275                 280                 285

Gln Gly Val Gly Trp Ala Asn Glu Leu Met Ala Arg Leu Thr Arg Ala
    290                 295                 300

Pro Val His Asp His Thr Cys Val Asn Asn Thr Leu Asp Ala Ser Pro
305                 310                 315                 320

Ala Thr Phe Pro Leu Asn Ala Thr Leu Tyr Ala Asp Phe Ser His Asp
                325                 330                 335

Ser Asn Leu Val Ser Ile Phe Trp Ala Leu Gly Leu Tyr Asn Gly Thr
                340                 345                 350

Ala Pro Leu Ser Gln Thr Ser Val Glu Ser Val Ser Gln Thr Asp Gly
                355                 360                 365

Tyr Ala Ala Trp Thr Val Pro Phe Ala Ala Arg Ala Tyr Val Glu
    370                 375                 380

Met Met Gln Cys Arg Ala Glu Lys Glu Pro Leu Val Arg Val Leu Val
385                 390                 395                 400

Asn Asp Arg Val Met Pro Leu His Gly Cys Pro Thr Asp Lys Leu Gly
                405                 410                 415

Arg Cys Lys Arg Asp Ala Phe Val Ala Gly Leu Ser Phe Ala Gln Ala
                420                 425                 430

Gly Gly Asn Trp Ala Asp Cys Phe
            435                 440
```

<210> SEQ ID NO 102
<211> LENGTH: 440
<212> TYPE: PRT
<213> ORGANISM: A. terreus cbs

<400> SEQUENCE: 102

```
Asn His Ser Asp Cys Thr Ser Val Asp Arg Gly Tyr Gln Cys Phe Pro
1               5                   10                  15

Glu Leu Ser His Lys Trp Gly Leu Tyr Ala Pro Tyr Phe Ser Leu Gln
                20                  25                  30

Asp Glu Ser Pro Phe Pro Leu Asp Val Pro Asp Asp Cys His Ile Thr
            35                  40                  45

Phe Val Gln Val Leu Ala Arg His Gly Ala Arg Ser Pro Thr Asp Ser
    50                  55                  60

Lys Thr Lys Ala Tyr Ala Ala Thr Ile Ala Ala Ile Gln Lys Asn Ala
65                  70                  75                  80

Thr Ala Leu Pro Gly Lys Tyr Ala Phe Leu Lys Ser Tyr Asn Tyr Ser
                85                  90                  95

Met Gly Ser Glu Asn Leu Thr Pro Phe Gly Arg Asn Gln Leu Gln Asp
            100                 105                 110

Leu Gly Ala Gln Phe Tyr Arg Arg Tyr Asp Thr Leu Thr Arg His Ile
    115                 120                 125

Asn Pro Phe Val Arg Ala Ala Asp Ser Ser Arg Val His Glu Ser Ala
            130                 135                 140
```

-continued

Glu Lys Phe Val Glu Gly Phe Gln Asn Ala Arg Gln Gly Asp Pro His
145                 150                 155                 160

Ala Asn Pro His Gln Pro Ser Pro Arg Val Asp Val Ile Pro Glu
            165                 170                 175

Gly Thr Ala Tyr Asn Asn Thr Leu Glu His Ser Ile Cys Thr Ala Phe
            180                 185                 190

Glu Ala Ser Thr Val Gly Asp Ala Ala Asp Asn Phe Thr Ala Val
        195                 200                 205

Phe Ala Pro Ala Ile Ala Lys Arg Leu Glu Ala Asp Leu Pro Gly Val
210                 215                 220

Gln Leu Ser Ala Asp Val Val Asn Leu Met Ala Met Cys Pro Phe
225                 230                 235                 240

Glu Thr Val Ser Leu Thr Asp Asp Ala His Thr Leu Ser Pro Phe Cys
            245                 250                 255

Asp Leu Phe Thr Ala Ala Glu Trp Thr Gln Tyr Asn Tyr Leu Leu Ser
            260                 265                 270

Leu Asp Lys Tyr Tyr Gly Tyr Gly Gly Asn Pro Leu Gly Pro Val
        275                 280                 285

Gln Gly Val Gly Trp Ala Asn Glu Leu Ile Ala Arg Leu Thr Arg Ser
290                 295                 300

Pro Val His Asp His Thr Cys Val Asn Asn Thr Leu Asp Ala Asn Pro
305                 310                 315                 320

Ala Thr Phe Pro Leu Asn Ala Thr Leu Tyr Ala Asp Phe Ser His Asp
            325                 330                 335

Ser Asn Leu Val Ser Ile Phe Trp Ala Leu Gly Leu Tyr Asn Gly Thr
            340                 345                 350

Lys Pro Leu Ser Gln Thr Thr Val Glu Asp Ile Thr Arg Thr Asp Gly
            355                 360                 365

Tyr Ala Ala Ala Trp Thr Val Pro Phe Ala Ala Arg Ala Tyr Ile Glu
370                 375                 380

Met Met Gln Cys Arg Ala Glu Lys Gln Pro Leu Val Arg Val Leu Val
385                 390                 395                 400

Asn Asp Arg Val Met Pro Leu His Gly Cys Ala Val Asp Asn Leu Gly
            405                 410                 415

Arg Cys Lys Arg Asp Asp Phe Val Glu Gly Leu Ser Phe Ala Arg Ala
            420                 425                 430

Gly Gly Asn Trp Ala Glu Cys Phe
            435                 440

<210> SEQ ID NO 103
<211> LENGTH: 441
<212> TYPE: PRT
<213> ORGANISM: A. niger var. awamori

<400> SEQUENCE: 103

Asn Gln Ser Thr Cys Asp Thr Val Asp Gln Gly Tyr Gln Cys Phe Ser
1               5                   10                  15

Glu Thr Ser His Leu Trp Gly Gln Tyr Ala Pro Phe Ser Leu Ala
            20                  25                  30

Asn Glu Ser Ala Ile Ser Pro Asp Val Pro Ala Gly Cys Arg Val Thr
        35                  40                  45

Phe Ala Gln Val Leu Ser Arg His Gly Ala Arg Tyr Pro Thr Glu Ser
    50                  55                  60

Lys Gly Lys Lys Tyr Ser Ala Leu Ile Glu Glu Ile Gln Gln Asn Val
65                  70                  75                  80

```
Thr Thr Phe Asp Gly Lys Tyr Ala Phe Leu Lys Thr Tyr Asn Tyr Ser
             85                  90                  95
Leu Gly Ala Asp Asp Leu Thr Pro Phe Gly Gln Glu Leu Val Asn
            100                 105                 110
Ser Gly Ile Lys Phe Tyr Gln Arg Tyr Glu Ser Leu Thr Arg Asn Ile
            115                 120                 125
Ile Pro Phe Ile Arg Ser Ser Gly Ser Ser Arg Val Ile Ala Ser Gly
130             135                 140
Glu Lys Phe Ile Glu Gly Phe Gln Ser Thr Lys Leu Lys Asp Pro Arg
145             150                 155                 160
Ala Gln Pro Gly Gln Ser Ser Pro Lys Ile Asp Val Ile Ser Glu
            165                 170                 175
Ala Ser Ser Asn Asn Thr Leu Asp Pro Gly Thr Cys Thr Val Phe
            180                 185                 190
Glu Asp Ser Glu Leu Ala Asp Thr Val Glu Ala Asn Phe Thr Ala Thr
            195                 200                 205
Phe Ala Pro Ser Ile Arg Gln Arg Leu Glu Asn Asp Leu Ser Gly Val
            210                 215                 220
Thr Leu Thr Asp Thr Glu Val Thr Tyr Leu Met Asp Met Cys Ser Phe
225             230                 235                 240
Asp Thr Ile Ser Thr Ser Thr Val Asp Thr Lys Leu Ser Pro Phe Cys
            245                 250                 255
Asp Leu Phe Thr His Asp Glu Trp Ile His Tyr Asp Tyr Leu Gln Ser
            260                 265                 270
Leu Lys Lys Tyr Tyr Gly His Gly Ala Gly Asn Pro Leu Gly Pro Thr
            275                 280                 285
Gln Gly Val Gly Tyr Ala Asn Glu Leu Ile Ala Arg Leu Thr His Ser
290             295                 300
Pro Val His Asp Asp Thr Ser Ser Asn His Thr Leu Asp Ser Asn Pro
305             310                 315                 320
Ala Thr Phe Pro Leu Asn Ser Thr Leu Tyr Ala Asp Phe Ser His Asp
            325                 330                 335
Asn Gly Ile Ile Ser Ile Leu Phe Ala Leu Gly Leu Tyr Asn Gly Thr
            340                 345                 350
Lys Pro Leu Ser Thr Thr Thr Val Glu Asn Ile Thr Gln Thr Asp Gly
            355                 360                 365
Phe Ser Ser Ala Trp Thr Val Pro Phe Ala Ser Arg Leu Tyr Val Glu
            370                 375                 380
Met Met Gln Cys Gln Ala Glu Gln Glu Pro Leu Val Arg Val Leu Val
385             390                 395                 400
Asn Asp Arg Val Val Pro Leu His Gly Cys Pro Ile Asp Ala Leu Gly
            405                 410                 415
Arg Cys Thr Arg Asp Ser Phe Val Arg Gly Leu Ser Phe Ala Arg Ser
            420                 425                 430
Gly Gly Asp Trp Ala Glu Cys Ser Ala
            435                 440
```

<210> SEQ ID NO 104
<211> LENGTH: 441
<212> TYPE: PRT
<213> ORGANISM: A. niger T213

<400> SEQUENCE: 104

Asn Gln Ser Ser Cys Asp Thr Val Asp Gln Gly Tyr Gln Cys Phe Ser

-continued

```
  1                   5                    10                   15
Glu Thr Ser His Leu Trp Gly Gln Tyr Ala Pro Phe Phe Ser Leu Ala
             20                  25                  30
Asn Glu Ser Val Ile Ser Pro Asp Val Pro Ala Gly Cys Arg Val Thr
             35                  40                  45
Phe Ala Gln Val Leu Ser Arg His Gly Ala Arg Tyr Pro Thr Glu Ser
     50                  55                  60
Lys Gly Lys Lys Tyr Ser Ala Leu Ile Glu Glu Ile Gln Gln Asn Val
 65                  70                  75                  80
Thr Thr Phe Asp Gly Lys Tyr Ala Phe Leu Lys Thr Tyr Asn Tyr Ser
                 85                  90                  95
Leu Gly Ala Asp Asp Leu Thr Pro Phe Gly Glu Gln Glu Leu Val Asn
                100                 105                 110
Ser Gly Ile Lys Phe Tyr Gln Arg Tyr Glu Ser Leu Thr Arg Asn Ile
            115                 120                 125
Ile Pro Phe Ile Arg Ser Ser Gly Ser Ser Arg Val Ile Ala Ser Gly
    130                 135                 140
Glu Lys Phe Ile Glu Gly Phe Gln Ser Thr Lys Leu Lys Asp Pro Arg
145                 150                 155                 160
Ala Gln Pro Gly Gln Ser Ser Pro Lys Ile Asp Val Val Ile Ser Glu
                165                 170                 175
Ala Ser Ser Asn Asn Thr Leu Asp Pro Gly Thr Cys Thr Val Phe
                180                 185                 190
Glu Asp Ser Glu Leu Ala Asp Thr Val Glu Ala Asn Phe Thr Ala Thr
            195                 200                 205
Phe Ala Pro Ser Ile Arg Gln Arg Leu Glu Asn Asp Leu Ser Gly Val
    210                 215                 220
Thr Leu Thr Asp Thr Glu Val Thr Tyr Leu Met Asp Met Cys Ser Phe
225                 230                 235                 240
Asp Thr Ile Ser Thr Ser Thr Val Asp Thr Lys Leu Ser Pro Phe Cys
                245                 250                 255
Asp Leu Phe Thr His Asp Glu Trp Ile His Tyr Asp Tyr Leu Arg Ser
            260                 265                 270
Leu Lys Lys Tyr Tyr Gly His Gly Ala Gly Asn Pro Leu Gly Pro Thr
    275                 280                 285
Gln Gly Val Gly Tyr Ala Asn Glu Leu Ile Ala Arg Leu Thr His Ser
290                 295                 300
Pro Val His Asp Asp Thr Ser Ser Asn His Thr Leu Asp Ser Asn Pro
305                 310                 315                 320
Ala Thr Phe Pro Leu Asn Ser Thr Leu Tyr Ala Asp Phe Ser His Asp
                325                 330                 335
Asn Gly Ile Ile Ser Ile Leu Phe Ala Leu Gly Leu Tyr Asn Gly Thr
            340                 345                 350
Lys Pro Leu Ser Thr Thr Val Glu Asn Ile Thr Gln Thr Asp Gly
    355                 360                 365
Phe Ser Ser Ala Trp Thr Val Pro Phe Ala Ser Arg Leu Tyr Val Glu
    370                 375                 380
Met Met Gln Cys Gln Ala Glu Gln Pro Leu Val Arg Val Leu Val
385                 390                 395                 400
Asn Asp Arg Val Val Pro Leu His Gly Cys Pro Ile Asp Ala Leu Gly
                405                 410                 415
Arg Cys Thr Arg Asp Ser Phe Val Arg Gly Leu Ser Phe Ala Arg Ser
            420                 425                 430
```

-continued

Gly Gly Asp Trp Ala Glu Cys Phe Ala
        435                 440

<210> SEQ ID NO 105
<211> LENGTH: 441
<212> TYPE: PRT
<213> ORGANISM: A. niger NRRL3135

<400> SEQUENCE: 105

Asn Gln Ser Ser Cys Asp Thr Val Asp Gln Gly Tyr Gln Cys Phe Ser
 1               5                  10                  15

Glu Thr Ser His Leu Trp Gly Gln Tyr Ala Pro Phe Phe Ser Leu Ala
            20                  25                  30

Asn Glu Ser Val Ile Ser Pro Glu Val Pro Ala Gly Cys Arg Val Thr
        35                  40                  45

Phe Ala Gln Val Leu Ser Arg His Gly Ala Arg Tyr Pro Thr Asp Ser
    50                  55                  60

Lys Gly Lys Lys Tyr Ser Ala Leu Ile Glu Ile Gln Gln Asn Ala
65                  70                  75                  80

Thr Thr Phe Asp Gly Lys Tyr Ala Phe Leu Lys Thr Tyr Asn Tyr Ser
                85                  90                  95

Leu Gly Ala Asp Asp Leu Thr Pro Phe Gly Glu Gln Glu Leu Val Asn
            100                 105                 110

Ser Gly Ile Lys Phe Tyr Gln Arg Tyr Glu Ser Leu Thr Arg Asn Ile
        115                 120                 125

Val Pro Phe Ile Arg Ser Ser Gly Ser Ser Arg Val Ile Ala Ser Gly
    130                 135                 140

Lys Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Ser Asn Asn Thr Leu Asp Pro Gly Thr Cys Thr Val Phe
            180                 185                 190

Glu Asp Ser Glu Leu Ala Asp Thr Val Glu Ala Asn Phe Thr Ala Thr
        195                 200                 205

Phe Val Pro Ser Ile Arg Gln Arg Leu Glu Asn Asp Leu Ser Gly Val
    210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile Asn Tyr Asp Tyr Leu Gln Ser
            260                 265                 270

Leu Lys Lys Tyr Tyr Gly His Gly Ala Gly Asn Pro Leu Gly Pro Thr
        275                 280                 285

Gln Gly Val Gly Tyr Ala Asn Glu Leu Ile Ala Arg Leu Thr His Ser
    290                 295                 300

Pro Val His Asp Asp Thr Ser Ser Asn His Thr Leu Asp Ser Ser Pro
305                 310                 315                 320

Ala Thr Phe Pro Leu Asn Ser Thr Leu Tyr Ala Asp Phe Ser His Asp
                325                 330                 335

Asn Gly Ile Ile Ser Ile Leu Phe Ala Leu Gly Leu Tyr Asn Gly Thr
            340                 345                 350

Lys Pro Leu Ser Thr Thr Thr Val Glu Asn Ile Thr Gln Thr Asp Gly

-continued

```
            355                 360                 365
Phe Ser Ser Ala Trp Thr Val Pro Phe Ala Ser Arg Leu Tyr Val Glu
        370                 375                 380

Met Met Gln Cys Gln Ala Glu Gln Pro Leu Val Arg Val Leu Val
385                 390                 395                 400

Asn Asp Arg Val Val Pro Leu His Gly Cys Pro Val Asp Ala Leu Gly
                405                 410                 415

Arg Cys Thr Arg Asp Ser Phe Val Arg Gly Leu Ser Phe Ala Arg Ser
                420                 425                 430

Gly Gly Asp Trp Ala Glu Cys Phe Ala
                435                 440

<210> SEQ ID NO 106
<211> LENGTH: 440
<212> TYPE: PRT
<213> ORGANISM: A. fumigatus 13073

<400> SEQUENCE: 106

Gly Ser Lys Ser Cys Asp Thr Val Asp Leu Gly Tyr Gln Cys Ser Pro
 1               5                  10                  15

Ala Thr Ser His Leu Trp Gly Gln Tyr Ser Pro Phe Phe Ser Leu Glu
                20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
        50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Gln Leu Val Asn
                100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
                165                 170                 175

Glu Thr Phe Asn Asn Thr Leu Asp His Gly Val Cys Thr Lys Phe Glu
                180                 185                 190

Ala Ser Gln Leu Gly Asp Glu Val Ala Ala Asn Phe Thr Ala Leu Phe
            195                 200                 205

Ala Pro Asp Ile Arg Ala Arg Ala Glu Lys His Leu Pro Gly Val Thr
        210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
            275                 280                 285
```

```
Gly Ile Gly Phe Thr Asn Glu Leu Ile Ala Arg Leu Thr Arg Ser Pro
            290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
            370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
            435                 440

<210> SEQ ID NO 107
<211> LENGTH: 440
<212> TYPE: PRT
<213> ORGANISM: A. fumigatus 32722

<400> SEQUENCE: 107

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
                20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
                165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
            195                 200                 205

Ala Pro Asp Ile Arg Ala Arg Ala Glu Lys His Leu Pro Gly Val Thr
210                 215                 220
```

-continued

```
Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
            245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Gly
            340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
            435                 440

<210> SEQ ID NO 108
<211> LENGTH: 440
<212> TYPE: PRT
<213> ORGANISM: A. fumigatus 58128

<400> SEQUENCE: 108

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
            85                  90                  95

Leu Gly Ala Asp Asp Leu Thr Pro Phe Gly Glu Gln Gln Leu Val Asn
                100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
        130                 135                 140

Glu Lys Phe Ile Glu Gly Phe Gln Gln Ala Lys Leu Ala Asp Pro Gly
```

```
                145                 150                 155                 160
Ala Thr Asn Arg Ala Ala Pro Ala Ile Ser Val Ile Ile Pro Glu Ser
                165                 170                 175

Glu Thr Phe Asn Asn Thr Leu Asp His Gly Val Cys Thr Lys Phe Glu
                180                 185                 190

Ala Ser Gln Leu Gly Asp Glu Val Ala Ala Asn Phe Thr Ala Leu Phe
                195                 200                 205

Ala Pro Asp Ile Arg Ala Arg Ala Glu Lys His Leu Pro Gly Val Thr
            210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
        290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
                340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
        370                 375                 380

Met Gln Cys Lys Ser Glu Lys Glu Ser Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
            435                 440

<210> SEQ ID NO 109
<211> LENGTH: 440
<212> TYPE: PRT
<213> ORGANISM: A. fumigatus 26906

<400> SEQUENCE: 109

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
                20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
        50                  55                  60

Lys Ser Lys Lys Tyr Lys Lys Leu Val Thr Ala Ile Gln Ala Asn Ala
65                  70                  75                  80
```

-continued

```
Thr Asp Phe Lys Gly Lys Phe Ala Phe Leu Lys Thr Tyr Asn Tyr Thr
             85                  90                  95

Leu Gly Ala Asp Asp Leu Thr Ala Phe Gly Glu Gln Gln Leu Val Asn
        100                 105                 110

Ser Gly Ile Lys Phe Tyr Gln Arg Tyr Lys Ala Leu Ala Arg Ser Val
        115                 120                 125

Val Pro Phe Ile Arg Ala Ser Gly Ser Asp Arg Val Ile Ala Ser Gly
    130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
                165                 170                 175

Glu Thr Phe Asn Asn Thr Leu Asp His Gly Val Cys Thr Lys Phe Glu
                180                 185                 190

Ala Ser Gln Leu Gly Asp Glu Val Ala Ala Asn Phe Thr Ala Leu Phe
            195                 200                 205

Ala Pro Asp Ile Arg Ala Arg Ala Lys Lys His Leu Pro Gly Val Thr
    210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
        275                 280                 285

Gly Ile Gly Phe Thr Asn Glu Leu Ile Ala Arg Leu Thr Arg Ser Pro
    290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
        355                 360                 365

Ser Ala Ser Trp Val Val Pro Phe Gly Ala Arg Ala Tyr Phe Glu Thr
    370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
            420                 425                 430

Gly Asn Trp Gly Glu Cys Phe Ser
        435                 440

<210> SEQ ID NO 110
<211> LENGTH: 440
<212> TYPE: PRT
<213> ORGANISM: A. fumigatus 32239

<400> SEQUENCE: 110

Gly Ser Lys Ala Cys Asp Thr Val Glu Leu Gly Tyr Gln Cys Ser Pro
  1               5                  10                  15
```

-continued

```
Gly Thr Ser His Leu Trp Gly Gln Tyr Ser Pro Phe Ser Leu Glu
             20                  25                  30

Asp Glu Leu Ser Val Ser Ser Asp Leu Pro Lys Asp Cys Arg Val Thr
             35                  40                  45

Phe Val Gln Val Leu Ser Arg His Gly Ala Arg Tyr Pro Thr Ala Ser
 50                  55                  60

Lys Ser Lys Lys Tyr Lys Lys Leu Val Thr Ala Ile Gln Lys Asn Ala
 65                  70                  75                  80

Thr Glu Phe Lys Gly Lys Phe Ala Phe Leu Glu Thr Tyr Asn Tyr Thr
                 85                  90                  95

Leu Gly Ala Asp Asp Leu Thr Pro Phe Gly Glu Gln Gln Met Val Asn
            100                 105                 110

Ser Gly Ile Lys Phe Tyr Gln Lys Tyr Lys Ala Leu Ala Gly Ser Val
            115                 120                 125

Val Pro Phe Ile Arg Ser Ser Gly Ser Asp Arg Val Ile Ala Ser Gly
            130                 135                 140

Glu Lys Phe Ile Glu Gly Phe Gln Gln Ala Asn Val Ala Asp Pro Gly
145                 150                 155                 160

Ala Thr Asn Arg Ala Ala Pro Val Ile Ser Val Ile Pro Glu Ser
            165                 170                 175

Glu Thr Tyr Asn Asn Thr Leu Asp His Ser Val Cys Thr Asn Phe Glu
            180                 185                 190

Ala Ser Glu Leu Gly Asp Glu Val Glu Ala Asn Phe Thr Ala Leu Phe
            195                 200                 205

Ala Pro Ala Ile Arg Ala Arg Ile Glu Lys His Leu Pro Gly Val Gln
            210                 215                 220

Leu Thr Asp Asp Val Val Ser Leu Met Asp Met Cys Ser Phe Asp
225                 230                 235                 240

Thr Val Ala Arg Thr Ala Asp Ala Ser Glu Leu Ser Pro Phe Cys Ala
            245                 250                 255

Ile Phe Thr His Asn Glu Trp Lys Lys Tyr Asp Tyr Leu Gln Ser Leu
            260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Asn Ser Pro
290                 295                 300

Val Gln Asp His Thr Ser Thr Asn Ser Thr Leu Asp Ser Asp Pro Ala
305                 310                 315                 320

Thr Phe Pro Leu Asn Ala Thr Ile Tyr Val Asp Phe Ser His Asp Asn
            325                 330                 335

Gly Met Ile Pro Ile Phe Phe Ala Met Gly Leu Tyr Asn Gly Thr Glu
            340                 345                 350

Pro Leu Ser Gln Thr Ser Glu Glu Ser Thr Lys Glu Ser Asn Gly Tyr
            355                 360                 365

Ser Ala Ser Trp Ala Val Pro Phe Gly Ala Arg Ala Tyr Phe Glu Thr
            370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Ala Val Asp Lys Leu Gly Arg
                405                 410                 415

Cys Lys Leu Lys Asp Phe Val Lys Gly Leu Ser Trp Ala Arg Ser Gly
            420                 425                 430
```

```
Gly Asn Ser Glu Gln Ser Phe Ser
        435                 440
```

<210> SEQ ID NO 111
<211> LENGTH: 439
<212> TYPE: PRT
<213> ORGANISM: E. nidulans

<400> SEQUENCE: 111

```
Gln Asn His Ser Cys Asn Thr Ala Asp Gly Gly Tyr Gln Cys Phe Pro
  1               5                  10                  15

Asn Val Ser His Val Trp Gly Gln Tyr Ser Pro Tyr Phe Ser Ile Glu
             20                  25                  30

Gln Glu Ser Ala Ile Ser Glu Asp Val Pro His Gly Cys Glu Val Thr
         35                  40                  45

Phe Val Gln Val Leu Ser Arg His Gly Ala Arg Tyr Pro Thr Glu Ser
     50                  55                  60

Lys Ser Lys Ala Tyr Ser Gly Leu Ile Glu Ala Ile Gln Lys Asn Ala
 65                  70                  75                  80

Thr Ser Phe Trp Gly Gln Tyr Ala Phe Leu Glu Ser Tyr Asn Tyr Thr
                 85                  90                  95

Leu Gly Ala Asp Asp Leu Thr Ile Phe Gly Glu Asn Gln Met Val Asp
            100                 105                 110

Ser Gly Ala Lys Phe Tyr Arg Arg Tyr Lys Asn Leu Ala Arg Lys Asn
        115                 120                 125

Thr Pro Phe Ile Arg Ala Ser Gly Ser Asp Arg Val Val Ala Ser Ala
    130                 135                 140

Glu Lys Phe Ile Asn Gly Phe Arg Lys Ala Gln Leu His Asp His Gly
145                 150                 155                 160

Ser Gly Gln Ala Thr Pro Val Val Asn Val Ile Ile Pro Glu Ile Asp
                165                 170                 175

Gly Phe Asn Asn Thr Leu Asp His Ser Thr Cys Val Ser Phe Glu Asn
            180                 185                 190

Asp Glu Arg Ala Asp Glu Ile Glu Ala Asn Phe Thr Ala Ile Met Gly
        195                 200                 205

Pro Pro Ile Arg Lys Arg Leu Glu Asn Asp Leu Pro Gly Ile Lys Leu
    210                 215                 220

Thr Asn Glu Asn Val Ile Tyr Leu Met Asp Met Cys Ser Phe Asp Thr
225                 230                 235                 240

Met Ala Arg Thr Ala His Gly Thr Glu Leu Ser Pro Phe Cys Ala Ile
                245                 250                 255

Phe Thr Glu Lys Glu Trp Leu Gln Tyr Asp Tyr Leu Gln Ser Leu Ser
            260                 265                 270

Lys Tyr Tyr Gly Tyr Gly Ala Gly Ser Pro Leu Gly Pro Ala Gln Gly
        275                 280                 285

Ile Gly Phe Thr Asn Glu Leu Ile Ala Arg Leu Thr Gln Ser Pro Val
    290                 295                 300

Gln Asp Asn Thr Ser Thr Asn His Thr Leu Asp Ser Asn Pro Ala Thr
305                 310                 315                 320

Phe Pro Leu Asp Arg Lys Leu Tyr Ala Asp Phe Ser His Asp Asn Ser
                325                 330                 335

Met Ile Ser Ile Phe Phe Ala Met Gly Leu Tyr Asn Gly Thr Gln Pro
            340                 345                 350

Leu Ser Met Asp Ser Val Glu Ser Ile Gln Glu Met Asp Gly Tyr Ala
        355                 360                 365
```

```
Ala Ser Trp Thr Val Pro Phe Gly Ala Arg Ala Tyr Phe Glu Leu Met
    370                 375                 380

Gln Cys Glu Lys Lys Glu Pro Leu Val Arg Val Leu Val Asn Asp Arg
385                 390                 395                 400

Val Val Pro Leu His Gly Cys Ala Val Asp Lys Phe Gly Arg Cys Thr
                405                 410                 415

Leu Asp Asp Trp Val Glu Gly Leu Asn Phe Ala Arg Ser Gly Gly Asn
                420                 425                 430

Trp Lys Thr Cys Phe Thr Leu
            435

<210> SEQ ID NO 112
<211> LENGTH: 443
<212> TYPE: PRT
<213> ORGANISM: T. thermophilus

<400> SEQUENCE: 112

Asp Ser His Ser Cys Asn Thr Val Glu Gly Gly Tyr Gln Cys Arg Pro
  1               5                  10                  15

Glu Ile Ser His Ser Trp Gly Gln Tyr Ser Pro Phe Phe Ser Leu Ala
                 20                  25                  30

Asp Gln Ser Glu Ile Ser Pro Asp Val Pro Gln Asn Cys Lys Ile Thr
             35                  40                  45

Phe Val Gln Leu Leu Ser Arg His Gly Ala Arg Tyr Pro Thr Ser Ser
         50                  55                  60

Lys Thr Glu Leu Tyr Ser Gln Leu Ile Ser Arg Ile Gln Lys Thr Ala
 65                  70                  75                  80

Thr Ala Tyr Lys Gly Tyr Tyr Ala Phe Leu Lys Asp Tyr Arg Tyr Gln
                 85                  90                  95

Leu Gly Ala Asn Asp Leu Thr Pro Phe Gly Glu Asn Gln Met Ile Gln
                100                 105                 110

Leu Gly Ile Lys Phe Tyr Asn His Tyr Lys Ser Leu Ala Arg Asn Ala
                115                 120                 125

Val Pro Phe Val Arg Cys Ser Gly Ser Asp Arg Val Ile Ala Ser Gly
            130                 135                 140

Arg Leu Phe Ile Glu Gly Phe Gln Ser Ala Lys Val Leu Asp Pro His
145                 150                 155                 160

Ser Asp Lys His Asp Ala Pro Pro Thr Ile Asn Val Ile Ile Glu Glu
                165                 170                 175

Gly Pro Ser Tyr Asn Asn Thr Leu Asp Thr Gly Ser Cys Pro Val Phe
                180                 185                 190

Glu Asp Ser Ser Gly Gly His Asp Ala Gln Glu Lys Phe Ala Lys Gln
            195                 200                 205

Phe Ala Pro Ala Ile Leu Glu Lys Ile Lys Asp His Leu Pro Gly Val
        210                 215                 220

Asp Leu Ala Val Ser Asp Val Pro Tyr Leu Met Asp Leu Cys Pro Phe
225                 230                 235                 240

Glu Thr Leu Ala Arg Asn His Thr Asp Thr Leu Ser Pro Phe Cys Ala
                245                 250                 255

Leu Ser Thr Gln Glu Glu Trp Gln Ala Tyr Asp Tyr Gln Ser Leu
                260                 265                 270

Gly Lys Tyr Tyr Gly Asn Gly Gly Asn Pro Leu Gly Pro Ala Gln
            275                 280                 285

Gly Val Gly Phe Val Asn Glu Leu Ile Ala Arg Met Thr His Ser Pro
```

```
                    290                 295                 300

Val Gln Asp Tyr Thr Thr Val Asn His Thr Leu Asp Ser Asn Pro Ala
305                 310                 315                 320

Thr Phe Pro Leu Asn Ala Thr Leu Tyr Ala Asp Phe Ser His Asp Asn
                325                 330                 335

Thr Met Thr Ser Ile Phe Ala Ala Leu Gly Leu Tyr Asn Gly Thr Ala
                340                 345                 350

Lys Leu Ser Thr Thr Glu Ile Lys Ser Ile Glu Glu Thr Asp Gly Tyr
                355                 360                 365

Ser Ala Ala Trp Thr Val Pro Phe Gly Gly Arg Ala Tyr Ile Glu Met
370                 375                 380

Met Gln Cys Asp Asp Ser Asp Glu Pro Val Val Arg Val Leu Val Asn
385                 390                 395                 400

Asp Arg Val Val Pro Leu His Gly Cys Glu Val Asp Ser Leu Gly Arg
                405                 410                 415

Cys Lys Arg Asp Asp Phe Val Arg Gly Leu Ser Phe Ala Arg Gln Gly
                420                 425                 430

Gly Asn Trp Glu Gly Cys Tyr Ala Ala Ser Glu
                435                 440

<210> SEQ ID NO 113
<211> LENGTH: 466
<212> TYPE: PRT
<213> ORGANISM: M. thermophila

<400> SEQUENCE: 113

Glu Ser Arg Pro Cys Asp Thr Pro Asp Leu Gly Phe Gln Cys Gly Thr
1                   5                   10                  15

Ala Ile Ser His Phe Trp Gly Gln Tyr Ser Pro Tyr Phe Ser Val Pro
                20                  25                  30

Ser Glu Leu Asp Ala Ser Ile Pro Asp Asp Cys Glu Val Thr Phe Ala
            35                  40                  45

Gln Val Leu Ser Arg His Gly Ala Arg Ala Pro Thr Leu Lys Arg Ala
        50                  55                  60

Ala Ser Tyr Val Asp Leu Ile Asp Arg Ile His His Gly Ala Ile Ser
65                  70                  75                  80

Tyr Gly Pro Gly Tyr Glu Phe Leu Arg Thr Tyr Asp Tyr Thr Leu Gly
                85                  90                  95

Ala Asp Glu Leu Thr Arg Thr Gly Gln Gln Gln Met Val Asn Ser Gly
            100                 105                 110

Ile Lys Phe Tyr Arg Arg Tyr Arg Ala Leu Ala Arg Lys Ser Ile Pro
        115                 120                 125

Phe Val Arg Thr Ala Gly Gln Asp Arg Val Val His Ser Ala Glu Asn
130                 135                 140

Phe Thr Gln Gly Phe His Ser Ala Leu Leu Ala Asp Arg Gly Ser Thr
145                 150                 155                 160

Val Arg Pro Thr Leu Pro Tyr Asp Met Val Val Ile Pro Glu Thr Ala
                165                 170                 175

Gly Ala Asn Asn Thr Leu His Asn Asp Leu Cys Thr Ala Phe Glu Glu
            180                 185                 190

Gly Pro Tyr Ser Thr Ile Gly Asp Asp Ala Gln Asp Thr Tyr Leu Ser
        195                 200                 205

Thr Phe Ala Gly Pro Ile Thr Ala Arg Val Asn Ala Asn Leu Pro Gly
210                 215                 220
```

-continued

```
Ala Asn Leu Thr Asp Ala Asp Thr Val Ala Leu Met Asp Leu Cys Pro
225                 230                 235                 240

Phe Glu Thr Val Ala Ser Ser Ser Asp Pro Ala Thr Ala Asp Ala
            245                 250                 255

Gly Gly Gly Asn Gly Arg Pro Leu Ser Pro Phe Cys Arg Leu Phe Ser
                260                 265                 270

Glu Ser Glu Trp Arg Ala Tyr Asp Tyr Leu Gln Ser Val Gly Lys Trp
            275                 280                 285

Tyr Gly Tyr Gly Pro Gly Asn Pro Leu Gly Pro Thr Gln Gly Val Gly
290                 295                 300

Phe Val Asn Glu Leu Leu Ala Arg Leu Ala Gly Val Pro Val Arg Asp
305                 310                 315                 320

Gly Thr Ser Thr Asn Arg Thr Leu Asp Gly Asp Pro Arg Thr Phe Pro
                325                 330                 335

Leu Gly Arg Pro Leu Tyr Ala Asp Phe Ser His Asp Asn Asp Met Met
            340                 345                 350

Gly Val Leu Gly Ala Leu Gly Ala Tyr Asp Gly Val Pro Pro Leu Asp
            355                 360                 365

Lys Thr Ala Arg Arg Asp Pro Glu Glu Leu Gly Gly Tyr Ala Ala Ser
370                 375                 380

Trp Ala Val Pro Phe Ala Ala Arg Ile Tyr Val Glu Lys Met Arg Cys
385                 390                 395                 400

Ser Gly Gly Gly Gly Gly Gly Gly Glu Gly Arg Gln Glu Lys
                405                 410                 415

Asp Glu Glu Met Val Arg Val Leu Val Asn Asp Arg Val Met Thr Leu
            420                 425                 430

Lys Gly Cys Gly Ala Asp Glu Arg Gly Met Cys Thr Leu Glu Arg Phe
            435                 440                 445

Ile Glu Ser Met Ala Phe Ala Arg Gly Asn Gly Lys Trp Asp Leu Cys
            450                 455                 460

Phe Ala
465

<210> SEQ ID NO 114
<211> LENGTH: 431
<212> TYPE: PRT
<213> ORGANISM: Consensus

<400> SEQUENCE: 114

Asn Ser His Ser Cys Asp Thr Val Asp Gly Gly Tyr Gln Cys Phe Pro
1               5                   10                  15

Glu Ile Ser His Leu Trp Gly Gln Tyr Ser Pro Tyr Phe Ser Leu Glu
            20                  25                  30

Asp Glu Ser Ala Ile Ser Pro Asp Val Pro Asp Asp Cys Val Thr Phe
        35                  40                  45

Val Gln Val Leu Ser Arg His Gly Ala Arg Tyr Pro Thr Ser Ser Lys
    50                  55                  60

Lys Ala Tyr Ser Ala Leu Ile Glu Ala Ile Gln Lys Asn Ala Thr Phe
65                  70                  75                  80

Lys Gly Lys Tyr Ala Phe Leu Lys Thr Tyr Asn Tyr Thr Leu Gly Ala
                85                  90                  95

Asp Asp Leu Thr Pro Phe Gly Glu Asn Gln Met Val Asn Ser Gly Ile
            100                 105                 110

Lys Phe Tyr Arg Arg Tyr Lys Ala Leu Ala Arg Lys Val Pro Phe Val
        115                 120                 125
```

```
Arg Ala Ser Gly Ser Asp Arg Val Ile Ala Ser Ala Glu Lys Phe Ile
    130                 135                 140

Glu Gly Phe Gln Ser Ala Lys Leu Ala Asp Pro Gly Ser Pro His Gln
145                 150                 155                 160

Ala Ser Pro Val Ile Asn Val Ile Pro Glu Gly Ser Gly Tyr Asn
                165                 170                 175

Asn Thr Leu Asp His Gly Thr Cys Thr Ala Phe Glu Asp Ser Glu Leu
                180                 185                 190

Gly Asp Asp Ala Glu Ala Asn Phe Thr Ala Thr Phe Ala Pro Ala Ile
                195                 200                 205

Arg Ala Arg Leu Glu Ala Asp Leu Pro Gly Val Thr Leu Thr Asp Glu
    210                 215                 220

Asp Val Val Leu Met Asp Met Cys Pro Phe Glu Thr Val Ala Arg Thr
225                 230                 235                 240

Ser Asp Ala Thr Glu Leu Ser Pro Phe Cys Ala Leu Phe Thr Glu Glu
                245                 250                 255

Trp Tyr Asp Tyr Leu Gln Ser Leu Gly Lys Tyr Tyr Gly Tyr Gly Ala
                260                 265                 270

Gly Asn Pro Leu Gly Pro Ala Gln Gly Val Gly Phe Asn Glu Leu Ile
                275                 280                 285

Ala Arg Leu Thr His Ser Pro Val Gln Asp His Thr Ser Thr Asn His
    290                 295                 300

Thr Leu Asp Ser Asn Pro Ala Thr Phe Pro Leu Asn Ala Thr Leu Tyr
305                 310                 315                 320

Ala Asp Phe Ser His Asp Asn Ser Met Ile Ser Ile Phe Phe Ala Leu
                325                 330                 335

Gly Leu Tyr Asn Gly Thr Ala Pro Leu Ser Thr Thr Ser Val Glu Ser
                340                 345                 350

Ile Glu Glu Thr Asp Gly Tyr Ala Ala Ser Trp Thr Val Pro Phe Gly
    355                 360                 365

Ala Arg Ala Tyr Val Glu Met Met Gln Cys Gln Ala Glu Lys Glu Pro
    370                 375                 380

Leu Val Arg Val Leu Val Asn Asp Arg Val Val Pro Leu His Gly Cys
385                 390                 395                 400

Ala Val Asp Lys Leu Gly Arg Cys Lys Leu Asp Asp Phe Val Glu Gly
                405                 410                 415

Leu Ser Phe Ala Arg Ser Gly Asn Trp Ala Glu Cys Phe Ala
                420                 425                 430

<210> SEQ ID NO 115
<211> LENGTH: 441
<212> TYPE: PRT
<213> ORGANISM: Consensus phytase

<400> SEQUENCE: 115

Asn Ser His Ser Cys Asp Thr Val Asp Gly Gly Tyr Gln Cys Phe Pro
  1               5                  10                 15

Glu Ile Ser His Leu Trp Gly Gln Tyr Ser Pro Tyr Phe Ser Leu Glu
                20                 25                 30

Asp Glu Ser Ala Ile Ser Pro Asp Val Pro Asp Asp Cys Arg Val Thr
            35                 40                 45

Phe Val Gln Val Leu Ser Arg His Gly Ala Arg Tyr Pro Thr Ser Ser
    50                 55                 60

Lys Ser Lys Ala Tyr Ser Ala Leu Ile Glu Ala Ile Gln Lys Asn Ala
```

```
                 65                  70                  75                  80
Thr Ala Phe Lys Gly Lys Tyr Ala Phe Leu Lys Thr Tyr Asn Tyr Thr
                         85                  90                  95

Leu Gly Ala Asp Asp Leu Thr Pro Phe Gly Glu Asn Gln Met Val Asn
            100                 105                 110

Ser Gly Ile Lys Phe Tyr Arg Arg Tyr Lys Ala Leu Ala Arg Lys Ile
            115                 120                 125

Val Pro Phe Ile Arg Ala Ser Gly Ser Asp Arg Val Ile Ala Ser Ala
            130                 135                 140

Glu Lys Phe Ile Glu Gly Phe Gln Ser Ala Lys Leu Ala Asp Pro Gly
145                 150                 155                 160

Ser Gln Pro His Gln Ala Ser Pro Val Ile Asp Val Ile Pro Glu
                165                 170                 175

Gly Ser Gly Tyr Asn Asn Thr Leu Asp His Gly Thr Cys Thr Ala Phe
                180                 185                 190

Glu Asp Ser Glu Leu Gly Asp Asp Val Glu Ala Asn Phe Thr Ala Leu
            195                 200                 205

Phe Ala Pro Ala Ile Arg Ala Arg Leu Glu Ala Asp Leu Pro Gly Val
            210                 215                 220

Thr Leu Thr Asp Glu Asp Val Val Tyr Leu Met Asp Met Cys Pro Phe
225                 230                 235                 240

Glu Thr Val Ala Arg Thr Ser Asp Ala Thr Glu Leu Ser Pro Phe Cys
                245                 250                 255

Ala Leu Phe Thr His Asp Glu Trp Arg Gln Tyr Asp Tyr Leu Gln Ser
                260                 265                 270

Leu Gly Lys Tyr Tyr Gly Tyr Gly Ala Gly Asn Pro Leu Gly Pro Ala
            275                 280                 285

Gln Gly Val Gly Phe Ala Asn Glu Leu Ile Ala Arg Leu Thr Arg Ser
            290                 295                 300

Pro Val Gln Asp His Thr Ser Thr Asn His Thr Leu Asp Ser Asn Pro
305                 310                 315                 320

Ala Thr Phe Pro Leu Asn Ala Thr Leu Tyr Ala Asp Phe Ser His Asp
                325                 330                 335

Asn Ser Met Ile Ser Ile Phe Phe Ala Leu Gly Leu Tyr Asn Gly Thr
            340                 345                 350

Ala Pro Leu Ser Thr Thr Ser Val Glu Ser Ile Glu Glu Thr Asp Gly
            355                 360                 365

Tyr Ser Ala Ser Trp Thr Val Pro Phe Gly Ala Arg Ala Tyr Val Glu
            370                 375                 380

Met Met Gln Cys Gln Ala Glu Lys Glu Pro Leu Val Arg Val Leu Val
385                 390                 395                 400

Asn Asp Arg Val Val Pro Leu His Gly Cys Ala Val Asp Lys Leu Gly
                405                 410                 415

Arg Cys Lys Arg Asp Asp Phe Val Glu Gly Leu Ser Phe Ala Arg Ser
            420                 425                 430

Gly Gly Asn Trp Ala Glu Cys Phe Ala
            435                 440

<210> SEQ ID NO 116
<211> LENGTH: 467
<212> TYPE: PRT
<213> ORGANISM: consensus phytase-1 gene

<400> SEQUENCE: 116
```

-continued

```
Met Gly Val Phe Val Leu Leu Ser Ile Ala Thr Leu Phe Gly Ser
 1               5                  10                 15

Thr Ser Gly Thr Ala Leu Gly Pro Arg Gly Asn Ser His Ser Cys Asp
             20                  25                  30

Thr Val Asp Gly Gly Tyr Gln Cys Phe Pro Glu Ile Ser His Leu Trp
         35                  40                  45

Gly Gln Tyr Ser Pro Tyr Phe Ser Leu Glu Asp Glu Ser Ala Ile Ser
     50                  55                  60

Pro Asp Val Pro Asp Asp Cys Arg Val Thr Phe Val Gln Val Leu Ser
 65                  70                  75                  80

Arg His Gly Ala Arg Tyr Pro Thr Ser Ser Lys Ser Lys Ala Tyr Ser
                 85                  90                  95

Ala Leu Ile Glu Ala Ile Gln Lys Asn Ala Thr Ala Phe Lys Gly Lys
                100                 105                 110

Tyr Ala Phe Leu Lys Thr Tyr Asn Tyr Thr Leu Gly Ala Asp Asp Leu
             115                 120                 125

Thr Pro Phe Gly Glu Asn Gln Met Val Asn Ser Gly Ile Lys Phe Tyr
         130                 135                 140

Arg Arg Tyr Lys Ala Leu Ala Arg Lys Ile Val Pro Phe Ile Arg Ala
145                 150                 155                 160

Ser Gly Ser Asp Arg Val Ile Ala Ser Glu Lys Phe Ile Glu Gly
                 165                 170                 175

Phe Gln Ser Ala Lys Leu Ala Asp Pro Gly Ser Gln Pro His Gln Ala
             180                 185                 190

Ser Pro Val Ile Asp Val Ile Pro Glu Gly Ser Gly Tyr Asn Asn
                 195                 200                 205

Thr Leu Asp His Gly Thr Cys Thr Ala Phe Glu Asp Ser Glu Leu Gly
    210                 215                 220

Asp Asp Val Glu Ala Asn Phe Thr Ala Leu Phe Ala Pro Ala Ile Arg
225                 230                 235                 240

Ala Arg Leu Glu Ala Asp Leu Pro Gly Val Thr Leu Thr Asp Glu Asp
                 245                 250                 255

Val Val Tyr Leu Met Asp Met Cys Pro Phe Glu Thr Val Ala Arg Thr
                 260                 265                 270

Ser Asp Ala Thr Glu Leu Ser Pro Phe Cys Ala Leu Phe Thr His Asp
             275                 280                 285

Glu Trp Arg Gln Tyr Asp Tyr Leu Gln Ser Leu Gly Lys Tyr Tyr Gly
    290                 295                 300

Tyr Gly Ala Gly Asn Pro Leu Gly Pro Ala Gln Gly Val Gly Phe Ala
305                 310                 315                 320

Asn Glu Leu Ile Ala Arg Leu Thr Arg Ser Pro Val Gln Asp His Thr
                 325                 330                 335

Ser Thr Asn His Thr Leu Asp Ser Asn Pro Ala Thr Phe Pro Leu Asn
             340                 345                 350

Ala Thr Leu Tyr Ala Asp Phe Ser His Asp Asn Ser Met Ile Ser Ile
             355                 360                 365

Phe Phe Ala Leu Gly Leu Tyr Asn Gly Thr Ala Pro Leu Ser Thr Thr
    370                 375                 380

Ser Val Glu Ser Ile Glu Glu Thr Asp Gly Tyr Ser Ala Ser Trp Thr
385                 390                 395                 400

Val Pro Phe Gly Ala Arg Ala Tyr Val Glu Met Met Gln Cys Gln Ala
                 405                 410                 415

Glu Lys Glu Pro Leu Val Arg Val Leu Val Asn Asp Arg Val Val Pro
```

```
                    420              425              430
Leu His Gly Cys Ala Val Asp Lys Leu Gly Arg Cys Lys Arg Asp Asp
        435              440              445

Phe Val Glu Gly Leu Ser Phe Ala Arg Ser Gly Gly Asn Trp Ala Glu
    450              455              460

Cys Phe Ala
465

<210> SEQ ID NO 117
<211> LENGTH: 1426
<212> TYPE: DNA
<213> ORGANISM: consensus phytase-1 gene

<400> SEQUENCE: 117
tatatgaatt catgggcgtg ttcgtcgtgc tactgtccat tgccaccttg ttcggttcca      60
catccggtac cgccttgggt cctcgtggta attctcactc ttgtgacact gttgacggtg     120
gttaccaatg tttcccagaa atttctcact gtggggtca atactctcca tacttctctt     180
tggaagacga atctgctatt tctccagacg ttccagacga ctgtagagtt actttcgttc     240
aagttttgtc tagacacggt gctagatacc caacttcttc taagtctaag gcttactctg     300
cttttgattga agctattcaa agaacgcta ctgctttcaa gggtaagtac gctttcttga     360
agacttacaa ctacactttg ggtgctgacg acttgactcc attcggtgaa accaaatgg      420
ttaactctgg tattaagttc tacagaagat acaaggcttt ggctagaaag attgttccat     480
tcattagagc ttctggttct gacagagtta ttgcttctgc tgaaaagttc attgaaggtt     540
tccaatctgc taagttggct gacccaggtt ctcaaccaca ccaagcttct ccagttattg     600
acgttattat tccagaagga tccggttaca caacactttt ggaccacggt acttgtactg     660
ctttcgaaga ctctgaattg ggtgacgacg ttgaagctaa cttcactgct ttgttcgctc     720
cagctattag agctagattg gaagctgact tgccaggtgt tactttgact gacgaagacg     780
ttgtttactt gatggacatg tgtccattcg aaactgttgc tagaacttct gacgctactg     840
aattgtctcc attctgtgct tgttcactc acgacgaatg gagacaatac gactacttgc     900
aatctttggg taagtactac ggttacggtg ctggtaaccc attgggtcca gctcaaggtg     960
ttggtttcgc taacgaattg attgctagat tgactagatc tccagttcaa gaccacactt    1020
ctactaacca cactttggac tctaacccag ctactttccc attgaacgct actttgtacg    1080
ctgacttctc tcacgacaac tctatgattt ctatttttctt cgctttgggt ttgtacaacg    1140
gtactgctcc attgtctact acttctgttg aatctattga agaaactgac ggttactctg    1200
cttcttggac tgttccattc ggtgctagag cttacgttga aatgatgcaa tgtcaagctg    1260
aaaaggaacc attggttaga gttttggtta acgacagagt tgttccattg cacggttgtg    1320
ctgttgacaa gttgggtaga tgtaagagag acgacttcgt tgaaggttg tctttcgcta    1380
gatctggtgg taactgggct gaatgtttcg cttaagaatt catata                 1426

<210> SEQ ID NO 118
<211> LENGTH: 422
<212> TYPE: PRT
<213> ORGANISM: P. involutus (phyA1)

<400> SEQUENCE: 118

Ser Val Pro Lys Asn Thr Ala Pro Thr Phe Pro Ile Pro Glu Ser Glu
  1               5                  10                  15

Gln Arg Asn Trp Ser Pro Tyr Ser Pro Tyr Phe Pro Leu Ala Glu Tyr
```

```
                    20                  25                  30
Lys Ala Pro Pro Ala Gly Cys Gln Ile Asn Gln Val Asn Ile Ile Gln
                35                  40                  45
Arg His Gly Ala Arg Phe Pro Thr Ser Gly Ala Thr Thr Arg Ile Lys
             50                  55                  60
Ala Gly Leu Thr Lys Leu Gln Gly Val Gln Asn Phe Thr Asp Ala Lys
 65                  70                  75                  80
Phe Asn Phe Ile Lys Ser Phe Lys Tyr Asp Leu Gly Asn Ser Asp Leu
                 85                  90                  95
Val Pro Phe Gly Ala Ala Gln Ser Phe Asp Ala Gly Gln Glu Ala Phe
                100                 105                 110
Ala Arg Tyr Ser Lys Leu Val Ser Lys Asn Asn Leu Pro Phe Ile Arg
            115                 120                 125
Ala Asp Gly Ser Asp Arg Val Val Asp Ser Ala Thr Asn Trp Thr Ala
        130                 135                 140
Gly Phe Ala Ser Ala Ser His Asn Thr Val Gln Pro Lys Leu Asn Leu
145                 150                 155                 160
Ile Leu Pro Gln Thr Gly Asn Asp Thr Leu Glu Asp Asn Met Cys Pro
                165                 170                 175
Ala Ala Gly Asp Ser Asp Pro Gln Val Asn Ala Trp Leu Ala Val Ala
            180                 185                 190
Phe Pro Ser Ile Thr Ala Arg Leu Asn Ala Ala Pro Ser Val Asn
            195                 200                 205
Leu Thr Asp Thr Asp Ala Phe Asn Leu Val Ser Leu Cys Ala Phe Leu
        210                 215                 220
Thr Val Ser Lys Glu Lys Lys Ser Asp Phe Cys Thr Leu Phe Glu Gly
225                 230                 235                 240
Ile Pro Gly Ser Phe Glu Ala Phe Ala Tyr Gly Gly Asp Leu Asp Lys
                245                 250                 255
Phe Tyr Gly Thr Gly Tyr Gly Gln Glu Leu Gly Pro Val Gln Gly Val
            260                 265                 270
Gly Tyr Val Asn Glu Leu Ile Ala Arg Leu Thr Asn Ser Ala Val Arg
        275                 280                 285
Asp Asn Thr Gln Thr Asn Arg Thr Leu Asp Ala Ser Pro Val Thr Phe
    290                 295                 300
Pro Leu Asn Lys Thr Phe Tyr Ala Asp Phe Ser His Asp Asn Leu Met
305                 310                 315                 320
Val Ala Val Phe Ser Ala Met Gly Leu Phe Arg Gln Pro Ala Pro Leu
                325                 330                 335
Ser Thr Ser Val Pro Asn Pro Trp Arg Thr Trp Arg Thr Ser Ser Leu
            340                 345                 350
Val Pro Phe Ser Gly Arg Met Val Val Glu Arg Leu Ser Cys Phe Gly
        355                 360                 365
Thr Thr Lys Val Arg Val Leu Val Gln Asp Gln Val Gln Pro Leu Glu
    370                 375                 380
Phe Cys Gly Gly Asp Arg Asn Gly Leu Cys Thr Leu Ala Lys Phe Val
385                 390                 395                 400
Glu Ser Gln Thr Phe Ala Arg Ser Asp Gly Ala Gly Asp Phe Glu Lys
                405                 410                 415
Cys Phe Ala Thr Ser Ala
            420

<210> SEQ ID NO 119
```

```
<211> LENGTH: 422
<212> TYPE: PRT
<213> ORGANISM: P. involutus (phyA2)

<400> SEQUENCE: 119
```

| | | | | | | | | | | | | | | |
|---|---|---|---|---|---|---|---|---|---|---|---|---|---|---|
| Ser | Val | Pro | Arg | Asn | Ile | Ala | Pro | Lys | Phe | Ser | Ile | Pro | Glu | Ser | Glu |
| 1 | | | | 5 | | | | | 10 | | | | | 15 | |

Gln Arg Asn Trp Ser Pro Tyr Ser Pro Tyr Phe Pro Leu Ala Glu Tyr
              20                  25                  30

Lys Ala Pro Pro Ala Gly Cys Glu Ile Asn Gln Val Asn Ile Ile Gln
        35                  40                  45

Arg His Gly Ala Arg Phe Pro Thr Ser Gly Ala Ala Thr Arg Ile Lys
    50                  55                  60

Ala Gly Leu Ser Lys Leu Gln Ser Val Gln Asn Phe Thr Asp Pro Lys
65                  70                  75                  80

Phe Asp Phe Ile Lys Ser Phe Thr Tyr Asp Leu Gly Thr Ser Asp Leu
            85                  90                  95

Val Pro Phe Gly Ala Ala Gln Ser Phe Asp Ala Gly Leu Glu Val Phe
            100              105              110

Ala Arg Tyr Ser Lys Leu Val Ser Ser Asp Asn Leu Pro Phe Ile Arg
        115                120              125

Ser Asp Gly Ser Asp Arg Val Val Asp Thr Ala Thr Asn Trp Thr Ala
130                  135                140

Gly Phe Ala Ser Ala Ser Arg Asn Ala Ile Gln Pro Lys Leu Asp Leu
145                150                155              160

Ile Leu Pro Gln Thr Gly Asn Asp Thr Leu Glu Asp Asn Met Cys Pro
            165              170              175

Ala Ala Gly Glu Ser Asp Pro Gln Val Asp Ala Trp Leu Ala Ser Ala
        180                185              190

Phe Pro Ser Val Thr Ala Gln Leu Asn Ala Ala Pro Gly Ala Asn
        195              200              205

Leu Thr Asp Ala Asp Ala Phe Asn Leu Val Ser Leu Cys Pro Phe Met
210                  215                220

Thr Val Ser Lys Glu Gln Lys Ser Asp Phe Cys Thr Leu Phe Glu Gly
225                230                235              240

Ile Pro Gly Ser Phe Glu Ala Phe Ala Tyr Ala Gly Asp Leu Asp Lys
            245              250              255

Phe Tyr Gly Thr Gly Tyr Gly Gln Ala Leu Gly Pro Val Gln Gly Val
        260                265              270

Gly Tyr Ile Asn Glu Leu Leu Ala Arg Leu Thr Asn Ser Ala Val Asn
        275                280              285

Asp Asn Thr Gln Thr Asn Arg Thr Leu Asp Ala Ala Pro Asp Thr Phe
    290                295              300

Pro Leu Asn Lys Thr Met Tyr Ala Asp Phe Ser His Asp Asn Leu Met
305                  310                315              320

Val Ala Val Phe Ser Ala Met Gly Leu Phe Arg Gln Ser Ala Pro Leu
            325              330              335

Ser Thr Ser Thr Pro Asp Pro Asn Arg Thr Trp Leu Thr Ser Ser Val
        340              345              350

Val Pro Phe Ser Ala Arg Met Ala Val Glu Arg Leu Ser Cys Ala Gly
        355              360              365

Thr Thr Lys Val Arg Val Leu Val Gln Asp Gln Val Gln Pro Leu Glu
    370              375              380

Phe Cys Gly Gly Asp Gln Asp Gly Leu Cys Ala Leu Asp Lys Phe Val

```
385             390             395             400
Glu Ser Gln Ala Tyr Ala Arg Ser Gly Gly Ala Gly Asp Phe Glu Lys
                    405             410             415
Cys Leu Ala Thr Thr Val
            420

<210> SEQ ID NO 120
<211> LENGTH: 420
<212> TYPE: PRT
<213> ORGANISM: T. pubescens

<400> SEQUENCE: 120

His Ile Pro Leu Arg Asp Thr Ser Ala Cys Leu Asp Val Thr Arg Asp
 1               5                  10                  15

Val Gln Gln Ser Trp Ser Met Tyr Ser Pro Tyr Phe Pro Ala Ala Thr
                20                  25                  30

Tyr Val Ala Pro Pro Ala Ser Cys Gln Ile Asn Gln Val His Ile Ile
            35                  40                  45

Gln Arg His Gly Ala Arg Phe Pro Thr Ser Gly Ala Ala Lys Arg Ile
    50                  55                  60

Gln Thr Ala Val Ala Lys Leu Lys Ala Ala Ser Asn Tyr Thr Asp Pro
65                  70                  75                  80

Leu Leu Ala Phe Val Thr Asn Tyr Thr Tyr Ser Leu Gly Gln Asp Ser
                85                  90                  95

Leu Val Glu Leu Gly Ala Thr Gln Ser Ser Glu Ala Gly Gln Glu Ala
            100                 105                 110

Phe Thr Arg Tyr Ser Ser Leu Val Ser Ala Asp Glu Leu Pro Phe Val
            115                 120                 125

Arg Ala Ser Gly Ser Asp Arg Val Val Ala Thr Ala Asn Asn Trp Thr
        130                 135                 140

Ala Gly Phe Ala Leu Ala Ser Ser Asn Ser Ile Thr Pro Val Leu Ser
145                 150                 155                 160

Val Ile Ile Ser Glu Ala Gly Asn Asp Thr Leu Asp Asp Asn Met Cys
                165                 170                 175

Pro Ala Ala Gly Asp Ser Asp Pro Gln Val Asn Gln Trp Leu Ala Gln
            180                 185                 190

Phe Ala Pro Pro Met Thr Ala Arg Leu Asn Ala Gly Ala Pro Gly Ala
        195                 200                 205

Asn Leu Thr Asp Thr Asp Thr Tyr Asn Leu Leu Thr Leu Cys Pro Phe
    210                 215                 220

Glu Thr Val Ala Thr Glu Arg Arg Ser Glu Phe Cys Asp Ile Tyr Glu
225                 230                 235                 240

Glu Leu Gln Ala Glu Asp Ala Phe Ala Tyr Asn Ala Asp Leu Asp Lys
                245                 250                 255

Phe Tyr Gly Thr Gly Tyr Gly Gln Pro Leu Gly Pro Val Gln Gly Val
            260                 265                 270

Gly Tyr Ile Asn Glu Leu Ile Ala Arg Leu Thr Ala Gln Asn Val Ser
        275                 280                 285

Asp His Thr Gln Thr Asn Ser Thr Leu Asp Ser Ser Pro Glu Thr Phe
    290                 295                 300

Pro Leu Asn Arg Thr Leu Tyr Ala Asp Phe Ser His Asp Asn Gln Met
305                 310                 315                 320

Val Ala Ile Phe Ser Ala Met Gly Leu Phe Asn Gln Ser Ala Pro Leu
                325                 330                 335
```

-continued

```
Asp Pro Thr Thr Pro Asp Pro Ala Arg Thr Phe Leu Val Lys Lys Ile
            340             345                 350
Val Pro Phe Ser Ala Arg Met Val Val Glu Arg Leu Asp Cys Gly Gly
            355             360                 365
Ala Gln Ser Val Arg Leu Leu Val Asn Asp Ala Val Gln Pro Leu Ala
            370             375                 380
Phe Cys Gly Ala Asp Thr Ser Gly Val Cys Thr Leu Asp Ala Phe Val
385             390             395                 400
Glu Ser Gln Ala Tyr Ala Arg Asn Asp Gly Glu Gly Asp Phe Glu Lys
            405             410                 415
Cys Phe Ala Thr
            420

<210> SEQ ID NO 121
<211> LENGTH: 435
<212> TYPE: PRT
<213> ORGANISM: A. pediades

<400> SEQUENCE: 121

Gly Gly Val Val Gln Ala Thr Phe Val Gln Pro Phe Pro Pro Gln
1               5                   10                  15
Ile Gln Asp Ser Trp Ala Ala Tyr Thr Pro Tyr Tyr Pro Val Gln Ala
            20                  25                  30
Tyr Thr Pro Pro Lys Asp Cys Lys Ile Thr Gln Val Asn Ile Ile
            35                  40                  45
Gln Arg His Gly Ala Arg Phe Pro Thr Ser Gly Ala Gly Thr Arg Ile
        50                  55                  60
Gln Ala Val Lys Lys Leu Gln Ser Ala Lys Thr Tyr Thr Asp Pro
65                  70                  75                  80
Arg Leu Asp Phe Leu Thr Asn Tyr Thr Tyr Thr Leu Gly His Asp Asp
                85                  90                  95
Leu Val Pro Phe Gly Ala Leu Gln Ser Ser Gln Ala Gly Glu Glu Thr
            100                 105                 110
Phe Gln Arg Tyr Ser Phe Leu Val Ser Lys Glu Asn Leu Pro Phe Val
            115                 120                 125
Arg Ala Ser Ser Ser Asn Arg Val Val Asp Ser Ala Thr Asn Trp Thr
        130                 135                 140
Glu Gly Phe Ser Ala Ala Ser His His Val Leu Asn Pro Ile Leu Phe
145                 150                 155                 160
Val Ile Leu Ser Glu Ser Leu Asn Asp Thr Leu Asp Ala Met Cys
                165                 170                 175
Pro Asn Ala Gly Ser Ser Asp Pro Gln Thr Gly Ile Trp Thr Ser Ile
            180                 185                 190
Tyr Gly Thr Pro Ile Ala Asn Arg Leu Asn Gln Gln Ala Pro Gly Ala
            195                 200                 205
Asn Ile Thr Ala Ala Asp Val Ser Asn Leu Ile Pro Leu Cys Ala Phe
        210                 215                 220
Glu Thr Ile Val Lys Glu Thr Pro Ser Pro Phe Cys Asn Leu Phe Thr
225                 230                 235                 240
Pro Glu Glu Phe Ala Gln Phe Glu Tyr Phe Gly Asp Leu Asp Lys Phe
                245                 250                 255
Tyr Gly Thr Gly Tyr Gly Gln Pro Leu Gly Pro Val Gln Gly Val Gly
            260                 265                 270
Tyr Ile Asn Glu Leu Leu Ala Arg Leu Thr Glu Met Pro Val Arg Asp
            275                 280                 285
```

Asn Thr Gln Thr Asn Arg Thr Leu Asp Ser Ser Pro Leu Thr Phe Pro
        290                 295                 300

Leu Asp Arg Ser Ile Tyr Ala Asp Leu Ser His Asp Asn Gln Met Ile
305                 310                 315                 320

Ala Ile Phe Ser Ala Met Gly Leu Phe Asn Gln Ser Ser Pro Leu Asp
                325                 330                 335

Pro Ser Phe Pro Asn Pro Lys Arg Thr Trp Val Thr Ser Arg Leu Thr
                340                 345                 350

Pro Phe Ser Ala Arg Met Val Thr Glu Arg Leu Leu Cys Gln Arg Asp
            355                 360                 365

Gly Thr Gly Ser Gly Gly Pro Ser Arg Ile Met Arg Asn Gly Asn Val
    370                 375                 380

Gln Thr Phe Val Arg Ile Leu Val Asn Asp Ala Leu Gln Pro Leu Lys
385                 390                 395                 400

Phe Cys Gly Gly Asp Met Asp Ser Leu Cys Thr Leu Glu Ala Phe Val
                405                 410                 415

Glu Ser Gln Lys Tyr Ala Arg Glu Asp Gly Gln Gly Asp Phe Glu Lys
            420                 425                 430

Cys Phe Asp
        435

<210> SEQ ID NO 122
<211> LENGTH: 419
<212> TYPE: PRT
<213> ORGANISM: P. lycii

<400> SEQUENCE: 122

Ser Thr Gln Phe Ser Phe Val Ala Ala Gln Leu Pro Ile Pro Ala Gln
1               5                   10                  15

Asn Thr Ser Asn Trp Gly Pro Tyr Asp Pro Phe Phe Pro Val Glu Pro
            20                  25                  30

Tyr Ala Ala Pro Pro Glu Gly Cys Thr Val Thr Gln Val Asn Leu Ile
        35                  40                  45

Gln Arg His Gly Ala Arg Trp Pro Thr Ser Gly Ala Arg Ser Arg Gln
    50                  55                  60

Val Ala Ala Val Ala Lys Ile Gln Met Ala Arg Pro Phe Thr Asp Pro
65                  70                  75                  80

Lys Tyr Glu Phe Leu Asn Asp Phe Val Tyr Lys Phe Gly Val Ala Asp
                85                  90                  95

Leu Leu Pro Phe Gly Ala Asn Gln Ser His Gln Thr Gly Thr Asp Met
                100                 105                 110

Tyr Thr Arg Tyr Ser Thr Leu Phe Glu Gly Gly Asp Val Pro Phe Val
            115                 120                 125

Arg Ala Ala Gly Asp Gln Arg Val Val Asp Ser Ser Thr Asn Trp Thr
    130                 135                 140

Ala Gly Phe Gly Asp Ala Ser Gly Glu Thr Val Leu Pro Thr Leu Gln
145                 150                 155                 160

Val Val Leu Gln Glu Glu Gly Asn Cys Thr Leu Cys Asn Asn Met Cys
                165                 170                 175

Pro Asn Glu Val Asp Gly Asp Glu Ser Thr Thr Trp Leu Gly Val Phe
            180                 185                 190

Ala Pro Asn Ile Thr Ala Arg Leu Asn Ala Ala Pro Ser Ala Asn
        195                 200                 205

Leu Ser Asp Ser Asp Ala Leu Thr Leu Met Asp Met Cys Pro Phe Asp

-continued

```
                210                 215                 220
Thr Leu Ser Ser Gly Asn Ala Ser Pro Phe Cys Asp Leu Phe Thr Ala
225                 230                 235                 240
Glu Glu Tyr Val Ser Tyr Glu Tyr Tyr Asp Leu Asp Lys Tyr Tyr
                245                 250                 255
Gly Thr Gly Pro Gly Asn Ala Leu Gly Pro Val Gln Gly Val Gly Tyr
                260                 265                 270
Val Asn Glu Leu Leu Ala Arg Leu Thr Gly Gln Ala Val Arg Asp Glu
                275                 280                 285
Thr Gln Thr Asn Arg Thr Leu Asp Ser Asp Pro Ala Thr Phe Pro Leu
                290                 295                 300
Asn Arg Thr Phe Tyr Ala Asp Phe Ser His Asp Asn Thr Met Val Pro
305                 310                 315                 320
Ile Phe Ala Ala Leu Gly Leu Phe Asn Ala Thr Ala Leu Asp Pro Leu
                325                 330                 335
Lys Pro Asp Glu Asn Arg Leu Trp Val Asp Ser Lys Leu Val Pro Phe
                340                 345                 350
Ser Gly His Met Thr Val Glu Lys Leu Ala Cys Ser Gly Lys Glu Ala
                355                 360                 365
Val Arg Val Leu Val Asn Asp Ala Val Gln Pro Leu Glu Phe Cys Gly
                370                 375                 380
Gly Val Asp Gly Val Cys Glu Leu Ser Ala Phe Val Glu Ser Gln Thr
385                 390                 395                 400
Tyr Ala Arg Glu Asn Gly Gln Gly Asp Phe Ala Lys Cys Gly Phe Val
                405                 410                 415
Pro Ser Glu

<210> SEQ ID NO 123
<211> LENGTH: 369
<212> TYPE: PRT
<213> ORGANISM: Basidio

<400> SEQUENCE: 123

Ser Pro Arg Thr Ala Ala Gln Leu Pro Ile Pro Gln Gln Trp Ser Pro
1               5                   10                  15
Tyr Ser Pro Tyr Phe Pro Val Ala Tyr Ala Pro Ala Gly Cys Gln
                20                  25                  30
Ile Gln Val Asn Ile Ile Gln Arg His Gly Ala Arg Phe Pro Thr Ser
                35                  40                  45
Gly Ala Ala Thr Arg Ile Gln Ala Ala Val Ala Lys Leu Gln Ser Ala
            50                  55                  60
Thr Asp Pro Lys Leu Asp Phe Leu Asn Thr Tyr Leu Gly Asp Asp Leu
65                  70                  75                  80
Val Pro Phe Gly Ala Gln Ser Ser Gln Ala Gly Gln Glu Ala Phe Thr
                85                  90                  95
Arg Tyr Ser Leu Val Ser Asp Asn Leu Pro Phe Val Arg Ala Ser Gly
                100                 105                 110
Ser Asp Arg Val Val Asp Ser Ala Thr Asn Trp Thr Ala Gly Phe Ala
            115                 120                 125
Ala Ser Asn Thr Pro Leu Val Ile Leu Ser Glu Gly Asn Asp Thr Leu
            130                 135                 140
Asp Asp Asn Met Cys Pro Ala Gly Asp Ser Asp Pro Gln Asn Trp Leu
145                 150                 155                 160
Ala Val Phe Ala Pro Pro Ile Thr Ala Arg Leu Asn Ala Ala Ala Pro
```

```
                    165                 170                 175
Gly Ala Asn Leu Thr Asp Asp Ala Asn Leu Leu Cys Pro Phe Glu Thr
                180                 185                 190

Val Ser Glu Ser Phe Cys Asp Leu Phe Glu Pro Glu Phe Ala Phe
            195                 200                 205

Tyr Gly Asp Leu Asp Lys Phe Tyr Gly Thr Gly Tyr Gly Gln Pro Leu
        210                 215                 220

Gly Pro Val Gln Gly Val Gly Tyr Ile Asn Glu Leu Leu Ala Arg Leu
225                 230                 235                 240

Thr Gln Ala Val Arg Asp Asn Thr Gln Thr Asn Arg Thr Leu Asp Ser
                245                 250                 255

Ser Pro Thr Phe Pro Leu Asn Arg Thr Phe Tyr Ala Asp Phe Ser His
            260                 265                 270

Asp Asn Gln Met Val Ala Ile Phe Ser Ala Met Gly Leu Phe Asn Gln
        275                 280                 285

Ser Ala Pro Leu Asp Pro Ser Pro Asp Pro Asn Arg Thr Trp Val Thr
    290                 295                 300

Ser Lys Leu Val Pro Phe Ser Ala Arg Met Val Val Glu Arg Leu Cys
305                 310                 315                 320

Gly Thr Val Arg Val Leu Val Asn Asp Ala Val Gln Pro Leu Glu Phe
                325                 330                 335

Cys Gly Gly Asp Asp Gly Cys Thr Leu Asp Ala Phe Val Glu Ser Gln
            340                 345                 350

Tyr Ala Arg Glu Asp Gly Gln Gly Asp Phe Glu Lys Cys Phe Ala Thr
        355                 360                 365

Pro

<210> SEQ ID NO 124
<211> LENGTH: 440
<212> TYPE: PRT
<213> ORGANISM: A. terreus 9a1

<400> SEQUENCE: 124

Lys His Ser Asp Cys Asn Ser Val Asp His Gly Tyr Gln Cys Phe Pro
 1               5                  10                  15

Glu Leu Ser His Lys Trp Gly Leu Tyr Ala Pro Tyr Phe Ser Leu Gln
                20                  25                  30

Asp Glu Ser Pro Phe Pro Leu Asp Val Pro Glu Asp Cys His Ile Thr
            35                  40                  45

Phe Val Gln Val Leu Ala Arg His Gly Ala Arg Ser Pro Thr His Ser
        50                  55                  60

Lys Thr Lys Ala Tyr Ala Ala Thr Ile Ala Ala Ile Gln Lys Ser Ala
65                  70                  75                  80

Thr Ala Phe Pro Gly Lys Tyr Ala Phe Leu Gln Ser Tyr Asn Tyr Ser
                85                  90                  95

Leu Asp Ser Glu Glu Leu Thr Pro Phe Gly Arg Asn Gln Leu Arg Asp
            100                 105                 110

Leu Gly Ala Gln Phe Tyr Glu Arg Tyr Asn Ala Leu Thr Arg His Ile
        115                 120                 125

Asn Pro Phe Val Arg Ala Thr Asp Ala Ser Arg Val His Glu Ser Ala
    130                 135                 140

Glu Lys Phe Val Glu Gly Phe Gln Thr Ala Arg Gln Asp Asp His His
145                 150                 155                 160

Ala Asn Pro His Gln Pro Ser Pro Arg Val Asp Val Ala Ile Pro Glu
```

-continued

```
                165                 170                 175
Gly Ser Ala Tyr Asn Asn Thr Leu Glu His Ser Leu Cys Thr Ala Phe
            180                 185                 190

Glu Ser Ser Thr Val Gly Asp Asp Ala Val Ala Asn Phe Thr Ala Val
        195                 200                 205

Phe Ala Pro Ala Ile Ala Gln Arg Leu Glu Ala Asp Leu Pro Gly Val
    210                 215                 220

Gln Leu Ser Thr Asp Asp Val Val Asn Leu Met Ala Met Cys Pro Phe
225                 230                 235                 240

Glu Thr Val Ser Leu Thr Asp Asp Ala His Thr Leu Ser Pro Phe Cys
                245                 250                 255

Asp Leu Phe Thr Ala Thr Glu Trp Thr Gln Tyr Asn Tyr Leu Leu Ser
            260                 265                 270

Leu Asp Lys Tyr Tyr Gly Tyr Gly Gly Asn Pro Leu Gly Pro Val
        275                 280                 285

Gln Gly Val Gly Trp Ala Asn Glu Leu Met Ala Arg Leu Thr Arg Ala
    290                 295                 300

Pro Val His Asp His Thr Cys Val Asn Asn Thr Leu Asp Ala Ser Pro
305                 310                 315                 320

Ala Thr Phe Pro Leu Asn Ala Thr Leu Tyr Ala Asp Phe Ser His Asp
                325                 330                 335

Ser Asn Leu Val Ser Ile Phe Trp Ala Leu Gly Leu Tyr Asn Gly Thr
            340                 345                 350

Ala Pro Leu Ser Gln Thr Ser Val Glu Ser Val Ser Gln Thr Asp Gly
        355                 360                 365

Tyr Ala Ala Ala Trp Thr Val Pro Phe Ala Ala Arg Ala Tyr Val Glu
    370                 375                 380

Met Met Gln Cys Arg Ala Glu Lys Glu Pro Leu Val Arg Val Leu Val
385                 390                 395                 400

Asn Asp Arg Val Met Pro Leu His Gly Cys Pro Thr Asp Lys Leu Gly
                405                 410                 415

Arg Cys Lys Arg Asp Ala Phe Val Ala Gly Leu Ser Phe Ala Gln Ala
            420                 425                 430

Gly Gly Asn Trp Ala Asp Cys Phe
        435                 440

<210> SEQ ID NO 125
<211> LENGTH: 440
<212> TYPE: PRT
<213> ORGANISM: A. terreus cbs

<400> SEQUENCE: 125

Asn His Ser Asp Cys Thr Ser Val Asp Arg Gly Tyr Gln Cys Phe Pro
1               5                   10                  15

Glu Leu Ser His Lys Trp Gly Leu Tyr Ala Pro Tyr Phe Ser Leu Gln
            20                  25                  30

Asp Glu Ser Pro Phe Pro Leu Asp Val Pro Asp Asp Cys His Ile Thr
        35                  40                  45

Phe Val Gln Val Leu Ala Arg His Gly Ala Arg Ser Pro Thr Asp Ser
    50                  55                  60

Lys Thr Lys Ala Tyr Ala Ala Thr Ile Ala Ala Ile Gln Lys Asn Ala
65                  70                  75                  80

Thr Ala Leu Pro Gly Lys Tyr Ala Phe Leu Lys Ser Tyr Asn Tyr Ser
                85                  90                  95
```

```
Met Gly Ser Glu Asn Leu Thr Pro Phe Gly Arg Asn Gln Leu Gln Asp
            100                 105                 110

Leu Gly Ala Gln Phe Tyr Arg Arg Tyr Asp Thr Leu Thr Arg His Ile
            115                 120                 125

Asn Pro Phe Val Arg Ala Ala Asp Ser Ser Arg Val His Glu Ser Ala
            130                 135             140

Glu Lys Phe Val Glu Gly Phe Gln Asn Ala Arg Gln Gly Asp Pro His
145                 150                 155                 160

Ala Asn Pro His Gln Pro Ser Pro Arg Val Asp Val Ile Pro Glu
                165                 170                 175

Gly Thr Ala Tyr Asn Asn Thr Leu Glu His Ser Ile Cys Thr Ala Phe
                180                 185                 190

Glu Ala Ser Thr Val Gly Asp Ala Ala Asp Asn Phe Thr Ala Val
            195                 200                 205

Phe Ala Pro Ala Ile Ala Lys Arg Leu Glu Ala Asp Leu Pro Gly Val
            210                 215                 220

Gln Leu Ser Ala Asp Val Val Asn Leu Met Ala Met Cys Pro Phe
225                 230                 235                 240

Glu Thr Val Ser Leu Thr Asp Ala His Thr Leu Ser Pro Phe Cys
                245                 250                 255

Asp Leu Phe Thr Ala Ala Glu Trp Thr Gln Tyr Asn Tyr Leu Leu Ser
                260                 265                 270

Leu Asp Lys Tyr Tyr Gly Tyr Gly Gly Asn Pro Leu Gly Pro Val
            275                 280                 285

Gln Gly Val Gly Trp Ala Asn Glu Leu Ile Ala Arg Leu Thr Arg Ser
290                 295                 300

Pro Val His Asp His Thr Cys Val Asn Asn Thr Leu Asp Ala Asn Pro
305                 310                 315                 320

Ala Thr Phe Pro Leu Asn Ala Thr Leu Tyr Ala Asp Phe Ser His Asp
                325                 330                 335

Ser Asn Leu Val Ser Ile Phe Trp Ala Leu Gly Leu Tyr Asn Gly Thr
            340                 345                 350

Lys Pro Leu Ser Gln Thr Thr Val Glu Asp Ile Thr Arg Thr Asp Gly
            355                 360                 365

Tyr Ala Ala Ala Trp Thr Val Pro Phe Ala Ala Arg Ala Tyr Ile Glu
370                 375                 380

Met Met Gln Cys Arg Ala Glu Lys Gln Pro Leu Val Arg Val Leu Val
385                 390                 395                 400

Asn Asp Arg Val Met Pro Leu His Gly Cys Ala Val Asp Asn Leu Gly
                405                 410                 415

Arg Cys Lys Arg Asp Asp Phe Val Glu Gly Leu Ser Phe Ala Arg Ala
                420                 425                 430

Gly Gly Asn Trp Ala Glu Cys Phe
            435                 440

<210> SEQ ID NO 126
<211> LENGTH: 441
<212> TYPE: PRT
<213> ORGANISM: A. niger var. awamori

<400> SEQUENCE: 126

Asn Gln Ser Thr Cys Asp Thr Val Asp Gln Gly Tyr Gln Cys Phe Ser
  1               5                  10                  15

Glu Thr Ser His Leu Trp Gly Gln Tyr Ala Pro Phe Phe Ser Leu Ala
            20                  25                  30
```

-continued

```
Asn Glu Ser Ala Ile Ser Pro Asp Val Pro Ala Gly Cys Arg Val Thr
     35                  40                  45

Phe Ala Gln Val Leu Ser Arg His Gly Ala Arg Tyr Pro Thr Glu Ser
 50                  55                  60

Lys Gly Lys Lys Tyr Ser Ala Leu Ile Glu Glu Ile Gln Gln Asn Val
 65                  70                  75                  80

Thr Thr Phe Asp Gly Lys Tyr Ala Phe Leu Lys Thr Tyr Asn Tyr Ser
                 85                  90                  95

Leu Gly Ala Asp Asp Leu Thr Pro Phe Gly Glu Gln Glu Leu Val Asn
             100                 105                 110

Ser Gly Ile Lys Phe Tyr Gln Arg Tyr Glu Ser Leu Thr Arg Asn Ile
             115                 120                 125

Ile Pro Phe Ile Arg Ser Ser Gly Ser Ser Arg Val Ile Ala Ser Gly
 130                 135                 140

Glu Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                 165                 170                 175

Ala Ser Ser Asn Asn Thr Leu Asp Pro Gly Thr Cys Thr Val Phe
             180                 185                 190

Glu Asp Ser Glu Leu Ala Asp Thr Val Glu Ala Asn Phe Thr Ala Thr
             195                 200                 205

Phe Ala Pro Ser Ile Arg Gln Arg Leu Glu Asn Asp Leu Ser Gly Val
 210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                 245                 250                 255

Asp Leu Phe Thr His Asp Glu Trp Ile His Tyr Asp Tyr Leu Gln Ser
             260                 265                 270

Leu Lys Lys Tyr Tyr Gly His Gly Ala Gly Asn Pro Leu Gly Pro Thr
             275                 280                 285

Gln Gly Val Gly Tyr Ala Asn Glu Leu Ile Ala Arg Leu Thr His Ser
290                 295                 300

Pro Val His Asp Asp Thr Ser Ser Asn His Thr Leu Asp Ser Asn Pro
305                 310                 315                 320

Ala Thr Phe Pro Leu Asn Ser Thr Leu Tyr Ala Asp Phe Ser His Asp
                 325                 330                 335

Asn Gly Ile Ile Ser Ile Leu Phe Ala Leu Gly Leu Tyr Asn Gly Thr
             340                 345                 350

Lys Pro Leu Ser Thr Thr Thr Val Glu Asn Ile Thr Gln Thr Asp Gly
             355                 360                 365

Phe Ser Ser Ala Trp Thr Val Pro Phe Ala Ser Arg Leu Tyr Val Glu
 370                 375                 380

Met Met Gln Cys Gln Ala Glu Gln Glu Pro Leu Val Arg Val Leu Val
385                 390                 395                 400

Asn Asp Arg Val Val Pro Leu His Gly Cys Pro Ile Asp Ala Leu Gly
                 405                 410                 415

Arg Cys Thr Arg Asp Ser Phe Val Arg Gly Leu Ser Phe Ala Arg Ser
             420                 425                 430

Gly Gly Asp Trp Ala Glu Cys Ser Ala
             435                 440
```

-continued

```
<210> SEQ ID NO 127
<211> LENGTH: 441
<212> TYPE: PRT
<213> ORGANISM: A. niger NRRL3135

<400> SEQUENCE: 127

Asn Gln Ser Ser Cys Asp Thr Val Asp Gln Gly Tyr Gln Cys Phe Ser
  1               5                  10                  15

Glu Thr Ser His Leu Trp Gly Gln Tyr Ala Pro Phe Phe Ser Leu Ala
             20                  25                  30

Asn Glu Ser Val Ile Ser Pro Glu Val Pro Ala Gly Cys Arg Val Thr
         35                  40                  45

Phe Ala Gln Val Leu Ser Arg His Gly Ala Arg Tyr Pro Thr Asp Ser
     50                  55                  60

Lys Gly Lys Lys Tyr Ser Ala Leu Ile Glu Ile Gln Gln Asn Ala
 65                  70                  75                  80

Thr Thr Phe Asp Gly Lys Tyr Ala Phe Leu Lys Thr Tyr Asn Tyr Ser
                 85                  90                  95

Leu Gly Ala Asp Asp Leu Thr Pro Phe Gly Glu Gln Glu Leu Val Asn
            100                 105                 110

Ser Gly Ile Lys Phe Tyr Gln Arg Tyr Glu Ser Leu Thr Arg Asn Ile
        115                 120                 125

Val Pro Phe Ile Arg Ser Ser Gly Ser Ser Arg Val Ile Ala Ser Gly
    130                 135                 140

Lys Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Asn Asn Thr Leu Asp Pro Gly Thr Cys Thr Val Phe
            180                 185                 190

Glu Asp Ser Glu Leu Ala Asp Thr Val Glu Ala Asn Phe Thr Ala Thr
        195                 200                 205

Phe Val Pro Ser Ile Arg Gln Arg Leu Glu Asn Asp Leu Ser Gly Val
    210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile Asn Tyr Asp Tyr Leu Gln Ser
            260                 265                 270

Leu Lys Lys Tyr Tyr Gly His Gly Ala Gly Asn Pro Leu Gly Pro Thr
        275                 280                 285

Gln Gly Val Gly Tyr Ala Asn Glu Leu Ile Ala Arg Leu Thr His Ser
    290                 295                 300

Pro Val His Asp Asp Thr Ser Ser Asn His Thr Leu Asp Ser Ser Pro
305                 310                 315                 320

Ala Thr Phe Pro Leu Asn Ser Thr Leu Tyr Ala Asp Phe Ser His Asp
                325                 330                 335

Asn Gly Ile Ile Ser Ile Leu Phe Ala Leu Gly Leu Tyr Asn Gly Thr
            340                 345                 350

Lys Pro Leu Ser Thr Thr Thr Val Glu Asn Ile Thr Gln Thr Asp Gly
        355                 360                 365

Phe Ser Ser Ala Trp Thr Val Pro Phe Ala Ser Arg Leu Tyr Val Glu
    370                 375                 380
```

```
Met Met Gln Cys Gln Ala Glu Gln Glu Pro Leu Val Arg Val Leu Val
385                 390                 395                 400

Asn Asp Arg Val Val Pro Leu His Gly Cys Pro Val Asp Ala Leu Gly
            405                 410                 415

Arg Cys Thr Arg Asp Ser Phe Val Arg Gly Leu Ser Phe Ala Arg Ser
            420                 425                 430

Gly Gly Asp Trp Ala Glu Cys Phe Ala
        435                 440

<210> SEQ ID NO 128
<211> LENGTH: 440
<212> TYPE: PRT
<213> ORGANISM: A. fumigatus 13073

<400> SEQUENCE: 128

Gly Ser Lys Ser Cys Asp Thr Val Asp Leu Gly Tyr Gln Cys Ser Pro
 1               5                  10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
 50                  55                  60

Lys Ser Lys Lys Tyr Lys Lys Leu Val Thr Ala Ile Gln Ala Asn Ala
 65                  70                  75                  80

Thr Asp Phe Lys Gly Lys Phe Ala Phe Leu Lys Thr Tyr Asn Tyr Thr
                 85                  90                  95

Leu Gly Ala Asp Asp Leu Thr Pro Phe Gly Glu Gln Leu Val Asn
                100                 105                 110

Ser Gly Ile Lys Phe Tyr Gln Arg Tyr Lys Ala Leu Ala Arg Ser Val
                115                 120                 125

Val Pro Phe Ile Arg Ala Ser Gly Ser Asp Arg Val Ile Ala Ser Gly
130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
                165                 170                 175

Glu Thr Phe Asn Asn Thr Leu Asp His Gly Val Cys Thr Lys Phe Glu
                180                 185                 190

Ala Ser Gln Leu Gly Asp Glu Val Ala Ala Asn Phe Thr Ala Leu Phe
                195                 200                 205

Ala Pro Asp Ile Arg Ala Arg Ala Glu Lys His Leu Pro Gly Val Thr
                210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
                275                 280                 285

Gly Ile Gly Phe Thr Asn Glu Leu Ile Ala Arg Leu Thr Arg Ser Pro
                290                 295                 300

Val Gln Asp His Thr Ser Thr Asn Ser Thr Leu Val Ser Asn Pro Ala
```

-continued

```
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
        355                 360                 365

Ser Ala Ser Trp Val Val Pro Phe Gly Ala Arg Ala Tyr Phe Glu Thr
370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
                435                 440

<210> SEQ ID NO 129
<211> LENGTH: 440
<212> TYPE: PRT
<213> ORGANISM: A. fumigatus 32722

<400> SEQUENCE: 129

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
        115                 120                 125

Val Pro Phe Ile Arg Ala Ser Gly Ser Asp Arg Val Ile Ala Ser Gly
    130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
                165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
        195                 200                 205

Ala Pro Asp Ile Arg Ala Arg Ala Glu Lys His Leu Pro Gly Val Thr
    210                 215                 220

Leu Thr Asp Glu Asp Val Val Ser Leu Met Asp Met Cys Ser Phe Asp
225                 230                 235                 240
```

-continued

```
Thr Val Ala Arg Thr Ser Asp Ala Ser Gln Leu Ser Pro Phe Cys Gln
            245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
        290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Gly
                340                 345                 350

Pro Leu Ser Arg Thr Ser Val Glu Ser Ala Lys Glu Leu Asp Gly Tyr
                355                 360                 365

Ser Ala Ser Trp Val Val Pro Phe Gly Ala Arg Ala Tyr Phe Glu Thr
        370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
        435                 440

<210> SEQ ID NO 130
<211> LENGTH: 440
<212> TYPE: PRT
<213> ORGANISM: A. fumigatus 58128

<400> SEQUENCE: 130

Gly Ser Lys Ser Cys Asp Thr Val Asp Leu Gly Tyr Gln Cys Ser Pro
 1               5                  10                  15

Ala Thr Ser His Leu Trp Gly Gln Tyr Ser Pro Phe Phe Ser Leu Glu
                20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Leu Val Asn
                100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
    130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
                165                 170                 175
```

```
Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
        195                 200                 205

Ala Pro Asp Ile Arg Ala Arg Ala Glu Lys His Leu Pro Gly Val Thr
    210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
        275                 280                 285

Gly Ile Gly Phe Thr Asn Glu Leu Ile Ala Arg Leu Thr Arg Ser Pro
    290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
        355                 360                 365

Ser Ala Ser Trp Val Val Pro Phe Gly Ala Arg Ala Tyr Phe Glu Thr
    370                 375                 380

Met Gln Cys Lys Ser Glu Lys Glu Ser Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
            420                 425                 430

Gly Asn Trp Gly Glu Cys Phe Ser
        435                 440

<210> SEQ ID NO 131
<211> LENGTH: 440
<212> TYPE: PRT
<213> ORGANISM: A. fumigatus 26906

<400> SEQUENCE: 131

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Ala Phe Gly Glu Gln Gln Leu Val Asn
```

```
                    100                 105                 110
Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
            165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
            195                 200                 205

Ala Pro Asp Ile Arg Ala Arg Ala Lys Lys His Leu Pro Gly Val Thr
            210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
            245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
            290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
            325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
            370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
            420                 425                 430

Gly Asn Trp Gly Glu Cys Phe Ser
            435                 440

<210> SEQ ID NO 132
<211> LENGTH: 440
<212> TYPE: PRT
<213> ORGANISM: A. fumigatus 32239

<400> SEQUENCE: 132

Gly Ser Lys Ala Cys Asp Thr Val Glu Leu Gly Tyr Gln Cys Ser Pro
1               5                   10                  15

Gly Thr Ser His Leu Trp Gly Gln Tyr Ser Pro Phe Phe Ser Leu Glu
            20                  25                  30
```

-continued

```
Asp Glu Leu Ser Val Ser Ser Asp Leu Pro Lys Asp Cys Arg Val Thr
         35                  40                  45

Phe Val Gln Val Leu Ser Arg His Gly Ala Arg Tyr Pro Thr Ala Ser
     50                  55                  60

Lys Ser Lys Lys Tyr Lys Lys Leu Val Thr Ala Ile Gln Lys Asn Ala
 65                  70                  75                  80

Thr Glu Phe Lys Gly Lys Phe Ala Phe Leu Glu Thr Tyr Asn Tyr Thr
                 85                  90                  95

Leu Gly Ala Asp Asp Leu Thr Pro Phe Gly Glu Gln Gln Met Val Asn
             100                 105                 110

Ser Gly Ile Lys Phe Tyr Gln Lys Tyr Lys Ala Leu Ala Gly Ser Val
             115                 120                 125

Val Pro Phe Ile Arg Ser Ser Gly Ser Asp Arg Val Ile Ala Ser Gly
         130                 135                 140

Glu Lys Phe Ile Glu Gly Phe Gln Gln Ala Asn Val Ala Asp Pro Gly
145                 150                 155                 160

Ala Thr Asn Arg Ala Ala Pro Val Ile Ser Val Ile Pro Glu Ser
             165                 170                 175

Glu Thr Tyr Asn Asn Thr Leu Asp His Ser Val Cys Thr Asn Phe Glu
             180                 185                 190

Ala Ser Glu Leu Gly Asp Glu Val Glu Ala Asn Phe Thr Ala Leu Phe
         195                 200                 205

Ala Pro Ala Ile Arg Ala Arg Ile Glu Lys His Leu Pro Gly Val Gln
     210                 215                 220

Leu Thr Asp Asp Asp Val Val Ser Leu Met Asp Met Cys Ser Phe Asp
225                 230                 235                 240

Thr Val Ala Arg Thr Ala Asp Ala Ser Glu Leu Ser Pro Phe Cys Ala
                 245                 250                 255

Ile Phe Thr His Asn Glu Trp Lys Lys Tyr Asp Tyr Leu Gln Ser Leu
             260                 265                 270

Gly Lys Tyr Tyr Gly Tyr Gly Ala Gly Asn Pro Leu Gly Pro Ala Gln
         275                 280                 285

Gly Ile Gly Phe Thr Asn Glu Leu Ile Ala Arg Leu Thr Asn Ser Pro
     290                 295                 300

Val Gln Asp His Thr Ser Thr Asn Ser Thr Leu Asp Ser Asp Pro Ala
305                 310                 315                 320

Thr Phe Pro Leu Asn Ala Thr Ile Tyr Val Asp Phe Ser His Asp Asn
                 325                 330                 335

Gly Met Ile Pro Ile Phe Phe Ala Met Gly Leu Tyr Asn Gly Thr Glu
             340                 345                 350

Pro Leu Ser Gln Thr Ser Glu Glu Ser Thr Lys Glu Ser Asn Gly Tyr
         355                 360                 365

Ser Ala Ser Trp Ala Val Pro Phe Gly Ala Arg Ala Tyr Phe Glu Thr
     370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Ala Val Asp Lys Leu Gly Arg
                 405                 410                 415

Cys Lys Leu Lys Asp Phe Val Lys Gly Leu Ser Trp Ala Arg Ser Gly
             420                 425                 430

Gly Asn Ser Glu Gln Ser Phe Ser
             435                 440
```

```
<210> SEQ ID NO 133
<211> LENGTH: 439
<212> TYPE: PRT
<213> ORGANISM: E. nidulans

<400> SEQUENCE: 133

Gln Asn His Ser Cys Asn Thr Ala Asp Gly Gly Tyr Gln Cys Phe Pro
  1               5                  10                  15

Asn Val Ser His Val Trp Gly Gln Tyr Ser Pro Tyr Phe Ser Ile Glu
             20                  25                  30

Gln Glu Ser Ala Ile Ser Glu Asp Val Pro His Gly Cys Glu Val Thr
         35                  40                  45

Phe Val Gln Val Leu Ser Arg His Gly Ala Arg Tyr Pro Thr Glu Ser
     50                  55                  60

Lys Ser Lys Ala Tyr Ser Gly Leu Ile Glu Ala Ile Gln Lys Asn Ala
 65                  70                  75                  80

Thr Ser Phe Trp Gly Gln Tyr Ala Phe Leu Glu Ser Tyr Asn Tyr Thr
                 85                  90                  95

Leu Gly Ala Asp Asp Leu Thr Ile Phe Gly Glu Asn Gln Met Val Asp
            100                 105                 110

Ser Gly Ala Lys Phe Tyr Arg Arg Tyr Lys Asn Leu Ala Arg Lys Asn
        115                 120                 125

Thr Pro Phe Ile Arg Ala Ser Gly Ser Asp Arg Val Val Ala Ser Ala
130                 135                 140

Glu Lys Phe Ile Asn Gly Phe Arg Lys Ala Gln Leu His Asp His Gly
145                 150                 155                 160

Ser Gly Gln Ala Thr Pro Val Val Asn Val Ile Ile Pro Glu Ile Asp
                165                 170                 175

Gly Phe Asn Asn Thr Leu Asp His Ser Thr Cys Val Ser Phe Glu Asn
            180                 185                 190

Asp Glu Arg Ala Asp Glu Ile Glu Ala Asn Phe Thr Ala Ile Met Gly
        195                 200                 205

Pro Pro Ile Arg Lys Arg Leu Glu Asn Asp Leu Pro Gly Ile Lys Leu
    210                 215                 220

Thr Asn Glu Asn Val Ile Tyr Leu Met Asp Met Cys Ser Phe Asp Thr
225                 230                 235                 240

Met Ala Arg Thr Ala His Gly Thr Glu Leu Ser Pro Phe Cys Ala Ile
                245                 250                 255

Phe Thr Glu Lys Glu Trp Leu Gln Tyr Asp Tyr Leu Gln Ser Leu Ser
            260                 265                 270

Lys Tyr Tyr Gly Tyr Gly Ala Gly Ser Pro Leu Gly Pro Ala Gln Gly
        275                 280                 285

Ile Gly Phe Thr Asn Glu Leu Ile Ala Arg Leu Thr Gln Ser Pro Val
    290                 295                 300

Gln Asp Asn Thr Ser Thr Asn His Thr Leu Asp Ser Asn Pro Ala Thr
305                 310                 315                 320

Phe Pro Leu Asp Arg Lys Leu Tyr Ala Asp Phe Ser His Asp Asn Ser
                325                 330                 335

Met Ile Ser Ile Phe Phe Ala Met Gly Leu Tyr Asn Gly Thr Gln Pro
            340                 345                 350

Leu Ser Met Asp Ser Val Glu Ser Ile Gln Glu Met Asp Gly Tyr Ala
        355                 360                 365

Ala Ser Trp Thr Val Pro Phe Gly Ala Arg Ala Tyr Phe Glu Leu Met
    370                 375                 380
```

-continued

Gln Cys Glu Lys Lys Glu Pro Leu Val Arg Val Leu Val Asn Asp Arg
385                 390                 395                 400

Val Val Pro Leu His Gly Cys Ala Val Asp Lys Phe Gly Arg Cys Thr
            405                 410                 415

Leu Asp Asp Trp Val Glu Gly Leu Asn Phe Ala Arg Ser Gly Gly Asn
            420                 425                 430

Trp Lys Thr Cys Phe Thr Leu
            435

<210> SEQ ID NO 134
<211> LENGTH: 443
<212> TYPE: PRT
<213> ORGANISM: T. thermophilus

<400> SEQUENCE: 134

Asp Ser His Ser Cys Asn Thr Val Glu Gly Gly Tyr Gln Cys Arg Pro
1               5                   10                  15

Glu Ile Ser His Ser Trp Gly Gln Tyr Ser Pro Phe Phe Ser Leu Ala
                20                  25                  30

Asp Gln Ser Glu Ile Ser Pro Asp Val Pro Gln Asn Cys Lys Ile Thr
            35                  40                  45

Phe Val Gln Leu Leu Ser Arg His Gly Ala Arg Tyr Pro Thr Ser Ser
    50                  55                  60

Lys Thr Glu Leu Tyr Ser Gln Leu Ile Ser Arg Ile Gln Lys Thr Ala
65                  70                  75                  80

Thr Ala Tyr Lys Gly Tyr Tyr Ala Phe Leu Lys Asp Tyr Arg Tyr Gln
                85                  90                  95

Leu Gly Ala Asn Asp Leu Thr Pro Phe Gly Glu Asn Gln Met Ile Gln
            100                 105                 110

Leu Gly Ile Lys Phe Tyr Asn His Tyr Lys Ser Leu Ala Arg Asn Ala
        115                 120                 125

Val Pro Phe Val Arg Cys Ser Gly Ser Asp Arg Val Ile Ala Ser Gly
    130                 135                 140

Arg Leu Phe Ile Glu Gly Phe Gln Ser Ala Lys Val Leu Asp Pro His
145                 150                 155                 160

Ser Asp Lys His Asp Ala Pro Pro Thr Ile Asn Val Ile Ile Glu Glu
                165                 170                 175

Gly Pro Ser Tyr Asn Asn Thr Leu Asp Thr Gly Ser Cys Pro Val Phe
            180                 185                 190

Glu Asp Ser Ser Gly Gly His Asp Ala Gln Glu Lys Phe Ala Lys Gln
        195                 200                 205

Phe Ala Pro Ala Ile Leu Glu Lys Ile Lys Asp His Leu Pro Gly Val
    210                 215                 220

Asp Leu Ala Val Ser Asp Val Pro Tyr Leu Met Asp Leu Cys Pro Phe
225                 230                 235                 240

Glu Thr Leu Ala Arg Asn His Thr Asp Thr Leu Ser Pro Phe Cys Ala
                245                 250                 255

Leu Ser Thr Gln Glu Glu Trp Gln Ala Tyr Asp Tyr Gln Ser Leu
            260                 265                 270

Gly Lys Tyr Tyr Gly Asn Gly Gly Asn Pro Leu Gly Pro Ala Gln
        275                 280                 285

Gly Val Gly Phe Val Asn Glu Leu Ile Ala Arg Met Thr His Ser Pro
    290                 295                 300

Val Gln Asp Tyr Thr Thr Val Asn His Thr Leu Asp Ser Asn Pro Ala
305                 310                 315                 320

```
Thr Phe Pro Leu Asn Ala Thr Leu Tyr Ala Asp Phe Ser His Asp Asn
            325                 330                 335

Thr Met Thr Ser Ile Phe Ala Ala Leu Gly Leu Tyr Asn Gly Thr Ala
            340                 345                 350

Lys Leu Ser Thr Thr Glu Ile Lys Ser Ile Glu Glu Thr Asp Gly Tyr
            355                 360                 365

Ser Ala Ala Trp Thr Val Pro Phe Gly Gly Arg Ala Tyr Ile Glu Met
    370                 375                 380

Met Gln Cys Asp Asp Ser Asp Glu Pro Val Val Arg Val Leu Val Asn
385                 390                 395                 400

Asp Arg Val Val Pro Leu His Gly Cys Glu Val Asp Ser Leu Gly Arg
                405                 410                 415

Cys Lys Arg Asp Asp Phe Val Arg Gly Leu Ser Phe Ala Arg Gln Gly
                420                 425                 430

Gly Asn Trp Glu Gly Cys Tyr Ala Ala Ser Glu
            435                 440

<210> SEQ ID NO 135
<211> LENGTH: 440
<212> TYPE: PRT
<213> ORGANISM: T. lanuginosa

<400> SEQUENCE: 135

Asn Val Asp Ile Ala Arg His Trp Gly Gln Tyr Ser Pro Phe Phe Ser
1               5                   10                  15

Leu Ala Glu Val Ser Glu Ile Ser Pro Ala Val Pro Lys Gly Cys Arg
            20                  25                  30

Val Glu Phe Val Gln Val Leu Ser Arg His Gly Ala Arg Tyr Pro Thr
        35                  40                  45

Ala His Lys Ser Glu Val Tyr Ala Glu Leu Leu Gln Arg Ile Gln Asp
    50                  55                  60

Thr Ala Thr Glu Phe Lys Gly Asp Phe Ala Phe Leu Arg Asp Tyr Ala
65                  70                  75                  80

Tyr His Leu Gly Ala Asp Asn Leu Thr Arg Phe Gly Glu Glu Gln Met
                85                  90                  95

Met Glu Ser Gly Arg Gln Phe Tyr His Arg Tyr Arg Glu Gln Ala Arg
            100                 105                 110

Glu Ile Val Pro Phe Val Arg Ala Ala Gly Ser Ala Arg Val Ile Ala
        115                 120                 125

Ser Ala Glu Phe Phe Asn Arg Gly Phe Gln Asp Ala Lys Asp Arg Asp
    130                 135                 140

Pro Arg Ser Asn Lys Asp Gln Ala Glu Pro Val Ile Asn Val Ile Ile
145                 150                 155                 160

Ser Glu Glu Thr Gly Ser Asn Asn Thr Leu Asp Gly Leu Thr Cys Pro
                165                 170                 175

Ala Ala Glu Glu Ala Pro Asp Pro Thr Gln Pro Ala Glu Phe Leu Gln
            180                 185                 190

Val Phe Gly Pro Arg Val Leu Lys Lys Ile Thr Lys His Met Pro Gly
        195                 200                 205

Val Asn Leu Thr Leu Glu Asp Val Pro Leu Phe Met Asp Leu Cys Pro
    210                 215                 220

Phe Asp Thr Val Gly Ser Asp Pro Val Leu Phe Pro Arg Gln Leu Ser
225                 230                 235                 240

Pro Phe Cys His Leu Phe Thr Ala Asp Asp Trp Met Ala Tyr Asp Tyr
```

```
                      245                 250                 255
Tyr Tyr Thr Leu Asp Lys Tyr Ser His Gly Gly Ser Ala Phe
            260                 265                 270

Gly Pro Ser Arg Gly Val Gly Phe Val Asn Glu Leu Ile Ala Arg Met
            275                 280                 285

Thr Gly Asn Leu Pro Val Lys Asp His Thr Val Asn His Thr Leu
            290                 295                 300

Asp Asp Asn Pro Glu Thr Phe Pro Leu Asp Ala Val Leu Tyr Ala Asp
305                 310                 315                 320

Phe Ser His Asp Asn Thr Met Thr Gly Ile Phe Ser Ala Met Gly Leu
                325                 330                 335

Tyr Asn Gly Thr Lys Pro Leu Ser Thr Ser Lys Ile Gln Pro Pro Thr
            340                 345                 350

Gly Ala Ala Asp Gly Tyr Ala Ala Ser Trp Thr Val Pro Phe Ala
            355                 360                 365

Ala Arg Ala Tyr Val Glu Leu Leu Arg Cys Glu Thr Glu Thr Ser Ser
370                 375                 380

Glu Glu Glu Glu Gly Glu Asp Glu Pro Phe Val Arg Val Leu Val
385                 390                 395                 400

Asn Asp Arg Val Val Pro Leu His Gly Cys Arg Val Asp Arg Trp Gly
            405                 410                 415

Arg Cys Arg Arg Asp Glu Trp Ile Lys Gly Leu Thr Phe Ala Arg Gln
            420                 425                 430

Gly Gly His Trp Asp Arg Cys Phe
            435                 440

<210> SEQ ID NO 136
<211> LENGTH: 466
<212> TYPE: PRT
<213> ORGANISM: M. thermophila

<400> SEQUENCE: 136

Glu Ser Arg Pro Cys Asp Thr Pro Asp Leu Gly Phe Gln Cys Gly Thr
1               5                   10                  15

Ala Ile Ser His Phe Trp Gly Gln Tyr Ser Pro Tyr Phe Ser Val Pro
            20                  25                  30

Ser Glu Leu Asp Ala Ser Ile Pro Asp Asp Cys Glu Val Thr Phe Ala
        35                  40                  45

Gln Val Leu Ser Arg His Gly Ala Arg Ala Pro Thr Leu Lys Arg Ala
    50                  55                  60

Ala Ser Tyr Val Asp Leu Ile Asp Arg Ile His Gly Ala Ile Ser
65                  70                  75              80

Tyr Gly Pro Gly Tyr Glu Phe Leu Arg Thr Tyr Asp Tyr Thr Leu Gly
                85                  90                  95

Ala Asp Glu Leu Thr Arg Thr Gly Gln Gln Met Val Asn Ser Gly
            100                 105                 110

Ile Lys Phe Tyr Arg Arg Tyr Arg Ala Leu Ala Arg Lys Ser Ile Pro
        115                 120                 125

Phe Val Arg Thr Ala Gly Gln Asp Arg Val Val His Ser Ala Glu Asn
130                 135                 140

Phe Thr Gln Gly Phe His Ser Ala Leu Leu Ala Asp Arg Gly Ser Thr
145                 150                 155                 160

Val Arg Pro Thr Leu Pro Tyr Asp Met Val Val Ile Pro Glu Thr Ala
                165                 170                 175
```

-continued

```
Gly Ala Asn Asn Thr Leu His Asn Asp Leu Cys Thr Ala Phe Glu Glu
                180                 185                 190

Gly Pro Tyr Ser Thr Ile Gly Asp Asp Ala Gln Asp Thr Tyr Leu Ser
            195                 200                 205

Thr Phe Ala Gly Pro Ile Thr Ala Arg Val Asn Ala Asn Leu Pro Gly
        210                 215                 220

Ala Asn Leu Thr Asp Ala Asp Thr Val Ala Leu Met Asp Leu Cys Pro
225                 230                 235                 240

Phe Glu Thr Val Ala Ser Ser Ser Asp Pro Ala Thr Ala Asp Ala
                245                 250                 255

Gly Gly Gly Asn Gly Arg Pro Leu Ser Pro Phe Cys Arg Leu Phe Ser
                260                 265                 270

Glu Ser Glu Trp Arg Ala Tyr Asp Tyr Leu Gln Ser Val Gly Lys Trp
            275                 280                 285

Tyr Gly Tyr Gly Pro Gly Asn Pro Leu Gly Pro Thr Gln Gly Val Gly
        290                 295                 300

Phe Val Asn Glu Leu Leu Ala Arg Leu Ala Gly Val Pro Val Arg Asp
305                 310                 315                 320

Gly Thr Ser Thr Asn Arg Thr Leu Asp Gly Asp Pro Arg Thr Phe Pro
                325                 330                 335

Leu Gly Arg Pro Leu Tyr Ala Asp Phe Ser His Asp Asn Asp Met Met
                340                 345                 350

Gly Val Leu Gly Ala Leu Gly Ala Tyr Asp Gly Val Pro Pro Leu Asp
            355                 360                 365

Lys Thr Ala Arg Arg Asp Pro Glu Glu Leu Gly Gly Tyr Ala Ala Ser
        370                 375                 380

Trp Ala Val Pro Phe Ala Ala Arg Ile Tyr Val Glu Lys Met Arg Cys
385                 390                 395                 400

Ser Gly Gly Gly Gly Gly Gly Gly Glu Gly Arg Gln Glu Lys
                405                 410                 415

Asp Glu Glu Met Val Arg Val Leu Val Asn Asp Arg Val Met Thr Leu
            420                 425                 430

Lys Gly Cys Gly Ala Asp Glu Arg Gly Met Cys Thr Leu Glu Arg Phe
        435                 440                 445

Ile Glu Ser Met Ala Phe Ala Arg Gly Asn Gly Lys Trp Asp Leu Cys
    450                 455                 460

Phe Ala
465

<210> SEQ ID NO 137
<211> LENGTH: 442
<212> TYPE: PRT
<213> ORGANISM: Basidio
<220> FEATURE:
<221> NAME/KEY: UNSURE
<222> LOCATION: (1)..(442)
<223> OTHER INFORMATION: n is unknown
<221> NAME/KEY: UNSURE
<222> LOCATION: (1)..(442)
<223> OTHER INFORMATION: x is unknown

<400> SEQUENCE: 137

Xaa Ser Xaa Pro Xaa Arg Xaa Thr Ala Ala Gln Leu Pro Ile Pro Xaa
  1               5                  10                  15

Gln Xaa Gln Xaa Xaa Trp Ser Pro Tyr Ser Pro Tyr Phe Pro Val Ala
                20                  25                  30

Xaa Tyr Xaa Ala Pro Pro Ala Gly Cys Gln Ile Xaa Gln Val Asn Ile
```

```
                 35                  40                  45
Ile Gln Arg His Gly Ala Arg Phe Pro Thr Ser Gly Ala Ala Thr Arg
 50                  55                  60

Ile Gln Ala Ala Val Ala Lys Leu Gln Ser Ala Xaa Xaa Xaa Thr Asp
 65                  70                  75                  80

Pro Lys Leu Asp Phe Leu Xaa Asn Xaa Thr Tyr Xaa Leu Gly Xaa Asp
                 85                  90                  95

Asp Leu Val Pro Phe Gly Ala Xaa Gln Ser Gln Ala Gly Gln Glu
                100                 105                 110

Ala Phe Thr Arg Tyr Ser Xaa Leu Val Ser Xaa Asp Asn Leu Pro Phe
                115                 120                 125

Val Arg Ala Ser Gly Ser Asp Arg Val Val Asp Ser Ala Thr Asn Trp
130                 135                 140

Thr Ala Gly Phe Ala Xaa Ala Ser Xaa Asn Thr Xaa Xaa Pro Xaa Leu
145                 150                 155                 160

Xaa Val Ile Leu Ser Glu Xaa Gly Asn Asp Thr Leu Asp Asp Asn Met
                165                 170                 175

Cys Pro Xaa Ala Gly Asp Ser Asp Pro Gln Xaa Asn Xaa Trp Leu Ala
                180                 185                 190

Val Phe Ala Pro Pro Ile Thr Ala Arg Leu Asn Ala Ala Pro Gly
                195                 200                 205

Ala Asn Leu Thr Asp Xaa Asp Ala Xaa Asn Leu Xaa Xaa Leu Cys Pro
210                 215                 220

Phe Glu Thr Val Ser Xaa Glu Xaa Xaa Ser Xaa Phe Cys Asp Leu Phe
225                 230                 235                 240

Glu Xaa Xaa Pro Glu Glu Phe Xaa Ala Phe Xaa Tyr Xaa Gly Asp Leu
                245                 250                 255

Asp Lys Phe Tyr Gly Thr Gly Tyr Gly Gln Pro Leu Gly Pro Val Gln
                260                 265                 270

Gly Val Gly Tyr Ile Asn Glu Leu Leu Ala Arg Leu Thr Xaa Gln Ala
                275                 280                 285

Val Arg Asp Asn Thr Gln Thr Asn Arg Thr Leu Asp Ser Ser Pro Xaa
                290                 295                 300

Thr Phe Pro Leu Asn Arg Thr Phe Tyr Ala Asp Phe Ser His Asp Asn
305                 310                 315                 320

Gln Met Val Ala Ile Phe Ser Ala Met Gly Leu Phe Asn Gln Ser Ala
                325                 330                 335

Pro Leu Asp Pro Ser Xaa Pro Asp Pro Asn Arg Thr Trp Val Thr Ser
                340                 345                 350

Lys Leu Val Pro Phe Ser Ala Arg Met Val Val Glu Arg Leu Xaa Cys
                355                 360                 365

Xaa Xaa Xaa Gly Thr Xaa Xaa Xaa Xaa Xaa Xaa Xaa Xaa Xaa Xaa Xaa
370                 375                 380

Xaa Xaa Xaa Xaa Xaa Xaa Val Arg Val Leu Val Asn Asp Ala Val Gln
385                 390                 395                 400

Pro Leu Glu Phe Cys Gly Gly Asp Xaa Asp Gly Xaa Cys Thr Leu Asp
                405                 410                 415

Ala Phe Val Glu Ser Gln Xaa Tyr Ala Arg Glu Asp Gly Gln Gly Asp
                420                 425                 430

Phe Glu Lys Cys Phe Ala Thr Pro Xaa Xaa
                435                 440

<210> SEQ ID NO 138
```

<211> LENGTH: 424
<212> TYPE: PRT
<213> ORGANISM: Consensus

<400> SEQUENCE: 138

```
Asn Ser His Ser Cys Asp Thr Val Asp Gly Gly Tyr Gln Cys Pro Glu
  1               5                  10                  15

Ile Ser His Leu Trp Gly Gln Tyr Ser Pro Phe Phe Ser Leu Ala Asp
             20                  25                  30

Glu Ser Ala Ile Ser Pro Asp Val Pro Gly Cys Arg Val Thr Phe Val
         35                  40                  45

Gln Val Leu Ser Arg His Gly Ala Arg Tyr Pro Thr Ser Ser Lys Ser
     50                  55                  60

Lys Lys Tyr Ser Ala Leu Ile Ala Ile Gln Lys Asn Ala Thr Phe Lys
 65                  70                  75                  80

Gly Lys Tyr Ala Phe Leu Lys Thr Tyr Asn Tyr Thr Leu Gly Ala Asp
                 85                  90                  95

Asp Leu Thr Pro Phe Gly Glu Gln Gln Met Val Asn Ser Gly Ile Lys
            100                 105                 110

Phe Tyr Arg Arg Tyr Lys Ala Leu Ala Arg Ile Val Pro Phe Val Arg
        115                 120                 125

Ala Ser Gly Ser Asp Arg Val Ile Ala Ser Ala Glu Lys Phe Ile Glu
    130                 135                 140

Gly Phe Gln Ser Ala Lys Leu Ala Asp Pro Ala Gln Ala Ser Pro Val
145                 150                 155                 160

Ile Asn Val Ile Ile Pro Glu Gly Gly Tyr Asn Asn Thr Leu Asp His
                165                 170                 175

Gly Leu Cys Thr Ala Phe Glu Pro Ser Glu Leu Gly Asp Asp Val Glu
            180                 185                 190

Ala Asn Phe Thr Ala Val Phe Ala Pro Pro Ile Arg Ala Arg Leu Glu
        195                 200                 205

Ala Leu Pro Gly Val Asn Leu Thr Asp Glu Asp Val Val Asn Leu Met
    210                 215                 220

Asp Met Cys Pro Phe Asp Thr Val Ala Thr Ser Asp Ala Thr Gln Leu
225                 230                 235                 240

Ser Pro Phe Cys Asp Leu Phe Thr His Glu Trp Gln Tyr Asp Tyr Leu
                245                 250                 255

Gln Ser Leu Lys Tyr Tyr Gly Tyr Gly Ala Gly Asn Pro Leu Gly Pro
            260                 265                 270

Ala Gln Gly Val Gly Phe Asn Glu Leu Ile Ala Arg Leu Thr His Ser
        275                 280                 285

Pro Val Gln Asp His Thr Ser Thr Asn His Thr Leu Asp Ser Asn Pro
    290                 295                 300

Ala Thr Phe Pro Leu Asn Ala Thr Leu Tyr Ala Asp Phe Ser His Asp
305                 310                 315                 320

Asn Thr Met Val Ser Ile Phe Ala Leu Gly Leu Tyr Asn Gly Thr
                325                 330                 335

Pro Leu Ser Thr Thr Ser Val Glu Pro Ser Glu Glu Thr Asp Gly Tyr
            340                 345                 350

Ala Ala Ser Trp Thr Val Pro Phe Ala Ala Arg Ala Tyr Val Glu Met
        355                 360                 365

Met Gln Cys Glu Glu Gly Glu Lys Glu Pro Leu Val Arg Val Leu Val
    370                 375                 380

Asn Asp Arg Val Val Pro Leu His Gly Cys Gly Val Asp Lys Leu Gly
```

```
                385                 390                 395                 400
Arg Cys Lys Asp Asp Phe Val Glu Gly Leu Ser Phe Ala Arg Ser Gly
                405                 410                 415

Gly Asn Trp Glu Glu Cys Phe Ala
            420

<210> SEQ ID NO 139
<211> LENGTH: 467
<212> TYPE: PRT
<213> ORGANISM: consensus phytase-10

<400> SEQUENCE: 139

Met Gly Val Phe Val Leu Leu Ser Ile Ala Thr Leu Phe Gly Ser
 1               5                  10                  15

Thr Ser Gly Thr Ala Leu Gly Pro Arg Gly Asn Ser His Ser Cys Asp
                20                  25                  30

Thr Val Asp Gly Gly Tyr Gln Cys Phe Pro Glu Ile Ser His Leu Trp
            35                  40                  45

Gly Gln Tyr Ser Pro Phe Phe Ser Leu Ala Asp Glu Ser Ala Ile Ser
        50                  55                  60

Pro Asp Val Pro Lys Gly Cys Arg Val Thr Phe Val Gln Val Leu Ser
65                  70                  75                  80

Arg His Gly Ala Arg Tyr Pro Thr Ser Ser Lys Ser Lys Tyr Ser
                85                  90                  95

Ala Leu Ile Glu Ala Ile Gln Lys Asn Ala Thr Ala Phe Lys Gly Lys
            100                 105                 110

Tyr Ala Phe Leu Lys Thr Tyr Asn Tyr Thr Leu Gly Ala Asp Asp Leu
        115                 120                 125

Thr Pro Phe Gly Glu Gln Gln Met Val Asn Ser Gly Ile Lys Phe Tyr
    130                 135                 140

Arg Arg Tyr Lys Ala Leu Ala Arg Lys Ile Val Pro Phe Val Arg Ala
145                 150                 155                 160

Ser Gly Ser Asp Arg Val Ile Ala Ser Ala Glu Lys Phe Ile Glu Gly
                165                 170                 175

Phe Gln Ser Ala Lys Leu Ala Asp Pro Gly Ala Asn Pro His Gln Ala
            180                 185                 190

Ser Pro Val Ile Asn Val Ile Ile Pro Glu Gly Ala Gly Tyr Asn Asn
        195                 200                 205

Thr Leu Asp His Gly Leu Cys Thr Ala Phe Glu Glu Ser Glu Leu Gly
    210                 215                 220

Asp Asp Val Glu Ala Asn Phe Thr Ala Val Phe Ala Pro Pro Ile Arg
225                 230                 235                 240

Ala Arg Leu Glu Ala His Leu Pro Gly Val Asn Leu Thr Asp Glu Asp
                245                 250                 255

Val Val Asn Leu Met Asp Met Cys Pro Phe Asp Thr Val Ala Arg Thr
            260                 265                 270

Ser Asp Ala Thr Gln Leu Ser Pro Phe Cys Asp Leu Phe Thr His Asp
        275                 280                 285

Glu Trp Ile Gln Tyr Asp Tyr Leu Gln Ser Leu Gly Lys Tyr Tyr Gly
    290                 295                 300

Tyr Gly Ala Gly Asn Pro Leu Gly Pro Ala Gln Gly Val Gly Phe Val
305                 310                 315                 320

Asn Glu Leu Ile Ala Arg Leu Thr His Ser Pro Val Gln Asp His Thr
                325                 330                 335
```

```
Ser Thr Asn His Thr Leu Asp Ser Asn Pro Ala Thr Phe Pro Leu Asn
            340                 345                 350

Ala Thr Leu Tyr Ala Asp Phe Ser His Asp Asn Thr Met Val Ser Ile
            355                 360                 365

Phe Phe Ala Leu Gly Leu Tyr Asn Gly Thr Lys Pro Leu Ser Thr Thr
    370                 375                 380

Ser Val Glu Ser Ile Glu Glu Thr Asp Gly Tyr Ala Ala Ser Trp Thr
385                 390                 395                 400

Val Pro Phe Ala Ala Arg Ala Tyr Val Glu Met Met Gln Cys Glu Ala
                405                 410                 415

Glu Lys Glu Pro Leu Val Arg Val Leu Val Asn Asp Arg Val Val Pro
                420                 425                 430

Leu His Gly Cys Gly Val Asp Lys Leu Gly Arg Cys Lys Arg Asp Asp
            435                 440                 445

Phe Val Glu Gly Leu Ser Phe Ala Arg Ser Gly Gly Asn Trp Glu Glu
    450                 455                 460

Cys Phe Ala
465

<210> SEQ ID NO 140
<211> LENGTH: 1426
<212> TYPE: DNA
<213> ORGANISM: consensus phytase-10

<400> SEQUENCE: 140
tatatgaatt catgggcgtg ttcgtcgtgc tactgtccat tgccaccttg ttcggttcca      60
catccggtac cgccttgggt cctcgtggta attctcactc ttgtgacact gttgacggtg     120
gttaccaatg tttcccagaa atttctcact gtgggtca atactctcca ttcttctctt      180
tggctgacga atctgctatt tctccagacg ttccaaaggg ttgtagagtt actttcgttc     240
aagttttgtc tagacacggt gctagatacc aacttcttc taagtctaag aagtactctg     300
ctttgattga agctattcaa agaacgcta ctgctttcaa gggtaagtac gctttcttga     360
agacttacaa ctacactttg ggtgctgacg acttgactcc attcggtgaa caacaaatgg     420
ttaactctgg tattaagttc tacagaagat acaaggcttt ggctagaaag attgttccat     480 cgttagagc ttctggttct gacagagtta ttgcttctgc tgaaaagttc attgaaggtt     540
tccaatctgc taagttggct gacccaggtg ctaaccccaca ccaagcttct ccagttatta     600
acgttattat tccagaaggt gctggttaca acaacacttt ggaccacggt ttgtgtactg     660
ctttcgaaga atctgaattg ggtgacgacg ttgaagctaa cttcactgct gttttcgctc     720
cacctattag agctagattg gaagctcact tgccaggtgt taacttgact gacgaagacg     780
ttgttaactt gatggacatg tgtccattcg acactgttgc tagaacttct gacgctactc     840
aattgtctcc attctgtgac ttgttcactc acgacgaatg gattcaatac gactacttgc     900
aatctttggg taagtactac ggttacggtg ctggtaaccc attgggtcca gctcaaggtg     960
ttggtttcgt taacgaattg attgctagat tgactcactc tccagttcaa gaccacactt    1020
ctactaacca cactttggac tctaacccag ctactttccc attgaacgct actttgtacg    1080
ctgacttctc tcacgacaac actatggttt ctatttctctt cgctttgggt ttgtacaacg    1140
gtactaagcc attgtctact acttctgttg aatctattga gaaactgac ggttacgctg    1200 cttcttggac tgtccattc gctgctagag cttacgttga aatgatgcaa tgtgaagctg    1260
aaaaggaacc attggttaga gttttggtta acgacagagt tgttccattg cacggttgtg    1320
```

```
gtgttgacaa gttgggtaga tgtaagagag acgacttcgt tgaaggtttg tctttcgcta    1380
gatctggtgg taactgggaa gaatgtttcg cttaagaatt catata                   1426
```

<210> SEQ ID NO 141
<211> LENGTH: 413
<212> TYPE: PRT
<213> ORGANISM: P. involutus (phyA1)

<400> SEQUENCE: 141

```
Phe Pro Ile Pro Glu Ser Glu Gln Arg Asn Trp Ser Pro Tyr Ser Pro
 1               5                  10                  15

Tyr Phe Pro Leu Ala Glu Tyr Lys Ala Pro Pro Ala Gly Cys Gln Ile
            20                  25                  30

Asn Gln Val Asn Ile Ile Gln Arg His Gly Ala Arg Phe Pro Thr Ser
        35                  40                  45

Gly Ala Thr Thr Arg Ile Lys Ala Gly Leu Thr Lys Leu Gln Gly Val
    50                  55                  60

Gln Asn Phe Thr Asp Ala Lys Phe Asn Phe Ile Lys Ser Phe Lys Tyr
65                  70                  75                  80

Asp Leu Gly Asn Ser Asp Leu Val Pro Phe Gly Ala Ala Gln Ser Phe
                85                  90                  95

Asp Ala Gly Gln Glu Ala Phe Ala Arg Tyr Ser Lys Leu Val Ser Lys
            100                 105                 110

Asn Asn Leu Pro Phe Ile Arg Ala Asp Gly Ser Asp Arg Val Val Asp
        115                 120                 125

Ser Ala Thr Asn Trp Thr Ala Gly Phe Ala Ser Ala Ser His Asn Thr
    130                 135                 140

Val Gln Pro Lys Leu Asn Leu Ile Leu Pro Gln Thr Gly Asn Asp Thr
145                 150                 155                 160

Leu Glu Asp Asn Met Cys Pro Ala Ala Gly Asp Ser Asp Pro Gln Val
                165                 170                 175

Asn Ala Trp Leu Ala Val Ala Phe Pro Ser Ile Thr Ala Arg Leu Asn
            180                 185                 190

Ala Ala Ala Pro Ser Val Asn Leu Thr Asp Thr Asp Ala Phe Asn Leu
        195                 200                 205

Val Ser Leu Cys Ala Phe Leu Thr Val Ser Lys Glu Lys Lys Ser Asp
    210                 215                 220

Phe Cys Thr Leu Phe Glu Gly Ile Pro Gly Ser Phe Glu Ala Phe Ala
225                 230                 235                 240

Tyr Gly Gly Asp Leu Asp Lys Phe Tyr Gly Thr Gly Tyr Gly Gln Glu
                245                 250                 255

Leu Gly Pro Val Gln Gly Val Gly Tyr Val Asn Glu Leu Ile Ala Arg
            260                 265                 270

Leu Thr Asn Ser Ala Val Arg Asp Asn Thr Gln Thr Asn Arg Thr Leu
        275                 280                 285

Asp Ala Ser Pro Val Thr Phe Pro Leu Asn Lys Thr Phe Tyr Ala Asp
    290                 295                 300

Phe Ser His Asp Asn Leu Met Val Ala Val Phe Ser Ala Met Gly Leu
305                 310                 315                 320

Phe Arg Gln Pro Ala Pro Leu Ser Thr Ser Val Pro Asn Pro Trp Arg
                325                 330                 335

Thr Trp Arg Thr Ser Ser Leu Val Pro Phe Ser Gly Arg Met Val Val
            340                 345                 350

Glu Arg Leu Ser Cys Phe Gly Thr Thr Lys Val Arg Val Leu Val Gln
```

```
                   355                 360                 365
Asp Gln Val Gln Pro Leu Glu Phe Cys Gly Gly Asp Arg Asn Gly Leu
                370                 375                 380

Cys Thr Leu Ala Lys Phe Val Glu Ser Gln Thr Phe Ala Arg Ser Asp
385                 390                 395                 400

Gly Ala Gly Asp Phe Glu Lys Cys Phe Ala Thr Ser Ala
                405                 410

<210> SEQ ID NO 142
<211> LENGTH: 413
<212> TYPE: PRT
<213> ORGANISM: P. involutus (phyA2)

<400> SEQUENCE: 142

Phe Ser Ile Pro Glu Ser Glu Gln Arg Asn Trp Ser Pro Tyr Ser Pro
  1               5                  10                  15

Tyr Phe Pro Leu Ala Glu Tyr Lys Ala Pro Ala Gly Cys Glu Ile
                 20                  25                  30

Asn Gln Val Asn Ile Ile Gln Arg His Gly Ala Arg Phe Pro Thr Ser
                 35                  40                  45

Gly Ala Ala Thr Arg Ile Lys Ala Gly Leu Ser Lys Leu Gln Ser Val
 50                  55                  60

Gln Asn Phe Thr Asp Pro Lys Phe Asp Phe Ile Lys Ser Phe Thr Tyr
 65                  70                  75                  80

Asp Leu Gly Thr Ser Asp Leu Val Pro Phe Gly Ala Ala Gln Ser Phe
                 85                  90                  95

Asp Ala Gly Leu Glu Val Phe Ala Arg Tyr Ser Lys Leu Val Ser Ser
                100                 105                 110

Asp Asn Leu Pro Phe Ile Arg Ser Asp Gly Ser Asp Arg Val Val Asp
                115                 120                 125

Thr Ala Thr Asn Trp Thr Ala Gly Phe Ala Ser Ala Ser Arg Asn Ala
130                 135                 140

Ile Gln Pro Lys Leu Asp Leu Ile Leu Pro Gln Thr Gly Asn Asp Thr
145                 150                 155                 160

Leu Glu Asp Asn Met Cys Pro Ala Ala Gly Glu Ser Asp Pro Gln Val
                165                 170                 175

Asp Ala Trp Leu Ala Ser Ala Phe Pro Ser Val Thr Ala Gln Leu Asn
                180                 185                 190

Ala Ala Ala Pro Gly Ala Asn Leu Thr Asp Ala Asp Ala Phe Asn Leu
                195                 200                 205

Val Ser Leu Cys Pro Phe Met Thr Val Ser Lys Glu Gln Lys Ser Asp
210                 215                 220

Phe Cys Thr Leu Phe Glu Gly Ile Pro Gly Ser Phe Glu Ala Phe Ala
225                 230                 235                 240

Tyr Ala Gly Asp Leu Asp Lys Phe Tyr Gly Thr Gly Tyr Gly Gln Ala
                245                 250                 255

Leu Gly Pro Val Gln Gly Val Tyr Ile Asn Glu Leu Leu Ala Arg
                260                 265                 270

Leu Thr Asn Ser Ala Val Asn Asp Asn Thr Gln Thr Asn Arg Thr Leu
                275                 280                 285

Asp Ala Ala Pro Asp Thr Phe Pro Leu Asn Lys Thr Met Tyr Ala Asp
                290                 295                 300

Phe Ser His Asp Asn Leu Met Val Ala Val Phe Ser Ala Met Gly Leu
305                 310                 315                 320
```

```
Phe Arg Gln Ser Ala Pro Leu Ser Thr Ser Thr Pro Asp Pro Asn Arg
                325                 330                 335

Thr Trp Leu Thr Ser Ser Val Val Pro Phe Ser Ala Arg Met Ala Val
            340                 345                 350

Glu Arg Leu Ser Cys Ala Gly Thr Thr Lys Val Arg Val Leu Val Gln
        355                 360                 365

Asp Gln Val Gln Pro Leu Glu Phe Cys Gly Gly Asp Gln Asp Gly Leu
    370                 375                 380

Cys Ala Leu Asp Lys Phe Val Glu Ser Gln Ala Tyr Ala Arg Ser Gly
385                 390                 395                 400

Gly Ala Gly Asp Phe Glu Lys Cys Leu Ala Thr Thr Val
                405                 410

<210> SEQ ID NO 143
<211> LENGTH: 410
<212> TYPE: PRT
<213> ORGANISM: T. pubescens

<400> SEQUENCE: 143

Leu Asp Val Thr Arg Asp Val Gln Gln Ser Trp Ser Met Tyr Ser Pro
  1               5                  10                  15

Tyr Phe Pro Ala Ala Thr Tyr Val Ala Pro Ala Ser Cys Gln Ile
                 20                  25                  30

Asn Gln Val His Ile Ile Gln Arg His Gly Ala Arg Phe Pro Thr Ser
             35                  40                  45

Gly Ala Ala Lys Arg Ile Gln Thr Ala Val Ala Lys Leu Lys Ala Ala
         50                  55                  60

Ser Asn Tyr Thr Asp Pro Leu Leu Ala Phe Val Thr Asn Tyr Thr Tyr
 65                  70                  75                  80

Ser Leu Gly Gln Asp Ser Leu Val Glu Leu Gly Ala Thr Gln Ser Ser
                 85                  90                  95

Glu Ala Gly Gln Glu Ala Phe Thr Arg Tyr Ser Ser Leu Val Ser Ala
            100                 105                 110

Asp Glu Leu Pro Phe Val Arg Ala Ser Gly Ser Asp Arg Val Val Ala
        115                 120                 125

Thr Ala Asn Asn Trp Thr Ala Gly Phe Ala Leu Ala Ser Ser Asn Ser
    130                 135                 140

Ile Thr Pro Val Leu Ser Val Ile Ser Glu Ala Gly Asn Asp Thr
145                 150                 155                 160

Leu Asp Asp Asn Met Cys Pro Ala Ala Gly Asp Ser Asp Pro Gln Val
                165                 170                 175

Asn Gln Trp Leu Ala Gln Phe Ala Pro Pro Met Thr Ala Arg Leu Asn
            180                 185                 190

Ala Gly Ala Pro Gly Ala Asn Leu Thr Asp Thr Asp Thr Tyr Asn Leu
        195                 200                 205

Leu Thr Leu Cys Pro Phe Glu Thr Val Ala Thr Glu Arg Arg Ser Glu
    210                 215                 220

Phe Cys Asp Ile Tyr Glu Glu Leu Gln Ala Glu Asp Ala Phe Ala Tyr
225                 230                 235                 240

Asn Ala Asp Leu Asp Lys Phe Tyr Gly Thr Gly Tyr Gly Gln Pro Leu
                245                 250                 255

Gly Pro Val Gln Gly Val Gly Tyr Ile Asn Glu Leu Ile Ala Arg Leu
            260                 265                 270

Thr Ala Gln Asn Val Ser Asp His Thr Gln Thr Asn Ser Thr Leu Asp
    275                 280                 285
```

```
Ser Ser Pro Glu Thr Phe Pro Leu Asn Arg Thr Leu Tyr Ala Asp Phe
    290                 295                 300

Ser His Asp Asn Gln Met Val Ala Ile Phe Ser Ala Met Gly Leu Phe
305                 310                 315                 320

Asn Gln Ser Ala Pro Leu Asp Pro Thr Thr Pro Asp Pro Ala Arg Thr
                325                 330                 335

Phe Leu Val Lys Lys Ile Val Pro Phe Ser Ala Arg Met Val Val Glu
                340                 345                 350

Arg Leu Asp Cys Gly Gly Ala Gln Ser Val Arg Leu Leu Val Asn Asp
            355                 360                 365

Ala Val Gln Pro Leu Ala Phe Cys Gly Ala Asp Thr Ser Gly Val Cys
    370                 375                 380

Thr Leu Asp Ala Phe Val Glu Ser Gln Ala Tyr Ala Arg Asn Asp Gly
385                 390                 395                 400

Glu Gly Asp Phe Glu Lys Cys Phe Ala Thr
                405                 410

<210> SEQ ID NO 144
<211> LENGTH: 425
<212> TYPE: PRT
<213> ORGANISM: A. pediades

<400> SEQUENCE: 144

Pro Phe Pro Pro Gln Ile Gln Asp Ser Trp Ala Ala Tyr Thr Pro
1               5                   10                  15

Tyr Tyr Pro Val Gln Ala Tyr Thr Pro Pro Lys Asp Cys Lys Ile
                20                  25                  30

Thr Gln Val Asn Ile Ile Gln Arg His Gly Ala Arg Phe Pro Thr Ser
            35                  40                  45

Gly Ala Gly Thr Arg Ile Gln Ala Ala Val Lys Lys Leu Gln Ser Ala
    50                  55                  60

Lys Thr Tyr Thr Asp Pro Arg Leu Asp Phe Leu Thr Asn Tyr Thr Tyr
65                  70                  75                  80

Thr Leu Gly His Asp Asp Leu Val Pro Phe Gly Ala Leu Gln Ser Ser
                85                  90                  95

Gln Ala Gly Glu Glu Thr Phe Gln Arg Tyr Ser Phe Leu Val Ser Lys
            100                 105                 110

Glu Asn Leu Pro Phe Val Arg Ala Ser Ser Ser Asn Arg Val Val Asp
        115                 120                 125

Ser Ala Thr Asn Trp Thr Glu Gly Phe Ser Ala Ala Ser His His Val
    130                 135                 140

Leu Asn Pro Ile Leu Phe Val Ile Leu Ser Glu Ser Leu Asn Asp Thr
145                 150                 155                 160

Leu Asp Asp Ala Met Cys Pro Asn Ala Gly Ser Ser Asp Pro Gln Thr
                165                 170                 175

Gly Ile Trp Thr Ser Ile Tyr Gly Thr Pro Ile Ala Asn Arg Leu Asn
            180                 185                 190

Gln Gln Ala Pro Gly Ala Asn Ile Thr Ala Ala Asp Val Ser Asn Leu
        195                 200                 205

Ile Pro Leu Cys Ala Phe Glu Thr Ile Val Lys Glu Thr Pro Ser Pro
    210                 215                 220

Phe Cys Asn Leu Phe Thr Pro Glu Glu Phe Ala Gln Phe Glu Tyr Phe
225                 230                 235                 240

Gly Asp Leu Asp Lys Phe Tyr Gly Thr Gly Tyr Gly Gln Pro Leu Gly
```

-continued

```
                245                 250                 255
Pro Val Gln Gly Val Gly Tyr Ile Asn Glu Leu Leu Ala Arg Leu Thr
                260                 265                 270

Glu Met Pro Val Arg Asp Asn Thr Gln Thr Asn Arg Thr Leu Asp Ser
            275                 280                 285

Ser Pro Leu Thr Phe Pro Leu Asp Arg Ser Ile Tyr Ala Asp Leu Ser
        290                 295                 300

His Asp Asn Gln Met Ile Ala Ile Phe Ser Ala Met Gly Leu Phe Asn
305                 310                 315                 320

Gln Ser Ser Pro Leu Asp Pro Ser Phe Pro Asn Pro Lys Arg Thr Trp
                325                 330                 335

Val Thr Ser Arg Leu Thr Pro Phe Ser Ala Arg Met Val Thr Glu Arg
            340                 345                 350

Leu Leu Cys Gln Arg Asp Gly Thr Gly Ser Gly Gly Pro Ser Arg Ile
        355                 360                 365

Met Arg Asn Gly Asn Val Gln Thr Phe Val Arg Ile Leu Val Asn Asp
    370                 375                 380

Ala Leu Gln Pro Leu Lys Phe Cys Gly Gly Asp Met Asp Ser Leu Cys
385                 390                 395                 400

Thr Leu Glu Ala Phe Val Glu Ser Gln Lys Tyr Ala Arg Glu Asp Gly
                405                 410                 415

Gln Gly Asp Phe Glu Lys Cys Phe Asp
            420                 425

<210> SEQ ID NO 145
<211> LENGTH: 409
<212> TYPE: PRT
<213> ORGANISM: P. lycii

<400> SEQUENCE: 145

Leu Pro Ile Pro Ala Gln Asn Thr Ser Asn Trp Gly Pro Tyr Asp Pro
  1               5                  10                  15

Phe Phe Pro Val Glu Pro Tyr Ala Ala Pro Pro Glu Gly Cys Thr Val
             20                  25                  30

Thr Gln Val Asn Leu Ile Gln Arg His Gly Ala Arg Trp Pro Thr Ser
         35                  40                  45

Gly Ala Arg Ser Arg Gln Val Ala Val Ala Lys Ile Gln Met Ala
     50                  55                  60

Arg Pro Phe Thr Asp Pro Lys Tyr Glu Phe Leu Asn Asp Phe Val Tyr
65                  70                  75                  80

Lys Phe Gly Val Ala Asp Leu Leu Pro Phe Gly Ala Asn Gln Ser His
                 85                  90                  95

Gln Thr Gly Thr Asp Met Tyr Thr Arg Tyr Ser Thr Leu Phe Glu Gly
            100                 105                 110

Gly Asp Val Pro Phe Val Arg Ala Gly Asp Gln Arg Val Val Asp
        115                 120                 125

Ser Ser Thr Asn Trp Thr Ala Gly Phe Gly Asp Ala Ser Gly Glu Thr
    130                 135                 140

Val Leu Pro Thr Leu Gln Val Leu Gln Glu Gly Asn Cys Thr
145                 150                 155                 160

Leu Cys Asn Asn Met Cys Pro Asn Glu Val Asp Gly Asp Glu Ser Thr
                165                 170                 175

Thr Trp Leu Gly Val Phe Ala Pro Asn Ile Thr Ala Arg Leu Asn Ala
            180                 185                 190
```

```
Ala Ala Pro Ser Ala Asn Leu Ser Asp Ser Asp Ala Leu Thr Leu Met
            195                 200                 205

Asp Met Cys Pro Phe Asp Thr Leu Ser Ser Gly Asn Ala Ser Pro Phe
        210                 215                 220

Cys Asp Leu Phe Thr Ala Glu Glu Tyr Val Ser Tyr Glu Tyr Tyr Tyr
225                 230                 235                 240

Asp Leu Asp Lys Tyr Tyr Gly Thr Gly Pro Gly Asn Ala Leu Gly Pro
                245                 250                 255

Val Gln Gly Val Gly Tyr Val Asn Glu Leu Leu Ala Arg Leu Thr Gly
            260                 265                 270

Gln Ala Val Arg Asp Glu Thr Gln Thr Asn Arg Thr Leu Asp Ser Asp
        275                 280                 285

Pro Ala Thr Phe Pro Leu Asn Arg Thr Phe Tyr Ala Asp Phe Ser His
290                 295                 300

Asp Asn Thr Met Val Pro Ile Phe Ala Ala Leu Gly Leu Phe Asn Ala
305                 310                 315                 320

Thr Ala Leu Asp Pro Leu Lys Pro Asp Glu Asn Arg Leu Trp Val Asp
                325                 330                 335

Ser Lys Leu Val Pro Phe Ser Gly His Met Thr Val Glu Lys Leu Ala
            340                 345                 350

Cys Ser Gly Lys Glu Ala Val Arg Val Leu Val Asn Asp Ala Val Gln
        355                 360                 365

Pro Leu Glu Phe Cys Gly Gly Val Asp Gly Val Cys Glu Leu Ser Ala
370                 375                 380

Phe Val Glu Ser Gln Thr Tyr Ala Arg Glu Asn Gly Gln Gly Asp Phe
385                 390                 395                 400

Ala Lys Cys Gly Phe Val Pro Ser Glu
                405

<210> SEQ ID NO 146
<211> LENGTH: 440
<212> TYPE: PRT
<213> ORGANISM: A. terreus 9a1

<400> SEQUENCE: 146

Lys His Ser Asp Cys Asn Ser Val Asp His Gly Tyr Gln Cys Phe Pro
1               5                   10                  15

Glu Leu Ser His Lys Trp Gly Leu Tyr Ala Pro Tyr Phe Ser Leu Gln
            20                  25                  30

Asp Glu Ser Pro Phe Pro Leu Asp Val Pro Glu Asp Cys His Ile Thr
        35                  40                  45

Phe Val Gln Val Leu Ala Arg His Gly Ala Arg Ser Pro Thr His Ser
    50                  55                  60

Lys Thr Lys Ala Tyr Ala Ala Thr Ile Ala Ala Ile Gln Lys Ser Ala
65                  70                  75                  80

Thr Ala Phe Pro Gly Lys Tyr Ala Phe Leu Gln Ser Tyr Asn Tyr Ser
                85                  90                  95

Leu Asp Ser Glu Glu Leu Thr Pro Phe Gly Arg Asn Gln Leu Arg Asp
            100                 105                 110

Leu Gly Ala Gln Phe Tyr Glu Arg Tyr Asn Ala Leu Thr Arg His Ile
        115                 120                 125

Asn Pro Phe Val Arg Ala Thr Asp Ala Ser Arg Val His Glu Ser Ala
    130                 135                 140

Glu Lys Phe Val Glu Gly Phe Gln Thr Ala Arg Gln Asp Asp His His
145                 150                 155                 160
```

-continued

```
Ala Asn Pro His Gln Pro Ser Pro Arg Val Asp Val Ala Ile Pro Glu
                165                 170                 175
Gly Ser Ala Tyr Asn Asn Thr Leu Glu His Ser Leu Cys Thr Ala Phe
            180                 185                 190
Glu Ser Ser Thr Val Gly Asp Asp Ala Val Ala Asn Phe Thr Ala Val
        195                 200                 205
Phe Ala Pro Ala Ile Ala Gln Arg Leu Glu Ala Asp Leu Pro Gly Val
    210                 215                 220
Gln Leu Ser Thr Asp Asp Val Val Asn Leu Met Ala Met Cys Pro Phe
225                 230                 235                 240
Glu Thr Val Ser Leu Thr Asp Asp Ala His Thr Leu Ser Pro Phe Cys
                245                 250                 255
Asp Leu Phe Thr Ala Thr Glu Trp Thr Gln Tyr Asn Tyr Leu Leu Ser
            260                 265                 270
Leu Asp Lys Tyr Tyr Gly Tyr Gly Gly Asn Pro Leu Gly Pro Val
        275                 280                 285
Gln Gly Val Gly Trp Ala Asn Glu Leu Met Ala Arg Leu Thr Arg Ala
    290                 295                 300
Pro Val His Asp His Thr Cys Val Asn Asn Thr Leu Asp Ala Ser Pro
305                 310                 315                 320
Ala Thr Phe Pro Leu Asn Ala Thr Leu Tyr Ala Asp Phe Ser His Asp
                325                 330                 335
Ser Asn Leu Val Ser Ile Phe Trp Ala Leu Gly Leu Tyr Asn Gly Thr
            340                 345                 350
Ala Pro Leu Ser Gln Thr Ser Val Glu Ser Val Ser Gln Thr Asp Gly
        355                 360                 365
Tyr Ala Ala Trp Thr Val Pro Phe Ala Ala Arg Ala Tyr Val Glu
    370                 375                 380
Met Met Gln Cys Arg Ala Glu Lys Glu Pro Leu Val Arg Val Leu Val
385                 390                 395                 400
Asn Asp Arg Val Met Pro Leu His Gly Cys Pro Thr Asp Lys Leu Gly
                405                 410                 415
Arg Cys Lys Arg Asp Ala Phe Val Ala Gly Leu Ser Phe Ala Gln Ala
            420                 425                 430
Gly Gly Asn Trp Ala Asp Cys Phe
        435                 440

<210> SEQ ID NO 147
<211> LENGTH: 440
<212> TYPE: PRT
<213> ORGANISM: A. terreus cbs

<400> SEQUENCE: 147

Asn His Ser Asp Cys Thr Ser Val Asp Arg Gly Tyr Gln Cys Phe Pro
1               5                   10                  15
Glu Leu Ser His Lys Trp Gly Leu Tyr Ala Pro Tyr Phe Ser Leu Gln
            20                  25                  30
Asp Glu Ser Pro Phe Pro Leu Asp Val Pro Asp Asp Cys His Ile Thr
        35                  40                  45
Phe Val Gln Val Leu Ala Arg His Gly Ala Arg Ser Pro Thr Asp Ser
    50                  55                  60
Lys Thr Lys Ala Tyr Ala Ala Thr Ile Ala Ala Ile Gln Lys Asn Ala
65                  70                  75                  80
Thr Ala Leu Pro Gly Lys Tyr Ala Phe Leu Lys Ser Tyr Asn Tyr Ser
```

-continued

```
                 85                  90                  95
Met Gly Ser Glu Asn Leu Thr Pro Phe Gly Arg Asn Gln Leu Gln Asp
            100                 105                 110
Leu Gly Ala Gln Phe Tyr Arg Arg Tyr Asp Thr Leu Thr Arg His Ile
        115                 120                 125
Asn Pro Phe Val Arg Ala Ala Asp Ser Ser Arg Val His Glu Ser Ala
    130                 135                 140
Glu Lys Phe Val Glu Gly Phe Gln Asn Ala Arg Gln Gly Asp Pro His
145                 150                 155                 160
Ala Asn Pro His Gln Pro Ser Pro Arg Val Asp Val Ile Pro Glu
                165                 170                 175
Gly Thr Ala Tyr Asn Asn Thr Leu Glu His Ser Ile Cys Thr Ala Phe
            180                 185                 190
Glu Ala Ser Thr Val Gly Asp Ala Ala Asp Asn Phe Thr Ala Val
        195                 200                 205
Phe Ala Pro Ala Ile Ala Lys Arg Leu Glu Ala Asp Leu Pro Gly Val
    210                 215                 220
Gln Leu Ser Ala Asp Asp Val Val Asn Leu Met Ala Met Cys Pro Phe
225                 230                 235                 240
Glu Thr Val Ser Leu Thr Asp Asp Ala His Thr Leu Ser Pro Phe Cys
            245                 250                 255
Asp Leu Phe Thr Ala Ala Glu Trp Thr Gln Tyr Asn Tyr Leu Leu Ser
        260                 265                 270
Leu Asp Lys Tyr Tyr Gly Tyr Gly Gly Asn Pro Leu Gly Pro Val
    275                 280                 285
Gln Gly Val Gly Trp Ala Asn Glu Leu Ile Ala Arg Leu Thr Arg Ser
            290                 295                 300
Pro Val His Asp His Thr Cys Val Asn Asn Thr Leu Asp Ala Asn Pro
305                 310                 315                 320
Ala Thr Phe Pro Leu Asn Ala Thr Leu Tyr Ala Asp Phe Ser His Asp
            325                 330                 335
Ser Asn Leu Val Ser Ile Phe Trp Ala Leu Gly Leu Tyr Asn Gly Thr
        340                 345                 350
Lys Pro Leu Ser Gln Thr Thr Val Glu Asp Ile Thr Arg Thr Asp Gly
    355                 360                 365
Tyr Ala Ala Trp Thr Val Pro Phe Ala Ala Arg Ala Tyr Ile Glu
    370                 375                 380
Met Met Gln Cys Arg Ala Glu Lys Gln Pro Leu Val Arg Val Leu Val
385                 390                 395                 400
Asn Asp Arg Val Met Pro Leu His Gly Cys Ala Val Asp Asn Leu Gly
            405                 410                 415
Arg Cys Lys Arg Asp Asp Phe Val Glu Gly Leu Ser Phe Ala Arg Ala
        420                 425                 430
Gly Gly Asn Trp Ala Glu Cys Phe
        435                 440

<210> SEQ ID NO 148
<211> LENGTH: 441
<212> TYPE: PRT
<213> ORGANISM: A. niger var. awamori

<400> SEQUENCE: 148

Asn Gln Ser Thr Cys Asp Thr Val Asp Gln Gly Tyr Gln Cys Phe Ser
  1               5                  10                  15
```

-continued

```
Glu Thr Ser His Leu Trp Gly Gln Tyr Ala Pro Phe Phe Ser Leu Ala
             20                  25                  30

Asn Glu Ser Ala Ile Ser Pro Asp Val Pro Ala Gly Cys Arg Val Thr
         35                  40                  45

Phe Ala Gln Val Leu Ser Arg His Gly Ala Arg Tyr Pro Thr Glu Ser
     50                  55                  60

Lys Gly Lys Lys Tyr Ser Ala Leu Ile Glu Ile Gln Gln Asn Val
 65                  70                  75                  80

Thr Thr Phe Asp Gly Lys Tyr Ala Phe Leu Lys Thr Tyr Asn Tyr Ser
                 85                  90                  95

Leu Gly Ala Asp Asp Leu Thr Pro Phe Gly Glu Gln Glu Leu Val Asn
                100                 105                 110

Ser Gly Ile Lys Phe Tyr Gln Arg Tyr Glu Ser Leu Thr Arg Asn Ile
            115                 120                 125

Ile Pro Phe Ile Arg Ser Ser Gly Ser Ser Arg Val Ile Ala Ser Gly
        130                 135                 140

Glu Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Asn Asn Thr Leu Asp Pro Gly Thr Cys Thr Val Phe
                180                 185                 190

Glu Asp Ser Glu Leu Ala Asp Thr Val Glu Ala Asn Phe Thr Ala Thr
            195                 200                 205

Phe Ala Pro Ser Ile Arg Gln Arg Leu Glu Asn Asp Leu Ser Gly Val
        210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile His Tyr Asp Tyr Leu Gln Ser
            260                 265                 270

Leu Lys Lys Tyr Tyr Gly His Gly Ala Gly Asn Pro Leu Gly Pro Thr
        275                 280                 285

Gln Gly Val Gly Tyr Ala Asn Glu Leu Ile Ala Arg Leu Thr His Ser
    290                 295                 300

Pro Val His Asp Asp Thr Ser Ser Asn His Thr Leu Asp Ser Asn Pro
305                 310                 315                 320

Ala Thr Phe Pro Leu Asn Ser Thr Leu Tyr Ala Asp Phe Ser His Asp
                325                 330                 335

Asn Gly Ile Ile Ser Ile Leu Phe Ala Leu Gly Leu Tyr Asn Gly Thr
            340                 345                 350

Lys Pro Leu Ser Thr Thr Val Glu Asn Ile Thr Gln Thr Asp Gly
        355                 360                 365

Phe Ser Ser Ala Trp Thr Val Pro Phe Ala Ser Arg Leu Tyr Val Glu
    370                 375                 380

Met Met Gln Cys Gln Ala Glu Gln Glu Pro Leu Val Arg Val Leu Val
385                 390                 395                 400

Asn Asp Arg Val Val Pro Leu His Gly Cys Pro Ile Asp Ala Leu Gly
                405                 410                 415

Arg Cys Thr Arg Asp Ser Phe Val Arg Gly Leu Ser Phe Ala Arg Ser
            420                 425                 430

Gly Gly Asp Trp Ala Glu Cys Ser Ala
```

435                 440

<210> SEQ ID NO 149
<211> LENGTH: 441
<212> TYPE: PRT
<213> ORGANISM: A. niger T213

<400> SEQUENCE: 149

Asn Gln Ser Ser Cys Asp Thr Val Asp Gln Gly Tyr Gln Cys Phe Ser
 1               5                  10                  15

Glu Thr Ser His Leu Trp Gly Gln Tyr Ala Pro Phe Phe Ser Leu Ala
            20                  25                  30

Asn Glu Ser Val Ile Ser Pro Asp Val Pro Ala Gly Cys Arg Val Thr
        35                  40                  45

Phe Ala Gln Val Leu Ser Arg His Gly Ala Arg Tyr Pro Thr Glu Ser
    50                  55                  60

Lys Gly Lys Lys Tyr Ser Ala Leu Ile Glu Ile Gln Gln Asn Val
65                  70                  75                  80

Thr Thr Phe Asp Gly Lys Tyr Ala Phe Leu Lys Thr Tyr Asn Tyr Ser
                85                  90                  95

Leu Gly Ala Asp Asp Leu Thr Pro Phe Gly Glu Gln Glu Leu Val Asn
            100                 105                 110

Ser Gly Ile Lys Phe Tyr Gln Arg Tyr Glu Ser Leu Thr Arg Asn Ile
        115                 120                 125

Ile Pro Phe Ile Arg Ser Gly Ser Ser Arg Val Ile Ala Ser Gly
    130                 135                 140

Glu Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Asn Asn Thr Leu Asp Pro Gly Thr Cys Thr Val Phe
            180                 185                 190

Glu Asp Ser Glu Leu Ala Asp Thr Val Glu Ala Asn Phe Thr Ala Thr
        195                 200                 205

Phe Ala Pro Ser Ile Arg Gln Arg Leu Glu Asn Asp Leu Ser Gly Val
    210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile His Tyr Asp Tyr Leu Arg Ser
            260                 265                 270

Leu Lys Lys Tyr Tyr Gly His Gly Ala Gly Asn Pro Leu Gly Pro Thr
        275                 280                 285

Gln Gly Val Gly Tyr Ala Asn Glu Leu Ile Ala Arg Leu Thr His Ser
    290                 295                 300

Pro Val His Asp Asp Thr Ser Asn His Thr Leu Asp Ser Asn Pro
305                 310                 315                 320

Ala Thr Phe Pro Leu Asn Ser Thr Leu Tyr Ala Asp Phe Ser His Asp
                325                 330                 335

Asn Gly Ile Ile Ser Ile Leu Phe Ala Leu Gly Leu Tyr Asn Gly Thr
            340                 345                 350

Lys Pro Leu Ser Thr Thr Val Glu Asn Ile Thr Gln Thr Asp Gly
        355                 360                 365

-continued

```
Phe Ser Ser Ala Trp Thr Val Pro Phe Ala Ser Arg Leu Tyr Val Glu
    370                 375                 380

Met Met Gln Cys Gln Ala Glu Gln Glu Pro Leu Val Arg Val Leu Val
385                 390                 395                 400

Asn Asp Arg Val Val Pro Leu His Gly Cys Pro Ile Asp Ala Leu Gly
                405                 410                 415

Arg Cys Thr Arg Asp Ser Phe Val Arg Gly Leu Ser Phe Ala Arg Ser
                420                 425                 430

Gly Gly Asp Trp Ala Glu Cys Phe Ala
            435                 440

<210> SEQ ID NO 150
<211> LENGTH: 441
<212> TYPE: PRT
<213> ORGANISM: A. niger NRRL3135

<400> SEQUENCE: 150

Asn Gln Ser Ser Cys Asp Thr Val Asp Gln Gly Tyr Gln Cys Phe Ser
  1               5                  10                  15

Glu Thr Ser His Leu Trp Gly Gln Tyr Ala Pro Phe Phe Ser Leu Ala
                 20                  25                  30

Asn Glu Ser Val Ile Ser Pro Glu Val Pro Ala Gly Cys Arg Val Thr
             35                  40                  45

Phe Ala Gln Val Leu Ser Arg His Gly Ala Arg Tyr Pro Thr Asp Ser
     50                  55                  60

Lys Gly Lys Lys Tyr Ser Ala Leu Ile Glu Glu Ile Gln Gln Asn Ala
 65                  70                  75                  80

Thr Thr Phe Asp Gly Lys Tyr Ala Phe Leu Lys Thr Tyr Asn Tyr Ser
                 85                  90                  95

Leu Gly Ala Asp Asp Leu Thr Pro Phe Gly Glu Gln Glu Leu Val Asn
                100                 105                 110

Ser Gly Ile Lys Phe Tyr Gln Arg Tyr Glu Ser Leu Thr Arg Asn Ile
            115                 120                 125

Val Pro Phe Ile Arg Ser Ser Gly Ser Ser Arg Val Ile Ala Ser Gly
    130                 135                 140

Lys Lys Phe Ile Glu Gly Phe Gln Ser Thr Lys Leu Lys Asp Pro Arg
145                 150                 155                 160

Ala Gln Pro Gly Gln Ser Ser Pro Lys Ile Asp Val Val Ile Ser Glu
                165                 170                 175

Ala Ser Ser Ser Asn Asn Thr Leu Asp Pro Gly Thr Cys Thr Val Phe
            180                 185                 190

Glu Asp Ser Glu Leu Ala Asp Thr Val Glu Ala Asn Phe Thr Ala Thr
    195                 200                 205

Phe Val Pro Ser Ile Arg Gln Arg Leu Glu Asn Asp Leu Ser Gly Val
    210                 215                 220

Thr Leu Thr Asp Thr Glu Val Thr Tyr Leu Met Asp Met Cys Ser Phe
225                 230                 235                 240

Asp Thr Ile Ser Thr Ser Thr Val Asp Thr Lys Leu Ser Pro Phe Cys
                245                 250                 255

Asp Leu Phe Thr His Asp Glu Trp Ile Asn Tyr Asp Tyr Leu Gln Ser
                260                 265                 270

Leu Lys Lys Tyr Tyr Gly His Gly Ala Gly Asn Pro Leu Gly Pro Thr
            275                 280                 285

Gln Gly Val Gly Tyr Ala Asn Glu Leu Ile Ala Arg Leu Thr His Ser
    290                 295                 300
```

-continued

```
Pro Val His Asp Asp Thr Ser Ser Asn His Thr Leu Asp Ser Ser Pro
305                 310                 315                 320

Ala Thr Phe Pro Leu Asn Ser Thr Leu Tyr Ala Asp Phe Ser His Asp
            325                 330                 335

Asn Gly Ile Ile Ser Ile Leu Phe Ala Leu Gly Leu Tyr Asn Gly Thr
                340                 345                 350

Lys Pro Leu Ser Thr Thr Thr Val Glu Asn Ile Thr Gln Thr Asp Gly
            355                 360                 365

Phe Ser Ser Ala Trp Thr Val Pro Phe Ala Ser Arg Leu Tyr Val Glu
    370                 375                 380

Met Met Gln Cys Gln Ala Glu Gln Pro Leu Val Arg Val Leu Val
385                 390                 395                 400

Asn Asp Arg Val Val Pro Leu His Gly Cys Pro Val Asp Ala Leu Gly
                405                 410                 415

Arg Cys Thr Arg Asp Ser Phe Val Arg Gly Leu Ser Phe Ala Arg Ser
                420                 425                 430

Gly Gly Asp Trp Ala Glu Cys Phe Ala
            435                 440
```

<210> SEQ ID NO 151
<211> LENGTH: 440
<212> TYPE: PRT
<213> ORGANISM: A. fumigatus 32722

<400> SEQUENCE: 151

```
Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
                20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
        115                 120                 125

Val Pro Phe Ile Arg Ala Ser Gly Ser Asp Arg Val Ile Ala Ser Gly
    130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Ile Pro Glu Ser
                165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
        195                 200                 205

Ala Pro Asp Ile Arg Ala Arg Ala Glu Lys His Leu Pro Gly Val Thr
    210                 215                 220

Leu Thr Asp Glu Asp Val Val Ser Leu Met Asp Met Cys Ser Phe Asp
```

```
                    225                 230                 235                 240

Thr Val Ala Arg Thr Ser Asp Ala Ser Gln Leu Ser Pro Phe Cys Gln
                    245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
        290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Glu
                340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
        370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
                435                 440

<210> SEQ ID NO 152
<211> LENGTH: 440
<212> TYPE: PRT
<213> ORGANISM: Artificial Sequence
<220> FEATURE:
<223> OTHER INFORMATION: Description of Artificial Sequence:
                A. fumigatus ATCC32722

<400> SEQUENCE: 152

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
        35                  40                  45

Leu Val Gln Val Leu Ser Arg His Gly Ala Arg Tyr Pro Thr Ser Ser
    50                  55                  60

Lys Ser Lys Lys Tyr Lys Lys Leu Val Thr Ala Ile Gln Ala Asn Ala
65                  70                  75                  80

Thr Asp Phe Lys Gly Lys Phe Ala Phe Leu Lys Thr Tyr Asn Tyr Thr
                85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
        115                 120                 125

Val Pro Phe Ile Arg Ala Ser Gly Ser Asp Arg Val Ile Ala Ser Gly
    130                 135                 140
```

```
Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
            165                 170                 175

Glu Thr Phe Asn Asn Thr Leu Asp His Gly Val Cys Thr Lys Phe Glu
                180                 185                 190

Ala Ser Gln Leu Gly Asp Glu Val Ala Ala Asn Phe Thr Ala Leu Phe
            195                 200                 205

Ala Pro Asp Ile Arg Ala Arg Ala Glu Lys His Leu Pro Gly Val Thr
            210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
                245                 250                 255

Leu Phe Thr His Asn Glu Trp Lys Lys Tyr Asn Tyr Leu Gln Ser Leu
                260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
            290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
                325                 330                 335

Ser Met Val Ser Ile Phe Phe Ala Leu Gly Leu Tyr Asn Gly Thr Gly
                340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
            370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Asp Val Asp Lys Leu Gly Arg
                405                 410                 415

Cys Lys Leu Asn Asp Phe Val Lys Gly Leu Ser Trp Ala Arg Ser Gly
                420                 425                 430

Gly Asn Trp Gly Glu Cys Phe Ser
            435                 440

<210> SEQ ID NO 153
<211> LENGTH: 440
<212> TYPE: PRT
<213> ORGANISM: A. fumigatus ATCC58128

<400> SEQUENCE: 153

Gly Ser Lys Ser Cys Asp Thr Val Asp Leu Gly Tyr Gln Cys Ser Pro
1               5                   10                  15

Ala Thr Ser His Leu Trp Gly Gln Tyr Ser Pro Phe Phe Ser Leu Glu
            20                  25                  30

Asp Glu Leu Ser Val Ser Ser Lys Leu Pro Lys Asp Cys Arg Ile Thr
            35                  40                  45

Leu Val Gln Val Leu Ser Arg His Gly Ala Arg Tyr Pro Thr Ser Ser
        50                  55                  60

Lys Ser Lys Lys Tyr Lys Lys Leu Val Thr Ala Ile Gln Ala Asn Ala
65                  70                  75                  80
```

```
Thr Asp Phe Lys Gly Lys Phe Ala Phe Leu Lys Thr Tyr Asn Tyr Thr
            85                  90                  95

Leu Gly Ala Asp Asp Leu Thr Pro Phe Gly Glu Gln Gln Leu Val Asn
            100                 105                 110

Ser Gly Ile Lys Phe Tyr Gln Arg Tyr Lys Ala Leu Ala Arg Ser Val
            115                 120                 125

Val Pro Phe Ile Arg Ala Ser Gly Ser Asp Arg Val Ile Ala Ser Gly
            130                 135                 140

Glu Lys Phe Ile Glu Gly Phe Gln Gln Ala Lys Leu Ala Asp Pro Gly
145                 150                 155                 160

Ala Thr Asn Arg Ala Ala Pro Ala Ile Ser Val Ile Pro Glu Ser
            165                 170                 175

Glu Thr Phe Asn Asn Thr Leu Asp His Gly Val Cys Thr Lys Phe Glu
            180                 185                 190

Ala Ser Gln Leu Gly Asp Glu Val Ala Ala Asn Phe Thr Ala Leu Phe
            195                 200                 205

Ala Pro Asp Ile Arg Ala Arg Ala Glu Lys His Leu Pro Gly Val Thr
            210                 215                 220

Leu Thr Asp Glu Asp Val Val Ser Leu Met Asp Met Cys Ser Phe Asp
225                 230                 235                 240

Thr Val Ala Arg Thr Ser Asp Ala Ser Gln Leu Ser Pro Phe Cys Gln
            245                 250                 255

Leu Phe Thr His Asn Glu Trp Lys Lys Tyr Asn Tyr Leu Gln Ser Leu
            260                 265                 270

Gly Lys Tyr Tyr Gly Tyr Gly Ala Gly Asn Pro Leu Gly Pro Ala Gln
            275                 280                 285

Gly Ile Gly Phe Thr Asn Glu Leu Ile Ala Arg Leu Thr Arg Ser Pro
            290                 295                 300

Val Gln Asp His Thr Ser Thr Asn Ser Thr Leu Val Ser Asn Pro Ala
305                 310                 315                 320

Thr Phe Pro Leu Asn Ala Thr Met Tyr Val Asp Phe Ser His Asp Asn
            325                 330                 335

Ser Met Val Ser Ile Phe Phe Ala Leu Gly Leu Tyr Asn Gly Thr Glu
            340                 345                 350

Pro Leu Ser Arg Thr Ser Val Glu Ser Ala Lys Glu Leu Asp Gly Tyr
            355                 360                 365

Ser Ala Ser Trp Val Val Pro Phe Gly Ala Arg Ala Tyr Phe Glu Thr
            370                 375                 380

Met Gln Cys Lys Ser Glu Lys Glu Ser Leu Val Arg Ala Leu Ile Asn
385                 390                 395                 400

Asp Arg Val Val Pro Leu His Gly Cys Asp Val Asp Lys Leu Gly Arg
            405                 410                 415

Cys Lys Leu Asn Asp Phe Val Lys Gly Leu Ser Trp Ala Arg Ser Gly
            420                 425                 430

Gly Asn Trp Gly Glu Cys Phe Ser
            435                 440

<210> SEQ ID NO 154
<211> LENGTH: 440
<212> TYPE: PRT
<213> ORGANISM: A. fumigatus ATCC26906

<400> SEQUENCE: 154

Gly Ser Lys Ser Cys Asp Thr Val Asp Leu Gly Tyr Gln Cys Ser Pro
```

```
  1               5                   10                  15
Ala Thr Ser His Leu Trp Gly Gln Tyr Ser Pro Phe Phe Ser Leu Glu
                20                  25                  30
Asp Glu Leu Ser Val Ser Ser Lys Leu Pro Lys Asp Cys Arg Ile Thr
                35                  40                  45
Leu Val Gln Val Leu Ser Arg His Gly Ala Arg Tyr Pro Thr Ser Ser
                50                  55                  60
Lys Ser Lys Lys Tyr Lys Lys Leu Val Thr Ala Ile Gln Ala Asn Ala
 65                  70                  75                  80
Thr Asp Phe Lys Gly Lys Phe Ala Phe Leu Lys Thr Tyr Asn Tyr Thr
                85                  90                  95
Leu Gly Ala Asp Asp Leu Thr Ala Phe Gly Glu Gln Gln Leu Val Asn
               100                 105                 110
Ser Gly Ile Lys Phe Tyr Gln Arg Tyr Lys Ala Leu Ala Arg Ser Val
               115                 120                 125
Val Pro Phe Ile Arg Ala Ser Gly Ser Asp Arg Val Ile Ala Ser Gly
               130                 135                 140
Glu Lys Phe Ile Glu Gly Phe Gln Gln Ala Lys Leu Ala Asp Pro Gly
145                 150                 155                 160
Ala Thr Asn Arg Ala Ala Pro Ala Ile Ser Val Ile Pro Glu Ser
               165                 170                 175
Glu Thr Phe Asn Asn Thr Leu Asp His Gly Val Cys Thr Lys Phe Glu
               180                 185                 190
Ala Ser Gln Leu Gly Asp Glu Val Ala Ala Asn Phe Thr Ala Leu Phe
               195                 200                 205
Ala Pro Asp Ile Arg Ala Arg Ala Lys Lys His Leu Pro Gly Val Thr
               210                 215                 220
Leu Thr Asp Glu Asp Val Val Ser Leu Met Asp Met Cys Ser Phe Asp
225                 230                 235                 240
Thr Val Ala Arg Thr Ser Asp Ala Ser Gln Leu Ser Pro Phe Cys Gln
               245                 250                 255
Leu Phe Thr His Asn Glu Trp Lys Lys Tyr Asn Tyr Leu Gln Ser Leu
               260                 265                 270
Gly Lys Tyr Tyr Gly Tyr Gly Ala Gly Asn Pro Leu Gly Pro Ala Gln
               275                 280                 285
Gly Ile Gly Phe Thr Asn Glu Leu Ile Ala Arg Leu Thr Arg Ser Pro
               290                 295                 300
Val Gln Asp His Thr Ser Thr Asn Ser Thr Leu Val Ser Asn Pro Ala
305                 310                 315                 320
Thr Phe Pro Leu Asn Ala Thr Met Tyr Val Asp Phe Ser His Asp Asn
               325                 330                 335
Ser Met Val Ser Ile Phe Phe Ala Leu Gly Leu Tyr Asn Gly Thr Glu
               340                 345                 350
Pro Leu Ser Arg Thr Ser Val Glu Ser Ala Lys Glu Leu Asp Gly Tyr
               355                 360                 365
Ser Ala Ser Trp Val Val Pro Phe Gly Ala Arg Ala Tyr Phe Glu Thr
               370                 375                 380
Met Gln Cys Lys Ser Glu Lys Glu Pro Leu Val Arg Ala Leu Ile Asn
385                 390                 395                 400
Asp Arg Val Val Pro Leu His Gly Cys Asp Val Asp Lys Leu Gly Arg
               405                 410                 415
Cys Lys Leu Asn Asp Phe Val Lys Gly Leu Ser Trp Ala Arg Ser Gly
               420                 425                 430
```

Gly Asn Trp Gly Glu Cys Phe Ser
            435                 440

<210> SEQ ID NO 155
<211> LENGTH: 440
<212> TYPE: PRT
<213> ORGANISM: A. fumigatus ATCC32239

<400> SEQUENCE: 155

Gly Ser Lys Ala Cys Asp Thr Val Glu Leu Gly Tyr Gln Cys Ser Pro
 1               5                  10                  15

Gly Thr Ser His Leu Trp Gly Gln Tyr Ser Pro Phe Ser Leu Glu
            20                  25                  30

Asp Glu Leu Ser Val Ser Ser Asp Leu Pro Lys Asp Cys Arg Val Thr
        35                  40                  45

Phe Val Gln Val Leu Ser Arg His Gly Ala Arg Tyr Pro Thr Ala Ser
    50                  55                  60

Lys Ser Lys Lys Tyr Lys Lys Leu Val Thr Ala Ile Gln Lys Asn Ala
65                  70                  75                  80

Thr Glu Phe Lys Gly Lys Phe Ala Phe Leu Glu Thr Tyr Asn Tyr Thr
                85                  90                  95

Leu Gly Ala Asp Asp Leu Thr Pro Phe Gly Glu Gln Met Val Asn
            100                 105                 110

Ser Gly Ile Lys Phe Tyr Gln Lys Tyr Lys Ala Leu Ala Gly Ser Val
        115                 120                 125

Val Pro Phe Ile Arg Ser Ser Gly Ser Asp Arg Val Ile Ala Ser Gly
    130                 135                 140

Glu Lys Phe Ile Glu Gly Phe Gln Gln Ala Asn Val Ala Asp Pro Gly
145                 150                 155                 160

Ala Thr Asn Arg Ala Ala Pro Val Ile Ser Val Ile Pro Glu Ser
            165                 170                 175

Glu Thr Tyr Asn Asn Thr Leu Asp His Ser Val Cys Thr Asn Phe Glu
        180                 185                 190

Ala Ser Glu Leu Gly Asp Glu Val Glu Ala Asn Phe Thr Ala Leu Phe
    195                 200                 205

Ala Pro Ala Ile Arg Ala Arg Ile Glu Lys His Leu Pro Gly Val Gln
    210                 215                 220

Leu Thr Asp Asp Val Val Ser Leu Met Asp Met Cys Ser Phe Asp
225                 230                 235                 240

Thr Val Ala Arg Thr Ala Asp Ala Ser Glu Leu Ser Pro Phe Cys Ala
                245                 250                 255

Ile Phe Thr His Asn Glu Trp Lys Lys Tyr Asp Tyr Leu Gln Ser Leu
            260                 265                 270

Gly Lys Tyr Tyr Gly Tyr Gly Ala Gly Asn Pro Leu Gly Pro Ala Gln
        275                 280                 285

Gly Ile Gly Phe Thr Asn Glu Leu Ile Ala Arg Leu Thr Asn Ser Pro
    290                 295                 300

Val Gln Asp His Thr Ser Thr Asn Ser Thr Leu Asp Ser Asp Pro Ala
305                 310                 315                 320

Thr Phe Pro Leu Asn Ala Thr Ile Tyr Val Asp Phe Ser His Asp Asn
                325                 330                 335

Gly Met Ile Pro Ile Phe Phe Ala Met Gly Leu Tyr Asn Gly Thr Glu
            340                 345                 350

Pro Leu Ser Gln Thr Ser Glu Glu Ser Thr Lys Glu Ser Asn Gly Tyr

```
                    355                 360                 365
Ser Ala Ser Trp Ala Val Pro Phe Gly Ala Arg Ala Tyr Phe Glu Thr
            370                 375                 380

Met Gln Cys Lys Ser Glu Lys Glu Pro Leu Val Arg Ala Leu Ile Asn
385                 390                 395                 400

Asp Arg Val Val Pro Leu His Gly Cys Ala Val Asp Lys Leu Gly Arg
                405                 410                 415

Cys Lys Leu Lys Asp Phe Val Lys Gly Leu Ser Trp Ala Arg Ser Gly
                420                 425                 430

Gly Asn Ser Glu Gln Ser Phe Ser
            435                 440

<210> SEQ ID NO 156
<211> LENGTH: 439
<212> TYPE: PRT
<213> ORGANISM: E. nidulans

<400> SEQUENCE: 156

Gln Asn His Ser Cys Asn Thr Ala Asp Gly Gly Tyr Gln Cys Phe Pro
 1               5                  10                  15

Asn Val Ser His Val Trp Gly Gln Tyr Ser Pro Tyr Phe Ser Ile Glu
            20                  25                  30

Gln Glu Ser Ala Ile Ser Glu Asp Val Pro His Gly Cys Glu Val Thr
        35                  40                  45

Phe Val Gln Val Leu Ser Arg His Gly Ala Arg Tyr Pro Thr Glu Ser
    50                  55                  60

Lys Ser Lys Ala Tyr Ser Gly Leu Ile Glu Ala Ile Gln Lys Asn Ala
65                  70                  75                  80

Thr Ser Phe Trp Gly Gln Tyr Ala Phe Leu Glu Ser Tyr Asn Tyr Thr
                85                  90                  95

Leu Gly Ala Asp Asp Leu Thr Ile Phe Gly Glu Asn Gln Met Val Asp
            100                 105                 110

Ser Gly Ala Lys Phe Tyr Arg Arg Tyr Lys Asn Leu Ala Arg Lys Asn
        115                 120                 125

Thr Pro Phe Ile Arg Ala Ser Gly Ser Asp Arg Val Val Ala Ser Ala
130                 135                 140

Glu Lys Phe Ile Asn Gly Phe Arg Lys Ala Gln Leu His Asp His Gly
145                 150                 155                 160

Ser Gly Gln Ala Thr Pro Val Val Asn Val Ile Ile Pro Glu Ile Asp
                165                 170                 175

Gly Phe Asn Asn Thr Leu Asp His Ser Thr Cys Val Ser Phe Glu Asn
            180                 185                 190

Asp Glu Arg Ala Asp Glu Ile Glu Ala Asn Phe Thr Ala Ile Met Gly
        195                 200                 205

Pro Pro Ile Arg Lys Arg Leu Glu Asn Asp Leu Pro Gly Ile Lys Leu
    210                 215                 220

Thr Asn Glu Asn Val Ile Tyr Leu Met Asp Met Cys Ser Phe Asp Thr
225                 230                 235                 240

Met Ala Arg Thr Ala His Gly Thr Glu Leu Ser Pro Phe Cys Ala Ile
                245                 250                 255

Phe Thr Glu Lys Glu Trp Leu Gln Tyr Asp Tyr Leu Gln Ser Leu Ser
            260                 265                 270

Lys Tyr Tyr Gly Tyr Gly Ala Gly Ser Pro Leu Gly Pro Ala Gln Gly
        275                 280                 285
```

-continued

```
Ile Gly Phe Thr Asn Glu Leu Ile Ala Arg Leu Thr Gln Ser Pro Val
    290                 295                 300

Gln Asp Asn Thr Ser Thr Asn His Thr Leu Asp Ser Asn Pro Ala Thr
305                 310                 315                 320

Phe Pro Leu Asp Arg Lys Leu Tyr Ala Asp Phe Ser His Asp Asn Ser
                325                 330                 335

Met Ile Ser Ile Phe Phe Ala Met Gly Leu Tyr Asn Gly Thr Gln Pro
            340                 345                 350

Leu Ser Met Asp Ser Val Glu Ser Ile Gln Glu Met Asp Gly Tyr Ala
        355                 360                 365

Ala Ser Trp Thr Val Pro Phe Gly Ala Arg Ala Tyr Phe Glu Leu Met
    370                 375                 380

Gln Cys Glu Lys Lys Glu Pro Leu Val Arg Val Leu Val Asn Asp Arg
385                 390                 395                 400

Val Val Pro Leu His Gly Cys Ala Val Asp Lys Phe Gly Arg Cys Thr
                405                 410                 415

Leu Asp Asp Trp Val Glu Gly Leu Asn Phe Ala Arg Ser Gly Gly Asn
            420                 425                 430

Trp Lys Thr Cys Phe Thr Leu
        435
```

```
<210> SEQ ID NO 157
<211> LENGTH: 443
<212> TYPE: PRT
<213> ORGANISM: T. thermophilus

<400> SEQUENCE: 157

Asp Ser His Ser Cys Asn Thr Val Glu Gly Gly Tyr Gln Cys Arg Pro
1               5                   10                  15

Glu Ile Ser His Ser Trp Gly Gln Tyr Ser Pro Phe Phe Ser Leu Ala
            20                  25                  30

Asp Gln Ser Glu Ile Ser Pro Asp Val Pro Gln Asn Cys Lys Ile Thr
        35                  40                  45

Phe Val Gln Leu Leu Ser Arg His Gly Ala Arg Tyr Pro Thr Ser Ser
    50                  55                  60

Lys Thr Glu Leu Tyr Ser Gln Leu Ile Ser Arg Ile Gln Lys Thr Ala
65                  70                  75                  80

Thr Ala Tyr Lys Gly Tyr Tyr Ala Phe Leu Lys Asp Tyr Arg Tyr Gln
                85                  90                  95

Leu Gly Ala Asn Asp Leu Thr Pro Phe Gly Glu Asn Gln Met Ile Gln
            100                 105                 110

Leu Gly Ile Lys Phe Tyr Asn His Tyr Lys Ser Leu Ala Arg Asn Ala
        115                 120                 125

Val Pro Phe Val Arg Cys Ser Gly Ser Asp Arg Val Ile Ala Ser Gly
    130                 135                 140

Arg Leu Phe Ile Glu Gly Phe Gln Ser Ala Lys Val Leu Asp Pro His
145                 150                 155                 160

Ser Asp Lys His Asp Ala Pro Pro Thr Ile Asn Val Ile Glu Glu
                165                 170                 175

Gly Pro Ser Tyr Asn Asn Thr Leu Asp Thr Gly Ser Cys Pro Val Phe
            180                 185                 190

Glu Asp Ser Ser Gly Gly His Asp Ala Gln Glu Lys Phe Ala Lys Gln
        195                 200                 205

Phe Ala Pro Ala Ile Leu Glu Lys Ile Lys Asp His Leu Pro Gly Val
    210                 215                 220
```

Asp Leu Ala Val Ser Asp Val Pro Tyr Leu Met Asp Leu Cys Pro Phe
225                 230                 235                 240

Glu Thr Leu Ala Arg Asn His Thr Asp Thr Leu Ser Pro Phe Cys Ala
            245                 250                 255

Leu Ser Thr Gln Glu Glu Trp Gln Ala Tyr Asp Tyr Gln Ser Leu
            260                 265                 270

Gly Lys Tyr Tyr Gly Asn Gly Gly Asn Pro Leu Gly Pro Ala Gln
            275                 280                 285

Gly Val Gly Phe Val Asn Glu Leu Ile Ala Arg Met Thr His Ser Pro
290                 295                 300

Val Gln Asp Tyr Thr Thr Val Asn His Thr Leu Asp Ser Asn Pro Ala
305                 310                 315                 320

Thr Phe Pro Leu Asn Ala Thr Leu Tyr Ala Asp Phe Ser His Asp Asn
                325                 330                 335

Thr Met Thr Ser Ile Phe Ala Ala Leu Gly Leu Tyr Asn Gly Thr Ala
            340                 345                 350

Lys Leu Ser Thr Thr Glu Ile Lys Ser Ile Glu Glu Thr Asp Gly Tyr
            355                 360                 365

Ser Ala Ala Trp Thr Val Pro Phe Gly Gly Arg Ala Tyr Ile Glu Met
370                 375                 380

Met Gln Cys Asp Asp Ser Asp Glu Pro Val Val Arg Val Leu Val Asn
385                 390                 395                 400

Asp Arg Val Val Pro Leu His Gly Cys Glu Val Asp Ser Leu Gly Arg
                405                 410                 415

Cys Lys Arg Asp Asp Phe Val Arg Gly Leu Ser Phe Ala Arg Gln Gly
                420                 425                 430

Gly Asn Trp Glu Gly Cys Tyr Ala Ala Ser Glu
            435                 440

<210> SEQ ID NO 158
<211> LENGTH: 440
<212> TYPE: PRT
<213> ORGANISM: T. lanuginosa

<400> SEQUENCE: 158

Asn Val Asp Ile Ala Arg His Trp Gly Gln Tyr Ser Pro Phe Phe Ser
1               5                   10                  15

Leu Ala Glu Val Ser Glu Ile Ser Pro Ala Val Pro Lys Gly Cys Arg
            20                  25                  30

Val Glu Phe Val Gln Val Leu Ser Arg His Gly Ala Arg Tyr Pro Thr
            35                  40                  45

Ala His Lys Ser Glu Val Tyr Ala Glu Leu Leu Gln Arg Ile Gln Asp
    50                  55                  60

Thr Ala Thr Glu Phe Lys Gly Asp Phe Ala Phe Leu Arg Asp Tyr Ala
65                  70                  75                  80

Tyr His Leu Gly Ala Asp Asn Leu Thr Arg Phe Gly Glu Glu Gln Met
                85                  90                  95

Met Glu Ser Gly Arg Gln Phe Tyr His Arg Tyr Arg Glu Gln Ala Arg
            100                 105                 110

Glu Ile Val Pro Phe Val Arg Ala Ala Gly Ser Ala Arg Val Ile Ala
            115                 120                 125

Ser Ala Glu Phe Phe Asn Arg Gly Phe Gln Asp Ala Lys Asp Arg Asp
    130                 135                 140

Pro Arg Ser Asn Lys Asp Gln Ala Glu Pro Val Ile Asn Val Ile Ile

-continued

```
            145                 150                 155                 160
        Ser Glu Glu Thr Gly Ser Asn Asn Thr Leu Asp Gly Leu Thr Cys Pro
                        165                 170                 175
        Ala Ala Glu Glu Ala Pro Asp Pro Thr Gln Pro Ala Glu Phe Leu Gln
                    180                 185                 190
        Val Phe Gly Pro Arg Val Leu Lys Lys Ile Thr Lys His Met Pro Gly
                195                 200                 205
        Val Asn Leu Thr Leu Glu Asp Val Pro Leu Phe Met Asp Leu Cys Pro
            210                 215                 220
        Phe Asp Thr Val Gly Ser Asp Pro Val Leu Phe Pro Arg Gln Leu Ser
        225                 230                 235                 240
        Pro Phe Cys His Leu Phe Thr Ala Asp Asp Trp Met Ala Tyr Asp Tyr
                        245                 250                 255
        Tyr Tyr Thr Leu Asp Lys Tyr Tyr Ser His Gly Gly Gly Ser Ala Phe
                    260                 265                 270
        Gly Pro Ser Arg Gly Val Gly Phe Val Asn Glu Leu Ile Ala Arg Met
                275                 280                 285
        Thr Gly Asn Leu Pro Val Lys Asp His Thr Thr Val Asn His Thr Leu
            290                 295                 300
        Asp Asp Asn Pro Glu Thr Phe Pro Leu Asp Ala Val Leu Tyr Ala Asp
        305                 310                 315                 320
        Phe Ser His Asp Asn Thr Met Thr Gly Ile Phe Ser Ala Met Gly Leu
                        325                 330                 335
        Tyr Asn Gly Thr Lys Pro Leu Ser Thr Ser Lys Ile Gln Pro Pro Thr
                    340                 345                 350
        Gly Ala Ala Ala Asp Gly Tyr Ala Ala Ser Trp Thr Val Pro Phe Ala
                355                 360                 365
        Ala Arg Ala Tyr Val Glu Leu Leu Arg Cys Glu Thr Glu Thr Ser Ser
            370                 375                 380
        Glu Glu Glu Glu Glu Gly Glu Asp Glu Pro Phe Val Arg Val Leu Val
        385                 390                 395                 400
        Asn Asp Arg Val Val Pro Leu His Gly Cys Arg Val Asp Arg Trp Gly
                        405                 410                 415
        Arg Cys Arg Arg Asp Glu Trp Ile Lys Gly Leu Thr Phe Ala Arg Gln
                    420                 425                 430
        Gly Gly His Trp Asp Arg Cys Phe
                435                 440

<210> SEQ ID NO 159
<211> LENGTH: 466
<212> TYPE: PRT
<213> ORGANISM: M. thermophila

<400> SEQUENCE: 159

Glu Ser Arg Pro Cys Asp Thr Pro Asp Leu Gly Phe Gln Cys Gly Thr
        1               5                   10                  15
        Ala Ile Ser His Phe Trp Gly Gln Tyr Ser Pro Tyr Phe Ser Val Pro
                    20                  25                  30
        Ser Glu Leu Asp Ala Ser Ile Pro Asp Asp Cys Glu Val Thr Phe Ala
                35                  40                  45
        Gln Val Leu Ser Arg His Gly Ala Arg Ala Pro Thr Leu Lys Arg Ala
            50                  55                  60
        Ala Ser Tyr Val Asp Leu Ile Asp Arg Ile His His Gly Ala Ile Ser
        65                  70                  75                  80
```

-continued

```
Tyr Gly Pro Gly Tyr Glu Phe Leu Arg Thr Tyr Asp Tyr Thr Leu Gly
                 85                  90                  95

Ala Asp Glu Leu Thr Arg Thr Gly Gln Gln Gln Met Val Asn Ser Gly
            100                 105                 110

Ile Lys Phe Tyr Arg Arg Tyr Arg Ala Leu Ala Arg Lys Ser Ile Pro
        115                 120                 125

Phe Val Arg Thr Ala Gly Gln Asp Arg Val Val His Ser Ala Glu Asn
    130                 135                 140

Phe Thr Gln Gly Phe His Ser Ala Leu Leu Ala Asp Arg Gly Ser Thr
145                 150                 155                 160

Val Arg Pro Thr Leu Pro Tyr Asp Met Val Ile Pro Glu Thr Ala
                165                 170                 175

Gly Ala Asn Asn Thr Leu His Asn Asp Leu Cys Thr Ala Phe Glu Glu
            180                 185                 190

Gly Pro Tyr Ser Thr Ile Gly Asp Asp Ala Gln Asp Thr Tyr Leu Ser
        195                 200                 205

Thr Phe Ala Gly Pro Ile Thr Ala Arg Val Asn Ala Asn Leu Pro Gly
    210                 215                 220

Ala Asn Leu Thr Asp Ala Asp Thr Val Ala Leu Met Asp Leu Cys Pro
225                 230                 235                 240

Phe Glu Thr Val Ala Ser Ser Ser Asp Pro Ala Thr Ala Asp Ala
                245                 250                 255

Gly Gly Gly Asn Gly Arg Pro Leu Ser Pro Phe Cys Arg Leu Phe Ser
            260                 265                 270

Glu Ser Glu Trp Arg Ala Tyr Asp Tyr Leu Gln Ser Val Gly Lys Trp
        275                 280                 285

Tyr Gly Tyr Gly Pro Gly Asn Pro Leu Gly Pro Thr Gln Gly Val Gly
    290                 295                 300

Phe Val Asn Glu Leu Leu Ala Arg Leu Ala Gly Val Pro Val Arg Asp
305                 310                 315                 320

Gly Thr Ser Thr Asn Arg Thr Leu Asp Gly Asp Pro Arg Thr Phe Pro
                325                 330                 335

Leu Gly Arg Pro Leu Tyr Ala Asp Phe Ser His Asp Asn Asp Met Met
            340                 345                 350

Gly Val Leu Gly Ala Leu Gly Ala Tyr Asp Gly Val Pro Pro Leu Asp
        355                 360                 365

Lys Thr Ala Arg Arg Asp Pro Glu Glu Leu Gly Gly Tyr Ala Ala Ser
    370                 375                 380

Trp Ala Val Pro Phe Ala Ala Arg Ile Tyr Val Glu Lys Met Arg Cys
385                 390                 395                 400

Ser Gly Gly Gly Gly Gly Gly Gly Glu Gly Arg Gln Glu Lys
                405                 410                 415

Asp Glu Glu Met Val Arg Val Leu Val Asn Asp Arg Val Met Thr Leu
            420                 425                 430

Lys Gly Cys Gly Ala Asp Glu Arg Gly Met Cys Thr Leu Glu Arg Phe
        435                 440                 445

Ile Glu Ser Met Ala Phe Ala Arg Gly Asn Gly Lys Trp Asp Leu Cys
    450                 455                 460

Phe Ala
465
```

<210> SEQ ID NO 160
<211> LENGTH: 440
<212> TYPE: PRT

-continued

<213> ORGANISM: Consensus Seq. 11

<400> SEQUENCE: 160

| | | | | | | | | | | | | | | |
|---|---|---|---|---|---|---|---|---|---|---|---|---|---|---|
Asn Ser His Ser Cys Asp Thr Val Asp Gly Tyr Gln Cys Pro Glu Ile
1               5                   10                  15

Ser His Leu Trp Gly Gln Tyr Ser Pro Phe Phe Ser Leu Ala Asp Glu
            20                  25                  30

Ser Ala Ile Ser Pro Asp Val Pro Lys Gly Cys Arg Val Thr Phe Val
            35                  40                  45

Gln Val Leu Ser Arg His Gly Ala Arg Tyr Pro Thr Ser Ser Lys Ser
    50                  55                  60

Lys Lys Tyr Ser Ala Leu Ile Glu Arg Ile Gln Lys Asn Ala Thr Phe
65                  70                  75                  80

Lys Gly Lys Tyr Ala Phe Leu Lys Thr Tyr Asn Tyr Thr Leu Gly Ala
                85                  90                  95

Asp Asp Leu Thr Pro Phe Gly Glu Asn Gln Met Val Asn Ser Gly Ile
            100                 105                 110

Lys Phe Tyr Arg Arg Tyr Lys Ala Leu Ala Arg Asn Ile Val Pro Phe
        115                 120                 125

Val Arg Ala Ser Gly Ser Asp Arg Val Ile Ala Ser Ala Glu Lys Phe
    130                 135                 140

Ile Glu Gly Phe Gln Ser Ala Lys Leu Ala Asp Pro Ala His Gln Ala
145                 150                 155                 160

Ser Pro Val Ile Asn Val Ile Pro Glu Gly Ser Gly Tyr Asn Asn
                165                 170                 175

Thr Leu Asp His Gly Leu Cys Thr Ala Phe Glu Asp Ser Thr Ser Glu
            180                 185                 190

Gln Leu Gly Asp Asp Ala Glu Ala Asn Phe Thr Ala Val Phe Ala Pro
    195                 200                 205

Pro Ile Arg Ala Arg Leu Glu Ala Leu Pro Gly Val Asn Leu Thr Asp
    210                 215                 220

Glu Asp Val Val Asn Leu Met Asp Met Cys Pro Phe Asp Thr Val Ala
225                 230                 235                 240

Arg Thr Ser Asp Ala Thr Gln Leu Ser Pro Phe Cys Asp Leu Phe Thr
            245                 250                 255

Ala Asp Glu Trp Gln Tyr Asp Tyr Leu Gln Ser Leu Lys Tyr Tyr Gly
            260                 265                 270

Tyr Gly Ala Gly Asn Pro Leu Gly Pro Ala Gln Gly Val Gly Phe Asn
        275                 280                 285

Glu Leu Ile Ala Arg Leu Thr His Ser Pro Val Gln Asp His Thr Ser
    290                 295                 300

Thr Asn His Thr Leu Asp Ser Asn Pro Ala Thr Phe Pro Leu Asn Ala
305                 310                 315                 320

Thr Leu Tyr Ala Asp Phe Ser His Asp Asn Thr Met Val Ser Ile Phe
            325                 330                 335

Phe Ala Leu Gly Leu Tyr Asn Gly Thr Lys Pro Leu Ser Thr Thr Ser
            340                 345                 350

Val Glu Ser Ile Glu Thr Asp Gly Tyr Ala Ala Ser Trp Thr Val Pro
        355                 360                 365

Phe Ala Ala Arg Ala Tyr Val Glu Met Met Gln Cys Glu Ala Gly Gly
    370                 375                 380

Gly Gly Gly Glu Gly Glu Lys Gly Pro Leu Val Arg Val Leu Val Asn
385                 390                 395                 400

Asp Arg Val Val Pro Leu His Gly Cys Gly Val Asp Lys Leu Gly Arg
             405                 410                 415

Cys Lys Leu Asp Asp Phe Val Glu Gly Leu Ser Phe Ala Arg Ser Gly
             420                 425                 430

Gly Asn Trp Ala Glu Cys Phe Ala
             435                 440

<210> SEQ ID NO 161
<211> LENGTH: 467
<212> TYPE: PRT
<213> ORGANISM: Artificial Sequence
<220> FEATURE:
<223> OTHER INFORMATION: Description of Artificial
      Sequence:phytase-1-thermo[8]-Q50T-K91A

<400> SEQUENCE: 161

Met Gly Val Phe Val Leu Leu Ser Ile Ala Thr Leu Phe Gly Ser
 1               5                  10                  15

Thr Ser Gly Thr Ala Leu Gly Pro Arg Gly Asn Ser His Ser Cys Asp
             20                  25                  30

Thr Val Asp Gly Gly Tyr Gln Cys Phe Pro Glu Ile Ser His Leu Trp
             35                  40                  45

Gly Thr Tyr Ser Pro Tyr Phe Ser Leu Ala Asp Glu Ser Ala Ile Ser
     50                  55                  60

Pro Asp Val Pro Asp Asp Cys Arg Val Thr Phe Val Gln Val Leu Ser
65                   70                  75                  80

Arg His Gly Ala Arg Tyr Pro Thr Ser Ser Ala Ser Lys Ala Tyr Ser
                 85                  90                  95

Ala Leu Ile Glu Ala Ile Gln Lys Asn Ala Thr Ala Phe Lys Gly Lys
             100                 105                 110

Tyr Ala Phe Leu Lys Thr Tyr Asn Tyr Thr Leu Gly Ala Asp Asp Leu
             115                 120                 125

Thr Pro Phe Gly Glu Asn Gln Met Val Asn Ser Gly Ile Lys Phe Tyr
             130                 135                 140

Arg Arg Tyr Lys Ala Leu Ala Arg Lys Ile Val Pro Phe Ile Arg Ala
145                 150                 155                 160

Ser Gly Ser Asp Arg Val Ile Ala Ser Ala Glu Lys Phe Ile Glu Gly
                 165                 170                 175

Phe Gln Ser Ala Lys Leu Ala Asp Pro Gly Ser Gln Pro His Gln Ala
             180                 185                 190

Ser Pro Val Ile Asn Val Ile Pro Glu Gly Ser Gly Tyr Asn Asn
             195                 200                 205

Thr Leu Asp His Gly Thr Cys Thr Ala Phe Glu Asp Ser Glu Leu Gly
     210                 215                 220

Asp Asp Val Glu Ala Asn Phe Thr Ala Leu Phe Ala Pro Ala Ile Arg
225                 230                 235                 240

Ala Arg Leu Glu Ala Asp Leu Pro Gly Val Thr Leu Thr Asp Glu Asp
                 245                 250                 255

Val Val Tyr Leu Met Asp Met Cys Pro Phe Asp Thr Val Ala Arg Thr
             260                 265                 270

Ser Asp Ala Thr Glu Leu Ser Pro Phe Cys Ala Leu Phe Thr His Asp
             275                 280                 285

Glu Trp Ile Gln Tyr Asp Tyr Leu Gln Ser Leu Gly Lys Tyr Tyr Gly
             290                 295                 300

Tyr Gly Ala Gly Asn Pro Leu Gly Pro Ala Gln Gly Val Gly Phe Ala
305                 310                 315                 320

Asn Glu Leu Ile Ala Arg Leu Thr His Ser Pro Val Gln Asp His Thr
              325                 330                 335

Ser Thr Asn His Thr Leu Asp Ser Asn Pro Ala Thr Phe Pro Leu Asn
          340                 345                 350

Ala Thr Leu Tyr Ala Asp Phe Ser His Asp Asn Thr Met Ile Ser Ile
              355                 360                 365

Phe Phe Ala Leu Gly Leu Tyr Asn Gly Thr Lys Pro Leu Ser Thr Thr
    370                 375                 380

Ser Val Glu Ser Ile Glu Glu Thr Asp Gly Tyr Ser Ala Ser Trp Thr
385                 390                 395                 400

Val Pro Phe Ala Ala Arg Ala Tyr Val Glu Met Met Gln Cys Gln Ala
              405                 410                 415

Glu Lys Glu Pro Leu Val Arg Val Leu Val Asn Asp Arg Val Val Pro
              420                 425                 430

Leu His Gly Cys Ala Val Asp Lys Leu Gly Arg Cys Lys Arg Asp Asp
              435                 440                 445

Phe Val Glu Gly Leu Ser Phe Ala Arg Ser Gly Gly Asn Trp Ala Glu
    450                 455                 460

Cys Phe Ala
465

<210> SEQ ID NO 162
<211> LENGTH: 1404
<212> TYPE: DNA
<213> ORGANISM: Artificial Sequence
<220> FEATURE:
<223> OTHER INFORMATION: Description of Artificial
      Sequence:phytase-1-thermo[8]-Q50T-K91A

<400> SEQUENCE: 162

| | | | | | |
|---|---|---|---|---|---|
| atgggcgtgt | cgtcgtgct | actgtccatt | gccaccttgt | tcggttccac | atccggtacc | 60 |
| gccttgggtc | ctcgtggtaa | ttctcactct | tgtgacactg | ttgacggtgg | ttaccaatgt | 120 |
| ttcccagaaa | tttctcactt | gtggggtacc | tactctccat | acttctcttt | ggcagacgaa | 180 |
| tctgctattt | ctccagacgt | tccagacgac | tgtagagtta | ctttcgttca | agttttgtct | 240 |
| agacacggtg | ctagataccc | aacttcttct | gcgtctaagg | cttactctgc | tttgattgaa | 300 |
| gctattcaaa | agaacgctac | tgctttcaag | ggtaagtacg | ctttcttgaa | gacttacaac | 360 |
| tacactttgg | gtgctgacga | cttgactcca | ttcggtgaaa | accaaatggt | taactctggt | 420 |
| attaagttct | acagaagata | caaggctttg | gctagaaaga | ttgttccatt | cattagagct | 480 |
| tctggttctg | acagagttat | tgcttctgct | gaaaagttca | ttgaaggttt | ccaatctgct | 540 |
| aagttggctg | acccaggttc | tcaaccacac | caagcttctc | agttattaa | cgtgatcatt | 600 |
| ccagaaggat | ccggttacaa | caacactttg | gaccacggta | cttgtactgc | tttcgaagac | 660 |
| tctgaattag | gtgacgacgt | tgaagctaac | ttcactgctt | tgttcgctcc | agctattaga | 720 |
| gctagattgg | aagctgactt | gccaggtgtt | actttgactg | acgaagacgt | tgtttacttg | 780 |
| atggacatgt | gtccattcga | cactgtcgct | agaacttctg | acgctactga | attgtctcca | 840 |
| ttctgtgctt | tgttcactca | cgacgaatgg | atccaatacg | actacttgca | aagcttgggt | 900 |
| aagtactacg | gttacggtgc | tggtaaccca | ttgggtccag | ctcaaggtgt | tggtttcgct | 960 |
| aacgaattga | ttgctagatt | gactcactct | ccagttcaag | accacacttc | tactaaccac | 1020 |
| actttggact | ctaacccagc | tactttccca | ttgaacgcta | cttgtacgc | tgacttctct | 1080 |
| cacgacaaca | ctatgatatc | tattttcttc | gctttgggtt | tgtacaacgg | taccaagcca | 1140 |

```
ttgtctacta cttctgttga atctattgaa gaaactgacg gttactctgc ttcttggact    1200
gttccattcg ctgctagagc ttacgttgaa atgatgcaat gtcaagctga aaaggaacca    1260
ttggttagag ttttggttaa cgacagagtt gttccattgc acggttgtgc tgttgacaag    1320
ttgggtagat gtaagagaga cgacttcgtt gaaggtttgt ctttcgctag atctggtggt    1380
aactgggctg aatgtttcgc ttaa                                            1404
```

<210> SEQ ID NO 163
<211> LENGTH: 467
<212> TYPE: PRT
<213> ORGANISM: Artificial Sequence
<220> FEATURE:
<223> OTHER INFORMATION: Description of Artificial Sequence:consensus
      phytase-10-thermo[3]-Q50T-K91A

<400> SEQUENCE: 163

```
Met Gly Val Phe Val Val Leu Leu Ser Ile Ala Thr Leu Phe Gly Ser
  1               5                  10                  15

Thr Ser Gly Thr Ala Leu Gly Pro Arg Gly Asn Ser His Ser Cys Asp
             20                  25                  30

Thr Val Asp Gly Gly Tyr Gln Cys Phe Pro Glu Ile Ser His Leu Trp
         35                  40                  45

Gly Thr Tyr Ser Pro Phe Phe Ser Leu Ala Asp Glu Ser Ala Ile Ser
     50                  55                  60

Pro Asp Val Pro Lys Gly Cys Arg Val Thr Phe Val Gln Val Leu Ser
 65                  70                  75                  80

Arg His Gly Ala Arg Tyr Pro Thr Ser Ser Ala Ser Lys Ala Tyr Ser
                 85                  90                  95

Ala Leu Ile Glu Ala Ile Gln Lys Asn Ala Thr Ala Phe Lys Gly Lys
            100                 105                 110

Tyr Ala Phe Leu Lys Thr Tyr Asn Tyr Thr Leu Gly Ala Asp Asp Leu
        115                 120                 125

Thr Pro Phe Gly Glu Gln Gln Met Val Asn Ser Gly Ile Lys Phe Tyr
    130                 135                 140

Arg Arg Tyr Lys Ala Leu Ala Arg Lys Ile Val Pro Phe Ile Arg Ala
145                 150                 155                 160

Ser Gly Ser Asp Arg Val Ile Ala Ser Ala Glu Lys Phe Ile Glu Gly
                165                 170                 175

Phe Gln Ser Ala Lys Leu Ala Asp Pro Gly Ala Asn Pro His Gln Ala
            180                 185                 190

Ser Pro Val Ile Asn Val Ile Ile Pro Glu Gly Ala Gly Tyr Asn Asn
        195                 200                 205

Thr Leu Asp His Gly Leu Cys Thr Ala Phe Glu Glu Ser Glu Leu Gly
    210                 215                 220

Asp Asp Val Glu Ala Asn Phe Thr Ala Val Phe Ala Pro Pro Ile Arg
225                 230                 235                 240

Ala Arg Leu Glu Ala His Leu Pro Gly Val Asn Leu Thr Asp Glu Asp
                245                 250                 255

Val Val Asn Leu Met Asp Met Cys Pro Phe Asp Thr Val Ala Arg Thr
            260                 265                 270

Ser Asp Ala Thr Gln Leu Ser Pro Phe Cys Asp Leu Phe Thr His Asp
        275                 280                 285

Glu Trp Ile Gln Tyr Asp Tyr Leu Gln Ser Leu Gly Lys Tyr Tyr Gly
    290                 295                 300
```

```
Tyr Gly Ala Gly Asn Pro Leu Gly Pro Ala Gln Gly Val Gly Phe Val
305                 310                 315                 320

Asn Glu Leu Ile Ala Arg Leu Thr His Ser Pro Val Gln Asp His Thr
                325                 330                 335

Ser Thr Asn His Thr Leu Asp Ser Asn Pro Ala Thr Phe Pro Leu Asn
                340                 345                 350

Ala Thr Leu Tyr Ala Asp Phe Ser His Asp Asn Thr Met Val Ser Ile
                355                 360                 365

Phe Phe Ala Leu Gly Leu Tyr Asn Gly Thr Lys Pro Leu Ser Thr Thr
370                 375                 380

Ser Val Glu Ser Ile Glu Glu Thr Asp Gly Tyr Ser Ala Ser Trp Thr
385                 390                 395                 400

Val Pro Phe Ala Ala Arg Ala Tyr Val Glu Met Met Gln Cys Glu Ala
                405                 410                 415

Glu Lys Glu Pro Leu Val Arg Val Leu Val Asn Asp Arg Val Val Pro
                420                 425                 430

Leu His Gly Cys Gly Val Asp Lys Leu Gly Arg Cys Lys Arg Asp Asp
                435                 440                 445

Phe Val Glu Gly Leu Ser Phe Ala Arg Ser Gly Gly Asn Trp Glu Glu
    450                 455                 460

Cys Phe Ala
465

<210> SEQ ID NO 164
<211> LENGTH: 1404
<212> TYPE: DNA
<213> ORGANISM: Artificial Sequence
<220> FEATURE:
<223> OTHER INFORMATION: Description of Artificial Sequence:consensus
      phytase-10-thermo[3]-Q50T-K91A

<400> SEQUENCE: 164
atgggcgtgt tcgtcgtgct actgtccatt gccaccttgt tcggttccac atccggtacc      60
gccttgggtc tcgtggtaa ctctcactct tgtgacactg ttgacggtgg ttaccaatgt     120
ttcccagaaa tttctcactt gtggggtaca tactctccat tcttctcttt ggctgacgaa     180
tctgctattt ctccagacgt tccaaagggt tgtagagtta ctttcgttca agttttgtct     240
agacacggtg ctagataccc aacttcttct gcgtctaagg cgtactctgc tttgattgaa     300
gctattcaaa agaacgctac tgctttcaag ggtaagtacg cttcttgaa gacttacaac     360 tacactttgg gtgctgacga cttgactcca ttcggtgaac aacaaatggt taactctggt     420
attaagttct acagaagata caaggctttg gctagaaaga ttgttccatt cattagagct     480
tctggttctg acagagttat tgcttctgct gaaaagttca ttgaaggttt ccaatctgct     540
aagttggctg acccaggtgc taacccacac caagcttctc cagttattaa cgttattatt     600
ccagaaggtg ctggttacaa caacactttg gaccacggtt tgtgtactgc tttcgaagaa     660
tctgaattgg gtgacgacgt tgaagctaac ttcactgctg ttttcgctcc accaattaga     720
gctagattgg aagctcactt gccaggtgtt aacttgactg acgaagacgt tgttaacttg     780
atggacatgt gtccattcga cactgttgct agaacttctg acgctactca attgtctcca     840
ttctgtgact tgttcactca cgacgaatgg attcaatacg actacttgca atctttgggt     900
aagtactacg ttacggtgc tggtaaccca ttgggtccag ctcaaggtgt tggtttcgtt     960
aacgaattga ttgctagatt gactcactct ccagttcaag accacacttc tactaaccac    1020
actttggact ctaacccagc tactttccca ttgaacgcta ctttgtacgc tgacttctct    1080
```

-continued

```
cacgacaaca ctatggtttc tattttcttc gctttgggtt tgtacaacgg tactaagcca      1140
ttgtctacta cttctgttga atctattgaa gaaactgacg gttactctgc ttcttggact      1200
gttccattcg ctgctagagc ttacgttgaa atgatgcaat gtgaagctga aaaggaacca      1260
ttggttagag ttttggttaa cgacagagtt gttccattgc acggttgtgg tgttgacaag      1320
ttgggtagat gtaagagaga cgacttcgtt gaaggtttgt ctttcgctag atctggtggt      1380
aactgggaag aatgtttcgc ttaa                                             1404
```

<210> SEQ ID NO 165
<211> LENGTH: 467
<212> TYPE: PRT
<213> ORGANISM: A. fumigatus ATCC13073

<400> SEQUENCE: 165

Met Gly Val Phe Val Leu Leu Ser Ile Ala Thr Leu Phe Gly Ser
 1               5                  10                  15

Thr Ser Gly Thr Ala Leu Gly Pro Arg Gly Asn His Ser Lys Ser Cys
            20                  25                  30

Asp Thr Val Asp Leu Gly Tyr Gln Cys Ser Pro Ala Thr Ser His Leu
        35                  40                  45

Trp Gly Thr Tyr Ser Pro Tyr Phe Ser Leu Glu Asp Glu Leu Ser Val
    50                  55                  60

Ser Ser Lys Leu Pro Lys Asp Cys Arg Ile Thr Leu Val Gln Val Leu
65                  70                  75                  80

Ser Arg His Gly Ala Arg Tyr Pro Thr Ser Ser Lys Ser Lys Tyr
                85                  90                  95

Lys Lys Leu Ile Thr Ala Ile Gln Ala Asn Ala Thr Asp Phe Lys Gly
            100                 105                 110

Lys Tyr Ala Phe Leu Lys Thr Tyr Asn Tyr Thr Leu Gly Ala Asp Asp
        115                 120                 125

Leu Thr Pro Phe Gly Glu Gln Gln Leu Val Asn Ser Gly Ile Lys Phe
    130                 135                 140

Tyr Gln Arg Tyr Lys Ala Leu Ala Arg Ser Val Val Pro Phe Ile Arg
145                 150                 155                 160

Ala Ser Gly Ser Asp Arg Val Ile Ala Ser Gly Glu Lys Phe Ile Glu
                165                 170                 175

Gly Phe Gln Gln Ala Lys Leu Ala Asp Pro Gly Ala Thr Asn Arg Ala
            180                 185                 190

Ala Pro Ala Ile Ser Val Ile Ile Pro Glu Ser Glu Thr Phe Asn Asn
        195                 200                 205

Thr Leu Asp His Gly Val Cys Thr Lys Phe Glu Ala Ser Gln Leu Gly
    210                 215                 220

Asp Glu Val Ala Ala Asn Phe Thr Ala Leu Phe Ala Pro Asp Ile Arg
225                 230                 235                 240

Ala Arg Leu Glu Lys His Leu Pro Gly Val Thr Leu Thr Asp Glu Asp
                245                 250                 255

Val Val Ser Leu Met Asp Met Cys Pro Phe Asp Thr Val Ala Arg Thr
            260                 265                 270

Ser Asp Ala Ser Gln Leu Ser Pro Phe Cys Gln Leu Phe Thr His Asn
        275                 280                 285

Glu Trp Lys Lys Tyr Asp Tyr Leu Gln Ser Leu Gly Lys Tyr Gly
    290                 295                 300

Tyr Gly Ala Gly Asn Pro Leu Gly Pro Ala Gln Gly Ile Gly Phe Thr

|     |     |     |     |     |     |     |     |     |     |     |     |
|-----|-----|-----|-----|-----|-----|-----|-----|-----|-----|-----|-----|
| 305 |     |     |     | 310 |     |     |     | 315 |     |     | 320 |
| Asn | Glu | Leu | Ile | Ala | Arg | Leu | Thr | Arg | Ser | Pro | Val | Gln | Asp | His | Thr |
|     |     |     |     | 325 |     |     |     | 330 |     |     |     | 335 |
| Ser | Thr | Asn | Ser | Thr | Leu | Val | Ser | Asn | Pro | Ala | Thr | Phe | Pro | Leu | Asn |
|     |     |     | 340 |     |     |     |     | 345 |     |     |     |     | 350 |
| Ala | Thr | Met | Tyr | Val | Asp | Phe | Ser | His | Asp | Asn | Ser | Met | Val | Ser | Ile |
|     |     |     | 355 |     |     |     |     | 360 |     |     |     |     | 365 |
| Phe | Phe | Ala | Leu | Gly | Leu | Tyr | Asn | Gly | Thr | Glu | Pro | Leu | Ser | Arg | Thr |
|     |     | 370 |     |     |     |     | 375 |     |     |     |     | 380 |
| Ser | Val | Glu | Ser | Ala | Lys | Glu | Leu | Asp | Gly | Tyr | Ser | Ala | Ser | Trp | Val |
| 385 |     |     |     |     | 390 |     |     |     |     | 395 |     |     |     |     | 400 |
| Val | Pro | Phe | Gly | Ala | Arg | Ala | Tyr | Phe | Glu | Thr | Met | Gln | Cys | Lys | Ser |
|     |     |     |     | 405 |     |     |     |     | 410 |     |     |     |     | 415 |
| Glu | Lys | Glu | Pro | Leu | Val | Arg | Ala | Leu | Ile | Asn | Asp | Arg | Val | Val | Pro |
|     |     |     | 420 |     |     |     |     | 425 |     |     |     |     | 430 |
| Leu | His | Gly | Cys | Asp | Val | Asp | Lys | Leu | Gly | Arg | Cys | Lys | Leu | Asn | Asp |
|     |     |     | 435 |     |     |     |     | 440 |     |     |     |     | 445 |
| Phe | Val | Lys | Gly | Leu | Ser | Trp | Ala | Arg | Ser | Gly | Gly | Asn | Trp | Gly | Glu |
|     | 450 |     |     |     |     | 455 |     |     |     |     | 460 |
| Cys | Phe | Ser |
| 465 |

<210> SEQ ID NO 166
<211> LENGTH: 1404
<212> TYPE: DNA
<213> ORGANISM: A. fumigatus ATCC13073

<400> SEQUENCE: 166

| | | | | | |
|---|---|---|---|---|---|
| atggggtttt | tcgtcgttct | attatctatc | gcgactctgt | tcggcagcac | atcgggcact | 60 |
| gcgctgggcc | cccgtggaaa | tcactccaag | tcctgcgata | cggtagacct | agggtaccag | 120 |
| tgctcccctg | cgacttctca | tctatggggc | acgtactcgc | catactttc | gctcgaggac | 180 |
| gagctgtccg | tgtcgagtaa | gcttcccaag | gattgccgga | tcaccttggt | acaggtgcta | 240 |
| tcgcgccatg | gagcgcggta | cccaaccagc | tccaagagca | aaagtataa | gaagcttatt | 300 |
| acggcgatcc | aggccaatgc | caccgacttc | aagggcaagt | acgcctttt | gaagacgtac | 360 |
| aactatactc | tgggtgcgga | tgacctcact | ccctttgggg | agcagcagct | ggtgaactcg | 420 |
| ggcatcaagt | tctaccagag | gtacaaggct | ctggcgcgca | gtgtggtgcc | gtttattcgc | 480 |
| gcctcaggct | cggaccgggt | tattgcttcg | ggagagaagt | tcatcgaggg | gttccagcag | 540 |
| gcgaagctgg | ctgatcctgg | cgcgacgaac | gcgccgctc | cggcgattag | tgtgattatt | 600 |
| ccggagagcg | agacgttcaa | caatacgctg | gaccacggtg | tgtgcacgaa | gtttgaggcg | 660 |
| agtcagctgg | gagatgaggt | tgcggccaat | ttcactgcgc | tctttgcacc | cgacatccga | 720 |
| gctcgcctcg | agaagcatct | tcctggcgtg | acgctgacag | acgaggacgt | tgtcagtcta | 780 |
| atggacatgt | gtccgtttga | tacggtagcg | cgcaccagcg | acgcaagtca | gctgtcaccg | 840 |
| ttctgtcaac | tcttcactca | caatgagtgg | aagaagtacg | actaccttca | gtccttgggc | 900 |
| aagtactacg | gctacggcgc | aggcaaccct | ctgggaccgg | ctcagggat | agggttcacc | 960 |
| aacgagctga | ttgcccggtt | gacgcgttcg | ccagtgcagg | accacaccag | cactaactcg | 1020 |
| actctagtct | ccaaccccggc | caccttcccg | ttgaacgcta | ccatgtacgt | cgactttca | 1080 |
| cacgacaaca | gcatggttc | catcttcttt | gcattgggcc | tgtacaacgg | cactgaaccc | 1140 |
| ttgtcccgga | cctcggtgga | aagcgccaag | gaattggatg | ggtattctgc | atcctgggtg | 1200 |

```
gtgcctttcg gcgcgcgagc ctacttcgag acgatgcaat gcaagtcgga aaaggagcct    1260
cttgttcgcg ctttgattaa tgaccgggtt gtgccactgc atggctgcga tgtggacaag    1320 ctgggcgat gcaagctgaa tgactttgtc aagggattga gttgggccag atctgggggc    1380
aactggggag agtgctttag ttga                                          1404
```

<210> SEQ ID NO 167
<211> LENGTH: 467
<212> TYPE: PRT
<213> ORGANISM: consensus phytase-7

<400> SEQUENCE: 167

```
Met Gly Val Phe Val Val Leu Leu Ser Ile Ala Thr Leu Phe Gly Ser
 1               5                  10                  15

Thr Ser Gly Thr Ala Leu Gly Pro Arg Gly Asn Ser His Ser Cys Asp
                20                  25                  30

Thr Val Asp Gly Gly Tyr Gln Cys Phe Pro Glu Ile Ser His Leu Trp
            35                  40                  45

Gly Gln Tyr Ser Pro Tyr Phe Ser Leu Glu Asp Glu Ser Ala Ile Ser
    50                  55                  60

Pro Asp Val Pro Asp Asp Cys Arg Val Thr Phe Val Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Ala Ile Gln Lys Asn Ala Thr Ala Phe Lys Gly Lys
            100                 105                 110

Tyr Ala Phe Leu Lys Thr Tyr Asn Tyr Thr Leu Gly Ala Asp Asp Leu
        115                 120                 125

Thr Pro Phe Gly Glu Asn Gln Met Val Asn Ser Gly Ile Lys Phe Tyr
    130                 135                 140

Arg Arg Tyr Lys Ala Leu Ala Arg Lys Ile Val Pro Phe Ile Arg Ala
145                 150                 155                 160

Ser Gly Ser Ser Arg Val Ile Ala Ser Ala Glu Lys Phe Ile Glu Gly
                165                 170                 175

Phe Gln Ser Ala Lys Leu Ala Asp Pro Gly Ser Gln Pro His Gln Ala
            180                 185                 190

Ser Pro Val Ile Asp Val Ile Ile Ser Glu Ala Ser Tyr Asn Asn
        195                 200                 205

Thr Leu Asp Pro Gly Thr Cys Thr Ala Phe Glu Asp Ser Glu Leu Ala
    210                 215                 220

Asp Thr Val Glu Ala Asn Phe Thr Ala Leu Phe Ala Pro Ala Ile Arg
225                 230                 235                 240

Ala Arg Leu Glu Ala Asp Leu Pro Gly Val Thr Leu Thr Asp Thr Glu
                245                 250                 255

Val Thr Tyr Leu Met Asp Met Cys Ser Phe Glu Thr Val Ala Arg Thr
            260                 265                 270

Ser Asp Ala Thr Glu Leu Ser Pro Phe Cys Ala Leu Phe Thr His Asp
        275                 280                 285

Glu Trp Arg His Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Phe Ala
305                 310                 315                 320

Asn Glu Leu Ile Ala Arg Leu Thr Arg Ser Pro Val Gln Asp His Thr
                325                 330                 335
```

```
Ser Thr Asn His Thr Leu Asp Ser Asn Pro Ala Thr Phe Pro Leu Asn
            340                 345                 350

Ala Thr Leu Tyr Ala Asp Phe Ser His Asp Asn Gly Ile Ile Ser Ile
            355                 360                 365

Phe Phe Ala Leu Gly Leu Tyr Asn Gly Thr Ala Pro Leu Ser Thr Thr
    370                 375                 380

Ser Val Glu Ser Ile Glu Glu Thr Asp Gly Tyr Ser Ser Ala Trp Thr
385                 390                 395                 400

Val Pro Phe Ala Ser Arg Ala Tyr Val Glu Met Met Gln Cys Gln Ala
                405                 410                 415

Glu Lys Glu Pro Leu Val Arg Val Leu Val Asn Asp Arg Val Val Pro
                420                 425                 430

Leu His Gly Cys Ala Val Asp Lys Leu Gly Arg Cys Lys Arg Asp Asp
            435                 440                 445

Phe Val Glu Gly Leu Ser Phe Ala Arg Ser Gly Gly Asn Trp Ala Glu
    450                 455                 460

Cys Phe Ala
465

<210> SEQ ID NO 168
<211> LENGTH: 1426
<212> TYPE: DNA
<213> ORGANISM: consensus phytase-7

<400> SEQUENCE: 168
tatatgaatt catgggcgtg ttcgtcgtgc tactgtccat tgccaccttg ttcggttcca      60
catccggtac cgccttgggt cctcgtggta attctcactc ttgtgacact gttgacggtg     120
gttaccaatg tttcccagaa atttctcact tgtggggtca atactctcca tacttctctt     180
tggaagacga atctgctatt tctccagacg ttccagacga ctgtagagtt actttcgttc     240
aagttttgtc tagacacggt gctagatacc aactgactc taagggtaag aagtactctg     300
ctttgattga agctattcaa agaacgcta ctgctttcaa gggtaagtac gctttcttga     360
agacttacaa ctacactttg ggtgctgacg acttgactcc attcggtgaa accaaatgg     420 ttaactctgg tattaagttc tacagaagat acaaggcttt ggctagaaag attgttccat     480
tcattagagc ttctggttct tctagagtta ttgcttctgc tgaaaagttc attgaaggtt     540
tccaatctgc taagttggct gacccaggtt ctcaaccaca ccaagcttct ccagttattg     600
acgttattat ttctgacgct tcttcttaca acaacacttt ggacccaggt acttgtactg     660 cttttcgaaga ctctgaattg gctgacactg ttgaagctaa cttcactgct ttgttcgctc     720
cagctattag agctagattg gaagctgact tgccaggtgt tactttgact gacactgaag     780
ttacttactt gatggacatg tgttcttttcg aaactgttgc tagaacttct gacgctactg     840
aattgtctcc attctgtgct tgttcactc acgacgaatg gagacactac gactacttgc     900
aatctttgaa gaagtactac ggtcacggtg ctggtaaccc attgggtcca actcaaggtg     960
ttggtttcgc taacgaattg attgctagat tgactagatc tccagttcaa gaccacactt    1020
ctactaacca cactttggac tctaacccag ctacttttccc attgaacgct actttgtacg    1080
ctgacttctc tcacgacaac ggtattattt ctatttttctt cgctttgggt ttgtacaacg    1140
gtactgctcc attgtctact acttctgttg aatctattga agaaactgac ggttactctt    1200
ctgcttggac tgttccattc gcttctagag cttacgttga aatgatgcaa tgtcaagctg    1260
aaaaggaacc attggttaga gttttggtta acgacagagt tgttccattg cacggttgtg    1320
```

```
ctgttgacaa gttgggtaga tgtaagagag acgacttcgt tgaaggtttg tctttcgcta    1380
gatctggtgg taactgggct gaatgtttcg cttaagaatt catata                   1426
```

<210> SEQ ID NO 169
<211> LENGTH: 467
<212> TYPE: PRT
<213> ORGANISM: Artificial Sequence
<220> FEATURE:
<223> OTHER INFORMATION: Description of Artificial Sequence:consensus phytase-12

<400> SEQUENCE: 169

```
Met Gly Val Phe Val Leu Leu Ser Ile Ala Thr Leu Phe Gly Ser
 1               5                  10                  15

Thr Ser Gly Thr Ala Leu Gly Pro Arg Gly Asn Ser His Ser Cys Asp
            20                  25                  30

Thr Val Asp Gly Gly Tyr Gln Cys Phe Pro Glu Ile Ser Ser Asn Trp
        35                  40                  45

Ser Pro Tyr Ser Pro Tyr Phe Ser Leu Ala Asp Glu Ser Ala Ile Ser
    50                  55                  60

Pro Asp Val Pro Lys Gly Cys Arg Val Thr Phe Val Gln Val Leu Gln
65                  70                  75                  80

Arg His Gly Ala Arg Phe Pro Thr Ser Gly Ala Ala Thr Arg Ile Ser
                85                  90                  95

Ala Leu Ile Glu Ala Ile Gln Lys Asn Ala Thr Ala Phe Lys Gly Lys
            100                 105                 110

Tyr Ala Phe Leu Lys Thr Tyr Asn Tyr Thr Leu Gly Ala Asp Asp Leu
        115                 120                 125

Val Pro Phe Gly Ala Asn Gln Ser Ser Gln Ala Gly Ile Lys Phe Tyr
    130                 135                 140

Arg Arg Tyr Lys Ala Leu Ala Arg Lys Ile Val Pro Phe Ile Arg Ala
145                 150                 155                 160

Ser Gly Ser Asp Arg Val Ile Asp Ser Ala Thr Asn Trp Ile Glu Gly
                165                 170                 175

Phe Gln Ser Ala Lys Leu Ala Asp Pro Gly Ala Asn Pro His Gln Ala
            180                 185                 190

Ser Pro Val Ile Asn Val Ile Ile Pro Glu Gly Ala Gly Tyr Asn Asn
        195                 200                 205

Thr Leu Asp His Gly Leu Cys Thr Ala Phe Glu Glu Ser Glu Leu Gly
    210                 215                 220

Asp Asp Val Glu Ala Asn Phe Thr Ala Val Phe Ala Pro Pro Ile Arg
225                 230                 235                 240

Ala Arg Leu Glu Ala His Leu Pro Gly Val Asn Leu Thr Asp Glu Asp
                245                 250                 255

Val Val Asn Leu Met Asp Met Cys Pro Phe Asp Thr Val Ala Arg Thr
            260                 265                 270

Ser Asp Ala Thr Glu Leu Ser Pro Phe Cys Asp Leu Phe Thr His Asp
        275                 280                 285

Glu Trp Ile Gln Tyr Asp Tyr Leu Gly Asp Leu Asp Lys Tyr Tyr Gly
    290                 295                 300

Thr Gly Ala Gly Asn Pro Leu Gly Pro Ala Gln Gly Val Gly Phe Val
305                 310                 315                 320

Asn Glu Leu Ile Ala Arg Leu Thr His Ser Pro Val Gln Asp His Thr
                325                 330                 335
```

```
-continued

Ser Thr Asn His Thr Leu Asp Ser Asn Pro Ala Thr Phe Pro Leu Asn
            340                 345                 350

Ala Thr Leu Tyr Ala Asp Phe Ser His Asp Asn Thr Met Val Ala Ile
            355                 360                 365

Phe Phe Ala Leu Gly Leu Tyr Asn Gly Thr Lys Pro Leu Ser Thr Thr
    370                 375                 380

Ser Val Glu Ser Ile Glu Glu Thr Asp Gly Tyr Ser Ala Ser Trp Leu
385                 390                 395                 400

Val Pro Phe Ser Ala Arg Met Tyr Val Glu Met Met Gln Cys Glu Ala
                405                 410                 415

Glu Lys Glu Pro Leu Val Arg Val Leu Val Asn Asp Arg Val Val Pro
                420                 425                 430

Leu His Gly Cys Gly Val Asp Lys Leu Gly Arg Cys Lys Arg Asp Asp
        435                 440                 445

Phe Val Glu Gly Leu Ser Phe Ala Arg Ser Gly Gly Asn Trp Glu Glu
    450                 455                 460

Cys Phe Ala
465
```